United States Patent
Angiolini et al.

(10) Patent No.: US 7,019,002 B2
(45) Date of Patent: Mar. 28, 2006

(54) PYRIDOPYRIMIDINONES DERIVATIVES AS TELOMERASE INHIBITORS

(75) Inventors: Mauro Angiolini, Bergamo (IT); Dario Ballinari, Milan (IT); Domenico Fusar Bassini, Montodine (IT); Luisella Bonomini, Cesano Maderno (IT); Markus Gude, Laufelfingen (CH); Maria Menichincheri, Milan (IT); Jurgen Moll, Appiano Gentile (IT); Jean-Yves Trosset, Issey-les-Moulineaux (FR)

(73) Assignee: Pharmacia & Upjohn, S.p.A., Milan (IT)

( * ) Notice: Subject to any disclaimer, the term of this patent is extended or adjusted under 35 U.S.C. 154(b) by 82 days.

(21) Appl. No.: 10/310,193

(22) Filed: Dec. 4, 2002

(65) Prior Publication Data

US 2004/0009993 A1 Jan. 15, 2004

Related U.S. Application Data

(60) Provisional application No. 60/339,420, filed on Dec. 11, 2001.

(51) Int. Cl.
  C07D 471/04 (2006.01)
  C07D 239/47 (2006.01)
  C07D 239/38 (2006.01)
  A61K 31/519 (2006.01)
  A61P 35/00 (2006.01)

(52) U.S. Cl. .................. 514/234.2; 544/117; 544/279; 544/317; 544/318; 514/264.11

(58) Field of Classification Search ................ 544/117, 544/279; 514/234.2, 264.11
  See application file for complete search history.

(56) References Cited

U.S. PATENT DOCUMENTS 6,242,452 B1 * 6/2001 Ogino et al. ............. 514/264.1

OTHER PUBLICATIONS

Incles et al, Current Opinion in Investigational Drugs. 2003 Jun.; 4(6):675-85.*
Rudolph, Cell, vol. 96, 701-712, Mar. 5, 1999.*
Titia de Lange et al, "For Better or Worse? Telomerase Inhibition and Cancer"(Cell, vol. 98, 273-275, Aug. 6, 1999), p. 274.*
Asai, Cancer Res. 63(14), 3931-9, Jul. 15, 2003.*
SCIFINDER printout for compound with registry No. 64224-21-1.*
SCIFINDER printout for compound with registry No. 797791-98-1.*
Herbert, et al., "*Inhibition of Human Telomerase in Immortal Human Cells Leads to Progressive Telomere Shortening and Cell Death*", PNAS, vol. 96, No. 25, pp. 14276-14281, Dec. 1999.
Hahn, et al., "*Inhibition of Telomerase Limits the Growth of Human Cancer Cells*", Nature Medicine, vol. 5, No. 10, pp. 1164-1170, Oct., 1999.
Nakamura, et al., "*Correlation of Telomere Lengths in Normal and Cancers Tissue in the Large Bowel*", Cancer Letters, 158, pp. 179-184, 2000.
Shay, et al., "*A Survey of Telomerase Activity in Human Cancer*", European Journal of Cancer, vol. 33, No. 5, pp. 787-791, 1997.
Blackburn, "*Telomerases*", Annu. Rev. Biochem., 61:113-29, 1992.
Shammas, et al., "*Telomerase Inhibition by Peptide Nucleic Acids Reverses 'Immorality' of Transformed Human Cells*", Oncogene, 18, pp. 6191-6200, 1999.
Feng, et al., "*The RNA Component of Human Telomerase*", Science, vol. 269, pp. 1236-1241, 1995.
Harley, "*Telomere loss: mitotic clock or genetic time bomb?*", Mutation Research, vol. 256, pp. 271-282, 1991.

* cited by examiner

*Primary Examiner*—Mark L. Berch
(74) *Attorney, Agent, or Firm*—Steve T. Zelson; Christian M. Smolizza

(57) ABSTRACT

The invention provides pyrido[2,3-d]pyrimidin-7(8H)-one telomerase inhibitors of the formula

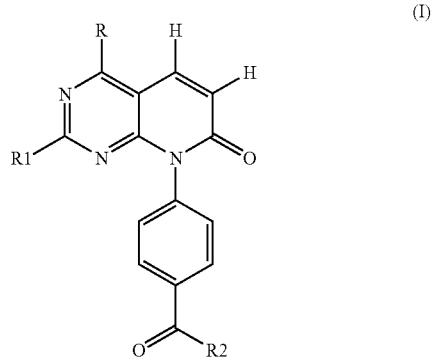

where R1, R2 are as defined herein. The invention also provides methods for preparing the compounds of formula I, methods of using the compounds to treat diseases such as cancer, and pharmaceutical compositions comprising the compounds.

9 Claims, No Drawings

PYRIDOPYRIMIDINONES DERIVATIVES AS TELOMERASE INHIBITORS

PRIORITY

This application claims the benefit of U.S. application Ser. No. 60/339,420, filed on Dec. 11, 2001, which is herein incorporated by reference in its entirety.

SUMMARY OF THE INVENTION

The present invention relates to novel pyrido[2,3-d]pyrimidin-7(8H)-ones derivatives active as Telomerase inhibitors, to the use of them as therapeutic agents, in particular as antitumoral agents, to a process for their preparation and to pharmaceutical compositions comprising them.

BACKGROUND OF THE INVENTION

Cancer is one of the major causes of disease and the second leading cause of death in the western world. Most cancer patients still die due to metastatic disease. Despite the great increase in the knowledge and understanding of the regulatory mechanisms involved in the onset of malignancy, currently available treatments (including surgery, radiation and a variety of cytoreductive and hormone-based drugs, used alone or in combination), are still highly non specific and toxic to the patient, causing severe side effects including nausea and vomiting, hair loss, diarrhea, fatigue and ulcerations. These evidences indicate the need for new and more effective anti-cancer therapies.

Recently an understanding of the mechanisms by which normal cells reach the state of replicative senescence, i.e. the loss of proliferative capacity that cells normally undergo in the cellular aging process, has begun to emerge and in this respect telomerase appears to have a central role.

Telomerase is a ribonucleoprotein enzyme responsible in most eukaryotes for the complete replication and maintenance of chromosome ends, or telomeres, which are composed of repeated DNA sequences (in particular human telomeres are formed by 5'-TTAAGGG repeats). Telomerase binds to telomeric DNA using as a template a sequence contained within the RNA component of the enzyme necessary for the addition of the short sequence repeats to the chromosome 3' end (see Blackburn 1992, *Annu. Rev. Biochem.*, 61, 113–129). In most human somatic cells telomerase activity cannot be detected and telomeres shorten with successive cell division: in fact actively dividing normal cells have the potential to lose 50–200 base pairs after each round of cell division, finally resulting in shortening of telomeres. Recently it has been hypothesized that the cumulative loss of telomeric DNA over repeated cell divisions can act as a trigger for cellular senescence and aging, and that regulation of telomerase can have important biological implications (see Harley 1991, *Mutation Research*, 256, 271–282). In fact in the absence of telomerase, telomeres shortening will eventually lead to cellular senescence by various mechanisms. This phenomenon, thought to be responsible for cellular aging, is termed the "mitotic clock" (see Holt et al. *Nat. Biotechnol.*, 1996, 15, 1734–1741).

Telomerase activity is restored in immortalised cell lines and in more than 85% of human tumors, thus maintaining telomeres length stable (see Shay, J. W. and Bacchetti, S. *Eur. J. Cancer*, 1997, 33, 787–791). Thus in cancer cells having telomerase activity and where the malignant phenotype is due to the loss of cell cycle or growth controls or other genetic damage, telomeric DNA is not lost during cell division and telomers are maintained, thereby allowing the cancer cells to become immortal, leading to a terminal prognosis for the patient.

Telomerase inhibition can lead to telomere shortening in tumors and subsequent senescent phenotype (see Feng et al. *Science*, 1995, 269, 1236–1241). Moreover it has been recently shown (Hahn et al. *Nature Med.*, 1999, 5, 1164–1170) that inhibition of telomerase activity by expressing in tumor cells a catalytically-inactive form of human TERT (TElomerase Reverse Transcriptase, the catalytic subunit of the enzyme) can cause telomere shortening and arrest of cell growth and apoptosis. In addition peptide-nucleic acids and 2'-O-MeRNA oligomers complementary to the template region of the RNA component of the enzyme have been reported to cause inhibition of telomerase activity, telomere shortening and cell death in certain tumor cell lines (see Herbert et al. *PNAS*, 1999, 96, 14276–14281; Shammas et al. *Oncogene*, 1999, 18, 6191–6200). These data strongly support inhibition of telomerase activity as an innovative, selective and useful method for the development of new anticancer agents.

Thus compounds that inhibit telomerase activity can be used to treat cancer, as cancer cells express telomerase activity, while normal human somatic cells usually do not express telomerase activity at biologically relevant levels (i.e., at levels sufficient to maintain telomere length over many cell divisions). Also telomere length in tumors is reduced compared with non-transformed cells giving the possibility of a therapeutic window (see Nakamura et al. *Cancer Letters* 158, 2000, 179–184).

Therefore, a need exists to find molecules that inhibit the activity of telomerase and interfere with the growth of many types of cancer.

The present invention fulfills such a need by providing a highly general method of treating many—if not most—malignancies, as demonstrated by the highly number of human tumor cell lines and tumors having telomerase activity.

The compounds of the present invention can be effective in providing treatments that discriminate between malignant and normal cells to a high degree, avoiding many of the deleterious side-effects present with most current chemotherapeutic regimes which rely on agents that kill dividing cells indiscriminately. Therefore they are expected to exhibit greater safety and lack of toxic effects in comparison with traditional chemotherapeutic anticancer agents.

DETAILED DESCRIPTION OF THE INVENTION

Embodiments of the present invention are pyrido[2,3-d]pyrimidin-7(8H)-ones derivatives having the following formula (I):

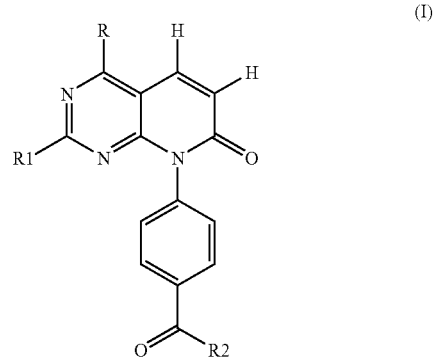

(I)

wherein
R represents C1–C6 alkyl or C1–C6 arylalkyl;
R1 represents NR3R4, wherein
R3 represents hydrogen, C1–C6 alkyl, alkenyl, aryl or acyl; and
R4 represents hydrogen; unsubstituted C1–C10 alkyl; C1–C10 alkyl substituted by cycloalkyl, C1–C6 alkoxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl or arylsulfonyl; C1–C10 alkyl substituted by phenyl unsubstituted or substituted by from 1 to 3 substituents chosen independently from halogen, C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C10 alkyl substituted by heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; alkenyl; cycloalkyl; cycloalkenyl; phenyl unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy) carbonyl, aryloxycarbonyl, amino, C1–C4 dialkylamino, or with heterocycles such as imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the like; fused bicycles comprising 1-naphthyl, 2-naphthyl and dihydronaphthalenyl; monocyclic heterocycles comprising imidazoles, pyrazoles, oxadiazoles, pyrroles, furans, thiadiazoles, oxazoles, thiazoles, triazoles, tetrazoles, pyridines, pyrimidines and pyrrolidines, unsubstituted or substituted by C1–C6 alkyl, aryl, C1–C6 acyl, or arylalkyl; or benzoheterocycles comprising benzofuranyl, benzothiazolyl, benzothiophenyl and benzimidazolyl, unsubstituted or substituted by C1–C6 alkyl, aryl, C1–C6 acyl, or arylalkyl; or NR3R4 represent a ring of the following type:

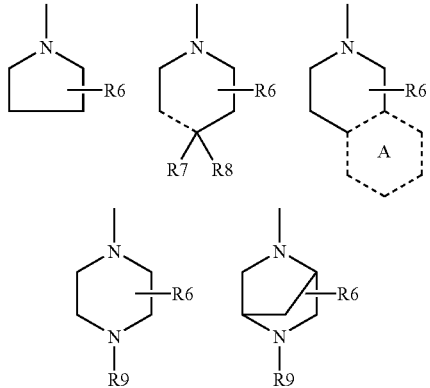

wherein the symbol ----- represents a single or a double bond;

A represents a saturated, unsaturated or aromatic six-membered ring;

R6 represents hydrogen; C1–C6 alkyl unsubstituted or substituted by alkoxy, dialkylamino, arylamino, alkylcarbonyl, arylcarbonyl, substituted or unsubstituted aryl, unsubstituted or substituted heterocycle, alkoxycarbonyl, carboxy, acylamino; alkenyl; cycloalkyl; cyano; alkoxycarbonyl; carboxy; alkylsulfanyl; arylsulfanyl; carbamoyl; alkylcarbamoyl; dialkylcarbamoyl; arylcarbamoyl; acylamino; phenyl unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy) carbonyl, aryloxycarbonyl, amino, C1–C4 dialkylamino, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; heterocycles comprising imidazoles, pyrazoles, oxazoles, oxadiazoles, pyrroles, furans, thiadiazoles, oxazoles, thiazoles, triazoles, tetrazoles, pyridines, pyrimidines, morpholines, piperidines, piperazines, pyrrolidines, indoles, benzofurans, benzothiazoles, benzothiophenes, benzimidazoles and phthalimido, unsubstituted or substituted by C1–C6 alkyl, aryl, C1–C6 acyl, or arylalkyl;

R7 and R8 represent, independently, hydrogen, C1–C6 alkyl (unsubstituted or substituted by alkoxy, hydroxy, amino, monoalkylamino, dialkylamino, arylamino, alkylcarbonyl, unsubstituted or substituted arylcarbonyl, substituted or unsubstituted aryl, unsubstituted or substituted heterocycle, alkoxycarbonyl, carboxy, acylamino); alkenyl; alkynyl; cycloalkyl; hydroxy; alkoxy; aryloxy; amino; alkylamino; arylamino; dialkylamino; diarylamino; alkylarylamino; acyloxy; alkoxycarbonyl; formyl; acyl; carboxy; acylamino; carbamoyl; alkylcarbamoyl; dialkylcarbamoyl; arylcarbamoyl; arylsulfonylamino; alkylaminosulfonyl; arylaminosulfonyl and cyano; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles comprising as imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; heterocycles, comprising imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofurans, benzothiazoles, benzothiophenes and benzimidazoles, unsubstituted or substituted by C1–C6 alkyl, aryl, C1–C6 acyl, or arylalkyl; or R7 and R8 taken together represent oxygen, a spirocyclized substituent comprising ethylidendioxy, propylidendioxy, cycloalkylidene or imidazolidindione;

R9 represents hydrogen; unsubstituted C1–C10 alkyl; C1–C10 alkyl substituted by cycloalkyl, C1–C6 alkoxy optionally substituted by hydroxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl or arylsulfonyl; C1–C10 alkyl substituted by phenyl unsubstituted or substituted by from 1 to 3 substituents, chosen independently from halogen, C1–C6 alkyl, C1–C6 alkoxy optionally substituted by hydroxy, methylenedioxy, hydroxy, carboxy, cyano, nitro, amino, monoalkylamino, monoarylamino, dialkylamino, alkylarylamino, diarylamino, C1–C6 trialkylammonium halides, alkylsulfanyl, alkylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl; C1–C10 alkyl substituted by heterocycles comprising imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofuranes, benzothiazoles, benzothiophenes, benzimidazoles, pyrazynes and quinolines, unsubstituted or substituted by C1–C6 alkyl, aryl, C1–C6 acyl, or arylalkyl; alkenyl; cycloalkyl; cycloalkenyl; formyl; acyl comprising optionally substituted C1–C6 alkylcarbonyl, optionally substituted arylcarbonyl and optionally substituted heterocyclylcarbonyl; C1–C6 alkoxycarbonyl optionally substituted by phenyl; carbamoyl; optionally substituted alkylcarbamoyl; dialkylcarbamoyl; optionally substituted arylcarbamoyl; alkylsulfonyl; arylsulfonyl; phenyl unsubstituted or substituted by from 1 to 3 substituents, chosen independently from halogen, C1–C6 alkyl, C1–C6 acyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, and piperidines, unsubstituted or substituted aryl, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles comprising 1-naphthyl and 2-naphthyl and dihydronaphthalenyls; heterocycles comprising imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofuranes, benzothiazoles, benzothiophenes, benzimidazoles, pyrazynes, and quinolines, unsubstituted or substituted by C1–C6 alkyl, aryl, C1–C6 acyl, or arylalkyl; or R1 represents OR5, SR5, SOR5 or SO2R5 wherein
  R5 represents unsubstituted C1–C6 alkyl; C1–C6 alkyl substituted by cycloalkyl, C1–C6 alkoxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl, arylsulfonyl; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl; C1–C6 alkyl substituted by heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; alkenyl; cycloalkyl; cycloalkenyl; phenyl unsubstituted or substituted by 1 to 3 substituents, chosen independently from halogen, C1–C6 alkyl, perhalogenated C1–C6 alkyl, C1–C6 alkyl substituted by aminocarbonyl or by OH, C1–C6 alkoxy, hydroxy, C1–C6 acyl, carboxy, cyano, nitro, amino, C1–C6 monoalkylamino, monoarylamino, C1–C6 dialkylamino, diarylamino, C1–C6 trialkylammonium halides, C1–C4 acylamino, (C1–C6 alkoxy)carbonyl, alkylsulfanyl, arylsulfanyl, alkylsulfinyl, arylsulfinyl, alkylsulfonyl, arylsulfonyl, alkylsulfonylamino, arylsulfonylamino, alkylaminosulfonyl, arylaminosulfonyl, aryloxy or arylalkyl; mono heterocles comprising imidazoles, pyrazoles, oxazoles, oxadiazoles, pyrroles, furans, thiadiazoles, oxazoles, thiazoles, triazoles, tetrazoles, pyridines, pyrimidines and pyrrolidines, unsubstituted or substituted by C1–C6 alkyl, aryl, C1–C6 acyl, or arylalkyl; or benzoheterocycles comprising benzofuranyl, benzothiazolyl, benzothiophenyl, benzimidazolyl, and the like unsubstituted or substituted by C1–C6 alkyl, aryl, C1–C6 acyl, or arylalkyl;

R2 represents:

OR', wherein R' is hydrogen, C1C6 alkyl, alkenyl, or aryl; NR"R'", wherein R" represents hydrogen or C1–C6 alkyl, and R'" represents hydrogen; unsubstituted C1–C10 alkyl; alkenyl; cycloalkyl; cycloalkenyl; C1–C6 alkyl substituted with cycloalkyl, C1–C6 alkoxy, C1–C6 acyl, amino, monoalkylamino and monoalkylamino-N-oxides, monoarylamino and monoarylamino N-oxides, dialkylamino and dialkylamino N-oxides, alkylarylamino and alkylarylamino N-oxides, mono heterocycles comprising unsubstituted or substituted morpholinyl, furyl, tetrahydrofuryl, pyridinyl, pyrimidinyl, imidazolyl, pyrazolyl, oxazolyl, pyrrolyl, thiazolyl, piperazinyl, N-alkyl piperazinyl, and the like and the corresponding N-oxides); fused bicycles comprising 1-naphthyl, 2-naphthyl and dihydronaphthalenyls; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C6 alkyl substituted by heterocycles comprising unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides;

phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles comprising imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles comprising 1-naphthyl, 2-naphthyl and dihydronaphthalenyls; heterocycles comprising unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides; and, if the case, the pharmaceutically acceptable salts thereof.

The present invention provides, in one embodiment, a compound of formula (I) wherein R represents C1–C4 alkyl for example, methyl, R1 and R2 are as defined above and, if the case, the pharmaceutically acceptable salts thereof.

In particular, the present invention relates to a compound of formula (I) wherein R represents C1–C4 alkyl for example, methyl, R1 is as defined above, R2 represents OR' wherein R' is as defined above and, if the case, the pharmaceutically acceptable salts thereof.

More in particular, the present invention relates to a compound of formula (I) wherein R represents C1–C4 alkyl, for example, methyl, R1 is as defined above, R2 represents OR' wherein R' represents hydrogen or C1–C6 alkyl, for example, methyl ethyl or t-butyl, and, if the case, the pharmaceutically acceptable salts thereof.

Still more in particular, the present invention relates to a compound of formula (I) wherein R represents C1–C4 alkyl for example, methyl, R1 represents SR5 or SO2R5 wherein R5 represents an unsubstituted C1–C6 alkyl for example, methyl, R2 represents OR' wherein R' represents hydrogen or C1–C6 alkyl, for example, methyl ethyl or t-butyl and, if the case, the pharmaceutically acceptable salts thereof.

Further in particular, the present invention relates to a compound of formula (I) wherein R represents C1–C4 alkyl for example, methyl, R1 represents NR3R4 wherein R3 represents hydrogen and R4 represents phenyl substituted by C1–C6 alkoxycarbonyl, or R1 represents NR3R4 wherein NR3R4 represents a ring of formula

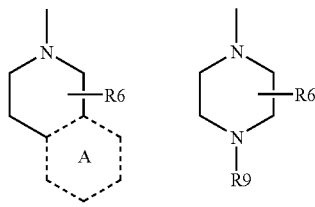

wherein R6 is hydrogen, the symbol ---- represents a single or double bond, A represents a phenyl ring, R9 is 2-pyridinyl, 2-pyrimidinyl, phenyl or p-fluorophenyl, R2 represents OR' wherein R' represents hydrogen or C1–C6 alkyl, for example, methyl ethyl or t-butyl and, if the case, the pharmaceutically acceptable salts thereof.

In a still another aspect the present invention relates to a compound of formula (I) wherein R represents C1–C4 alkyl for example, methyl, R1 represents OR5 wherein R5 represents a group selected from

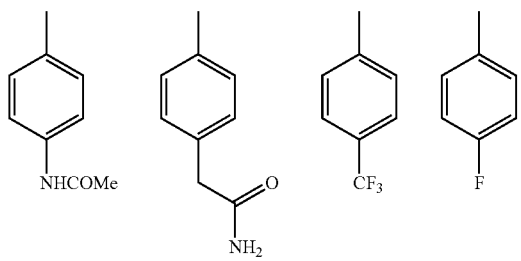

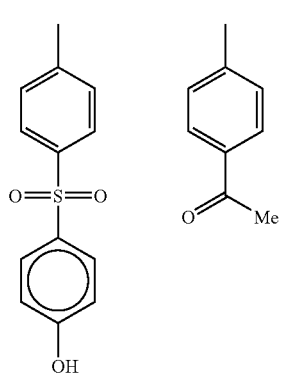

or R1 represents SR5 wherein R5 is a group selected from:

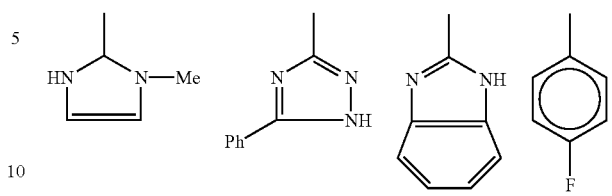

R2 represents NR"R'" wherein R" represents hydrogen and R'" represents hydrogen; unsubstituted C1–C8 alkyl, for example, n-C8H17 or iso-butyl; C1–C6 cycloalkyl, for example, cyclopropyl; or a substituent selected from:

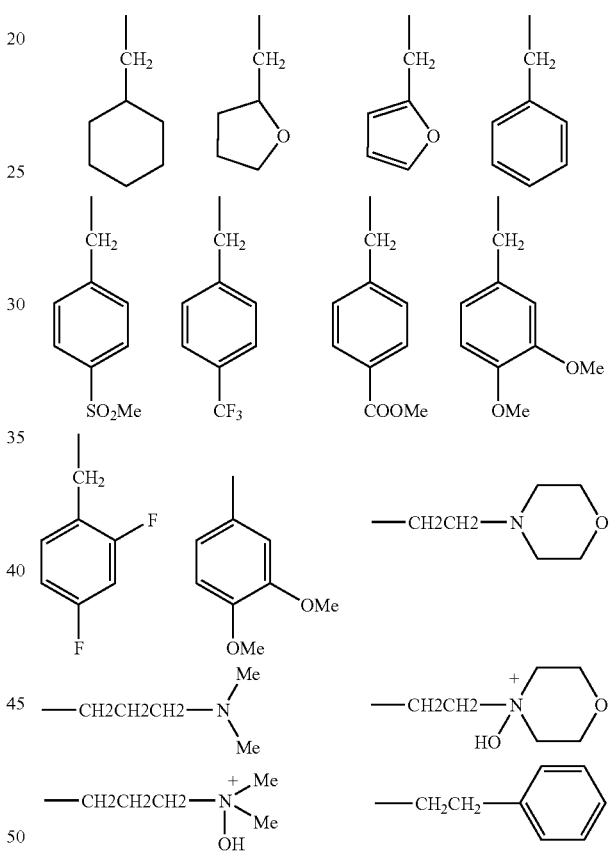

and, if the case, the pharmaceutically acceptable salts thereof.

In a further aspect, the present invention relates to a compounds of formula (I) wherein R represents methyl, R1 represents NR3R4 wherein R3 represents hydrogen and R4 represents a group selected from:

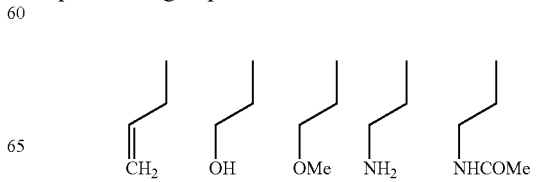

-continued

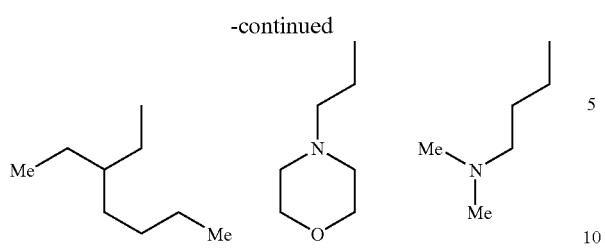

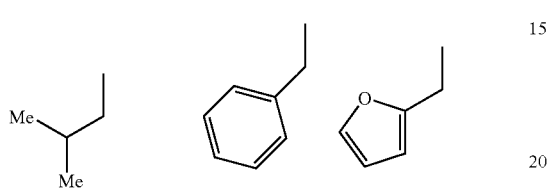

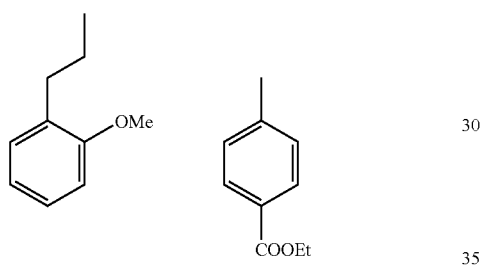

or R1 represents NR3R4 wherein NR3R4 represents:
(i) a group of formula

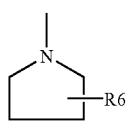

wherein $R_6$ represents hydrogen or carboxy;
(ii) a group of formula

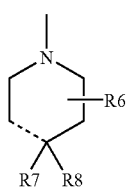

wherein the symbol --- represents a single or double bond, $R_6$ represents hydrogen, alkoxy carbonyl and $R_7$ and $R_8$ represent, each independently, hydrogen, hydroxy, unsubstituted phenyl, $C_1$–$C_4$ alkyl carbonyl, $C_1$–$C_4$ alkyl substituted by hydroxy, phenyl or phenylcarbonyl in which phenyl is substituted with halogen, or $R_7$ and $R_8$, taken together represent oxygen, in particular it represents a group selected from:

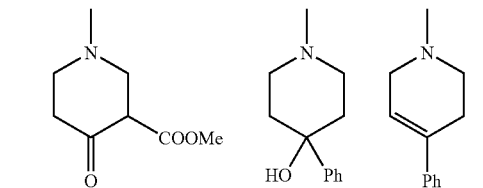

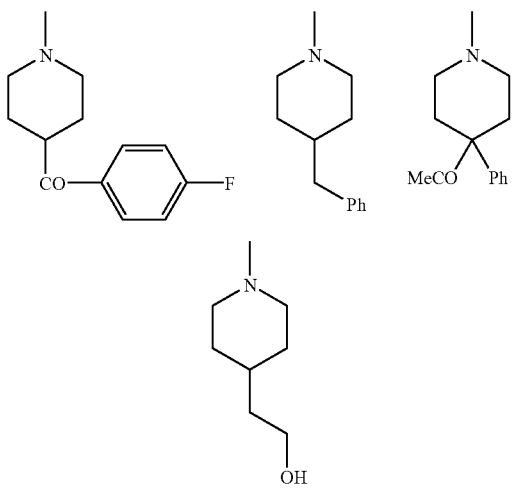

(iii) a group of formula

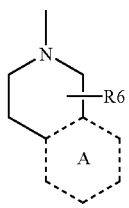

wherein the symbol ---- represents a single or double bond, A represent an unsubstituted phenyl ring or cyclohexyl and $R_6$ represents hydrogen;
(iv) a group of formula

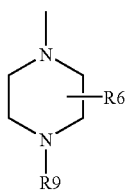

wherein R6 represents hydrogen and R$_9$ represents a group selected from
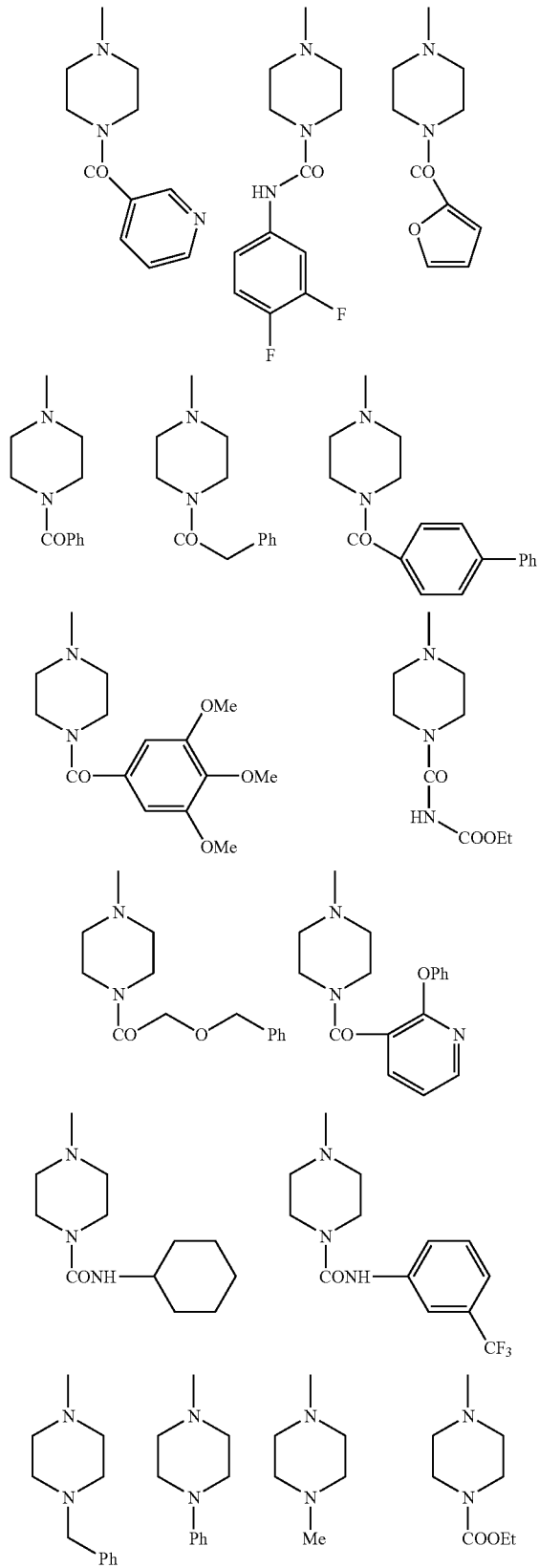
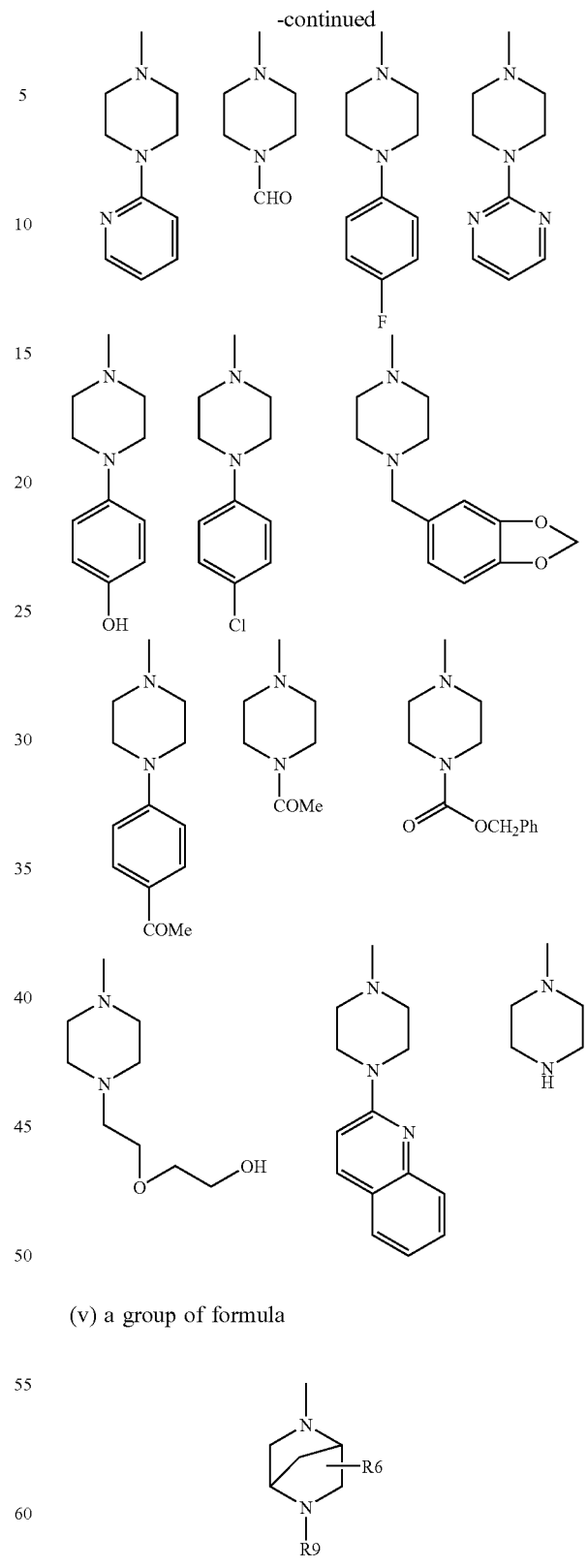
(v) a group of formula
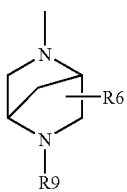
wherein R$_6$ is hydrogen and R$_9$ is C1–C4 alkyl substituted by phenyl, or phenyl substituted by halogen; and R2 represents NR"R'" wherein R" represents hydrogen and R'" represents hydrogen; unsubstituted C1–C8 alkyl, for example, n-C8H17 or iso-butyl; C1–C6 cycloalkyl, for example, cyclopropyl; or R''' represents a substituent selected from:

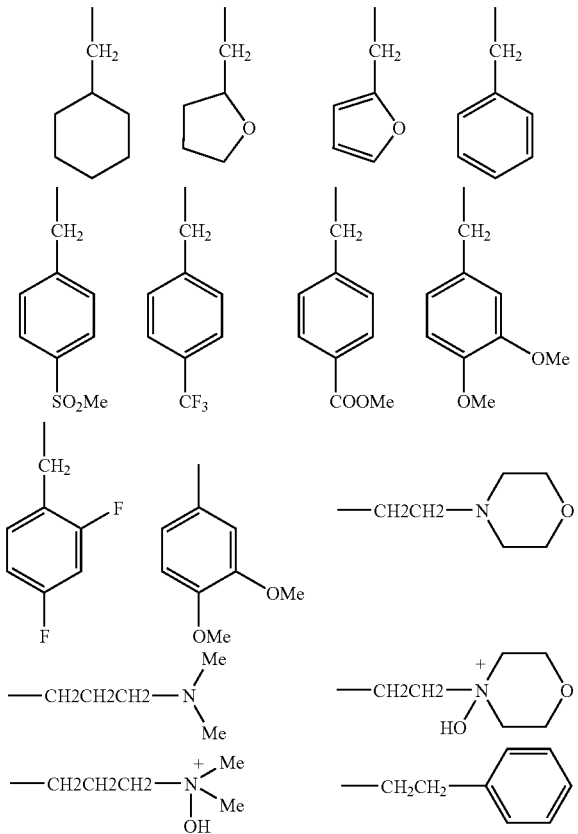

and, if the case, the pharmaceutically acceptable salts thereof.

The symbols "Me", "Et" and "Ph" means, as herein reported, methyl, ethyl and phenyl, respectively.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium bases, or alkaline-earth metal, especially calcium or magnesium bases, or with organic bases, e.g. alkylamines, for example, triethyl-amine.

The present invention includes within its scope all possible isomers, stereoisomers and optical isomers and their mixtures, and the metabolites and the metabolic precursors or bioprecursors of the compounds of formula (I).

In the written descriptions of molecules and groups, molecular descriptors can be combined to produce words or phrases that describe structural groups or are combined to describe structural groups. Such descriptors are used in this document. Common illustrative examples include such terms as aralkyl (or arylalkyl), alkylarylamino, aryloxycarbonyl, and the like. It is also to be noted that a structural group can have more than one descriptive word or phrase in the art, for example, alkylcarbonyl can also be termed alkanoyl. Such combinations are used herein in the description of the processes, compounds and compositions of this invention and further examples are described below. The following list is not intended to be exhaustive or drawn out but provide illustrative examples of words or phrases (terms) that are used herein.

As utilized herein, the term "alkyl", alone or in combination means, unless otherwise specified, a straight-chain or branched-chain alkyl radical containing one to about twelve carbon atoms, for example, one to about ten carbon atoms, and for example, one to about six carbon atoms. Examples of such radicals include methyl, ethyl, n-propyl, isopropyl, n-butyl, isobutyl, sec-butyl, tert-butyl, pentyl, iso-amyl, hexyl, octyl, and the like.

The term "alkenyl", alone or in combination means, unless otherwise specified, a straight-chain or branched-chain hydrocarbon radical having one or more double bonds and containing two to about to about twelve carbon atoms, and for example, two to about six carbon atoms. Examples of suitable alkenyl radicals include ethenyl (vinyl), 2-propenyl, 3-propenyl, allyl, 1,4-pentadienyl, 1,4-butadienyl, 1-butenyl, 2-butenyl, 3-butenyl, 4-methylbutenyl, decenyl, and the like.

The term "alkenyl" embrace radicals having "cis" and "trans" orientations, or alternatively, "E" and "Z" orientations.

The term "alkynyl", alone or in combination means, unless otherwise specified, a straight-chain or branched-chain hydrocarbon radical having one or more triple bonds and containing two to about twelve carbon atoms, for example, two to about ten carbon atoms, and for example, two to about six carbon atoms. Examples of alkynyl radicals include ethynyl, 2-propynyl, 3-propynyl, decynyl, 1-butynyl, 2-butynyl, 3-butynyl, propargyl, and the like.

The term "acyl", alone or in combination means, unless otherwise specified, a radical provided by the residue after removal of hydroxyl from an organic acid. Examples of such acyl radicals include alkanoyl and aroyl radicals. Examples of such alkanoyl radicals include formyl, acetyl, propionyl, butyryl, isobutyryl, valeryl, isovaleryl, pivaloyl, hexanoyl, trifluoroacetyl, and the like.

The term "carbonyl" or "oxo", alone or in combination, i.e., used with other terms, such as "alkoxycarbonyl", means a —C(=O)— group wherein the remaining two bonds (valences) can be independently substituted. The term carbonyl is also intended to encompass a hydrated carbonyl group —C(OH)$_2$—.

The term "carbamoyl", alone or in combination means, unless otherwise specified, a R—NH—C=O— group wherein R represents an alkyl or an aryl substituent, where the terms alkyl or aryl are as defined above.

The term "alkylcarbamoyl" alone or in combination, means a radical of the formula R—NH—C=O— in which R represents an alkyl group as defined above.

The term "arylcarbamoyl" alone or in combination, means a radical of the formula R—NH—C=O— in which R represents an aryl group as defined above.

The term "halogen", alone or in combination, means fluoride, chloride, bromide or iodide.

The term "amino", alone or in combination, means an amine or —NH$_2$ group whereas the term mono-substituted amino, alone or in combination, means a substituted amine —N(H)(substituent) group wherein one hydrogen atom is replaced with a substituent, and disubstituted amine means a —N(substituent)$_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or N,N-disubstituted depending on the degree of substitution of the amino nitrogen. Quaternary amine (ammonium) (IV°) means a nitrogen with four substituents [—N⁺(substituent)₄] that is positively charged and accompanied by a counter ion, whereas N-oxide means one substituent is oxygen and the group is represented as [—N⁺(substituent)₃—O⁻]; i.e., the charges are internally compensated.

The term "cyano", alone or in combination, means a —C-triple bond-N (—C≡N) group.

The term "hydroxy", alone or in combination, means a —OH group.

The term "nitro", alone or in combination, means a —NO2 group.

The term "sulfonyl", alone or in combination, i.e., linked to other terms such as alkylsulfonyl, means a —SO₂— group wherein the depicted remaining two bonds (valences) can be independently substituted.

The term "sulfinyl", alone or in combination, i.e., linked to other terms such as alkylsulfonyl, means a —S(=O)— group wherein the depicted remaining two bonds (valences) can be independently substituted.

The term "sulfanyl", alone or in combination, i.e., linked to other terms such as alkylsulfonyl, means a —S— group wherein the depicted remaining two bonds (valences) can be independently substituted.

The term "alkoxy" or "alkoxy", alone or in combination mean, unless otherwise specified, an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy, and the like.

The term "cycloalkyl", alone or in combination means, unless otherwise specified, a cyclic alkyl radical that contains three to about twelve carbon atoms. For example, cycloalkyl radicals are cycloalkyl radicals having three to about eight carbon atoms. Examples of such radicals include cyclopropyl, cyclobutyl, cyclopentyl, cyclohexyl, and the like.

The term "heterocycle" embraces saturated, partially unsaturated and unsaturated heteroatom-containing ring-shaped radicals, where the heteroatoms can be selected from nitrogen, sulfur and oxygen. Examples of saturated heterocycle radicals include saturated three- to six-membered heteromonocylic group containing one to four nitrogen atoms (e.g. pyrrolidinyl, imidazolidinyl, piperidino, piperazinyl, etc.); saturated three- to six-membered heteromonocyclic group containing one to two oxygen atoms and one to three nitrogen atoms (e.g. morpholinyl, etc.); saturated three- to six-membered heteromonocyclic group containing one to two sulfur atoms and one to three nitrogen atoms (e.g., thiazolidinyl, etc.). Examples of partially unsaturated heterocycle radicals include dihydrothiophene, dihydropyran, dihydrofuran and dihydrothiazole. Heterocycle compounds include benzofused heterocyclic compounds such as benzofurane.

The term "aryl", alone or in combination means, unless otherwise specified, a five- or six-membered carbocyclic aromatic ring-containing moiety or a five- or six-membered carbocyclic aromatic system containing two or three rings wherein such rings are attached together in a pendent manner, or a fused ring system containing two or three rings that have all carbon atoms in the ring; i.e., a carbocyclic aryl radical. The term "aryl" embraces aromatic radicals such as phenyl, indenyl, naphthyl, tetrahydronaphthyl, indane and biphenyl.

The term "heteroaryl", alone or in combination means a five- or six-membered aromatic ring-containing moiety or a fused ring system (radical) containing two or three rings that have carbon atoms and also one or more heteroatoms in the ring(s) such as sulfur, oxygen and nitrogen. Examples of such heterocyclic or heteroaryl groups are pyrrolidinyl, piperidyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, tetrazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like radicals.

The term "aralkyl", alone or in combination, means an alkyl radical as defined above in which one hydrogen atom is replaced by an aryl radical as defined above, such as benzyl, diphenylmethyl, triphenylmethyl, phenylethyl, diphenylethyl 2-phenylethyl, and the like.

The term "aryloxy", alone or in combination, means a radical of the formula aryl-O— in which the term aryl has the significance given above. The phenoxy radical is an exemplary aryloxy radical.

The term "alkylamino", alone or in combination, means an amino group which has been substituted with one or two alkyl radicals. In one example, N-alkylamino radicals have alkyl portions having one to six carbon atoms. Suitable alkylamino can be mono or dialkylamino such as N-methylamino, N-ethylamino, N,N-dimethylamino, N,N-diethylamino, and the like.

The term "arylamino", alone or in combination, means an amino group which has been substituted with one or two aryl radicals, such as N-phenylamino. The "arylamino" radicals can be further substituted on the aryl ring portion of the radical.

The term "aralkylamino", alone or in combination, means an aralkyl radical attached through a nitrogen atom to other radicals.

The terms "alkanoyl" or "alkylcarbonyl", alone or in combination, mean an acyl radical derived from an alkanecarboxylic acid, examples of which include formyl, acetyl, propionyl, butyryl, valeryl, 4-methylvaleryl, and the like.

The terms "aroyl" or "arylcarbonyl", alone or in combination, mean an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The terms "carboxy" or "carboxyl", whether used alone or in combination, i.e., with other terms, such as "carboxyalkyl", mean a —CO₂H radical.

The term "alkoxycarbonyl", alone or in combination, means a radical containing an alkoxy radical, as defined above, attached via an oxygen atom to a carbonyl radical. In one embodiment, alkoxycarbonyl radicals have alkyl portions having one to six carbons. Examples of such alkoxycarbonyl (ester) radicals include methoxycarbonyl, ethoxycarbonyl, propoxycarbonyl, butoxycarbonyl, hexyloxycarbonyl, and the like.

Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

The terms "malignant neoplasm", "cancer", "tumor" and "solid tumor cancer" are used interchangeably herein to refer to the condition well known to those skilled in the art as the life-threatening disease commonly referred to simply as "cancer". The term "cancer" as used herein, is meant a disease characterized by excessive, uncontrolled growth of abnormal cells, which invades and destroys other tissues and includes all human cancers such as carcinomas, sarcomas, leukemias and lymphomas. For example, the term "cancer" comprises prostate, breast, lung, colorectal, bladder, uterine, skin, kidney, pancreatic, ovarian, liver and stomach cancer.

By the term "chemotherapeutic agent" as used herein, is meant a chemical substance or drug used to treat a disease; the term is most often applied to such substances or drugs which are used primarily for the treatment of cancer.

By the term "treating" as used herein, is meant reversing, alleviating, ameliorating, limiting, inhibiting the progress of, or preventing the disorder or condition to which such term applies, or one or more symptoms of such disorder or condition. The term "treatment" as used herein, refers to the act of treating as "treating" is defined immediately above.

By the term "method" as used herein, is meant manners, means, techniques and procedures for accomplishing a given task including, but not limited to, those manners, means, techniques and procedures either known to, or readily developed from known manners, means, techniques and procedures by, practitioners of the chemical, pharmacological, biological, biochemical and medical arts.

By the term "administered" or "administering" as used herein, is meant standard delivery methods, e.g, parenteral administration, including continuous infusion and intravenous, intramuscular and subcutaneous injections, and oral administration.

The term "modulated" as used herein, includes governed, controlled, provoked, modulated and induced.

By the term "mammal" as used herein, is meant any of a class of warm-blooded higher vertebrates, that nourish their young with milk secreted by mammary glands, have the skin usually more or less covered with hair, and includes humans.

By the term "physiologically acceptable carrier" as used herein, is meant a carrier or diluent that does not cause significant irritation to an organism and does not abrogate the biological activity and properties of the administered compound.

By the term "excipient" as used herein, is meant an inert substance added to a pharmaceutical composition to further facilitate administration of a compound.

By the term "disease" as used herein, is meant a kind or instance of impairment of a living being that interferes with normal bodily function.

As stated above, the present invention also includes within its scope pharmaceutically acceptable bio-precursors (otherwise known as pro-drugs) of the compounds of formula (I), i.e. compounds which have a different formula (I) above, but which nevertheless upon administration to a human being are converted directly or indirectly in vivo into a compound of formula (I).

Examples of compounds of the invention are reported in Table 1:

TABLE 1

| N° | Compound name |
|---|---|
| 1 | tert-butyl 4-(4-methyl-2-(methylsulfanyl)-7-oxopyrido[2,3-d]pyrimidin-8(7H)-yl)benzoate (1) |
| 2 | tert-butyl 4-(4-methyl-2-(methylsulfonyl)-7-oxopyrido[2,3-d]pyrimidin-8(7H)-yl)benzoate (2) |
| 3 | tert-butyl 4-(2-[4-(ethoxycarbonyl)anilino]-4-methyl-7-oxopyrido[2,3-d]pyrimidin-8(7H)-yl)benzoate (3) |
| 4 | tert-butyl 4-(4-methyl-7-oxo-2-(4-phenyl-1-piperazinyl)pyrido[2,3-d]pyrimidin-8(7H)-yl)benzoate (4) |
| 5 | tert-butyl 4-(2-[4-(4-fluorophenyl)-1-piperazinyl]-4-methyl-7-oxopyrido[2,3-d]pyrimidin-8(7H)-yl)benzoate (5) |
| 6 | tert-butyl 4-(4-methyl-7-oxo-2-[4-(2-pyridinyl)-1-piperazinyl]pyrido[2,3-d]pyrimidin-8(7H)-yl)benzoate (6) |
| 7 | tert-butyl 4-(4-methyl-7-oxo-2-[4-(2-pyrimidinyl)-1-piperazinyl]pyrido[2,3-d]pyrimidin-8(7H)-yl)benzoate (7) |
| 8 | tert-butyl 4-(2-(3,4-dihydro-2(1H)-isoquinolinyl)-4-methyl-7-oxopyrido[2,3-d]pyrimidin-8(7H)-yl)benzoate (8) |
| 9 | 4-(2-[4-(ethoxycarbonyl)anilino]-4-methyl-7-oxopyrido[2,3-d]pyrimidin-8(7H)-yl)benzoic acid (9) |
| 10 | 4-(4-methyl-7-oxo-2-(4-phenyl-1-piperazinyl)pyrido[2,3-d]pyrimidin-8(7H)-yl)benzoic acid (10) |
| 11 | 4-(2-[4-(4-fluorophenyl)-1-piperazinyl]-4-methyl-7-oxopyrido[2,3-d]pyrimidin-8(7H)-yl)benzoic acid (11) |
| 12 | 4-(4-methyl-7-oxo-2-[4-(2-pyridinyl)-1-piperazinyl]pyrido[2,3-d]pyrimidin-8(7H)-yl)benzoic acid (12) |
| 13 | 4-(4-methyl-7-oxo-2-[4-(2-pyrimidinyl)-1-piperazinyl]pyrido[2,3-d]pyrimidin-8(7H)-yl)benzoic acid (13) |
| 14 | 4-(2-(3,4-dihydro-2(1H)-isoquinolinyl)-4-methyl-7-oxopyrido[2,3-d]pyrimidin-8(7H)-yl)benzoic acid (14) |
| 15 | N-benzyl-4-(4-methyl-7-oxo-2-(4-phenyl-1-piperazinyl)pyrido[2,3-d]pyrimidin-8(7H)-yl)benzamide (15) |
| 16 | N-(2-furylmethyl)-4-(4-methyl-7-oxo-2-(4-phenyl-1-piperazinyl)pyrido[2,3-d]pyrimidin-8(7H)-yl)benzamide (16) |
| 17 | 4-(4-methyl-7-oxo-2-(4-phenyl-1-piperazinyl)pyrido[2,3-d]pyrimidin-8(7H)-yl)-N-(3-pyridinylmethyl)benzamide (17) |
| 18 | 4-(4-methyl-7-oxo-2-(4-phenyl-1-piperazinyl)pyrido[2,3-d]pyrimidin-8(7H)-yl)-N-(1-naphthylmethyl)benzamide (18) |
| 19 | N-(3,4-dimethoxybenzyl)-4-(4-methyl-7-oxo-2-(4-phenyl-1-piperazinyl)pyrido[2,3-d]pyrimidin-8(7H)-yl)benzamide (19) |
| 20 | N-benzyl-4-(2-[4-(4-fluorophenyl)-1-piperazinyl]-4-methyl-7-oxopyrido[2,3-d]pyrimidin-8(7H)-yl)benzamide (20) |
| 21 | 4-(2-[4-(4-fluorophenyl)-1-piperazinyl]-4-methyl-7-oxopyrido[2,3-d]pyrimidin-8(7H)-yl)-N-(2-furylmethyl)benzamide (21) |
| 22 | N-benzyl-4-(4-methyl-7-oxo-2-[4-(2-pyridinyl)-1-piperazinyl]pyrido[2,3-d]pyrimidin-8(7H)-yl)benzamide (22) |
| 23 | 4-(4-methyl-7-oxo-2-[4-(2-pyridinyl)-1-piperazinyl]pyrido[2,3-d]pyrimidin-8(7H)-yl)-N-(3-pyridinylmethyl)benzamide (23) |
| 24 | N-(2-furylmethyl)-4-(4-methyl-7-oxo-2-[4-(2-pyridinyl)-1-piperazinyl]pyrido[2,3-d]pyrimidin-8(7H)-yl)benzamide (24) |

TABLE 1-continued

| N° | Compound name |
|---|---|
| 25 | N-(3,4-dimethoxybenzyl)-4-(4-methyl-7-oxo-2-[4-(2-pyridinyl)-1-piperazinyl]pyrido[2,3-d]pyrimidin-8(7H)-yl)benzamide (25) |
| 26 | 4-(4-methyl-7-oxo-2-[4-(2-pyridinyl)-1-piperazinyl]pyrido[2,3-d]pyrimidin-8(7H)-yl)-N-(2-naphthylmethyl)benzamide (26) |
| 27 | N-benzyl-4-(4-methyl-7-oxo-2-[4-(2-pyrimidinyl)-1-piperazinyl]pyrido[2,3-d]pyrimidin-8(7H)-yl)benzamide (27) |
| 28 | N-(2-furylmethyl)-4-(4-methyl-7-oxo-2-[4-(2-pyrimidinyl)-1-piperazinyl]pyrido[2,3-d]pyrimidin-8(7H)-yl)benzamide (28) |
| 29 | N-(3,4-dimethoxybenzyl)-4-(4-methyl-7-oxo-2-[4-(2-pyrimidinyl)-1-piperazinyl]pyrido[2,3-d]pyrimidin-8(7H)-yl)benzamide (29) |
| 30 | 4-(4-methyl-7-oxo-2-[4-(2-pyrimidinyl)-1-piperazinyl]pyrido[2,3-d]pyrimidin-8(7H)-yl)-N-(3-pyridinylmethyl)benzamide (30) |
| 31 | N-(2,4-difluorobenzyl)-4-(4-methyl-7-oxo-2-[4-(2-pyrimidinyl)-1-piperazinyl]pyrido[2,3-d]pyrimidin-8(7H)-yl)benzamide (31) |
| 32 | 4-(4-methyl-7-oxo-2-[4-(2-pyrimidinyl)-1-piperazinyl]pyrido[2,3-d]pyrimidin-8(7H)-yl)-N-(1-naphthylmethyl)benzamide (32) |
| 33 | N-cyclopropyl-4-(2-(3,4-dihydro-2(1H)-isoquinolinyl)-4-methyl-7-oxopyrido[2,3-d]pyrimidin-8(7H)-yl)benzamide (33) |
| 34 | 4-(2-(3,4-dihydro-2(1H)-isoquinolinyl)-4-methyl-7-oxopyrido[2,3-d]pyrimidin-8(7H)-yl)-N-(3,4-dimethoxyphenyl)benzamide (34) |
| 35 | 4-(2-(3,4-dihydro-2(1H)-isoquinolinyl)-4-methyl-7-oxopyrido[2,3-d]pyrimidin-8(7H)-yl)-N,N-dimethylbenzamide (35) |
| 36 | 4-(2-(3,4-dihydro-2(1H)-isoquinolinyl)-4-methyl-7-oxopyrido[2,3-d]pyrimidin-8(7H)-yl)-N-(3,4-dimethoxybenzyl)benzamide (36) |
| 37 | Ethyl 4-{[4-(2-(3,4-dihydro-2(1H)-isoquinolinyl)-4-methyl-7-oxopyrido[2,3-d]pyrimidin-8(7H)-yl)benzoyl]amino}benzoate (37) |
| 38 | N-(3-cyanophenyl)-4-(2-(3,4-dihydro-2(1H)-isoquinolinyl)-4-methyl-7-oxopyrido[2,3-d]pyrimidin-8(7H)-yl)benzamide (38) |
| 39 | N-cyclohexyl-4-(2-(3,4-dihydro-2(1H)-isoquinolinyl)-4-methyl-7-oxopyrido[2,3-d]pyrimidin-8(7H)-yl)benzamide (39) |
| 40 | N-(3,4-dichlorophenyl)-4-(2-(3,4-dihydro-2(1H)-isoquinolinyl)-4-methyl-7-oxopyrido[2,3-d]pyrimidin-8(7H)-yl)benzamide (40) |
| 41 | methyl 4-({8-[4-(methoxycarbonyl)phenyl]-4-methyl-7-oxo-7,8-dihydropyrido[2,3-d]pyrimidin-2-yl}amino)benzoate (41) |
| 42 | Ethyl 4-({8-[4-(ethoxycarbonyl)phenyl]-4-methyl-7-oxo-7,8-dihydropyrido[2,3-d]pyrimidin-2-yl}amino)benzoate (42) |
| 43 | 4-2-Isobutylamino-4-methyl-7-oxo-7H-pyrido[2,3-d]pyrimidin-8-yl)-N-octyl-benzamide (43) |
| 44 | 4-2-Isobutylamino-4-methyl-7-oxo-7H-pyrido[2,3-d]pyrimidin-8-yl)-N-phenyl-benzamide (44) |
| 45 | 4-[2-(3,4-Dihydro-1H-isoquinolin-2-yl)-4-methyl-7-oxo-7H-pyrido[2,3-d]pyrimidin-8-yl]-N-[2-(4-oxy-morpholin-4-yl)-ethyl]-benzamide (45) |
| 46 | 4-(2-(3,4-dihydro-2(1H)-isoquinolinyl)-4-methyl-7-oxopyrido[2,3-d]pyrimidin-8(7H)-yl)-N-[3-(dimethylamino-N-oxido)propyl]benzamide (46) |
| 47 | 4-[2-2-Methoxy-ethylamino)-4-methyl-7-oxo-7H-pyrido[2,3-d]pyrimidin-8-yl]-N-[2-(4-oxy-morpholin-4-yl)-ethyl]-benzamide (47) |
| 48 | N-[3-(dimethylamino-N-oxido)propyl]-4-(2-[(2-methoxyethyl)amino]-4-methyl-7-oxopyrido[2,3-d]pyrimidin-8(7H)-yl)benzamide (48) |
| 49 | N-[3-(dimethylamino-N-oxido)propyl]-4-(2-[(2-furylmethyl)amino]-4-methyl-7-oxopyrido[2,3-d]pyrimidin-8(7H)-yl)benzamide (49) |
| 50 | 4-(2-[(2-furylmethyl)amino]-4-methyl-7-oxopyrido[2,3-d]pyrimidin-8(7H)-yl)-N-(2-phenylethyl)benzamide (50) |
| 51 | 4-(2-[(2-furylmethyl)amino]-4-methyl-7-oxopyrido[2,3-d]pyrimidin-8(7H)-yl)-N-isobutylbenzamide (51) |
| 52 | N-[3-(dimethylamino-N-oxido)propyl]-4-(2-[(2-ethylhexyl)amino]-4-methyl-7-oxopyrido[2,3-d]pyrimidin-8(7H)-yl)benzamide (52) |
| 53 | 4-(2-[(2-ethylhexyl)amino]-4-methyl-7-oxopyrido[2,3-d]pyrimidin-8(7H)-yl)-N-(2-phenylethyl)benzamide (53) |
| 54 | 4-(2-{[2-(acetylamino)ethyl]amino}-4-methyl-7-oxopyrido[2,3-d]pyrimidin-8(7H)-yl)-N-[3-(dimethylamino-N-oxido)propyl]benzamide (54) |
| 55 | 4-(2-{[2-(acetylamino)ethyl]amino}-4-methyl-7-oxopyrido[2,3-d]pyrimidin-8(7H)-yl)-N-(tetrahydro-2-furanylmethyl)benzamide (55) |
| 56 | 4-(2-(benzylamino)-4-methyl-7-oxopyrido[2,3-d]pyrimidin-8(7H)-yl)-N-[3-(dimethylamino-N-oxido)propyl]benzamide (56) |
| 57 | 4-(2-(benzylamino)-4-methyl-7-oxopyrido[2,3-d]pyrimidin-8(7H)-yl)-N-isobutylbenzamide (57) |
| 58 | 4-(2-[(2-aminoethyl)amino]-4-methyl-7-oxopyrido[2,3-d]pyrimidin-8(7H)-yl)-N-[3-(dimethylamino-N-oxido)propyl]benzamide (58) |
| 59 | 4-(2-[(2-aminoethyl)amino]-4-methyl-7-oxopyrido[2,3-d]pyrimidin-8(7H)-yl)-N-(2-furylmethyl)benzamide (59) |
| 60 | 4-(4-methyl-7-oxo-2-[4-(2-pyrimidinyl)-1-piperazinyl]pyrido[2,3-d]pyrimidin-8(7H)-yl)-N-[2-(4-oxido-4-morpholinyl)ethyl]benzamide (60) |
| 61 | N-[3-(dimethylamino-N-oxido)propyl]-4-(4-methyl-7-oxo-2-[4-(2-pyrimidinyl)-1-piperazinyl]pyrido[2,3-d]pyrimidin-8(7H)-yl)benzamide (61) |
| 62 | 4-(4-methyl-7-oxo-2-(1-piperazinyl)pyrido[2,3-d]pyrimidin-8(7H)-yl)-N-[2-(4-oxido-4-morpholinyl)ethyl]benzamide (62) |
| 63 | 4-(4-methyl-7-oxo-2-(1-pyrrolidinyl)pyrido[2,3-d]pyrimidin-8(7H)-yl)-N-[2-(4-oxido-4-morpholinyl)ethyl]benzamide (63) |
| 64 | 4-(2-[(2-hydroxyethyl)amino]-4-methyl-7-oxopyrido[2,3-d]pyrimidin-8(7H)-yl)-N-(tetrahydro-2-furanylmethyl)benzamide (64) |
| 65 | 4-(2-{[2-(2-methoxyphenyl)ethyl]amino}-4-methyl-7-oxopyrido[2,3-d]pyrimidin-8(7H)-yl)-N-[2-(4-oxido-4-morpholinyl)ethyl]benzamide (65) |
| 66 | N-[3-(dimethylamino-N-oxido)propyl]-4-(2-{[2-(2-methoxyphenyl)ethyl]amino}-4-methyl-7-oxopyrido[2,3-d]pyrimidin-8(7H)-yl)benzamide (66) |
| 67 | N-(2-furylmethyl)-4-(2-{[2-(2-methoxyphenyl)ethyl]amino}-4-methyl-7-oxopyrido[2,3-d]pyrimidin-8(7H)-yl)benzamide (67) |
| 68 | 4-(2-(3,4-dihydro-2(1H)-isoquinolinyl)-4-methyl-7-oxopyrido[2,3-d]pyrimidin-8(7H)-yl)-N-(2-furylmethyl)benzamide (68) |
| 69 | 4-(2-(3,4-dihydro-2(1H)-isoquinolinyl)-4-methyl-7-oxopyrido[2,3-d]pyrimidin-8(7H)-yl)-N-octylbenzamide (69) |
| 70 | N-benzyl-4-(2-(3,4-dihydro-2(1H)-isoquinolinyl)-4-methyl-7-oxopyrido[2,3-d]pyrimidin-8(7H)-yl)benzamide (70) |
| 71 | 4-(2-(3,4-dihydro-2(1H)-isoquinolinyl)-4-methyl-7-oxopyrido[2,3-d]pyrimidin-8(7H)-yl)-N-(2-phenylethyl)benzamide (71) |
| 72 | 4-(2-(3,4-dihydro-2(1H)-isoquinolinyl)-4-methyl-7-oxopyrido[2,3-d]pyrimidin-8(7H)-yl)-N-isobutylbenzamide (72) |
| 73 | 4-(2-(3,4-dihydro-2(1H)-isoquinolinyl)-4-methyl-7-oxopyrido[2,3-d]pyrimidin-8(7H)-yl)-N-(tetrahydro-2-furanylmethyl)benzamide (73) |
| 74 | N-(cyclohexylmethyl)-4-(2-(3,4-dihydro-2(1H)-isoquinolinyl)-4-methyl-7-oxopyrido[2,3-d]pyrimidin-8(7H)-yl)benzamide (74) |
| 75 | N-cyclopropyl-4-(4-methyl-2-{[2-(4-morpholinyl)ethyl]amino}-7-oxopyrido[2,3-d]pyrimidin-8(7H)-yl)benzamide (75) |

TABLE 1-continued

| N° | Compound name |
|---|---|
| 76 | 4-(4-methyl-2-{[2-(4-morpholinyl)ethyl]amino}-7-oxopyrido[2,3-d]pyrimidin-8(7H)-yl)-N-octylbenzamide (76) |
| 77 | N-(2-furylmethyl)-4-(4-methyl-2-{[2-(4-morpholinyl)ethyl]amino}-7-oxopyrido[2,3-d]pyrimidin-8(7H)-yl)benzamide (77) |
| 78 | N-(3,4-dimethoxyphenyl)-4-(4-methyl-2-{[2-(4-morpholinyl)ethyl]amino}-7-oxopyrido[2,3-d]pyrimidin-8(7H)-yl)benzamide (78) |
| 79 | N-benzyl-4-(4-methyl-2-{[2-(4-morpholinyl)ethyl]amino}-7-oxopyrido[2,3-d]pyrimidin-8(7H)-yl)benzamide (79) |
| 80 | 4-(4-methyl-2-{[2-(4-morpholinyl)ethyl]amino}-7-oxopyrido[2,3-d]pyrimidin-8(7H)-yl)-N-(2-phenylethyl)benzamide (80) |
| 81 | N-isobutyl-4-(4-methyl-2-{[2-(4-morpholinyl)ethyl]amino}-7-oxopyrido[2,3-d]pyrimidin-8(7H)-yl)benzamide (81) |
| 82 | 4-(4-methyl-2-{[2-(4-morpholinyl)ethyl]amino}-7-oxopyrido[2,3-d]pyrimidin-8(7H)-yl)-N-(tetrahydro-2-furanylmethyl)benzamide (82) |
| 83 | N-(cyclohexylmethyl)-4-(4-methyl-2-{[2-(4-morpholinyl)ethyl]amino}-7-oxopyrido[2,3-d]pyrimidin-8(7H)-yl)benzamide (83) |
| 84 | N-cyclopropyl-4-(2-[(2-methoxyethyl)amino]-4-methyl-7-oxopyrido[2,3-d]pyrimidin-8(7H)-yl)benzamide (84) |
| 85 | 4-(2-[(2-methoxyethyl)amino]-4-methyl-7-oxopyrido[2,3-d]pyrimidin-8(7H)-yl)-N-octylbenzamide (85) |
| 86 | N-(2-furylmethyl)-4-(2-[(2-methoxyethyl)amino]-4-methyl-7-oxopyrido[2,3-d]pyrimidin-8(7H)-yl)benzamide (86) |
| 87 | N-(3,4-dimethoxyphenyl)-4-(2-[(2-methoxyethyl)amino]-4-methyl-7-oxopyrido[2,3-d]pyrimidin-8(7H)-yl)benzamide (87) |
| 88 | N-benzyl-4-(2-[(2-methoxyethyl)amino]-4-methyl-7-oxopyrido[2,3-d]pyrimidin-8(7H)-yl)benzamide (88) |
| 89 | 4-(2-[(2-methoxyethyl)amino]-4-methyl-7-oxopyrido[2,3-d]pyrimidin-8(7H)-yl)-N-(2-phenylethyl)benzamide (89) |
| 90 | N-isobutyl-4-(2-[(2-methoxyethyl)amino]-4-methyl-7-oxopyrido[2,3-d]pyrimidin-8(7H)-yl)benzamide (90) |
| 91 | 4-(2-[(2-methoxyethyl)amino]-4-methyl-7-oxopyrido[2,3-d]pyrimidin-8(7H)-yl)-N-(tetrahydro-2-furanylmethyl)benzamide (91) |
| 92 | N-(cyclohexylmethyl)-4-(2-[(2-methoxyethyl)amino]-4-methyl-7-oxopyrido[2,3-d]pyrimidin-8(7H)-yl)benzamide (92) |
| 93 | N-cyclopropyl-4-(2-[(2-furylmethyl)amino]-4-methyl-7-oxopyrido[2,3-d]pyrimidin-8(7H)-yl)benzamide (93) |
| 94 | 4-(2-[(2-furylmethyl)amino]-4-methyl-7-oxopyrido[2,3-d]pyrimidin-8(7H)-yl)-N-octylbenzamide (94) |
| 95 | N-(2-furylmethyl)-4-(2-[(2-furylmethyl)amino]-4-methyl-7-oxopyrido[2,3-d]pyrimidin-8(7H)-yl)benzamide (95) |
| 96 | N-(3,4-dimethoxyphenyl)-4-(2-[(2-furylmethyl)amino]-4-methyl-7-oxopyrido[2,3-d]pyrimidin-8(7H)-yl)benzamide (96) |
| 97 | N-benzyl-4-(2-[(2-furylmethyl)amino]-4-methyl-7-oxopyrido[2,3-d]pyrimidin-8(7H)-yl)benzamide (97) |
| 98 | 4-(2-[(2-furylmethyl)amino]-4-methyl-7-oxopyrido[2,3-d]pyrimidin-8(7H)-yl)-N-(tetrahydro-2-furanylmethyl)benzamide (98) |
| 99 | N-(cyclohexylmethyl)-4-(2-[(2-furylmethyl)amino]-4-methyl-7-oxopyrido[2,3-d]pyrimidin-8(7H)-yl)benzamide (99) |
| 100 | N-cyclopropyl-4-(2-[(2-ethylhexyl)amino]-4-methyl-7-oxopyrido[2,3-d]pyrimidin-8(7H)-yl)benzamide (100) |
| 101 | N-benzyl-4-(2-[(2-ethylhexyl)amino]-4-methyl-7-oxopyrido[2,3-d]pyrimidin-8(7H)-yl)benzamide (101) |
| 102 | 4-(2-[(2-ethylhexyl)amino]-4-methyl-7-oxopyrido[2,3-d]pyrimidin-8(7H)-yl)-N-(2-furylmethyl)benzamide (102) |
| 103 | N-(3,4-dimethoxyphenyl)-4-(2-[(2-ethylhexyl)amino]-4-methyl-7-oxopyrido[2,3-d]pyrimidin-8(7H)-yl)benzamide (103) |
| 104 | 4-(2-[(2-ethylhexyl)amino]-4-methyl-7-oxopyrido[2,3-d]pyrimidin-8(7H)-yl)-N-isobutylbenzamide (104) |
| 105 | N-(cyclohexylmethyl)-4-(2-[(2-ethylhexyl)amino]-4-methyl-7-oxopyrido[2,3-d]pyrimidin-8(7H)-yl)benzamide (105) |
| 106 | 4-(2-{[2-(acetylamino)ethyl]amino}-4-methyl-7-oxopyrido[2,3-d]pyrimidin-8(7H)-yl)-N-cyclopropylbenzamide (106) |
| 107 | 4-(2-{[2-(acetylamino)ethyl]amino}-4-methyl-7-oxopyrido[2,3-d]pyrimidin-8(7H)-yl)-N-octylbenzamide (107) |
| 108 | 4-(2-{[2-(acetylamino)ethyl]amino}-4-methyl-7-oxopyrido[2,3-d]pyrimidin-8(7H)-yl)-N-(2-furylmethyl)benzamide (108) |
| 109 | 4-(2-{[2-(acetylamino)ethyl]amino}-4-methyl-7-oxopyrido[2,3-d]pyrimidin-8(7H)-yl)-N-(3,4-dimethoxyphenyl)benzamide (109) |
| 110 | 4-(2-{[2-(acetylamino)ethyl]amino}-4-methyl-7-oxopyrido[2,3-d]pyrimidin-8(7H)-yl)-N-benzylbenzamide (110) |
| 111 | 4-(2-{[2-(acetylamino)ethyl]amino}-4-methyl-7-oxopyrido[2,3-d]pyrimidin-8(7H)-yl)-N-(2-phenylethyl)benzamide (111) |
| 112 | 4-(2-{[2-(acetylamino)ethyl]amino}-4-methyl-7-oxopyrido[2,3-d]pyrimidin-8(7H)-yl)-N-isobutylbenzamide (112) |
| 113 | 4-(2-{[2-(acetylamino)ethyl]amino}-4-methyl-7-oxopyrido[2,3-d]pyrimidin-8(7H)-yl)-N-(cyclohexylmethyl)benzamide (113) |
| 114 | 4-(2-(benzylamino)-4-methyl-7-oxopyrido[2,3-d]pyrimidin-8(7H)-yl)-N-cyclopropylbenzamide (114) |
| 115 | 4-(2-(benzylamino)-4-methyl-7-oxopyrido[2,3-d]pyrimidin-8(7H)-yl)-N-octylbenzamide (115) |
| 116 | 4-(2-(benzylamino)-4-methyl-7-oxopyrido[2,3-d]pyrimidin-8(7H)-yl)-N-(2-furylmethyl)benzamide (116) |
| 117 | 4-(2-(benzylamino)-4-methyl-7-oxopyrido[2,3-d]pyrimidin-8(7H)-yl)-N-(3,4-dimethoxyphenyl)benzamide (117) |
| 118 | N-benzyl-4-(2-(benzylamino)-4-methyl-7-oxopyrido[2,3-d]pyrimidin-8(7H)-yl)benzamide (118) |
| 119 | 4-(2-(benzylamino)-4-methyl-7-oxopyrido[2,3-d]pyrimidin-8(7H)-yl)-N-(2-phenylethyl)benzamide (119) |
| 120 | 4-(2-(benzylamino)-4-methyl-7-oxopyrido[2,3-d]pyrimidin-8(7H)-yl)-N-(tetrahydro-2-furanylmethyl)benzamide (120) |
| 121 | 4-(2-(benzylamino)-4-methyl-7-oxopyrido[2,3-d]pyrimidin-8(7H)-yl)-N-(cyclohexylmethyl)benzamide (121) |
| 122 | 4-(2-[(2-aminoethyl)amino]-4-methyl-7-oxopyrido[2,3-d]pyrimidin-8(7H)-yl)-N-cyclopropylbenzamide (122) |
| 123 | 4-(2-[(2-aminoethyl)amino]-4-methyl-7-oxopyrido[2,3-d]pyrimidin-8(7H)-yl)-N-octylbenzamide (123) |
| 124 | 4-(2-[(2-aminoethyl)amino]-4-methyl-7-oxopyrido[2,3-d]pyrimidin-8(7H)-yl)-N-(3,4-dimethoxyphenyl)benzamide (124) |
| 125 | 4-(2-[(2-aminoethyl)amino]-4-methyl-7-oxopyrido[2,3-d]pyrimidin-8(7H)-yl)-N-benzylbenzamide (125) |
| 126 | 4-(2-[(2-aminoethyl)amino]-4-methyl-7-oxopyrido[2,3-d]pyrimidin-8(7H)-yl)-N-(2-phenylethyl)benzamide (126) |

TABLE 1-continued

| N° | Compound name |
|---|---|
| 127 | 4-(2-[(2-aminoethyl)amino]-4-methyl-7-oxopyrido[2,3-d]pyrimidin-8(7H)-yl)-N-isobutylbenzamide (127) |
| 128 | N-cyclopropyl-4-(4-methyl-7-oxo-2-[4-(2-pyrimidinyl)-1-piperazinyl]pyrido[2,3-d]pyrimidin-8(7H)-yl)benzamide (128) |
| 129 | 4-(2-[(2-aminoethyl)amino]-4-methyl-7-oxopyrido[2,3-d]pyrimidin-8(7H)-yl)-N-(cyclohexylmethyl)benzamide (129) |
| 130 | 4-(4-methyl-7-oxo-2-[4-(2-pyrimidinyl)-1-piperazinyl]pyrido[2,3-d]pyrimidin-8(7H)-yl)-N-octylbenzamide (130) |
| 131 | N-(3,4-dimethoxyphenyl)-4-(4-methyl-7-oxo-2-yl)benzamide (131) |
| 132 | 4-(4-methyl-7-oxo-2-[4-(2-pyrimidinyl)-1-piperazinyl]pyrido[2,3-d]pyrimidin-8(7H)-yl)-N-(2-phenylethyl)benzamide (132) |
| 133 | N-isobutyl-4-(4-methyl-7-oxo-2-[4-(2-pyrimidinyl)-1-piperazinyl]pyrido[2,3-d]pyrimidin-8(7H)-yl)benzamide (133) |
| 134 | 4-(4-methyl-7-oxo-2-[4-(2-pyrimidinyl)-1-piperazinyl]pyrido[2,3-d]pyrimidin-8(7H)-yl)-N-(tetrahydro-2-furanylmethyl)benzamide (134) |
| 135 | N-(cyclohexylmethyl)-4-(4-methyl-7-oxo-2-[4-(2-pyrimidinyl)-1-piperazinyl]pyrido[2,3-d]pyrimidin-8(7H)-yl)benzamide (135) |
| 136 | N-cyclopropyl-4-(4-methyl-7-oxo-2-(1-piperazinyl)pyrido[2,3-d]pyrimidin-8(7H)-yl)benzamide (136) |
| 137 | 4-(4-methyl-7-oxo-2-(1-piperazinyl)pyrido[2,3-d]pyrimidin-8(7H)-yl)-N-octylbenzamide (137) |
| 138 | N-(2-furylmethyl)-4-(4-methyl-7-oxo-2-(1-piperazinyl)pyrido[2,3-d]pyrimidin-8(7H)-yl)benzamide (138) |
| 139 | N-(3,4-dimethoxyphenyl)-4-(4-methyl-7-oxo-2-(1-piperazinyl)pyrido[2,3-d]pyrimidin-8(7H)-yl)benzamide (139) |
| 140 | N-benzyl-4-(4-methyl-7-oxo-2-(1-piperazinyl)pyrido[2,3-d]pyrimidin-8(7H)-yl)benzamide (140) |
| 141 | 4-(4-methyl-7-oxo-2-(1-piperazinyl)pyrido[2,3-d]pyrimidin-8(7H)-yl)-N-(2-phenylethyl)benzamide (141) |
| 142 | N-isobutyl-4-(4-methyl-7-oxo-2-(1-piperazinyl)pyrido[2,3-d]pyrimidin-8(7H)-yl)benzamide (142) |
| 143 | 4-(4-methyl-7-oxo-2-(1-piperazinyl)pyrido[2,3-d]pyrimidin-8(7H)-yl)-N-(tetrahydro-2-furanylmethyl)benzamide (143) |
| 144 | N-(cyclohexylmethyl)-4-(4-methyl-7-oxo-2-(1-piperazinyl)pyrido[2,3-d]pyrimidin-8(7H)-yl)benzamide (144) |
| 145 | 4-(2-(allylamino)-4-methyl-7-oxopyrido[2,3-d]pyrimidin-8(7H)-yl)-N-cyclopropylbenzamide (145) |
| 146 | 4-(2-(allylamino)-4-methyl-7-oxopyrido[2,3-d]pyrimidin-8(7H)-yl)-N-octylbenzamide (146) |
| 147 | 4-(2-(allylamino)-4-methyl-7-oxopyrido[2,3-d]pyrimidin-8(7H)-yl)-N-(2-furylmethyl)benzamide (147) |
| 148 | 4-(2-(allylamino)-4-methyl-7-oxopyrido[2,3-d]pyrimidin-8(7H)-yl)-N-(3,4-dimethoxyphenyl)benzamide (148) |
| 149 | 4-(2-(allylamino)-4-methyl-7-oxopyrido[2,3-d]pyrimidin-8(7H)-yl)-N-benzylbenzamide (149) |
| 150 | 4-(2-(allylamino)-4-methyl-7-oxopyrido[2,3-d]pyrimidin-8(7H)-yl)-N-(2-phenylethyl)benzamide (150) |
| 151 | 4-(2-(allylamino)-4-methyl-7-oxopyrido[2,3-d]pyrimidin-8(7H)-yl)-N-isobutylbenzamide (151) |
| 152 | 4-(2-(allylamino)-4-methyl-7-oxopyrido[2,3-d]pyrimidin-8(7H)-yl)-N-(tetrahydro-2-furanylmethyl)benzamide (152) |
| 153 | 4-(2-(allylamino)-4-methyl-7-oxopyrido[2,3-d]pyrimidin-8(7H)-yl)-N-(cyclohexylmethyl)benzamide (153) |
| 154 | N-cyclopropyl-4-(4-methyl-7-oxo-2-(1-pyrrolidinyl)pyrido[2,3-d]pyrimidin-8(7H)-yl)benzamide (154) |
| 155 | 4-(4-methyl-7-oxo-2-(1-pyrrolidinyl)pyrido[2,3-d]pyrimidin-8(7H)-yl)-N-octylbenzamide (155) |
| 156 | N-(2-furylmethyl)-4-(4-methyl-7-oxo-2-(1-pyrrolidinyl)pyrido[2,3-d]pyrimidin-8(7H)-yl)benzamide (156) |
| 157 | N-(3,4-dimethoxyphenyl)-4-(4-methyl-7-oxo-2-(1-pyrrolidinyl)pyrido[2,3-d]pyrimidin-8(7H)-yl)benzamide (157) |
| 158 | N-benzyl-4-(4-methyl-7-oxo-2-(1-pyrrolidinyl)pyrido[2,3-d]pyrimidin-8(7H)-yl)benzamide (158) |
| 159 | 4-(4-methyl-7-oxo-2-(1-pyrrolidinyl)pyrido[2,3-d]pyrimidin-8(7H)-yl)-N-(2-phenylethyl)benzamide (159) |
| 160 | N-isobutyl-4-(4-methyl-7-oxo-2-(1-pyrrolidinyl)pyrido[2,3-d]pyrimidin-8(7H)-yl)benzamide (160) |
| 161 | 4-(4-methyl-7-oxo-2-(1-pyrrolidinyl)pyrido[2,3-d]pyrimidin-8(7H)-yl)-N-(tetrahydro-2-furanylmethyl)benzamide (161) |
| 162 | N-(cyclohexylmethyl)-4-(4-methyl-7-oxo-2-(1-pyrrolidinyl)pyrido[2,3-d]pyrimidin-8(7H)-yl)benzamide (162) |
| 163 | N-benzyl-4-(2-{[2-(2-methoxyphenyl)ethyl]amino}-4-methyl-7-oxopyrido[2,3-d]pyrimidin-8(7H)-yl)benzamide (163) |
| 164 | N-cyclopropyl-4-(2-[(2-hydroxyethyl)amino]-4-methyl-7-oxopyrido[2,3-d]pyrimidin-8(7H)-yl)benzamide (164) |
| 165 | 4-(2-[(2-hydroxyethyl)amino]-4-methyl-7-oxopyrido[2,3-d]pyrimidin-8(7H)-yl)-N-octylbenzamide (165) |
| 166 | N-(2-furylmethyl)-4-(2-[(2-hydroxyethyl)amino]-4-methyl-7-oxopyrido[2,3-d]pyrimidin-8(7H)-yl)benzamide (166) |
| 167 | N-(3,4-dimethoxyphenyl)-4-(2-[(2-hydroxyethyl)amino]-4-methyl-7-oxopyrido[2,3-d]pyrimidin-8(7H)-yl)benzamide (167) |
| 168 | N-benzyl-4-(2-[(2-hydroxyethyl)amino]-4-methyl-7-oxopyrido[2,3-d]pyrimidin-8(7H)-yl)benzamide (168) |
| 169 | 4-(2-[(2-hydroxyethyl)amino]-4-methyl-7-oxopyrido[2,3-d]pyrimidin-8(7H)-yl)-N-(2-phenylethyl)benzamide (169) |
| 170 | 4-(2-[(2-hydroxyethyl)amino]-4-methyl-7-oxopyrido[2,3-d]pyrimidin-8(7H)-yl)-N-isobutylbenzamide (170) |
| 171 | N-(cyclohexylmethyl)-4-(2-[(2-hydroxyethyl)amino]-4-methyl-7-oxopyrido[2,3-d]pyrimidin-8(7H)-yl)benzamide (171) |
| 172 | N-cyclopropyl-4-(2-{[2-(2-methoxyphenyl)ethyl]amino}-4-methyl-7-oxopyrido[2,3-d]pyrimidin-8(7H)-yl)benzamide (172) |
| 173 | 4-(2-{[2-(2-methoxyphenyl)ethyl]amino}-4-methyl-7-oxopyrido[2,3-d]pyrimidin-8(7H)-yl)-N-octylbenzamide (173) |
| 174 | N-(3,4-dimethoxyphenyl)-4-(2-{[2-(2-methoxyphenyl)ethyl]amino}-4-methyl-7-oxopyrido[2,3-d]pyrimidin-8(7H)-yl)benzamide (174) |
| 175 | 4-(2-{[2-(2-methoxyphenyl)ethyl]amino}-4-methyl-7-oxopyrido[2,3-d]pyrimidin-8(7H)-yl)-N-(2-phenylethyl)benzamide (175) |
| 176 | N-isobutyl-4-(2-{[2-(2-methoxyphenyl)ethyl]amino}-4-methyl-7-oxopyrido[2,3-d]pyrimidin-8(7H)-yl)benzamide (176) |
| 177 | 4-(2-{[2-(2-methoxyphenyl)ethyl]amino}-4-methyl-7-oxopyrido[2,3-d]pyrimidin-8(7H)-yl)-N-(tetrahydro-2-furanylmethyl)benzamide (177) |

TABLE 1-continued

| N° | Compound name |
|---|---|
| 178 | N-(cyclohexylmethyl)-4-(2-{[2-(2-methoxyphenyl)ethyl]amino}-4-methyl-7-oxopyrido[2,3-d]pyrimidin-8(7H)-yl)benzamide (178) |
| 179 | (2S)-1-(8-{4-[(cyclopropylamino)carbonyl]phenyl}-4-methyl-7-oxo-7,8-dihydropyrido[2,3-d]pyrimidin-2-yl)-2-pyrrolidinecarboxylic acid (179) |
| 180 | (2S)-1-(4-methyl-8-{4-[(octylamino)carbonyl]phenyl}-7-oxo-7,8-dihydropyrido[2,3-d]pyrimidin-2-yl)-2-pyrrolidinecarboxylic acid (180) |
| 181 | (2S)-1-[8-(4-{[(2-furylmethyl)amino]carbonyl}phenyl)-4-methyl-7-oxo-7,8-dihydropyrido[2,3-d]pyrimidin-2-yl]-2-pyrrolidinecarboxylic acid (181) |
| 182 | (2S)-1-(8-{4-[(3,4-dimethoxyanilino)carbonyl]phenyl}-4-methyl-7-oxo-7,8-dihydropyrido[2,3-d]pyrimidin-2-yl)-2-pyrrolidinecarboxylic acid (182) |
| 183 | (2S)-1-(8-{4-[(benzylamino)carbonyl]phenyl}-4-methyl-7-oxo-7,8-dihydropyrido[2,3-d]pyrimidin-2-yl)-2-pyrrolidinecarboxylic acid (183) |
| 184 | (2S)-1-[4-methyl-7-oxo-8-(4-{[(2-phenylethyl)amino]carbonyl}phenyl)-7,8-dihydropyrido[2,3-d]pyrimidin-2-yl]-2-pyrrolidinecarboxylic acid (184) |
| 185 | (2S)-1-(8-{4-[(isobutylamino)carbonyl]phenyl}-4-methyl-7-oxo-7,8-dihydropyrido[2,3-d]pyrimidin-2-yl)-2-pyrrolidinecarboxylic acid (185) |
| 186 | (2S)-1-[4-methyl-7-oxo-8-(4-{[(tetrahydro-2-furanylmethyl)amino]carbonyl}phenyl)-7,8-dihydropyrido[2,3-d]pyrimidin-2-yl]-2-pyrrolidinecarboxylic acid (186) |
| 187 | (2S)-1-[8-(4-{[(cyclohexylmethyl)amino]carbonyl}phenyl)-4-methyl-7-oxo-7,8-dihydropyrido[2,3-d]pyrimidin-2-yl]-2-pyrrolidinecarboxylic acid (187) |
| 188 | N-cyclopropyl-4-(2-{[3-(dimethylamino)propyl]amino}-4-methyl-7-oxopyrido[2,3-d]pyrimidin-8(7H)-yl)benzamide (188) |
| 189 | 4-(2-{[3-(dimethylamino)propyl]amino}-4-methyl-7-oxopyrido[2,3-d]pyrimidin-8(7H)-yl)-N-octylbenzamide (189) |
| 190 | 4-(2-{[3-(dimethylamino)propyl]amino}-4-methyl-7-oxopyrido[2,3-d]pyrimidin-8(7H)-yl)-N-(2-furylmethyl)benzamide (190) |
| 191 | N-(3,4-dimethoxyphenyl)-4-(2-{[3-(dimethylamino)propyl]amino}-4-methyl-7-oxopyrido[2,3-d]pyrimidin-8(7H)-yl)benzamide (191) |
| 192 | N-benzyl-4-(2-{[3-(dimethylamino)propyl]amino}-4-methyl-7-oxopyrido[2,3-d]pyrimidin-8(7H)-yl)benzamide (192) |
| 193 | 4-(2-{[3-(dimethylamino)propyl]amino}-4-methyl-7-oxopyrido[2,3-d]pyrimidin-8(7H)-yl)-N-(2-phenylethyl)benzamide (193) |
| 194 | 4-(2-{[3-(dimethylamino)propyl]amino}-4-methyl-7-oxopyrido[2,3-d]pyrimidin-8(7H)-yl)-N-isobutylbenzamide (194) |
| 195 | 4-(2-{[3-(dimethylamino)propyl]amino}-4-methyl-7-oxopyrido[2,3-d]pyrimidin-8(7H)-yl)-N-(tetrahydro-2-furanylmethyl)benzamide (195) |
| 196 | N-(cyclohexylmethyl)-4-(2-{[3-(dimethylamino)propyl]amino}-4-methyl-7-oxopyrido[2,3-d]pyrimidin-8(7H)-yl)benzamide (196) |
| 197 | 4-(2-[(2-ethylhexyl)amino]-4-methyl-7-oxopyrido[2,3-d]pyrimidin-8(7H)-yl)-N-octylbenzamide (197) |
| 198 | 4-(2-[(2-aminoethyl)amino]-4-methyl-7-oxopyrido[2,3-d]pyrimidin-8(7H)-yl)-N-(tetrahydro-2-furanylmethyl)benzamide (198) |
| 199 | 4-[2-(4-Benzyl-piperazin-1-yl)-4-methyl-7-oxo-7H-pyrido[2,3-d]pyrimidin-8-yl]-benzamide; |
| 200 | 4-[4-Methyl-7-oxo-2-(4-phenyl-piperazin-1-yl)-7H-pyrido[2,3-d]pyrimidin-8-yl]-benzamide; |
| 201 | 4-[4-Methyl-2-(4-methyl-piperazin-1-yl)-7-oxo-7H-pyrido[2,3-d]pyrimidin-8-yl]-benzamide; |
| 202 | 4-[8-(4-Carbamoyl-phenyl)-4-methyl-7-oxo-7,8-dihydro-pyrido[2,3-d]pyrimidin-2-yl]-piperazine-1-carboxylic acid ethyl ester; |
| 203 | 4-[4-Methyl-7-oxo-2-(4-pyridin-2-yl-piperazin-1-yl)-7H-pyrido[2,3-d]pyrimidin-8-yl]-benzamide; |
| 204 | 4-[2-(4-Formyl-piperazin-1-yl)-4-methyl-7-oxo-7H-pyrido[2,3-d]pyrimidin-8-yl]-benzamide; |
| 205 | 4-{2-[4-(4-Fluoro-phenyl)-piperazin-1-yl]-4-methyl-7-oxo-7H-pyrido[2,3-d]pyrimidin-8-yl}-benzamide; |
| 206 | 4-{2-[4-(4-Hydroxy-phenyl)-piperazin-1-yl]-4-methyl-7-oxo-7H-pyrido[2,3-d]pyrimidin-8-yl}-benzamide; |
| 207 | 4-[2-(4-Benzyl-piperazin-1-yl)-4-methyl-7-oxo-7H-pyrido[2,3-d]pyrimidin-8-yl]-N-(3,4-dimethoxy-benzyl)-benzamide; |
| 208 | N-(3,4-Dimethoxy-benzyl)-4-[4-methyl-7-oxo-2-(4-phenyl-piperazin-1-yl)-7H-pyrido[2,3-d]pyrimidin-8-yl]-benzamide; |
| 209 | N-(3,4-Dimethoxy-benzyl)-4-[4-methyl-2-(4-methyl-piperazin-1-yl)-7-oxo-7H-pyrido[2,3-d]pyrimidin-8-yl]-benzamide; |
| 210 | 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid ethyl ester; |
| 211 | N-(3,4-Dimethoxy-benzyl)-4-[4-methyl-7-oxo-2-(4-pyridin-2-yl-piperazin-1-yl)-7H-pyrido[2,3-d]pyrimidin-8-yl]-benzamide; |
| 212 | N-(3,4-Dimethoxy-benzyl)-4-[2-(4-formyl-piperazin-1-yl)-4-methyl-7-oxo-7H-pyrido[2,3-d]pyrimidin-8-yl]-benzamide; |
| 213 | N-(3,4-Dimethoxy-benzyl)-4-{2-[4-(4-fluoro-phenyl)-piperazin-1-yl]-4-methyl-7-oxo-7H-pyrido[2,3-d]pyrimidin-8-yl}-benzamide; |
| 214 | N-(3,4-Dimethoxy-benzyl)-4-{2-[4-(4-hydroxy-phenyl)-piperazin-1-yl]-4-methyl-7-oxo-7H-pyrido[2,3-d]pyrimidin-8-yl}-benzamide; |
| 215 | N-Benzyl-4-[2-(4-benzyl-piperazin-1-yl)-4-methyl-7-oxo-7H-pyrido[2,3-d]pyrimidin-8-yl]-benzamide |
| 216 | N-Benzyl-4-[4-methyl-7-oxo-2-(4-phenyl-piperazin-1-yl)-7H-pyrido[2,3-d]pyrimidin-8-yl]-benzamide; |
| 217 | N-Benzyl-4-[4-methyl-2-(4-methyl-piperazin-1-yl)-7-oxo-7H-pyrido[2,3-d]pyrimidin-8-yl]-benzamide; |
| 218 | 4-[8-(4-Benzylcarbamoyl-phenyl)-4-methyl-7-oxo-7,8-dihydro-pyrido[2,3-d]pyrimidin-2-yl]-piperazine-1-carboxylic acid ethyl ester; |
| 219 | N-Benzyl-4-[4-methyl-7-oxo-2-(4-pyridin-2-yl-piperazin-1-yl)-7H-pyrido[2,3-d]pyrimidin-8-yl]-benzamide; |
| 220 | N-Benzyl-4-[2-(4-formyl-piperazin-1-yl)-4-methyl-7-oxo-7H-pyrido[2,3-d]pyrimidin-8-yl]-benzamide; |
| 221 | N-Benzyl-4-{2-[4-(4-fluoro-phenyl)-piperazin-1-yl]-4-methyl-7-oxo-7H-pyrido[2,3-d]pyrimidin-8-yl}-benzamide; |
| 222 | N-Benzyl-4-{2-[4-(4-hydroxy-phenyl)-piperazin-1-yl]-4-methyl-7-oxo-7H-pyrido[2,3-d]pyrimidin-8-yl}-benzamide; |
| 223 | 4-[2-(4-Benzyl-piperazin-1-yl)-4-methyl-7-oxo-7H-pyrido[2,3-d]pyrimidin-8-yl]-N-cyclopropyl-benzamide; |
| 224 | N-Cyclopropyl-4-[4-methyl-7-oxo-2-(4-phenyl-piperazin-1-yl)-7H-pyrido[2,3-d]pyrimidin-8-yl]-benzamide; |
| 225 | N-Cyclopropyl-4-[4-methyl-2-(4-methyl-piperazin-1-yl)-7-oxo-7H-pyrido[2,3-d]pyrimidin-8-yl]-benzamide; |

TABLE 1-continued

| N° | Compound name |
|---|---|
| 226 | 4-[8-(4-Cyclopropylcarbamoyl-phenyl)-4-methyl-7-oxo-7,8-dihydro-pyrido[2,3-d]pyrimidin-2-yl]-piperazine-1-carboxylic acid ethyl ester; |
| 227 | N-Cyclopropyl-4-[4-methyl-7-oxo-2-(4-pyridin-2-yl-piperazin-1-yl)-7H-pyrido[2,3-d]pyrimidin-8-yl]-benzamide; |
| 228 | N-Cyclopropyl-4-{2-[4-(4-fluoro-phenyl)-piperazin-1-yl]-4-methyl-7-oxo-7H-pyrido[2,3-d]pyrimidin-8-yl}-benzamide; |
| 229 | N-Cyclopropyl-4-{2-[4-(4-hydroxy-phenyl)-piperazin-1-yl]-4-methyl-7-oxo-7H-pyrido[2,3-d]pyrimidin-8-yl}-benzamide; |
| 230 | 4-[2-(4-Benzyl-piperazin-1-yl)-4-methyl-7-oxo-7H-pyrido[2,3-d]pyrimidin-8-yl]-N-(4-trifluoromethyl-benzyl)-benzamide; |
| 231 | 4-[4-Methyl-7-oxo-2-(4-phenyl-piperazin-1-yl)-7H-pyrido[2,3-d]pyrimidin-8-yl]-N-(4-trifluoromethyl-benzyl)-benzamide; |
| 232 | 4-[4-Methyl-2-(4-methyl-piperazin-1-yl)-7-oxo-7H-pyrido[2,3-d]pyrimidin-8-yl]-N-(4-trifluoromethyl-benzyl)-benzamide; |
| 233 | 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid ethyl ester; |
| 234 | 4-[4-Methyl-7-oxo-2-(4-pyridin-2-yl-piperazin-1-yl)-7H-pyrido[2,3-d]pyrimidin-8-yl]-N-(4-trifluoromethyl-benzyl)-benzamide; |
| 235 | 4-[2-(4-Formyl-piperazin-1-yl)-4-methyl-7-oxo-7H-pyrido[2,3-d]pyrimidin-8-yl]-N-(4-trifluoromethyl-benzyl)-benzamide; |
| 236 | 4-{2-[4-(4-Hydroxy-phenyl)-piperazin-1-yl]-4-methyl-7-oxo-7H-pyrido[2,3-d]pyrimidin-8-yl}-N-(4-trifluoromethyl-benzyl)-benzamide; |
| 237 | 4-({4-[2-(4-Benzyl-piperazin-1-yl)-4-methyl-7-oxo-7H-pyrido[2,3-d]pyrimidin-8-yl]-benzoylamino}-methyl)-benzoic acid methyl ester; |
| 238 | 4-({4-[4-Methyl-7-oxo-2-(4-phenyl-piperazin-1-yl)-7H-pyrido[2,3-d]pyrimidin-8-yl]-benzoylamino}-methyl)-benzoic acid methyl ester; |
| 239 | 4-({4-[4-Methyl-2-(4-methyl-piperazin-1-yl)-7-oxo-7H-pyrido[2,3-d]pyrimidin-8-yl]-benzoylamino}-methyl)-benzoic acid methyl ester; |
| 240 | 4-{8-[4-(4-Methoxycarbonyl-benzylcarbamoyl)-phenyl]-4-methyl-7-oxo-7,8-dihydro-pyrido[2,3-d]pyrimidin-2-yl}-piperazine-1-carboxylic acid ethyl ester; |
| 241 | 4-({4-[4-Methyl-7-oxo-2-(4-pyridin-2-yl-piperazin-1-yl)-7H-pyrido[2,3-d]pyrimidin-8-yl]-benzoylamino}-methyl)-benzoic acid methyl ester; |
| 242 | 4-[(4-{2-[4-(4-Hydroxy-phenyl)-piperazin-1-yl]-4-methyl-7-oxo-7H-pyrido[2,3-d]pyrimidin-8-yl}-benzoylamino)-methyl]-benzoic acid methyl ester; |
| 243 | 4-[2-(4-Benzyl-piperazin-1-yl)-4-methyl-7-oxo-7H-pyrido[2,3-d]pyrimidin-8-yl]-N-(2,4-difluoro-benzyl)-benzamide; |
| 244 | N-(2,4-Difluoro-benzyl)-4-[4-methyl-7-oxo-2-(4-phenyl-piperazin-1-yl)-7H-pyrido[2,3-d]pyrimidin-8-yl]-benzamide; |
| 245 | N-(2,4-Difluoro-benzyl)-4-[4-methyl-2-(4-methyl-piperazin-1-yl)-7-oxo-7H-pyrido[2,3-d]pyrimidin-8-yl]-benzamide; |
| 246 | 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid ethyl ester; |
| 247 | N-(2,4-Difluoro-benzyl)-4-[4-methyl-7-oxo-2-(4-pyridin-2-yl-piperazin-1-yl)-7H-pyrido[2,3-d]pyrimidin-8-yl]-benzamide; |
| 248 | N-(2,4-Difluoro-benzyl)-4-{2-[4-(4-fluoro-phenyl)-piperazin-1-yl]-4-methyl-7-oxo-7H-pyrido[2,3-d]pyrimidin-8-yl}-benzamide; |
| 249 | N-(2,4-Difluoro-benzyl)-4-{2-[4-(4-hydroxy-phenyl)-piperazin-1-yl]-4-methyl-7-oxo-7H-pyrido[2,3-d]pyrimidin-8-yl}-benzamide; |
| 250 | 4-[2-(4-Benzyl-piperazin-1-yl)-4-methyl-7-oxo-7H-pyrido[2,3-d]pyrimidin-8-yl]-N-(4-methanesulfonyl-benzyl)-benzamide; |
| 251 | N-(4-Methanesulfonyl-benzyl)-4-[4-methyl-7-oxo-2-(4-phenyl-piperazin-1-yl)-7H-pyrido[2,3-d]pyrimidin-8-yl]-benzamide; |
| 252 | N-(4-Methanesulfonyl-benzyl)-4-[4-methyl-2-(4-methyl-piperazin-1-yl)-7-oxo-7H-pyrido[2,3-d]pyrimidin-8-yl]-benzamide; |
| 253 | 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid ethyl ester; |
| 254 | N-(4-Methanesulfonyl-benzyl)-4-[4-methyl-7-oxo-2-(4-pyridin-2-yl-piperazin-1-yl)-7H-pyrido[2,3-d]pyrimidin-8-yl]-benzamide; |
| 255 | 4-{2-[4-(4-Fluoro-phenyl)-piperazin-1-yl]-4-methyl-7-oxo-7H-pyrido[2,3-d]pyrimidin-8-yl}-N-(4-methanesulfonyl-benzyl)-benzamide; |
| 256 | 4-{2-[4-(4-Hydroxy-phenyl)-piperazin-1-yl]-4-methyl-7-oxo-7H-pyrido[2,3-d]pyrimidin-8-yl}-N-(4-methanesulfonyl-benzyl)-benzamide; |
| 257 | 4-{2-[4-(4-Fluoro-benzoyl)-piperidin-1-yl]-4-methyl-7-oxo-7H-pyrido[2,3-d]pyrimidin-8-yl}-benzamide; |
| 258 | 4-[2-(4-Benzyl-piperidin-1-yl)-4-methyl-7-oxo-7H-pyrido[2,3-d]pyrimidin-8-yl]-benzamide; |
| 259 | 4-{2-[4-(4-Acetyl-phenyl)-piperazin-1-yl]-4-methyl-7-oxo-7H-pyrido[2,3-d]pyrimidin-8-yl}-benzamide; |
| 260 | 4-[2-(5-Benzyl-2,5-diaza-bicyclo[2.2.1]hept-2-yl)-4-methyl-7-oxo-7H-pyrido[2,3-d]pyrimidin-8-yl]-benzamide; |
| 261 | 4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-benzamide; |
| 262 | 4-[2-(4-Acetyl-4-phenyl-piperidin-1-yl)-4-methyl-7-oxo-7H-pyrido[2,3-d]pyrimidin-8-yl]-benzamide; |
| 263 | 4-[2-(4-Acetyl-piperazin-1-yl)-4-methyl-7-oxo-7H-pyrido[2,3-d]pyrimidin-8-yl]-benzamide; |
| 264 | 4-[8-(4-Carbamoyl-phenyl)-4-methyl-7-oxo-7,8-dihydro-pyrido[2,3-d]pyrimidin-2-yl]-piperazine-1-carboxylic acid benzyl ester; |
| 265 | 4-(2-{4-[2-(2-Hydroxy-ethoxy)-ethyl]-piperazin-1-yl}-4-methyl-7-oxo-7H-pyrido[2,3-d]pyrimidin-8-yl)-benzamide; |
| 266 | 4-[4-Methyl-7-oxo-2-(4-quinolin-2-yl-piperazin-1-yl)-7H-pyrido[2,3-d]pyrimidin-8-yl]-benzamide; |
| 267 | N-(3,4-Dimethoxy-benzyl)-4-{2-[4-(4-fluoro-benzoyl)-piperidin-1-yl]-4-methyl-7-oxo-7H-pyrido[2,3-d]pyrimidin-8-yl}-benzamide; |
| 268 | 4-[2-(4-Benzyl-piperidin-1-yl)-4-methyl-7-oxo-7H-pyrido[2,3-d]pyrimidin-8-yl]-N-(3,4-dimethoxy-benzyl)-benzamide; |
| 269 | 4-[2-(4-Benzo[1,3]dioxol-5-ylmethyl-piperazin-1-yl)-4-methyl-7-oxo-7H-pyrido[2,3-d]pyrimidin-8-yl]-N-(3,4-dimethoxy-benzyl)-benzamide; |
| 270 | 4-{2-[4-(4-Acetyl-phenyl)-piperazin-1-yl]-4-methyl-7-oxo-7H-pyrido[2,3-d]pyrimidin-8-yl}-N-(3,4-dimethoxy-benzyl)-benzamide; |
| 271 | 4-[2-(5-Benzyl-2,5-diaza-bicyclo[2.2.1]hept-2-yl)-4-methyl-7-oxo-7H-pyrido[2,3-d]pyrimidin-8-yl]-N-(3,4-dimethoxy-benzyl)-benzamide; |
| 272 | N-(3,4-Dimethoxy-benzyl)-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; |
| 273 | 4-[2-(4-Acetyl-4-phenyl-piperidin-1-yl)-4-methyl-7-oxo-7H-pyrido[2,3-d]pyrimidin-8-yl]-N-(3,4-dimethoxy-benzyl)-benzamide; |
| 274 | 4-[2-(4-Acetyl-piperazin-1-yl)-4-methyl-7-oxo-7H-pyrido[2,3-d]pyrimidin-8-yl]-N-(3,4-dimethoxy-benzyl)-benzamide; |
| 275 | N-(3,4-Dimethoxy-benzyl)-4-{2-[4-(2-hydroxy-ethyl)-piperidin-1-yl]-4-methyl-7-oxo-7H-pyrido[2,3-d]pyrimidin-8-yl}-benzamide; |

TABLE 1-continued

| N° | Compound name |
|---|---|
| 276 | 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid benzyl ester; |
| 277 | N-(3,4-Dimethoxy-benzyl)-4-(2-{4-[2-(2-hydroxy-ethoxy)-ethyl]-piperazin-1-yl}-4-methyl-7-oxo-7H-pyrido[2,3-d]pyrimidin-8-yl)-benzamide; |
| 278 | N-Benzyl-4-{2-[4-(4-fluoro-benzoyl)-piperidin-1-yl]-4-methyl-7-oxo-7H-pyrido[2,3-d]pyrimidin-8-yl}-benzamide; |
| 279 | N-Benzyl-4-[2-(4-benzyl-piperidin-1-yl)-4-methyl-7-oxo-7H-pyrido[2,3-d]pyrimidin-8-yl]-benzamide; |
| 280 | 4-[2-(4-Benzo[1,3]dioxol-5-ylmethyl-piperazin-1-yl)-4-methyl-7-oxo-7H-pyrido[2,3-d]pyrimidin-8-yl]-N-benzyl-benzamide; |
| 281 | 4-{2-[4-(4-Acetyl-phenyl)-piperazin-1-yl]-4-methyl-7-oxo-7H-pyrido[2,3-d]pyrimidin-8-yl}-N-benzyl-benzamide; |
| 282 | N-Benzyl-4-[2-(5-benzyl-2,5-diaza-bicyclo[2.2.1]hept-2-yl)-4-methyl-7-oxo-7H-pyrido[2,3-d]pyrimidin-8-yl]-benzamide; |
| 283 | N-Benzyl-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; |
| 284 | 4-[2-(4-Acetyl-4-phenyl-piperidin-1-yl)-4-methyl-7-oxo-7H-pyrido[2,3-d]pyrimidin-8-yl]-N-benzyl-benzamide; |
| 285 | 4-[2-(4-Acetyl-piperazin-1-yl)-4-methyl-7-oxo-7H-pyrido[2,3-d]pyrimidin-8-yl]-N-benzyl-benzamide; |
| 286 | N-Benzyl-4-{2-[4-(2-hydroxy-ethyl)-piperidin-1-yl]-4-methyl-7-oxo-7H-pyrido[2,3-d]pyrimidin-8-yl}-benzamide; |
| 287 | 4-[8-(4-Benzylcarbamoyl-phenyl)-4-methyl-7-oxo-7,8-dihydro-pyrido[2,3-d]pyrimidin-2-yl]-piperazine-1-carboxylic acid benzyl ester; |
| 288 | N-Benzyl-4-(2-{4-[2-(2-hydroxy-ethoxy)-ethyl]-piperazin-1-yl}-4-methyl-7-oxo-7H-pyrido[2,3-d]pyrimidin-8-yl)-benzamide; |
| 289 | N-Cyclopropyl-4-{2-[4-(4-fluoro-benzoyl)-piperidin-1-yl]-4-methyl-7-oxo-7H-pyrido[2,3-d]pyrimidin-8-yl}-benzamide; |
| 290 | 4-[2-(4-Benzyl-piperidin-1-yl)-4-methyl-7-oxo-7H-pyrido[2,3-d]pyrimidin-8-yl]-N-cyclopropyl-benzamide; |
| 291 | 4-{2-[4-(4-Acetyl-phenyl)-piperazin-1-yl]-4-methyl-7-oxo-7H-pyrido[2,3-d]pyrimidin-8-yl}-N-cyclopropyl-benzamide; |
| 292 | 4-[2-(5-Benzyl-2,5-diaza-bicyclo[2.2.1]hept-2-yl)-4-methyl-7-oxo-7H-pyrido[2,3-d]pyrimidin-8-yl]-N-cyclopropyl-benzamide; |
| 293 | N-Cyclopropyl-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; |
| 294 | 4-[2-(4-Acetyl-4-phenyl-piperidin-1-yl)-4-methyl-7-oxo-7H-pyrido[2,3-d]pyrimidin-8-yl]-N-cyclopropyl-benzamide; |
| 295 | 4-[2-(4-Acetyl-piperazin-1-yl)-4-methyl-7-oxo-7H-pyrido[2,3-d]pyrimidin-8-yl]-N-cyclopropyl-benzamide; |
| 296 | N-Cyclopropyl-4-{2-[4-(2-hydroxy-ethyl)-piperidin-1-yl]-4-methyl-7-oxo-7H-pyrido[2,3-d]pyrimidin-8-yl}-benzamide; |
| 297 | 4-[8-(4-Cyclopropylcarbamoyl-phenyl)-4-methyl-7-oxo-7,8-dihydro-pyrido[2,3-d]pyrimidin-2-yl]-piperazine-1-carboxylic acid benzyl ester; |
| 298 | 4-{2-[4-(4-Fluoro-benzoyl)-piperidin-1-yl]-4-methyl-7-oxo-7H-pyrido[2,3-d]pyrimidin-8-yl}-N-(4-trifluoromethyl-benzyl)-benzamide; |
| 299 | 4-[2-(4-Benzyl-piperidin-1-yl)-4-methyl-7-oxo-7H-pyrido[2,3-d]pyrimidin-8-yl]-N-(4-trifluoromethyl-benzyl)-benzamide; |
| 300 | 4-{2-[4-(4-Acetyl-phenyl)-piperazin-1-yl]-4-methyl-7-oxo-7H-pyrido[2,3-d]pyrimidin-8-yl}-N-(4-trifluoromethyl-benzyl)-benzamide; |
| 301 | 4-[2-(5-Benzyl-2,5-diaza-bicyclo[2.2.1]hept-2-yl)-4-methyl-7-oxo-7H-pyrido[2,3-d]pyrimidin-8-yl]-N-(4-trifluoromethyl-benzyl)-benzamide; |
| 302 | 4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-N-(4-trifluoromethyl-benzyl)-benzamide; |
| 303 | 4-[2-(4-Acetyl-4-phenyl-piperidin-1-yl)-4-methyl-7-oxo-7H-pyrido[2,3-d]pyrimidin-8-yl]-N-(4-trifluoromethyl-benzyl)-benzamide; |
| 304 | 4-[2-(4-Acetyl-piperazin-1-yl)-4-methyl-7-oxo-7H-pyrido[2,3-d]pyrimidin-8-yl]-N-(4-trifluoromethyl-benzyl)-benzamide; |
| 305 | 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid benzyl ester; |
| 306 | 4-(2-{4-[2-(2-Hydroxy-ethoxy)-ethyl]-piperazin-1-yl}-4-methyl-7-oxo-7H-pyrido[2,3-d]pyrimidin-8-yl)-N-(4-trifluoromethyl-benzyl)-benzamide; |
| 307 | 4-[(4-{2-[4-(4-Fluoro-benzoyl)-piperidin-1-yl]-4-methyl-7-oxo-7H-pyrido[2,3-d]pyrimidin-8-yl}-benzoylamino)-methyl]-benzoic acid methyl ester; |
| 308 | 4-({4-[2-(4-Benzyl-piperidin-1-yl)-4-methyl-7-oxo-7H-pyrido[2,3-d]pyrimidin-8-yl]-benzoylamino}-methyl)-benzoic acid methyl ester; |
| 309 | 4-({4-[2-(4-Benzo[1,3]dioxol-5-ylmethyl-piperazin-1-yl)-4-methyl-7-oxo-7H-pyrido[2,3-d]pyrimidin-8-yl]-benzoylamino}-methyl)-benzoic acid methyl ester; |
| 310 | 4-[(4-{2-[4-(4-Acetyl-phenyl)-piperazin-1-yl]-4-methyl-7-oxo-7H-pyrido[2,3-d]pyrimidin-8-yl}-benzoylamino)-methyl]-benzoic acid methyl ester; |
| 311 | 4-({4-[2-(5-Benzyl-2,5-diaza-bicyclo[2.2.1]hept-2-yl)-4-methyl-7-oxo-7H-pyrido[2,3-d]pyrimidin-8-yl]-benzoylamino}-methyl)-benzoic acid methyl ester; |
| 312 | 4-[(4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-benzoylamino)-methyl]-benzoic acid methyl ester; |
| 313 | 4-({4-[2-(4-Acetyl-4-phenyl-piperidin-1-yl)-4-methyl-7-oxo-7H-pyrido[2,3-d]pyrimidin-8-yl]-benzoylamino}-methyl)-benzoic acid methyl ester; |
| 314 | 4-({4-[2-(4-Acetyl-piperazin-1-yl)-4-methyl-7-oxo-7H-pyrido[2,3-d]pyrimidin-8-yl]-benzoylamino}-methyl)-benzoic acid methyl ester; |
| 315 | 4-[(4-{2-[4-(2-Hydroxy-ethyl)-piperidin-1-yl]-4-methyl-7-oxo-7H-pyrido[2,3-d]pyrimidin-8-yl}-benzoylamino)-methyl]-benzoic acid methyl ester; |
| 316 | 4-{8-[4-(4-Methoxycarbonyl-benzylcarbamoyl)-phenyl]-4-methyl-7-oxo-7,8-dihydro-pyrido[2,3-d]pyrimidin-2-yl}-piperazine-1-carboxylic acid benzyl ester; |
| 317 | 4-{[4-(2-{4-[2-(2-Hydroxy-ethoxy)-ethyl]-piperazin-1-yl}-4-methyl-7-oxo-7H-pyrido[2,3-d]pyrimidin-8-yl)-benzoylamino]-methyl}-benzoic acid methyl ester; |
| 318 | N-(2,4-Difluoro-benzyl)-4-{2-[4-(4-fluoro-benzoyl)-piperidin-1-yl]-4-methyl-7-oxo-7H-pyrido[2,3-d]pyrimidin-8-yl}-benzamide; |
| 319 | 4-[2-(4-Benzyl-piperidin-1-yl)-4-methyl-7-oxo-7H-pyrido[2,3-d]pyrimidin-8-yl]-N-(2,4-difluoro-benzyl)-benzamide; |
| 320 | 4-[2-(4-Benzo[1,3]dioxol-5-ylmethyl-piperazin-1-yl)-4-methyl-7-oxo-7H-pyrido[2,3-d]pyrimidin-8-yl]-N-(2,4-difluoro-benzyl)-benzamide; |
| 321 | 4-{2-[4-(4-Acetyl-phenyl)-piperazin-1-yl]-4-methyl-7-oxo-7H-pyrido[2,3-d]pyrimidin-8-yl}-N-(2,4-difluoro-benzyl)-benzamide; |
| 322 | 4-[2-(5-Benzyl-2,5-diaza-bicyclo[2.2.1]hept-2-yl)-4-methyl-7-oxo-7H-pyrido[2,3-d]pyrimidin-8-yl]-N-(2,4-difluoro-benzyl)-benzamide; |
| 323 | N-(2,4-Difluoro-benzyl)-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; |

TABLE 1-continued

| N° | Compound name |
|---|---|
| 324 | 4-[2-(4-Acetyl-4-phenyl-piperidin-1-yl)-4-methyl-7-oxo-7H-pyrido[2,3-d]pyrimidin-8-yl]-N-(2,4-difluoro-benzyl)-benzamide; |
| 325 | 4-[2-(4-Acetyl-piperazin-1-yl)-4-methyl-7-oxo-7H-pyrido[2,3-d]pyrimidin-8-yl]-N-(2,4-difluoro-benzyl)-benzamide; |
| 326 | 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid benzyl ester; |
| 327 | N-(2,4-Difluoro-benzyl)-4-(2-{4-[2-(2-hydroxy-ethoxy)-ethyl]-piperazin-1-yl}-4-methyl-7-oxo-7H-pyrido[2,3-d]pyrimidin-8-yl)-benzamide; |
| 328 | 4-{2-[4-(4-Fluoro-benzoyl)-piperidin-1-yl]-4-methyl-7-oxo-7H-pyrido[2,3-d]pyrimidin-8-yl}-N-(4-methanesulfonyl-benzyl)-benzamide; |
| 329 | 4-[2-(4-Benzyl-piperidin-1-yl)-4-methyl-7-oxo-7H-pyrido[2,3-d]pyrimidin-8-yl]-N-(4-methanesulfonyl-benzyl)-benzamide; |
| 330 | 4-[2-(4-Benzo[1,3]dioxol-5-ylmethyl-piperazin-1-yl)-4-methyl-7-oxo-7H-pyrido[2,3-d]pyrimidin-8-yl]-N-(4-methanesulfonyl-benzyl)-benzamide; |
| 331 | 4-{2-[4-(4-Acetyl-phenyl)-piperazin-1-yl]-4-methyl-7-oxo-7H-pyrido[2,3-d]pyrimidin-8-yl}-N-(4-methanesulfonyl-benzyl)-benzamide; |
| 332 | 4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-N-(4-methanesulfonyl-benzyl)-benzamide; |
| 333 | 4-[2-(4-Acetyl-4-phenyl-piperidin-1-yl)-4-methyl-7-oxo-7H-pyrido[2,3-d]pyrimidin-8-yl]-N-(4-methanesulfonyl-benzyl)-benzamide; |
| 334 | 4-[2-(4-Acetyl-piperazin-1-yl)-4-methyl-7-oxo-7H-pyrido[2,3-d]pyrimidin-8-yl]-N-(4-methanesulfonyl-benzyl)-benzamide; |
| 335 | 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid benzyl ester; |
| 336 | 4-[2-(4-Acetylamino-phenoxy)-4-methyl-7-oxo-7H-pyrido[2,3-d]pyrimidin-8-yl]-benzamide; |
| 337 | 4-[2-(4-Carbamoylmethyl-phenoxy)-4-methyl-7-oxo-7H-pyrido[2,3-d]pyrimidin-8-yl]-benzamide; |
| 338 | 4-[8-(4-Carbamoyl-phenyl)-4-methyl-7-oxo-7,8-dihydro-pyrido[2,3-d]pyrimidin-2-yloxy]-benzoic acid ethyl ester; |
| 339 | 4-[4-Methyl-7-oxo-2-(4-trifluoromethyl-phenoxy)-7H-pyrido[2,3-d]pyrimidin-8-yl]-benzamide; |
| 340 | 4-[2-(4-Fluoro-phenoxy)-4-methyl-7-oxo-7H-pyrido[2,3-d]pyrimidin-8-yl]-benzamide; |
| 341 | 4-{2-[4-(4-Hydroxy-benzenesulfonyl)-phenoxy]-4-methyl-7-oxo-7H-pyrido[2,3-d]pyrimidin-8-yl}-benzamide; |
| 342 | 4-[2-(4-Acetyl-phenoxy)-4-methyl-7-oxo-7H-pyrido[2,3-d]pyrimidin-8-yl]-benzamide; |
| 343 | 4-[2-(4-Carbamoylmethyl-phenoxy)-4-methyl-7-oxo-7H-pyrido[2,3-d]pyrimidin-8-yl]-N-(3,4-dimethoxy-benzyl)-benzamide; |
| 344 | N-(3,4-Dimethoxy-benzyl)-4-[4-methyl-7-oxo-2-(4-trifluoromethyl-phenoxy)-7H-pyrido[2,3-d]pyrimidin-8-yl]-benzamide; |
| 345 | N-(3,4-Dimethoxy-benzyl)-4-[2-(4-fluoro-phenoxy)-4-methyl-7-oxo-7H-pyrido[2,3-d]pyrimidin-8-yl]-benzamide; |
| 346 | N-(3,4-Dimethoxy-benzyl)-4-{2-[4-(4-hydroxy-benzenesulfonyl)-phenoxy]-4-methyl-7-oxo-7H-pyrido[2,3-d]pyrimidin-8-yl}-benzamide; |
| 347 | 4-[2-(4-Acetyl-phenoxy)-4-methyl-7-oxo-7H-pyrido[2,3-d]pyrimidin-8-yl]-N-(3,4-dimethoxy-benzyl)-benzamide; |
| 348 | N-Benzyl-4-[2-(4-carbamoylmethyl-phenoxy)-4-methyl-7-oxo-7H-pyrido[2,3-d]pyrimidin-8-yl]-benzamide; |
| 349 | N-Benzyl-4-[2-(4-fluoro-phenoxy)-4-methyl-7-oxo-7H-pyrido[2,3-d]pyrimidin-8-yl]-benzamide; |
| 350 | 4-[2-(4-Acetyl-phenoxy)-4-methyl-7-oxo-7H-pyrido[2,3-d]pyrimidin-8-yl]-N-benzyl-benzamide; |
| 351 | 4-[2-(4-Acetylamino-phenoxy)-4-methyl-7-oxo-7H-pyrido[2,3-d]pyrimidin-8-yl]-N-cyclopropyl-benzamide; |
| 352 | N-(3,4-Dimethoxy-benzyl)-4-[2-(4-fluoro-phenylsulfanyl)-4-methyl-7-oxo-7H-pyrido[2,3-d]pyrimidin-8-yl]-benzamide; |
| 353 | N-Benzyl-4-[4-methyl-2-(1-methyl-1H-imidazol-2-ylsulfanyl)-7-oxo-7H-pyrido[2,3-d]pyrimidin-8-yl]-benzamide; |
| 354 | N-Benzyl-4-[2-(4-fluoro-phenylsulfanyl)-4-methyl-7-oxo-7H-pyrido[2,3-d]pyrimidin-8-yl]-benzamide; |
| 355 | N-Cyclopropyl-4-[2-(4-fluoro-phenylsulfanyl)-4-methyl-7-oxo-7H-pyrido[2,3-d]pyrimidin-8-yl]-benzamide; |
| 356 | 4-[4-Methyl-2-(1-methyl-1H-imidazol-2-ylsulfanyl)-7-oxo-7H-pyrido[2,3-d]pyrimidin-8-yl]-N-(4-trifluoromethyl-benzyl)-benzamide; |
| 357 | 4-[2-(4-Fluoro-phenylsulfanyl)-4-methyl-7-oxo-7H-pyrido[2,3-d]pyrimidin-8-yl]-N-(4-trifluoromethyl-benzyl)-benzamide; |
| 358 | 4-({4-[4-Methyl-2-(1-methyl-1H-imidazol-2-ylsulfanyl)-7-oxo-7H-pyrido[2,3-d]pyrimidin-8-yl]-benzoylamino}-methyl)-benzoic acid methyl ester; |
| 359 | 4-({4-[2-(4-Fluoro-phenylsulfanyl)-4-methyl-7-oxo-7H-pyrido[2,3-d]pyrimidin-8-yl]-benzoylamino}-methyl)-benzoic acid methyl ester; |
| 360 | N-(2,4-Difluoro-benzyl)-4-[4-methyl-2-(1-methyl-1H-imidazol-2-ylsulfanyl)-7-oxo-7H-pyrido[2,3-d]pyrimidin-8-yl]-benzamide; |
| 361 | N-(2,4-Difluoro-benzyl)-4-[2-(4-fluoro-phenylsulfanyl)-4-methyl-7-oxo-7H-pyrido[2,3-d]pyrimidin-8-yl]-benzamide; |
| 362 | 4-[2-(4-Fluoro-phenylsulfanyl)-4-methyl-7-oxo-7H-pyrido[2,3-d]pyrimidin-8-yl]-N-(4-methanesulfonyl-benzyl)-benzamide; |
| 363 | N-(3,4-Dimethoxy-benzyl)-4-[4-methyl-2-(1-methyl-1H-imidazol-2-ylsulfanyl)-7-oxo-7H-pyrido[2,3-d]pyrimidin-8-yl]-benzamide; |
| 364 | 4-[2-(4-Carbamoylmethyl-phenoxy)-4-methyl-7-oxo-7H-pyrido[2,3-d]pyrimidin-8-yl]-N-cyclopropyl-benzamide; |
| 365 | N-Cyclopropyl-4-[4-methyl-7-oxo-2-(4-trifluoromethyl-phenoxy)-7H-pyrido[2,3-d]pyrimidin-8-yl]-benzamide; |
| 366 | N-Cyclopropyl-4-[2-(4-fluoro-phenoxy)-4-methyl-7-oxo-7H-pyrido[2,3-d]pyrimidin-8-yl]-benzamide; |
| 367 | N-Cyclopropyl-4-{2-[4-(4-hydroxy-benzenesulfonyl)-phenoxy]-4-methyl-7-oxo-7H-pyrido[2,3-d]pyrimidin-8-yl}-benzamide; |
| 368 | 4-[2-(4-Acetyl-phenoxy)-4-methyl-7-oxo-7H-pyrido[2,3-d]pyrimidin-8-yl]-N-cyclopropyl-benzamide; |
| 369 | 4-[2-(4-Carbamoylmethyl-phenoxy)-4-methyl-7-oxo-7H-pyrido[2,3-d]pyrimidin-8-yl]-N-(4-trifluoromethyl-benzyl)-benzamide; |
| 370 | 4-{4-Methyl-7-oxo-8-[4-(4-trifluoromethyl-benzylcarbamoyl)-phenyl]-7,8-dihydro-pyrido[2,3-d]pyrimidin-2-yloxy}-benzoic acid ethyl ester; |
| 371 | 4-[4-Methyl-7-oxo-2-(4-trifluoromethyl-phenoxy)-7H-pyrido[2,3-d]pyrimidin-8-yl]-N-(4-trifluoromethyl-benzyl)-benzamide; |
| 372 | 4-[2-(4-Fluoro-phenoxy)-4-methyl-7-oxo-7H-pyrido[2,3-d]pyrimidin-8-yl]-N-(4-trifluoromethyl-benzyl)-benzamide; |
| 373 | 4-[2-(4-Acetyl-phenoxy)-4-methyl-7-oxo-7H-pyrido[2,3-d]pyrimidin-8-yl]-N-(4-trifluoromethyl-benzyl)-benzamide; |
| 374 | 4-({4-[2-(4-Carbamoylmethyl-phenoxy)-4-methyl-7-oxo-7H-pyrido[2,3-d]pyrimidin-8-yl]-benzoylamino}-methyl)-benzoic acid methyl ester; |
| 375 | 4-({4-[4-Methyl-7-oxo-2-(4-trifluoromethyl-phenoxy)-7H-pyrido[2,3-d]pyrimidin-8-yl]-benzoylamino}-methyl)-benzoic acid methyl ester; |

TABLE 1-continued

| N° | Compound name |
|---|---|
| 376 | 4-({4-[2-(4-Acetyl-phenoxy)-4-methyl-7-oxo-7H-pyrido[2,3-d]pyrimidin-8-yl]-benzoylamino}-methyl)-benzoic acid methyl ester; |
| 377 | 4-[2-(4-Carbamoylmethyl-phenoxy)-4-methyl-7-oxo-7H-pyrido[2,3-d]pyrimidin-8-yl]-N-(2,4-difluoro-benzyl)-benzamide; |
| 378 | N-(2,4-Difluoro-benzyl)-4-[4-methyl-7-oxo-2-(4-trifluoromethyl-phenoxy)-7H-pyrido[2,3-d]pyrimidin-8-yl]-benzamide; |
| 379 | 4-[2-(4-Acetyl-phenoxy)-4-methyl-7-oxo-7H-pyrido[2,3-d]pyrimidin-8-yl]-N-(2,4-difluoro-benzyl)-benzamide; |
| 380 | 4-[2-(4-Carbamoylmethyl-phenoxy)-4-methyl-7-oxo-7H-pyrido[2,3-d]pyrimidin-8-yl]-N-(4-methanesulfonyl-benzyl)-benzamide; |
| 381 | 4-{8-[4-(4-Methanesulfonyl-benzylcarbamoyl)-phenyl]-4-methyl-7-oxo-7,8-dihydro-pyrido[2,3-d]pyrimidin-2-yloxy}-benzoic acid ethyl ester; |
| 382 | N-(4-Methanesulfonyl-benzyl)-4-[4-methyl-7-oxo-2-(4-trifluoromethyl-phenoxy)-7H-pyrido[2,3-d]pyrimidin-8-yl]-benzamide; |
| 383 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 384 | 4-[2-(4-Acetyl-phenoxy)-4-methyl-7-oxo-7H-pyrido[2,3-d]pyrimidin-8-yl]-N-(4-methanesulfonyl-benzyl)-benzamide; |
| 385 | 4-[4-Methyl-2-(octahydro-isoquinolin-2-yl)-7-oxo-7H-pyrido[2,3-d]pyrimidin-8-yl]-benzamide; |
| 386 | N-(3,4-Dimethoxy-benzyl)-4-[4-methyl-2-(octahydro-isoquinolin-2-yl)-7-oxo-7H-pyrido[2,3-d]pyrimidin-8-yl]-benzamide; |
| 387 | N-Benzyl-4-[4-methyl-2-(octahydro-isoquinolin-2-yl)-7-oxo-7H-pyrido[2,3-d]pyrimidin-8-yl]-benzamide; |
| 388 | N-Cyclopropyl-4-[4-methyl-2-(octahydro-isoquinolin-2-yl)-7-oxo-7H-pyrido[2,3-d]pyrimidin-8-yl]-benzamide; |
| 389 | 4-[4-Methyl-2-(octahydro-isoquinolin-2-yl)-7-oxo-7H-pyrido[2,3-d]pyrimidin-8-yl]-N-(4-trifluoromethyl-benzyl)-benzamide; |
| 390 | 4-({4-[4-Methyl-2-(octahydro-isoquinolin-2-yl)-7-oxo-7H-pyrido[2,3-d]pyrimidin-8-yl]-benzoylamino}-methyl)-benzoic acid methyl ester; |
| 391 | N-(2,4-Difluoro-benzyl)-4-[4-methyl-2-(octahydro-isoquinolin-2-yl)-7-oxo-7H-pyrido[2,3-d]pyrimidin-8-yl]-benzamide; |
| 392 | N-(4-Methanesulfonyl-benzyl)-4-[4-methyl-2-(octahydro-isoquinolin-2-yl)-7-oxo-7H-pyrido[2,3-d]pyrimidin-8-yl]-benzamide; |
| 393 | 4-[4-Methyl-2-(1-methyl-1H-imidazol-2-ylsulfanyl)-7-oxo-7H-pyrido[2,3-d]pyrimidin-8-yl]-benzamide; |
| 394 | 4-[2-(1H-Benzoimidazol-2-ylsulfanyl)-4-methyl-7-oxo-7H-pyrido[2,3-d]pyrimidin-8-yl]-benzamide; |
| 395 | 4-[2-(4-Fluoro-phenylsulfanyl)-4-methyl-7-oxo-7H-pyrido[2,3-d]pyrimidin-8-yl]-benzamide; |
| 396 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 397 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 398 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 399 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 400 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 401 | 4-[4-Methyl-7-oxo-2-(5-phenyl-1H-[1,2,4]triazol-3-ylsulfanyl)-7H-pyrido[2,3-d]pyrimidin-8-yl]-benzamide; |
| 402 | N-(3,4-Dimethoxy-benzyl)-4-[4-methyl-7-oxo-2-(5-phenyl-1H-[1,2,4]triazol-3-ylsulfanyl)-7H-pyrido[2,3-d]pyrimidin-8-yl]-benzamide; |
| 403 | 4-[2-(1H-Benzoimidazol-2-ylsulfanyl)-4-methyl-7-oxo-7H-pyrido[2,3-d]pyrimidin-8-yl]-N-(3,4-dimethoxy-benzyl)-benzamide; |
| 404 | N-Benzyl-4-[4-methyl-7-oxo-2-(5-phenyl-1H-[1,2,4]triazol-3-ylsulfanyl)-7H-pyrido[2,3-d]pyrimidin-8-yl]-benzamide; |
| 405 | 4-[2-(1H-Benzoimidazol-2-ylsulfanyl)-4-methyl-7-oxo-7H-pyrido[2,3-d]pyrimidin-8-yl]-N-benzyl-benzamide; |
| 406 | N-Cyclopropyl-4-[4-methyl-7-oxo-2-(5-phenyl-1H-[1,2,4]triazol-3-ylsulfanyl)-7H-pyrido[2,3-d]pyrimidin-8-yl]-benzamide; |
| 407 | 4-[4-Methyl-7-oxo-2-(5-phenyl-1H-[1,2,4]triazol-3-ylsulfanyl)-7H-pyrido[2,3-d]pyrimidin-8-yl]-N-(4-trifluoromethyl-benzyl)-benzamide; |
| 408 | 4-[2-(1H-Benzoimidazol-2-ylsulfanyl)-4-methyl-7-oxo-7H-pyrido[2,3-d]pyrimidin-8-yl]-N-(4-trifluoromethyl-benzyl)-benzamide; |
| 409 | 4-({4-[4-Methyl-7-oxo-2-(5-phenyl-1H-[1,2,4]triazol-3-ylsulfanyl)-7H-pyrido[2,3-d]pyrimidin-8-yl]-benzoylamino}-methyl)-benzoic acid methyl ester; |
| 410 | 4-({4-[2-(1H-Benzoimidazol-2-ylsulfanyl)-4-methyl-7-oxo-7H-pyrido[2,3-d]pyrimidin-8-yl]-benzoylamino}-methyl)-benzoic acid methyl ester; |
| 411 | N-(2,4-Difluoro-benzyl)-4-[4-methyl-7-oxo-2-(5-phenyl-1H-[1,2,4]triazol-3-ylsulfanyl)-7H-pyrido[2,3-d]pyrimidin-8-yl]-benzamide; |
| 412 | 4-[2-(1H-Benzoimidazol-2-ylsulfanyl)-4-methyl-7-oxo-7H-pyrido[2,3-d]pyrimidin-8-yl]-N-(2,4-difluoro-benzyl)-benzamide; |
| 413 | N-(4-Methanesulfonyl-benzyl)-4-[4-methyl-2-(1-methyl-1H-imidazol-2-ylsulfanyl)-7-oxo-7H-pyrido[2,3-d]pyrimidin-8-yl]-benzamide; |
| 414 | N-(4-Methanesulfonyl-benzyl)-4-[4-methyl-7-oxo-2-(5-phenyl-1H-[1,2,4]triazol-3-ylsulfanyl)-7H-pyrido[2,3-d]pyrimidin-8-yl]-benzamide; |
| 415 | 4-[2-(1H-Benzoimidazol-2-ylsulfanyl)-4-methyl-7-oxo-7H-pyrido[2,3-d]pyrimidin-8-yl]-N-(4-methanesulfonyl-benzyl)-benzamide; |
| 416 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 417 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 418 | 4-[2-(4-Fluoro-phenoxy)-4-methyl-7-oxo-7H-pyrido[2,3-d]pyrimidin-8-yl]-N-(4-methanesulfonyl-benzyl)-benzamide; |
| 419 | N-(2,4-Difluoro-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide; |
| 420 | 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid cyclohexylamide; |
| 421 | 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide; |
| 422 | N-(4-Methanesulfonyl-benzyl)-4-{4-methyl-7-oxo-2-[4-(pyridine-3-carbonyl)-piperazin-1-yl]-7H-pyrido[2,3-d]pyrimidin-8-yl}-benzamide; |
| 423 | 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide; |
| 424 | 4-{2-[4-(Furan-2-carbonyl)-piperazin-1-yl]-4-methyl-7-oxo-7H-pyrido[2,3-d]pyrimidin-8-yl}-N-(4-methanesulfonyl-benzyl)-benzamide; |
| 425 | 4-[2-(4-Benzoyl-piperazin-1-yl)-4-methyl-7-oxo-7H-pyrido[2,3-d]pyrimidin-8-yl]-N-(4-methanesulfonyl-benzyl)-benzamide; |

TABLE 1-continued

| N° | Compound name |
|---|---|
| 426 | N-(4-Methanesulfonyl-benzyl)-4-[4-methyl-7-oxo-2-(4-phenylacetyl-piperazin-1-yl)-7H-pyrido[2,3-d]pyrimidin-8-yl]-benzamide; |
| 427 | N-(4-Methanesulfonyl-benzyl)-4-{methyl-7-oxo-2-[4-(3,4,5-trimethoxy-benzoyl)-piperazin-1-yl]-7H-pyrido[2,3-d]pyrimidin-8-yl}-benzamide; |
| 428 | 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid cyclohexylamide; |
| 429 | 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide; |
| 430 | 4-{2-[4-(Furan-2-carbonyl)-piperazin-1-yl]-4-methyl-7-oxo-7H-pyrido[2,3-d]pyrimidin-8-yl}-benzamide; |
| 431 | 4-[2-(4-Benzoyl-piperazin-1-yl)-4-methyl-7-oxo-7H-pyrido[2,3-d]pyrimidin-8-yl]-benzamide; |
| 432 | 4-{4-Methyl-7-oxo-2-[4-(3,4,5-trimethoxy-benzoyl)-piperazin-1-yl]-7H-pyrido[2,3-d]pyrimidin-8-yl}-benzamide; |
| 433 | N-(3,4-Dimethoxy-benzyl)-4-{4-methyl-7-oxo-2-[4-(pyridine-3-carbonyl)-piperazin-1-yl]-7H-pyrido[2,3-d]pyrimidin-8-yl}-benzamide; |
| 434 | 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide; |
| 435 | N-(3,4-Dimethoxy-benzyl)-4-{2-[4-(furan-2-carbonyl)-piperazin-1-yl]-4-methyl-7-oxo-7H-pyrido[2,3-d]pyrimidin-8-yl}-benzamide; |
| 436 | 4-[2-(4-Benzoyl-piperazin-1-yl)-4-methyl-7-oxo-7H-pyrido[2,3-d]pyrimidin-8-yl]-N-(3,4-dimethoxy-benzyl)-benzamide; |
| 437 | N-(3,4-Dimethoxy-benzyl)-4-[4-methyl-7-oxo-2-(4-phenylacetyl-piperazin-1-yl)-7H-pyrido[2,3-d]pyrimidin-8-yl]-benzamide; |
| 438 | N-(3,4-Dimethoxy-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide; |
| 439 | 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid cyclohexylamide; |
| 440 | N-Benzyl-4-{4-methyl-7-oxo-2-[4-(pyridine-3-carbonyl)-piperazin-1-yl]-7H-pyrido[2,3-d]pyrimidin-8-yl}-benzamide; |
| 441 | 4-{8-(4-Benzylcarbamoyl-phenyl)-4-methyl-7-oxo-7,8-dihydro-pyrido[2,3-d]pyrimidin-2-yl]-piperazine-1-carboxylic acid (3,4-difluoro-phenyl)-amide; |
| 442 | N-Benzyl-4-{2-[4-(furan-2-carbonyl)-piperazin-1-yl]-4-methyl-7-oxo-7H-pyrido[2,3-d]pyrimidin-8-yl}-benzamide; |
| 443 | 4-[2-(4-Benzoyl-piperazin-1-yl)-4-methyl-7-oxo-7H-pyrido[2,3-d]pyrimidin-8-yl]-N-benzyl-benzamide; |
| 444 | N-Benzyl-4-[4-methyl-7-oxo-2-(4-phenylacetyl-piperazin-1-yl)-7H-pyrido[2,3-d]pyrimidin-8-yl]-benzamide; |
| 445 | 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide; |
| 446 | N-Benzyl-4-{4-methyl-7-oxo-2-[4-(3,4,5-trimethoxy-benzoyl)-piperazin-1-yl]-7H-pyrido[2,3-d]pyrimidin-8-yl}-benzamide; |
| 447 | 4-[8-(4-Benzylcarbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide; |
| 448 | N-Cyclopropyl-4-{4-methyl-7-oxo-2-[4-(pyridine-3-carbonyl)-piperazin-1-yl]-7H-pyrido[2,3-d]pyrimidin-8-yl}-benzamide; |
| 449 | 4-[8-(4-Cyclopropylcarbamoyl-phenyl)-4-methyl-7-oxo-7,8-dihydro-pyrido[2,3-d]pyrimidin-2-yl]-piperazine-1-carboxylic acid (3,4-difluoro-phenyl)-amide; |
| 450 | N-Cyclopropyl-4-{2-[4-(furan-2-carbonyl)-piperazin-1-yl]-4-methyl-7-oxo-7H-pyrido[2,3-d]pyrimidin-8-yl}-benzamide; |
| 451 | 4-[2-(4-Benzoyl-piperazin-1-yl)-4-methyl-7-oxo-7H-pyrido[2,3-d]pyrimidin-8-yl]-N-cyclopropyl-benzamide; |
| 452 | N-Cyclopropyl-4-[4-methyl-7-oxo-2-(4-phenylacetyl-piperazin-1-yl)-7H-pyrido[2,3-d]pyrimidin-8-yl]-benzamide; |
| 453 | N-Cyclopropyl-4-{4-methyl-7-oxo-2-[4-(3,4,5-trimethoxy-benzoyl)-piperazin-1-yl]-7H-pyrido[2,3-d]pyrimidin-8-yl}-benzamide; |
| 454 | 4-[8-(4-Cyclopropylcarbamoyl-phenyl)-4-methyl-7-oxo-7,8-dihydro-pyrido[2,3-d]pyrimidin-2-yl]-piperazine-1-carboxylic acid cyclohexylamide |
| 455 | 4-[8-(4-Cyclopropylcarbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide |
| 456 | 4-{4-Methyl-7-oxo-2-[4-(3,4,5-trimethoxy-benzoyl)-piperazin-1-yl]-7H-pyrido[2,3-d]pyrimidin-8-yl}-N-(4-trifluoromethyl-benzyl)-benzamide; |
| 457 | 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid cyclohexylamide; |
| 458 | 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid (3-trifluoromethyl-phenyl)-amide; |
| 459 | 4-[(4-{4-Methyl-7-oxo-2-[4-(pyridine-3-carbonyl)-piperazin-1-yl]-7H-pyrido[2,3-d]pyrimidin-8-yl}-benzoylamino)-methyl]-benzoic acid methyl ester; |
| 460 | 4-[(4-{2-[4-(3,4-Difluoro-phenylcarbamoyl)-piperazin-1-yl]-4-methyl-7-oxo-7H-pyrido[2,3-d]pyrimidin-8-yl}-benzoylamino)-methyl]-benzoic acid methyl ester; |
| 461 | 4-[(4-{2-[4-(Furan-2-carbonyl)-piperazin-1-yl]-4-methyl-7-oxo-7H-pyrido[2,3-d]pyrimidin-8-yl}-benzoylamino)-methyl]-benzoic acid methyl ester; |
| 462 | 4-({4-[2-(4-Benzoyl-piperazin-1-yl)-4-methyl-7-oxo-7H-pyrido[2,3-d]pyrimidin-8-yl]-benzoylamino}-methyl)-benzoic acid methyl ester; |
| 463 | 4-({4-[4-Methyl-7-oxo-2-(4-phenylacetyl-piperazin-1-yl)-7H-pyrido[2,3-d]pyrimidin-8-yl]-benzoylamino}-methyl)-benzoic acid methyl ester; |
| 464 | 4-[(4-{4-Methyl-7-oxo-2-[4-(3,4,5-trimethoxy-benzoyl)-piperazin-1-yl]-7H-pyrido[2,3-d]pyrimidin-8-yl}-benzoylamino)-methyl]-benzoic acid methyl ester; |
| 465 | 4-({4-[2-(4-Cyclohexylcarbamoyl-piperazin-1-yl)-4-methyl-7-oxo-7H-pyrido[2,3-d]pyrimidin-8-yl]-benzoylamino}-methyl)-benzoic acid methyl ester; |
| 466 | 4-[(4-{4-Methyl-7-oxo-2-[4-(3-trifluoromethyl-phenylcarbamoyl)-piperazin-1-yl]-7H-pyrido[2,3-d]pyrimidin-8-yl}-benzoylamino)-methyl]-benzoic acid methyl ester; |
| 467 | N-(2,4-Difluoro-benzyl)-4-{4-methyl-7-oxo-2-[4-(pyridine-3-carbonyl)-piperazin-1-yl]-7H-pyrido[2,3-d]pyrimidin-8-yl}-benzamide; |
| 468 | 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide; |
| 469 | 4-[8-(4-Carbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide; |

TABLE 1-continued

| N° | Compound name |
|---|---|
| 470 | N-(2,4-Difluoro-benzyl)-4-{2-[4-(furan-2-carbonyl)-piperazin-1-yl]-4-methyl-7-oxo-7H-pyrido[2,3-d]pyrimidin-8-yl}-benzamide; |
| 471 | 4-[2-(4-Benzoyl-piperazin-1-yl)-4-methyl-7-oxo-7H-pyrido[2,3-d]pyrimidin-8-yl]-N-(2,4-difluoro-benzyl)-benzamide; |
| 472 | N-(2,4-Difluoro-benzyl)-4-[4-methyl-7-oxo-2-(4-phenylacetyl-piperazin-1-yl)-7H-pyrido[2,3-d]pyrimidin-8-yl]-benzamide; |
| 473 | 4-{4-Methyl-7-oxo-2-[4-(pyridine-3-carbonyl)-piperazin-1-yl]-7H-pyrido[2,3-d]pyrimidin-8-yl}-benzamide; |
| 474 | 4-[8-(4-Carbamoyl-phenyl)-4-methyl-7-oxo-7,8-dihydro-pyrido[2,3-d]pyrimidin-2-yl]-piperazine-1-carboxylic acid (3,4-difluoro-phenyl)-amide; |
| 475 | 4-[4-Methyl-7-oxo-2-(4-phenylacetyl-piperazin-1-yl)-7H-pyrido[2,3-d]pyrimidin-8-yl]-benzamide; |
| 476 | 4-[8-(4-Carbamoyl-phenyl)-4-methyl-7-oxo-7,8-dihydro-pyrido[2,3-d]pyrimidin-2-yl]-piperazine-1-carboxylic acid cyclohexylamide; |
| 477 | 4-[8-(4-Benzylcarbamoyl-phenyl)-4-methyl-7-oxo-7,8-dihydro-pyrido[2,3-d]pyrimidin-2-yl]-piperazine-1-carboxylic acid cyclohexylamide; |
| 478 | 4-{4-Methyl-7-oxo-2-[4-(pyridine-3-carbonyl)-piperazin-1-yl]-7H-pyrido[2,3-d]pyrimidin-8-yl}-N-(4-trifluoromethyl-benzyl)-benzamide; |
| 479 | 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid (3,4-difluoro-phenyl)-amide; |
| 480 | 4-{2-[4-(Furan-2-carbonyl)-piperazin-1-yl]-4-methyl-7-oxo-7H-pyrido[2,3-d]pyrimidin-8-yl}-N-(4-trifluoromethyl-benzyl)-benzamide; |
| 481 | 4-[2-(4-Benzoyl-piperazin-1-yl)-4-methyl-7-oxo-7H-pyrido[2,3-d]pyrimidin-8-yl]-N-(4-trifluoromethyl-benzyl)-benzamide; |
| 482 | 4-[4-Methyl-7-oxo-2-(4-phenylacetyl-piperazin-1-yl)-7H-pyrido[2,3-d]pyrimidin-8-yl]-N-(4-trifluoromethyl-benzyl)-benzamide; |
| 483 | 4-(4-methyl-2-(methylsulfanyl)-7-oxopyrido[2,3-d]pyrimidin-8(7H)-yl)benzoic acid |

It is another embodiment of the present invention to provide a method for inhibiting telomerase enzyme, which comprises contacting said enzyme with an effective amount of a compound having the above formula (I).

It is a further embodiment of the present invention to provide a method for treating a telomerase-modulated disease, which comprises administering to a mammal a therapeutically effective amount of a compound having the above formula (I).

It is a still further embodiment of the present invention to provide a method for treating a cancer disease related to a deranged cancer cell growth mediated by telomerase enzyme activity, which comprises administering to a mammal a therapeutically effective amount of a compound having the above formula (I).

It is still another embodiment of the present invention to provide a method for treating a cancer, which comprises administering to a mammal a therapeutic effective amount of a compound having the above formula (I).

According to still another aspect of the invention, a method is provided which involves the use of a compound having the above formula (I) in the preparation of a medicament. In particular embodiments, the medicament is for treating a proliferative disorder (e.g. a cancer). The present invention therefore also provides a compound having the above formula (I) for use in the preparation of a medicament having anticancer activity.

A still further embodiment of the present invention is to provide a pharmaceutical composition comprising a pharmaceutically acceptable carrier and/or diluent and, as an active principle, a compound of formula (I) as defined above.

A further embodiment of the present invention is to provide a method for the preparation of compounds of formula (I).

According to one embodiment of the invention a compound of formula (I) can be prepared by a process as reported in Scheme 1.

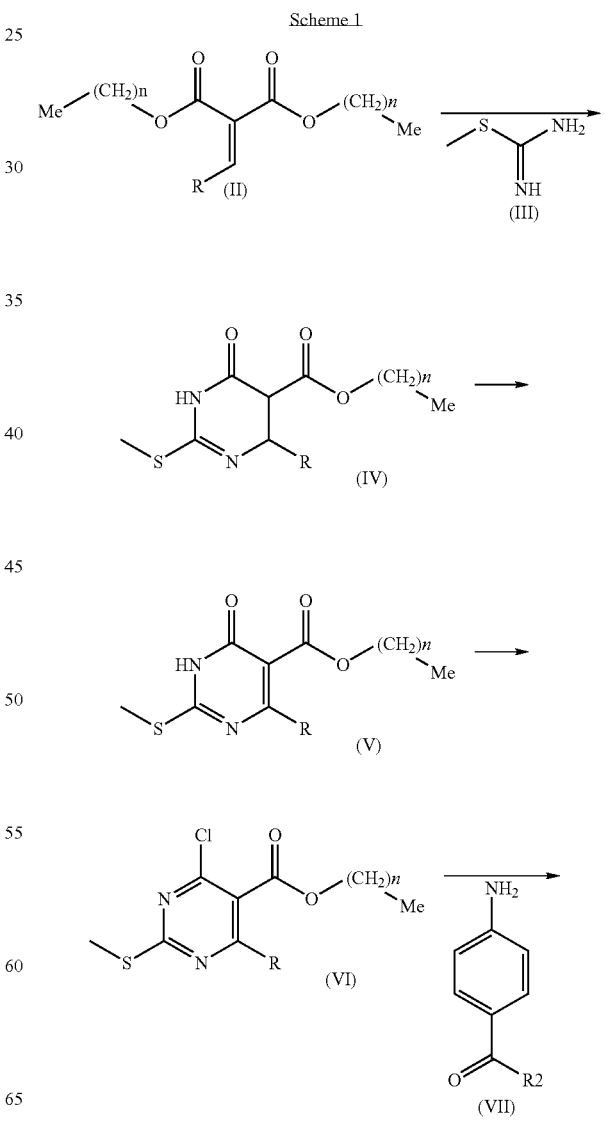

-continued

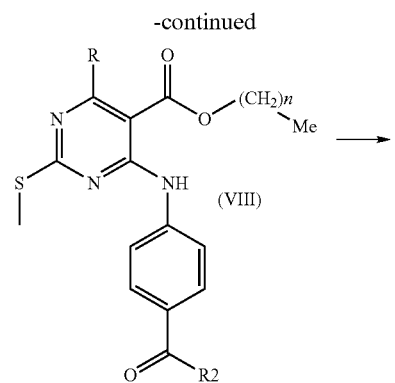

(VIII)

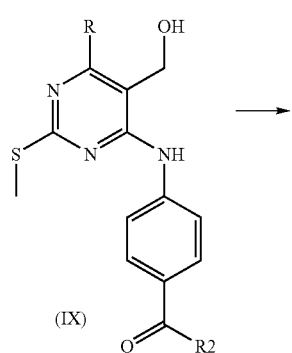

(IX)

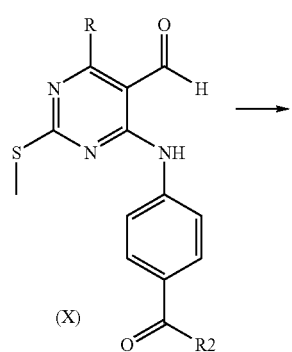

(X)

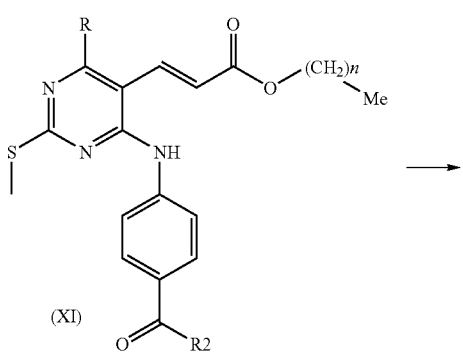

(XI)

-continued

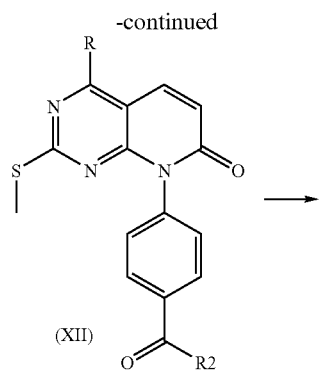

(XII)

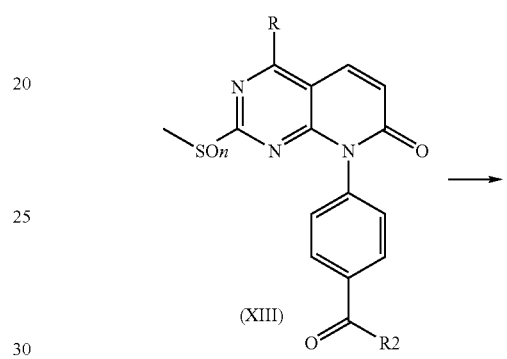

(XIII)

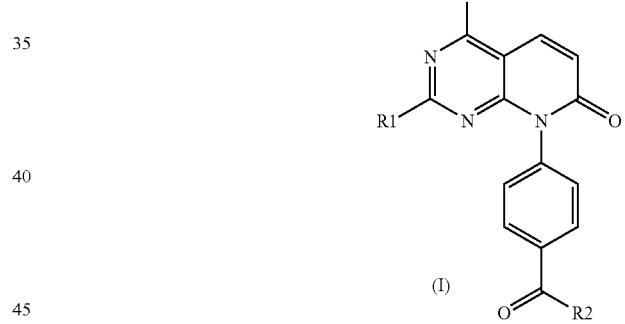

(I)

As described in scheme 1, the process for the typical preparation of compounds of formula (I) involves treatment of a dialkyl alkylidene malonate derivatives of formula (II), where R is as defined above and is, for example, methyl, with S-methyl isothiourea (III) to yield the novel compounds of formula (IV). (CH2)n-Me represents an alkyl group where n=0 to 6, for example, methyl or ethyl. Such condensation can be run at temperatures ranging from r.t. to reflux conditions in an organic solvent such as methanol, ethanol, isopropanol, n-buthanol, t-buthanol, and the like, and in the presence of a base such as triethylamine, N,N-diisopropylethylamine, pyridine and the like, for 30' to 24 h.

Compounds of formula (II) are commercially available (such as for example diethyl ethylidene malonate where R=methyl) or can be easily prepared from dialkyl malonate (IIa) and an appropriate aldehyde (IIb) as reported in scheme 2:

Scheme 2

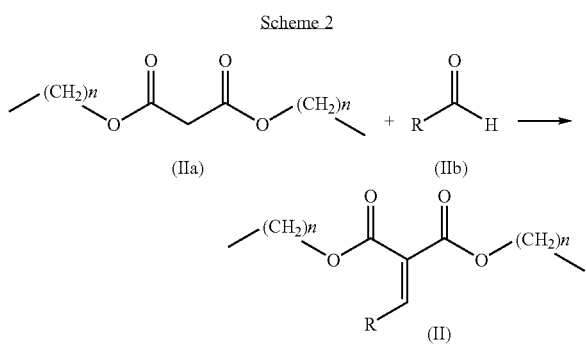

Tetrahydropyrimidine derivatives (IV) can be transformed into novel compounds of formula (V) under a variety of different reaction conditions. One procedure provides the use of N-bromosuccinimide in the presence of a radical initiator, such as benzoyl peroxide, and of an inorganic base, such as anhydrous potassium carbonate, in a suitable organic solvent, like dioxane, dimethoxyethane, diglyme, and the like, at temperatures ranging from r.t. to 150° C. for 1 to 12 h (see for example *J. Org. Chem.* 1993, 58, 4490).

Treatment of compound (V) with halogenating agents such as $POCl_3$, $SOCl_2$, $PCl_5$ and the like, at temperatures ranging from r.t. to reflux conditions for 1 to 12 h, furnishes novel compounds of formula (VI).

Compounds of formula (VI) are then treated with anilino derivatives of formula (VII), where R2 is as defined above, to afford novel compounds of formula (VIII). In this reaction reactants VII are those where R2 is an alkoxy or aryloxy group, for example, a tert-buthoxy group. The reaction is typically run in the presence of a base, such as N,N-diisopropylethylamine, triethyl amine, pyridine, 2,6-dimethylaminopyridine and the like, and in a suitable organic solvent, such as dimethoxyethane, diglyme, dioxane, N,N-dimethylformamide and the like at temperatures from r.t. to reflux for 1 to 96 h.

Derivatives of formula (VIII) are converted into novel compounds of formula (IX) by the use of a reducing agent such as $NaBH_4$ at 0° to 100° C. in an appropriate organic solvent such as methanol, ethanol, and the like, for 1 to 24 h. Other reducing agents can be used to reduce the ester group, such as Lithium Aluminum hydride, diisobutylaluminum hydride, and the like, as reported in the literature [see for example J. March "Advanced Organic Chemistry"—Wiley-Interscience Publ.], but they can not be compatible with other functional groups in the molecule (for example when R2 is an alkoxy group). In cases where R2 is for example tert-butoxy, very clean chemoselectivity is observed by using $NaBH_4$ when the other ester group to be reduced is methyl or ethyl.

Alcohol (IX) can be transformed into the novel aldehyde of formula (X) by the use of an oxidizing agent that can convert an alcohol into an aldehyde, such as PCC, $MnO_2$, or by Swern reaction conditions and the like, and many other methods known in the art [see for example J. March "Advanced Organic Chemistry"—Wiley-Interscience Publ.]. One of the reagents is $MnO_2$ that can be used in a suitable organic solvent, such as methylene chloride, chloroform, and the like, for 1 to 48 h at 0° to 50° C.

Aldehyde of formula (X) is then reacted with a stabilized phosphorane, such as (carbethoxymethylene)triphenyl phosphorane, or any other Wittig or Horner-Emmons reagent, to provide the novel compound of formula (XI), where (CH2)n-Me represents an alkyl group (where n=0 to 6), such as methyl or ethyl. The new double bond formed can have stereochemistry E or Z or a mixture of the two, mainly E when the reagent used is (carbethoxymethylene)triphenyl phosphorane. The reaction is run in a suitable organic solvent like THF, diethyl ether, dioxane, and the like, at r.t. to reflux temperatures for 1 to 48 h.

Compound (XI) is then cyclized to compound of formula (XII) (that represents a compound of formula (I) where R1=MeS—) by refluxing in the presence of DBU (1,8-diazabicyclo[5.4.0]undec-7-ene) (1 to 5 equivalents) and by using a tertiary base such as triethylamine or N,N-diisopropylethylamine as the solvents at reflux temperatures for 1 to 48 h.

Oxidation of compound (XII) by the use of several oxidizing agents, such as m-chloroperbenzoic acid, an oxaziridine, or dimethyldioxirane, and the like, in a suitable organic solvent such as chloroform, methylene chloride, acetone and the like, at 0° to r.t. for 1 to 12 h, affords compounds of formula (XIII) (that represents a compound of formula I where R1=$MeSO_n$—), where n=1 or 2, for example, 2.

Compound (XIII) can then be converted into different compounds of formula I where R1 is as defined above, by displacing the methylsulphonyl group with various nucleophiles, such as ammonia, primary or secondary amines, alcohols, thiols and the like. For example when R1 is NR3R4, i.e. when the displacement is made with an amine, the reaction can be carried out with the necessary amine in an appropriate solvent such as DMF, dioxane, dimethylethyl ether, and the like, under heating conditions such as under reflux, for 1 to 48 h.

A particular case of compounds of formula I is when R2 is OR' (where R' is as defined above), i.e. compounds of formula (Ib) (scheme 3). Compounds (Ib) can be obtained for example from another ester derivative of formula (I), such as compound (Ia), by transesterification in R'OH as the solvent, like methanol or ethanol, and in the presence of an acidic catalyst such as concentrated sulphuric acid, according to the methods of the literature [see for example J. March "Advanced Organic Chemistry"—Wiley-Interscience Publ.] and as reported in scheme below.

Scheme 3

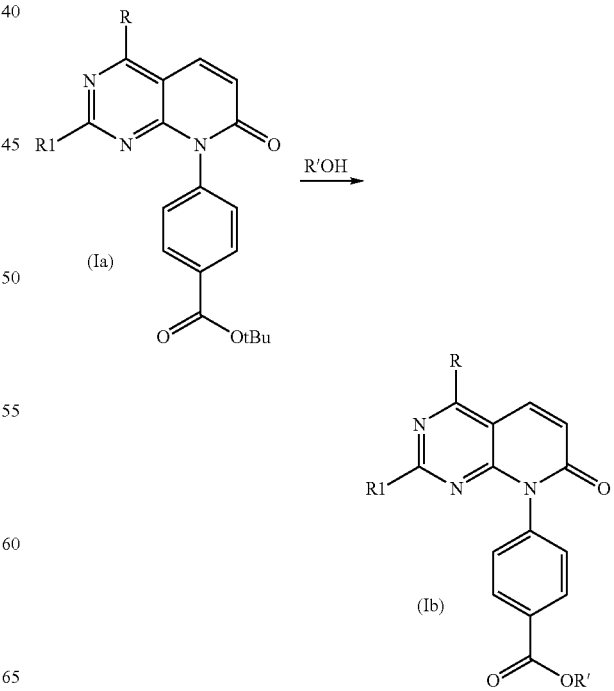

In cases where other ester groups are present in structure (Ia), the transesterification reaction might affect them as well.

Compounds of formula (I) where R2 is OH, i.e. compounds (Ic) in scheme below, can be obtained from compounds of formula (Ia) by treatment with an acid, such as trifluoroacetic acid in a suitable organic solvent such as methylene chloride, THF, diethyl ether, and the like at 0° to r.t. for 1 to 12 h.

Scheme 4

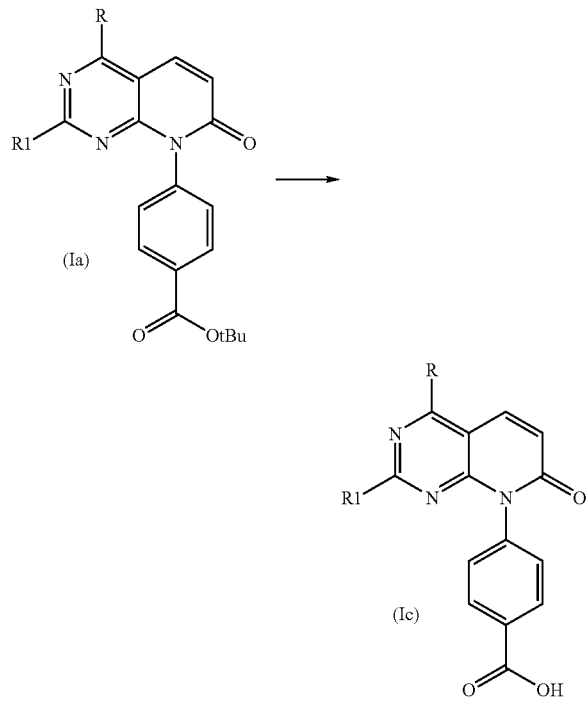

Compounds of formula (I) can be also obtained from compounds of formula (Ic), either directly or through the acyl chlorides (Id), as reported in scheme below.

Scheme 5

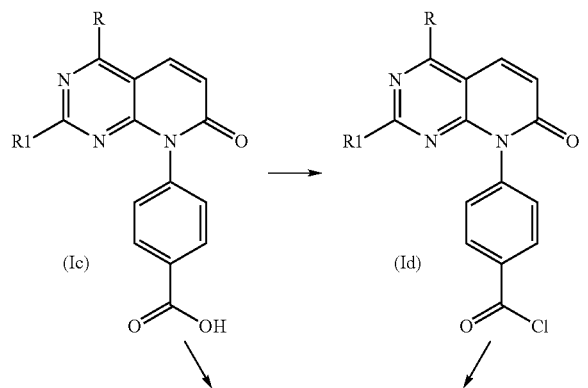

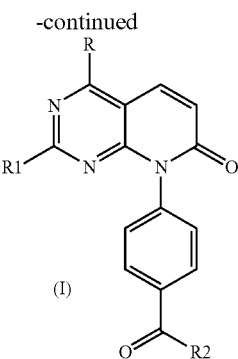

In fact compounds (I) where R2 is as defined above, can be obtained by treatment of the corresponding acyl chlorides Id with the appropriate nucleophile, such as an alcohol or a primary or secondary amine (R'OH, or R"R'" NH) in a suitable organic solvent such as methylene chloride, chloroform, THF, diethyl ether, DMF, dioxane, acetonitrile, ethyl acetate, and the like, and in the presence of an organic base such as triethylamine, 2,6-dimethylaminopyridine, N,N-diisopropylethylamine, and the like at 0° to reflux temperatures for 1 to 12 h. Compounds (Id) in turn can be obtained by treatment of compounds Ic with oxalyl chloride in the presence of anhydrous N,N-dimethylformamide, or with $SOCl_2$ in a suitable organic solvent such as THF, toluene, and the like at r.t. to reflux temperature for 1 to 12 h.

Compounds (I) where R2 is as defined above, can be also obtained by treatment of compounds (Ic) with a nucleophile such as an alcohol or a primary or secondary amine (R'OH, or R"R'"NH), in the presence of a condensing agent such as DCC (dicyclohexylcarbodiimmide), EDC (1-ethyl-3-3'-dimethylaminopropyl)carbodiimide), DCC in the presence of HOBt (1-hydroxybenzotriazole), or N,N'-carbonyldiimidazole and the like.

According to another embodiment of the invention compounds of formula (I) and in particular a library of compounds of formula (I) can be prepared by using a combinatorial solid phase method. In particular starting material for such a method can be a compound of formula (XIIa), i.e. a compound of formula (I) where R is as defined above, R1=MeS— and R2=OH, as depicted in scheme 6. The solid phase method reported in scheme 6 is particularly suited, but it is not limited to the obtainement of compounds of formula (I) where R2=—NR"R'", and more in particular where R"=H, i.e. compounds of formula (If).

Scheme 6

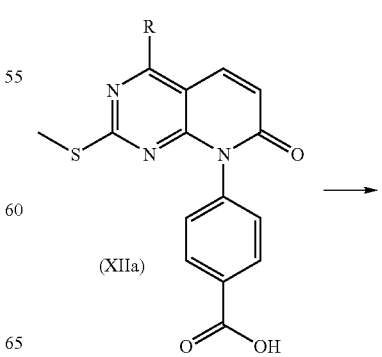

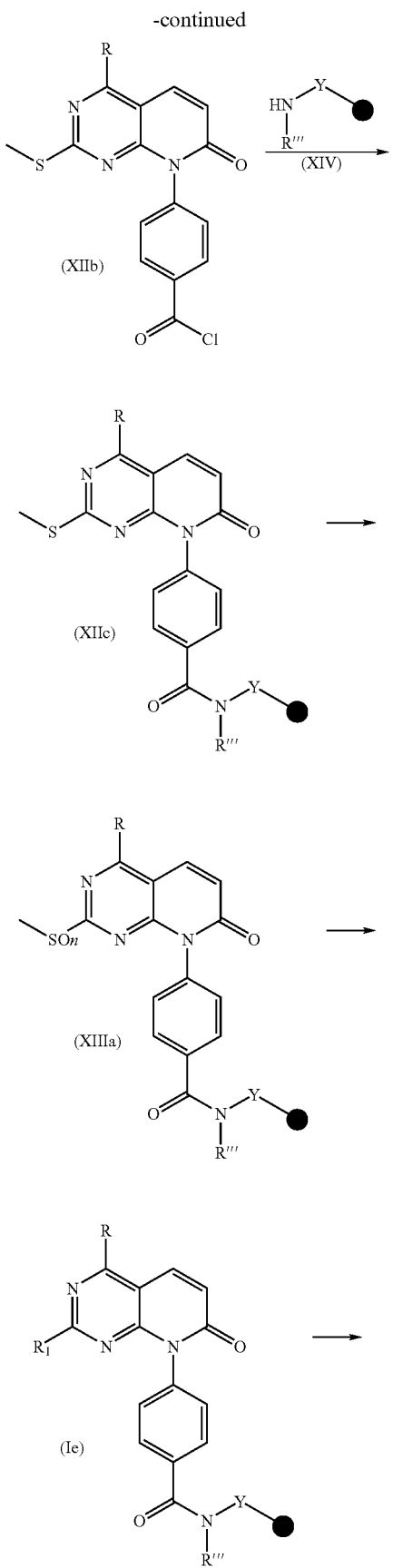

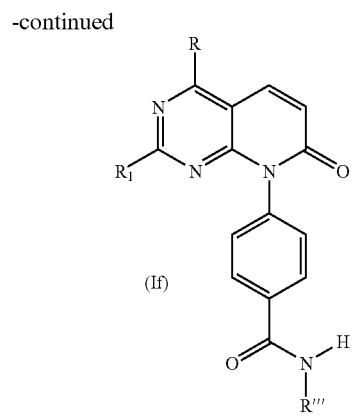

The symbol ● represents the solid support.

The compounds of formula (If), and the salts thereof, can be obtained, for example, by a process comprising:

(a) synthesizing the solid supported amino residue —NHR''', where R''' is as defined above; in particular synthesizing the resin of formula XIV containing the amino residue —NHR''' attached to the Merrifield resin through Y, where Y can be an alkylic chain or an aromatic residue. Such solid supported amino residues can be introduced, for example, by treatment of resins containing aldehydic linkers (e.g. FMPB resin, Novabiochem) with primary amines under reductive amination conditions (such as using NaHB(OAc)$_3$);

(b) reacting a compound represented by formula (XIIa), where R is as defined above, with an halogenating agent, to obtain a compound represented by formula (XIIb), where R is as defined above; such a reaction can be carried out under neat conditions, methylene chloride or $CCl_4$ with $SOCl_2$, $(COCl)_2$, $PCl_3$ as halogenating agent at a temperature ranging from 0° C. to room temperature;

(c) reacting a compound represented by formula (XIIb) with polymer supported sec. amines (XIV) to obtain an immobilized compound represented by formula (XIIc), where R and R''' are defined above and Y represents a linker; such a reaction can be carried out with the acylchloride in presence of $NEt_3$, $EtNiPr_2$ in a solvent like DMF, THF or methylene chloride at room temperature. Another possibility is the activation of acid (XIIa) with DCC (dicyclohexylcarbodiimmide), EDC (1-ethyl-3-(3'-dimethylaminopropyl)carbodiimide), or DCC in the presence of HOBt (1-hydroxybenzotriazole) and the like, in solvents like DMF or methylene chloride at a temperature ranging from 0° C. to room temperature followed by coupling of the activated acid to the immobilized amine. This amine is part of a linker which is defined above;

(d) reacting a compound represented by formula (XIIc) with an oxidizing agent to obtain a compound represented by formula (XIIIa), where R, R''' and Y are as defined above; this reaction can be carried out by oxidation with oxone® or another oxidizing agent like hydrogen peroxide or m-chlorperbenzoic acid in a suitable solvent such as a mixture of water-acetone or methylene chloride;

(e) reacting a compound represented by formula (XIIIa), where R and R''' are as defined above and Y represents a linker, with nucleophiles (R1) in organic solvents in presence of a basic agent, to obtain a compound represented by formula (Ie); such reactions can be carried out with amines, alcohols or thiols in presence of bases like $NEt_3$, $EtNiPr_2$ or NaH in suitable solvents like DMF, THF or methylene chloride at room temperature;

(f) reacting a compound represented by formula (Ie) with a diluted acid, to obtain the final compound represented by formula (If), where R, R1 and R''' are as defined above; this reaction can be carried out in a suitable solvents like methylene chloride or dioxane in presence of TFA or HCl.

The compounds of formula (I) are herein defined as the "compounds of the present invention", the "compounds of the invention" and/or the "active principles of the pharmaceutical compositions of the invention".

The compounds of the invention can be administered in a variety of dosage forms, e.g. orally, in the form of tablets, capsules, lozenges, liquid solutions or suspensions; rectally, in the form of suppositories; parenterally, e.g. intramuscularly, intravenously, intradermally or subcuteneously; or topically.

The dosage depends upon, for example, the compound of the invention employed, the age, weight, condition of the patient and administration route; specific dosage regimens can be fit to any particular subject on the basis of the individual need and the professional judgement of the person administering or supervising the administration of the aforesaid compounds.

For humans, therapy with the disclosed compounds includes doses of a pharmaceutical formulation comprising one or more of the compounds of the invention that are from about 0.001 to about 100 mg/kg. For example, the dosage is about 0.1 to 10 mg/kg. The dosages will vary in accordance with, for example, the condition of the patient and the type of disease being treated. A dosage can be administered once or can be divided into a number of smaller doses to be administered at varying intervals of time. This therapy is effective in the treatment of telomerase-modulated diseases, including, for example, cancer related to abnormal cancer cell growth mediated by telomerase enzyme activity. For example, the dosage adopted for the administration to adult humans can range from 0.001 to 100 mg of compound of the invention per kg of body weight; a particularly preferred range can be from 0.1 to 10 mg of compound of the invention per kg of body weight. The dosages can be administered at once or can be divided into a number of smaller doses to be administered at varying intervals of time.

Pharmaceutical compositions containing, as an active ingredient, a compound of formula (I) or a pharmaceutically acceptable salt thereof in association with a pharmaceutically acceptable carrier and/or diluent, are also within the scope of the present invention.

These pharmaceutical compositions contain an amount of active ingredient, which is therapeutically effective to display antileukemic and/or antitumor activity. There can also be included as a part of the pharmaceutical compositions according to the invention, pharmaceutically acceptable binding agents and/or adjuvant materials. The active ingredients can also be mixed with other active principles, which do not impair the desired action and/or supplement the desired action.

The pharmaceutical compositions containing the compounds of the invention are usually prepared following conventional methods and can be administered in a pharmaceutically suitable form.

For example, the solid oral forms can contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, microcrystalline cellulose, carboxymethylcellulose or polyvinyl pyrrolidone; diaggregating agents, e.g. a starch, alginic acid, alginates or sodium starch glycolate; effervescing mixtures; dyestuffs; sweetening agents, e.g. sucrose or saccharin; flavouring agents, e.g. peppermint, methylsalicylate or orange flavouring; wetting agents, such as lecithin, polysorbates, laurylsulphates; and, in general, non-toxic and pharmacologically inactive substances used in pharmaceutical formulations.

When the dosage unit form is a capsule, it can contain, in addition to material of the above type, a liquid carrier such as, e.g., a fatty oil.

Said pharmaceutical preparations can be manufactured in known manners, for example, by means of mixing, granulating, tabletting, sugar-coating or film-coating processes. The liquid dispersions for oral administration can be, e.g. syrups, emulsions and suspensions.

The syrups can contain as carrier, for example, saccharose or saccharose with glycerine and/or mannitol and/or sorbitol; in particular, a syrup to be administered to diabetic patients can contain as carriers only products not metabolizable to glucose, or metabolizable in very small amount to glucose, for example sorbitol.

The suspensions and the emulsions can contain as carrier, for example, a natural gum, agar, sodium alginate, pectin, methylcellulose, carboxymethylcellulose, or polyvinyl alcohol. The suspensions or solutions for intramuscular injections can contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions can contain as a carrier, for example, sterile water, or they can be in the form of sterile, aqueous, isotonic saline solution. The solutions or suspensions for parenteral therapeutic administration can also contain antibacterial agents, such as benzyl alcohol or methyl parabens; antioxidants, such as ascorbic acid or sodium bisulphite; chelating agents, such as ethylenediaminetetraacetic acid; buffers, such as acetates, citrates or phosphates and agents for the adjustment of tonicity, such as sodium chloride or dextrose. The parenteral preparation can be enclosed in ampoules, disposable syringes or multiple dose vials made of glass or plastic.

The suppositories can contain together with the active compound a pharmaceutically acceptable carrier, e.g., cocabutter, polyethylene glycol, a polyoxyethylene sorbitan fatty acid ester surfactant or lecithin.

Compositions for topical application, such as, e.g., creams, lotions or pastes, can be, e.g., prepared by admixing the active ingredient with a conventional oleaginous or emulsifying excipient.

Biological Activity

The telomerase activity of compounds of the invention have been evaluated using a Flash Plate-based assay. The method proved to be sensitive, accurate and able to reproducibly identify compounds that inhibit telomerase activity in a dose-dependent manner.

Briefly the assay mixture is constituted of:
telomerase enzyme diluted in a buffer, the composition of which has been selected to maintain the enzyme activity stable along the duration of the assay.
dNTPs, deoxynucleotides 5'-triphosphate.
biotinylated oligo as primer.
increasing concentrations of test compounds/positive control.

After two hours of incubation at 37° degrees the telomeric repeats added are evaluated by hybridization in solution with a 3'-labeled short oligonucleotide probe.

The extent of hybridization is then quantitated by transferring the reaction mixture in a streptavidin-coated flash plate, where the binding between biotin and streptavidin occurs.

The telomerase activity is proportional to the radioactivity measured and the inhibitory activity of the compounds is evaluated as $IC_{50}$ using the Sigma Plot fit program.

With the above-described method $IC_{50}$ values of the compounds of the present invention were determined.

The results relative to a representative selection of compounds of the invention are shown in Table 2.

TABLE 2

| Compound | $IC_{50}$ (µM) |
|---|---|
| 20 | 6.1 |
| 21 | 21.8 |
| 24 | 3.8 |
| 25 | 1.7 |
| 27 | 3.9 |
| 28 | 16.6 |
| 30 | 9.4 |
| 31 | 9.4 |
| 32 | 1.25 |
| 33 | 1.1 |
| 34 | 8.2 |
| 35 | 1.9 |
| 36 | 2 |
| 37 | 2.9 |
| 38 | 1.6 |
| 39 | 1.4 |
| 41 | 3.1 |
| 42 | 4.6 |
| 43 | 6.1 |
| 44 | 19.1 |
| 45 | 7.3 |
| 46 | 2.6 |

The data reported in Table 2 clearly show the activity of the compounds according to the invention as telomerase inhibitors.

A human or animal body can thus be treated by a method, which comprises the administration thereto of a pharmaceutically effective amount of a compound of formula (I) or a salt thereof. The condition of the human or animal can thereby be improved.

The compounds of the invention can be administered either as single agents or, alternatively, in combination with one or more anti-cancer agent including, for example, topoisomerase inhibitors, antimetabolites, alkylating agents, antibiotics, antimicrotubule agents, hormonal agents, immunological agents, interferon-type agents, cyclooxygenase inhibitors (e.g. COX-2 inhibitors), metallomatrixprotease inhibitors, kinase inhibitors, tyrosine kinase inhibitors, antigrowth factor receptor agents, anti-HER agents, anti-EGFR agents, farnesyl transferase inhibitors, ras-raf signal transduction pathway inhibitors, cell cycle inhibitors, tubulin binding agents and anti-angiogenesis agents.

Combinations of drugs are administered in an attempt to obtain a synergistic effect on most cancers, e.g., carcinomas, melanomas, sarcomas, lymphomas and leukemias and/or to reduce or eliminate emergence of drug-resistant cells and/or to reduce side effects to each drug.

It is therefore a still further aspect of the present invention to provide a combined anti-cancer therapy which comprises administering a compound according to the invention with at least one other anti-cancer agent. The combined use of active substances provides an improved therapeutic effect than employing the single agents alone.

Compounds of formula (I) can be combined with at least one other anti-cancer agent in a fixed pharmaceutical formulation or can be administered with at least one other anti-cancer agent in any desired order.

It is therefore a further embodiment of the invention to provide a product or kit comprising a compound of formula (I) of the invention and one or more anti-cancer agents for simultaneous, separate or sequential use in anticancer therapy.

Anti-cancer agents suitable for combination with the compounds of the present invention include, but are not limited to:
topoisomerase I inhibitors comprising, for example, epipodophyllotoxins such as, e.g. etoposide and teniposide; camptothecin and camptothecin derivatives including, e.g., irinotecan, SN-38, topotecan, 9-aminocamptothecin, 10,11-Methylenedioxy camptothecin and 9-nitro-camptothecin (rubitecan);
alkylating agents including nitrogen mustards such as, e.g., mechlorethamine, chlorambucil, melphalan, uracil mustard and estramustine; alkylsulfonates such as, e.g., busulfan improsulfan and piposulfan; oxazaphosphorines such as e.g., ifosfamide, cyclophosphamide, perfosfamide, and trophosphamide; platinum derivatives such as, e.g., oxaliplatin, carboplatin and cisplatin; nitrosoureas such as, e.g., carmustine, lomustine and streptozocin;
antimitotic agents including taxanes such as, e.g., paclitaxel and docetaxel; vinca alkaloids such as, e.g., vincristine, vinblastine, vinorelbine and vindesine; and novel microtubule agents such as, e.g., epothilone analogs, discodermolide analogs and eleutherobin analogs;
antimetabolites including purines such as, e.g., 6-mercaptopurine, thioguanine, azathioprine, allopurinol, cladribine, fludarabine, pentostatin, and 2-chloro adenosine; fluoropyrimidines such as, e.g., 5-FU, fluorodeoxyuridine, ftorafur, 5'-deoxyfluorouridine, UFT, S-1 and capecitabine; and pyrimidine nucleosides such as, e.g., deoxycytidine, cytosine arabinoside, 5-azacytosine, gemcitabine, and 5-azacytosine-arabinoside; antimetabolites (for example antifolates like methotrexate, fluoropyrimidines like 5-fluorouracil, purine and adenosine analogues, cytosine arabinoside;
hormones, hormonal analogues and hormonal antagonists including antiestrogens (for example tamoxifen, toremifen, raloxifene, droloxifene and iodoxyfene), progestogens (for example megestrol and acetate), aromatase inhibitors (for example anastrozole, letrazole, borazole and exemestane), antiprogestogens, antiandrogens (for example flutamide, nilutamide, bicalutamide and cyproterone acetate), LHRH agonists and antagonists (for example gosereline acetate and luprolide) and inhibitors of testosterone 5a-dihydroreductase (for example finasteride);
antitumor antibiotics including anthracyclines and anthracenediones such as, e.g., doxorubicin, daunorubicin, epirubicin, idarubicin and mitoxantrone;
farnesyltransferase inhibitors including, for example, SCH 44342, RPR 113228, BZA 5B and PD 161956;

anti-invasion agents (for example metalloproteinase inhibitors such as, e.g., marimastat and inhibitors of urokinase plasminogen activator receptor functions);

inhibitors of growth factor (for example, EGF, FGF, platelet derived growth factor and hepatocyte growth factor) functions including growth factor antibodies, growth factor receptor antibodies, tyrosine kinase inhibitors and serine/threonine kinase inhibitors;

antiangiogenic agents such as, for example, linomide, inhibitors of integrin avβ3 function, angiostatin, razoxin, SU 5416, SU 6668, AGM 1470 (TNP-470), a synthetic analogue of fumagillin a naturally secreted product of the fungus *Aspergillus fumigates fresenius*, platelet factor 4 (endostatin), thalidomide, marimastat (BB-2516) and batimastat (BB-94);

cyclooxygenase (COX) inhibitors, for example, COX-2 inhibitors such as, for example, celecoxib, parecoxib, rofecoxib, valecoxib and JTE 5222; and cell cycle inhibitors such as, e.g., flavopyridols.

In a further aspect of this invention, a method is provided for treating a cancer comprising administering to a patient in need of such treatment a therapeutically effective amount of a compound of formula (I) as defined above and a therapeutically effective amount of at least another anti-cancer agent. In one aspect of the present invention, the combination of a compound of formula (I) as defined above with at least one antiangiogenesis agent is contemplated.

The following examples illustrate but do not limit the invention. All references cited herein are incorporated by reference in their entirety.

EXAMPLES

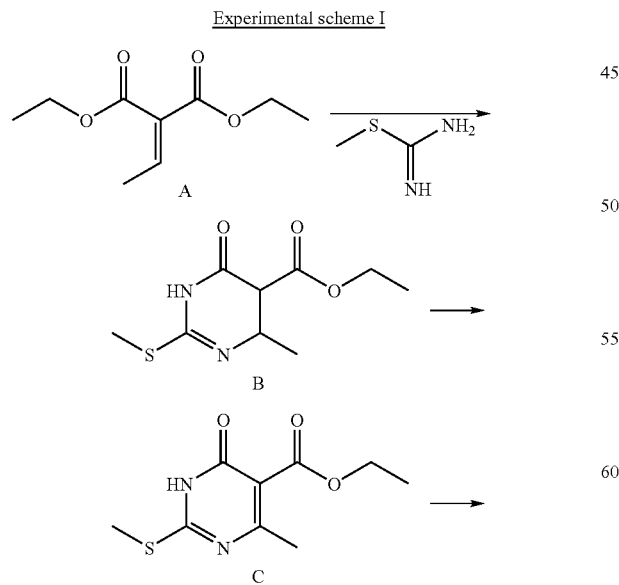

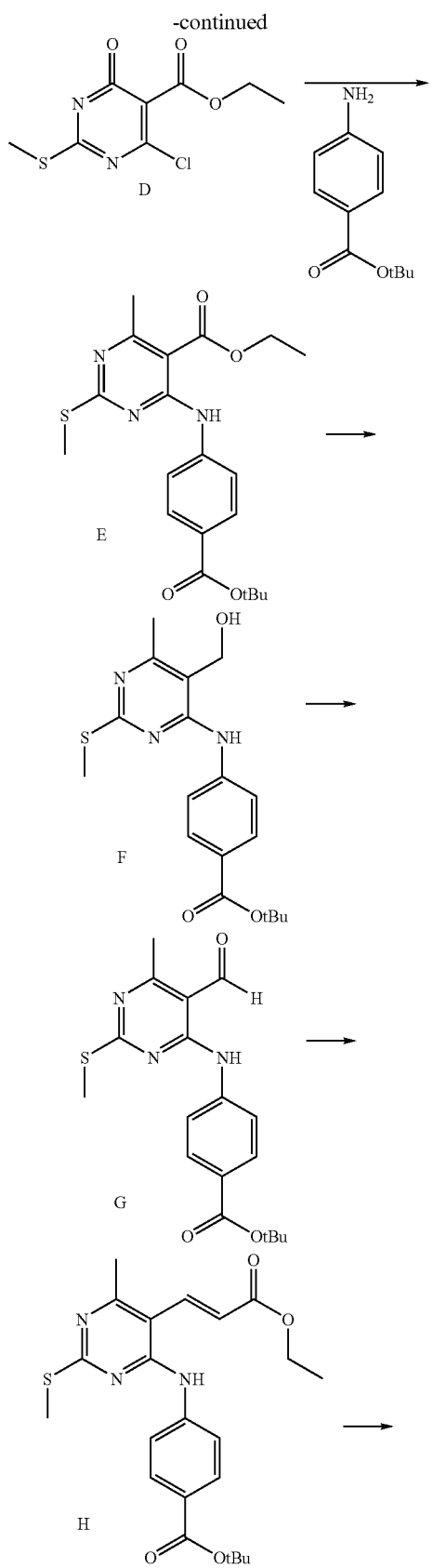

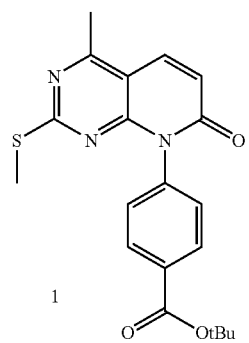

1

Example 1 ethyl 4-methyl-2-(methylsulfanyl)-6-oxo-1,4,5,6-tetrahydro-5-pyrimidinecarboxylate (B)

A solution of diethyl ethylidene malonate A (96 g; 0.51 mol), S-methyl isothiourea (71.1 g; 0.79 mol) and triethylamine (80 mL) in 530 mL of abs. ethanol, was refluxed for 3 h under magnetic stirring. The reaction mixture was filtered, and the ethanol concentrated under vacuum, water was added (400 mL) and extracted with ethyl acetate. The organic phase was dried over anhydrous sodium sulphate and concentrated. The crude reaction mixture was purified by silica gel column chromatography (eluant: n-hexane/ethyl acetate=7/3) to yield compound B (63.7 g; 55%) as a pure solid.

$^1$H-NMR (400 Mhz, DMSO-$d_6$), ppm: 1.16 (d, j=6.6 Hz, 3H); 1.17 (t, j=7.2 Hz, 3H); 3.29 (d, j=10.5 Hz, 1H); 3.84 (dq, j=6.6, 10.5 Hz, 1H); 4.21 (m, 2H);

Example 2 ethyl 4-methyl-2-(methylsulfanyl)-6-oxo-1,6-dihydro-5-pyrimidinecarboxylate (C)

To a solution of compound B (65.5; 0.285 mol) in 2000 mL of anhydrous dioxane, finely powdered anhydrous potassium carbonate (314; 2.27 mol) was added under vigorous mechanic stirring. Then benzoyl peroxide (3.79 g; 0.016 mol) was added followed by N-bromosuccinimide (50.78 g; 0.285 mol). The reaction mixture was stirred at 90° C. for 3 h., and after cooling to room temperature, the solution was filtered and the precipitate was washed with ethyl acetate. The collected organic phases were concentrated, treated with water and neutralized to pH 7 with acetic acid. The aqueous solution was extracted with ethyl acetate (6×500 mL), the organic phase washed with brine, dried over anhydrous sodium sulphate and concentrated to yield compound C (60 g; 91.6%) as a white solid sufficiently pure for the next step. A sample was purified for analysis.

$^1$H-NMR (400 Mhz, DMSO-$d_6$), ppm: 1.24 (t, j=7.1 Hz, 3H); 2.21 (s, 3H); 2.48 (s, 3H); 4.21 (q, j=7.1 Hz, 2H); 13.0 (bs, 1H);

Example 3 ethyl 4-chloro-6-methyl-2-(methylsulfanyl)-5-pyrimidinecarboxylate (D)

A mixture of compound C (60 g; 0.263 mol) and POCl$_3$ (300 mL) was vigorously stirred under reflux temperature for 2 h. Then POCl$_3$ was distilled off under vacuum, the crude solid triturated with water and ethyl acetate and filtered on a Celite pad. The filtrate was neutralized with sodium bicarbonate and extracted with ethyl acetate. The organic phase was washed with a saturated aqueous solution of sodium bicarbonate, washed with brine and dried over anhydrous sodium sulphate. After concentration the crude reaction mixture was purified by silica gel column chromatography (eluant: n-hexane/ethyl acetate=9/1) to yield compound D (31.8 g; 49%) as an orange oil.

$^1$H-NMR (400 Mhz, DMSO-$d_6$), ppm: 1.22 (t, j=7.1 Hz, 3H); 2.50 (s, 3H); 2.57 (s, 3H); 4.41 (q, j=7.1 Hz, 2H);

Example 4 ethyl 4-[4-(tert-butoxycarbonyl)anilino]-6-methyl-2-(methylsulfanyl)-5-pyrimidinecarboxylate (E)

A solution of compound D (31.5 g; 0.1278 mol), tert-butyl 4-aminobenzoate (48 g; 0.248 mol), N,N-diisopropylethylamine (50.3 g; 0.39 mol) in 400 mL of dioxane was refluxed for 72 h under magnetic stirring. The reaction mixture was filtered, concentrated and taken up with ethyl acetate. The organic phase was washed with water and brine, dried over anhydrous sodium sulphate and concentrated. The crude mixture was purified by silica gel column chromatography (eluant: n-hexane/ethyl acetate=9/1) to yield compound E (41.8 g; 81%).

$^1$H-NMR (400 Mhz, DMSO-$d_6$), ppm: 1.60 (s, 9H); 1.43 (t, j=7.1 Hz, 3H); 2.56 (s, 3H); 2.66 (s, 3H); 7.70 (m, 2H); 7.96 (m, 2H); 10.8 (s, 1H);

Example 5 tert-butyl 4-{[5-(hydroxymethyl)-6-methyl-2-(methylsulfanyl)-4-pyrimidinyl]amino}benzoate (F)

To a suspension of compound E (30 g; 0.0743 mol) in 500 mL of anhydrous ethanol at 45° C. NaBH$_4$ (15 g; 0.397 mol) was added portion-wise under vigorous stirring. After 4 h the reaction mixture was brought to room temperature and was poured into 2 L of iced water, vigorously stirred for 10' and extracted with ethyl acetate (2×600 mL). The organic phase was washed with water until neutral pH, with brine and dried over anhydrous sodium sulphate. After evaporation the crude compound F (22 g; 82%) was used without further purification in the next step.

$^1$H-NMR (400 Mhz, DMSO-$d_6$), ppm: 1.53 (s, 9H); 2.44 (s, 3H); 2.35 (s, 3H); 4.60 (d, j=5.4 Hz, 2H); 7.75 (m, 2H); 7.84 (m, 2H); 8.98 (s, 1H);

Example 6 tert-butyl 4-{[5-formyl-6-methyl-2-(methylsulfanyl)-4-pyrimidinyl]amino}benzoate (G)

A mixture of compound F (22 g; 0.0545 mol) and MnO$_2$ (69 g; 0.7936 mol) in 600 mL of methylene chloride was stirred at room temperature overnight. Further MnO$_2$ (30 g; 0.03451 mol) was added and the reaction mixture was stirred for additional 5 h. The reaction mixture was diluted with methylene chloride (1 L), filtered and the solid washed carefully with solvent. The filtrate was concentrated to a small volume and the precipitated orange/yellow solid collected and washed carefully with n-hexane to yield pure aldehyde G (15.4 g; 70%).

$^1$H-NMR (400 Mhz, DMSO-d$_6$), ppm: 1.61 (s, 9H); 2.59 (s, 3H); 2.70 (s, 3H); 7.78 (m, 2H); 7.98 (m, 2H); 10.30 (s, 1H); 11.4 (s, 1H);

Example 7 tert-butyl 4-{[5-[(1E)-3-ethoxy-3-oxo-1-propenyl]-6-methyl-2-(methylsulfanyl)-4-pyrimidinyl]amino}benzoate (H)

A solution of compound G (28.8 g; 0.0801 mol) and Ph$_3$PCHCOOEt (34 g; 0.0976 mol) in 400 mL of anhydrous THF was stirred under reflux for 2 h 30'. The reaction mixture was cooled to room temperature, filtered and concentrated. The crude mixture was purified by silica gel column chromatography (eluant: n-hexane/ethyl acetate=3/1 to 1/1) to yield compound H (32.5 g; 94.4%) as a yellow solid.

Example 8 tert-butyl 4-(4-methyl-2-(methylsulfanyl)-7-oxopyrido[2,3-d]pyrimidin-8(7H)-yl)benzoate (1)

A mixture of compound H (19 g; 0.04423 mol) and DBU (14 mL; 0.0936) in 110 mL of N,N-diisopropylethylamine and 30 mL of THF was refluxed for 30 h. The reaction mixture was poured into 600 mL of iced water and extracted with ethyl acetate (3×500 mL). The organic phase was washed with water and brine, dried over anhydrous sodium sulphate and concentrated. The crude was purified by silica gel column chromatography (eluant: n-hexane/ethyl acetate=2/1 to 1/2) to yield compound 1 (12 g; 71%) as a yellow solid.

$^1$H-NMR (400 Mhz, DMSO-d$_6$), ppm: 1.57 (s, 9H); 2.12 (s, 3H); 2.66 (s, 3H); 6.67 (d, j=9.7 Hz, 1H); 7.43 (m, 2H); 8.02 (m, 2H); 8.20 (d, j=9.7 Hz, 1H);

Example 9 tert-butyl 4-(4-methyl-2-(methylsulfonyl)-7-oxopyrido[2,3-d]pyrimidin-8(7H)-yl)benzoate (2)

Experimental scheme II

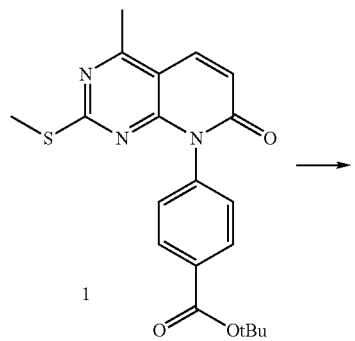

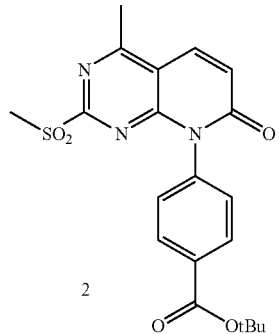

A mixture of compound 1 (1.917 g; 5 mmol) and 70% MCPBA (3.35 g; 15 mmol) in 100 mL of methylene chloride was stirred at room temperature for 90'. The reaction mixture was washed several times with a saturated solution of sodium bicarbonate, filtered, dried over anhydrous CaCl$_2$, and concentrated. The crude solid was purified by silica gel column chromatography (eluant: n-hexane/ethyl acetate=1/3) to yield compound 2 (1.8 g; 87%).

$^1$H-NMR (400 Mhz, DMSO-d$_6$), ppm: 1.57 (s, 9H); 2.85 (s, 3H); 3.08 (s, 3H); 6.97 (d, j=9.9 Hz, 1H); 7.48 (m, 2H); 8.05 (m, 2H); 8.37 (d, j=9.9 Hz, 1H);

Example 10 tert-butyl 4-(2-[4-(ethoxycarbonyl)anilino]-4-methyl-7-oxopyrido[2,3-d]pyrimidin-8(7H)-yl)benzoate (3)

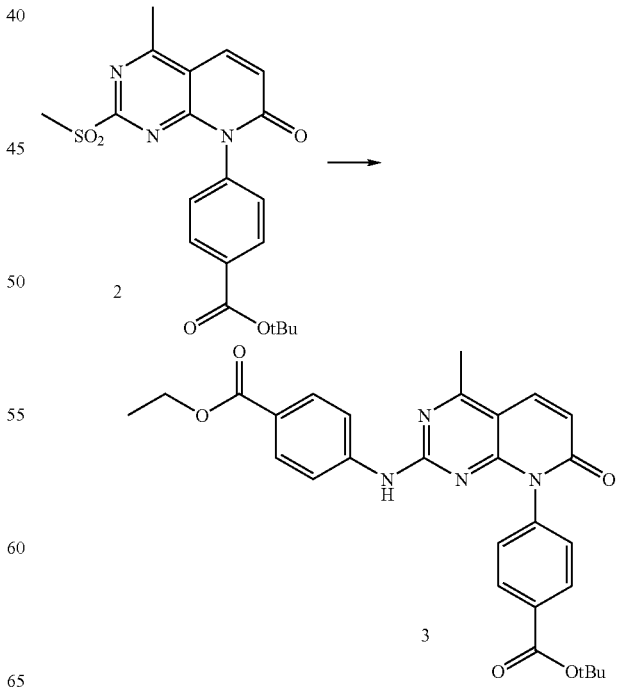

A solution of compound 2 (0.5 g; 1.2 mmol) and ethyl p-aminobenzoate (1 g; 6 mmol) in 10 mL of dioxane was refluxed under stirring for 14 h. The reaction mixture was concentrated, purified by silica gel column chromatography (eluant: n-hexane/ethyl acetate=1/1 to 1/2) to yield compound 3 (0.38 g; 63%).

$^1$H-NMR (400 Mhz, DMSO-d$_6$), ppm: 1.25 (t, j=7.1 Hz, 2H); 1.61 (s, 9H); 2.65 (s, 3H); 6.51 (d, j=9.6 Hz, 1H); 7.29 (m, 2H); 7.48 (m, 4H); 8.13 (m, 3H); 10.32 (s, 3H);

Analogously the following compounds have been prepared by reacting compound (9) with the corresponding amines:

tert-butyl 4-(4-methyl-7-oxo-2-(4-phenyl-1-piperazinyl)pyrido[2,3-d]pyrimidin-8(7H)-yl)benzoate (4)

$^1$H-NMR (400 Mhz, DMSO-d$_6$), ppm: 1.58 (s, 9H); 2.58 (s, 3H); 3.6, 3.1 (two bs, 8H); 6.33 (d, j=9.6 Hz, 1H); 6.11 (m, 2H); 7.38 (m, 2H); 8.03 (m, 4H);

tert-butyl 4-(2-[4-(4-fluorophenyl)-1-piperazinyl]-4-methyl-7-oxopyrido[2,3-d]pyrimidin-8(7H)-yl)benzoate (5)

$^1$H-NMR (400 Mhz, DMSO-d$_6$), ppm: 1.57 (s, 9H); 2.58 (s, 3H); 3.0 (bs, 4H); 3.6 (bs, 4H); 6.34 (d, j=9.6 Hz, 1H); 6.97 (m, 4H); 7.38 (m, 2H); 8.02 (m, 3H);

tert-butyl 4-(4-methyl-7-oxo-2-[4-(2-pyridinyl)-1-piperazinyl]pyrido[2,3-d]pyrimidin-8(7H)-yl)benzoate (6)

$^1$H-NMR (400 Mhz, DMSO-d$_6$), ppm: 1.58 (s, 9H); 2.58 (s, 3H); 3.40 (bs, 4H); 6.34 (d, j=9.6 Hz, 1H); 6.61 (ddd, j=7.0, 5.5, 0.7 Hz, 1H); 7.39 (m, 2H); 8.05 (m, 4H);

tert-butyl 4-(4-methyl-7-oxo-2-[4-(2-pyrimidinyl)-1-piperazinyl]pyrido[2,3-d]pyrimidin-8(7H)-yl)benzoate (7)

$^1$H-NMR (400 Mhz, DMSO-d$_6$), ppm: 1.58 (s, 9H); 2.58 (s, 3H); 3.67 (bs, 4H); 6.34 (d, j=9.6 Hz, 1H); 6.62 (t, j=4.7 Hz, 1H); 7.38 (m, 2H); 8.04 (m, 3H);

tert-butyl 4-(2-(3,4-dihydro-2(1H)-isoquinolinyl)-4-methyl-7-oxopyrido[2,3-d]pyrimidin-8(7H)-yl)benzoate (8)

$^1$H-NMR (400 Mhz, DMSO-d$_6$), ppm: 1.59 (s, 9H); 2.58 (s, 3H); 3.3–5.1 (bs, 4H); 6.34 (d, j=9.6 Hz, 1H); 7.11 (m, 3H); 7.39 (m, 2H); 8.04 (m, 3H)

Example 11

4-(2-[4-(ethoxycarbonyl)anilino]-4-methyl-7-oxopyrido[2,3-d]pyrimidin-8(7H)-yl)benzoic acid (9)

Experimental scheme IV

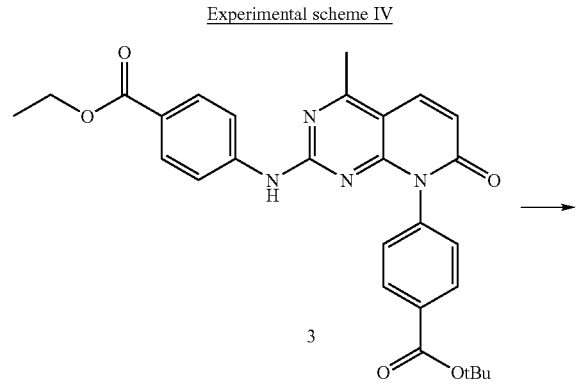

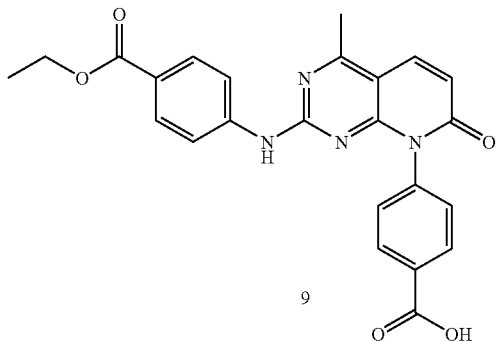

A solution of compound 3 (0.12 g; 0.2397 mmol) and trifluoroacetic acid (0.2 mL; 2.62 mmol) in 3 mL of methylene chloride was stirred at room temperature for 2 h. The reaction mixture was concentrated and the crude product taken up with ethyl acetate and n-hexane to yield compound 9 (0.09 g; 84%).

$^1$H-NMR (400 Mhz, DMSO-d$_6$), ppm: 1.28 (t, j=7.1 Hz, 3H); 2.65 (s, 3H); 6.51 (d, j=9.6 Hz, 1H); 7.31 (m, 2H); 7.47 (m, 4H); 8.15 (m, 3H); 10.33 (s, 1H);

Analogously the following compounds have been prepared:

4-(4-methyl-7-oxo-2-(4-phenyl-1-piperazinyl)pyrido[2,3-d]pyrimidin-8 (7H)-yl)benzoic acid (10)

4-(2-[4-(4-fluorophenyl)-1-piperazinyl]-4-methyl-7-oxopyrido[2,3-d]pyrimidin-8 (7H)-yl)benzoic acid (11)

4-(4-methyl-7-oxo-2-[4-(2-pyridinyl)-1-piperazinyl]pyrido[2,3-d]pyrimidin-8 (7H)-yl)benzoic acid (12)

4-(4-methyl-7-oxo-2-[4-(2-pyrimidinyl)-1-piperazinyl]pyrido[2,3-d]pyrimidin-8 (7H)-yl)benzoic acid (13)

$^1$H-NMR (400 Mhz, DMSO-d$_6$), ppm: 2.58 (s, 3H); 3.0–4.0 (bs, 8H); 6.35 (d, j=9.6 Hz, 1H); 6.62 (t, j=4.7 Hz, 1H); 7.38 (m, 2H); 8.05 (m, 3H)

4-(2-(3,4-dihydro-2(1H)-isoquinolinyl)-4-methyl-7-oxopyrido[2,3-d]pyrimidin-8(7H)-yl)benzoic acid (14)

4-(4-methyl-2-(methylsulfanyl)-7-oxopyrido[2,3-d]pyrimidin-8(7H)-yl)benzoic acid (483)

Example 12

4-(4-methyl-7-oxo-2-(4-phenyl-1-piperazinyl)pyrido[2,3-d]pyrimidin-8(7H)-yl)benzoyl chloride (L)

Example 13

N-benzyl-4-(4-methyl-7-oxo-2-(4-phenyl-1-piperazinyl)pyrido[2,3-d]pyrimidin-8(7H)-yl)benzamide (15)

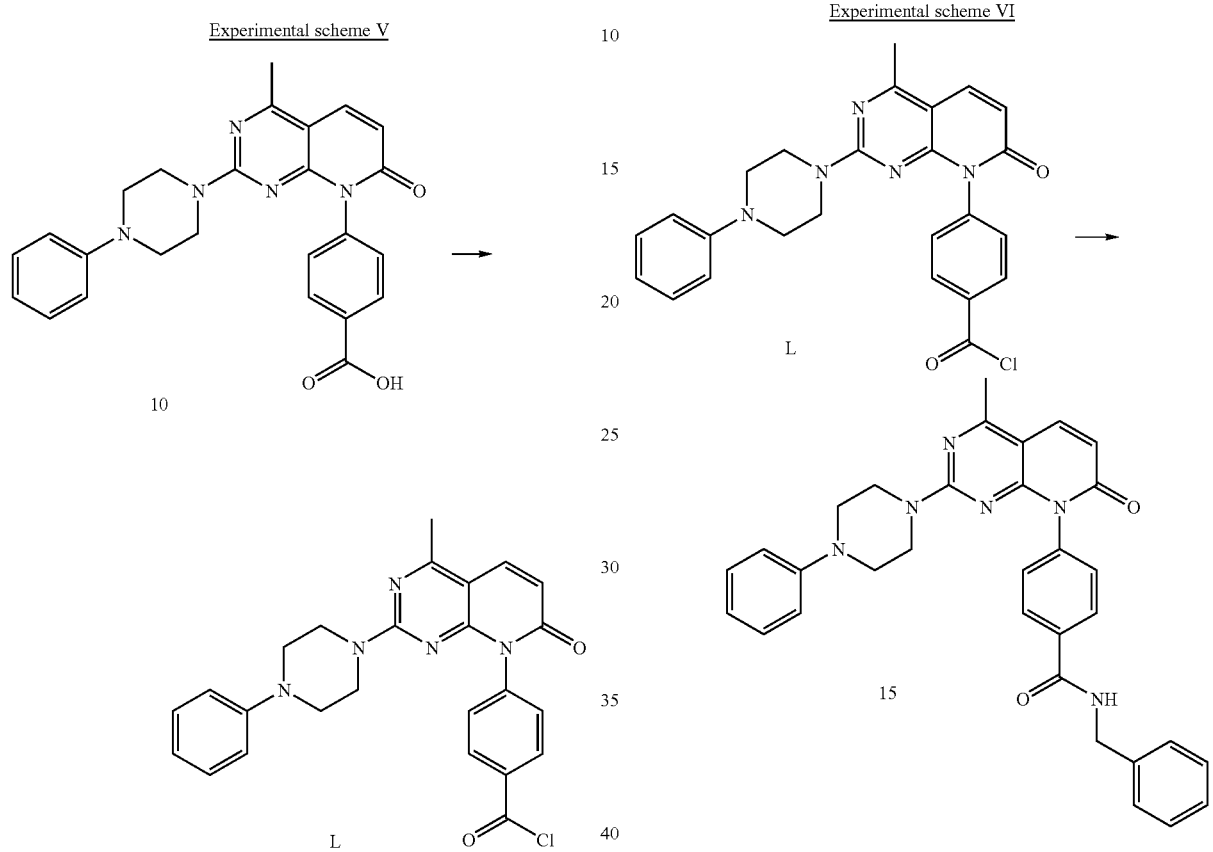

To a solution of compound 10 (0.215 g; 0.487 mmol) and anhydrous DMF (120 uL) in 8 mL of methylene chloride, oxalyl chloride (0.18 g; 5 mmol) was added dropwise at room temperature and the reaction mixture was stirred for 2 h. Then it was concentrated and the oxalyl chloride carefully removed by distillation to yield compound L (0.217 g; 97%). The compound was used in the next step without further purification.

Analogously the following compounds have been prepared:

4-(2-[4-(4-fluorophenyl)-1-piperazinyl]-4-methyl-7-oxopyrido[2,3-d]pyrimidin-8(7H)-yl)benzoyl chloride;

4-(4-methyl-7-oxo-2-[4-(2-pyridinyl)-1-piperazinyl]pyrido[2,3-d]pyrimidin-8(7H)-yl)benzoyl chloride;

4-(4-methyl-7-oxo-2-[4-(2-pyrimidinyl)-1-piperazinyl]pyrido[2,3-d]pyrimidin-8(7H)-yl)benzoyl chloride;

4-(2-(3,4-dihydro-2(1H)-isoquinolinyl)-4-methyl-7-oxopyrido[2,3-d]pyrimidin-8(7H)-yl)benzoyl chloride;

4-(4-methyl-2-(methylsulfanyl)-7-oxopyrido[2,3-d]pyrimidin-8(7H)-yl)benzoyl chloride (M);

To a solution of benzylamine (0.0536 g; 0.50mmol) and a drop of triethylamine in 5 mL of methylene chloride, compound L (0.043 g; 0.094 mmol) in 3 mL of methylene chloride was added at room temperature. The reaction mixture was stirred for 2 h and then diluted with 10 mL of methylene chloride and 10 mL of water. The organic phase was dried over $CaCl_2$, concentrated and the crude reaction mixture purified by silica gel column chromatography (eluant: $CH_2Cl_2/CH_3OH=190/10$) to yield compound 15 (0.039 g; 78%).

$^1$H-NMR (400 Mhz, DMSO-$d_6$), ppm: 2.58 (s, 3H); 3.05 (bs, 4H); 3.7 (bs, 4H); 4.51 (d, j=5.9 Hz, 1H); 6.34 (d, j=9.6 Hz, 1H); 7.1–7.4 (m, 7H); 8.02 (m, 3H); 9.10 (t, j=5.9 Hz, 1H);

Analogously starting from the corresponding acyl chloride, the following compounds have been prepared:

From 4-(4-methyl-7-oxo-2-(4-phenyl-1-piperazinyl)pyrido[2,3-d]pyrimidin-8(7H)-yl)benzoyl chloride (L):

N-(2-furylmethyl)-4-(4-methyl-7-oxo-2-(4-phenyl-1-piperazinyl)pyrido[2,3-d]pyrimidin-8(7H)-yl)benzamide (16)

$^1$H-NMR (400 Mhz, DMSO-$d_6$), ppm: 2.58 (s, 3H); 3.05 (bs, 4H); 3.7 (bs, 4H); 4.49 (d, j=5.8 Hz, 1H); 6.34 (d, j=9.6 Hz, 1H); 7.34 (m, 2H); 7.57 (dd, j=0.9, 1.9 Hz, 1H); 7.99 (m, 2H); 8.03 (d, j=9.6 Hz, 1H); 9.07 (t, j=5.8 Hz, 1H);

4-(4-methyl-7-oxo-2-(4-phenyl-1-piperazinyl)pyrido[2,3-d]pyrimidin-8(7H)-yl)-N-(3-pyridinylmethyl)benzamide (17)

$^1$H-NMR (400 Mhz, DMSO-d$_6$), ppm: 2.58 (s, 3H); 3.05 (bs, 4H); 3.6 (bs, 4H); 4.52 (d, j=5.9 Hz, 2H); 6.34 (d, j=9.6 Hz, 1H); 6.91 (m, 2H); 7.36 (m, 3H); 8.00 (m, 2H); 8.04 (d, j=9.6 Hz, 1H); 8.46 (dd, j=4.7, 1.6 Hz, 1H); 9.20 (t, j=5.9 Hz, 1H);

4-(4-methyl-7-oxo-2-(4-phenyl-1-piperazinyl)pyrido[2,3-d]pyrimidin-8(7H)-yl)-N-(1-naphthylmethyl)benzamide (18)

$^1$H-NMR (400 Mhz, DMSO-d$_6$), ppm: 2.58 (s, 3H); 3.0, 3.6 (two bs, 8H); 6.34 (d, j=9.6 Hz, 1H); 6.90 (m, 2H); 7.36 (m, 2H); 8.04 (m, 4H); 8.21 (d, j=8.0 Hz, 1H); 9.17 (t, j=5.7 Hz, 1H);

N-(3,4-dimethoxybenzyl)-4-(4-methyl-7-oxo-2-(4-phenyl-1-piperazinyl)pyrido[2,3-d]pyrimidin-8(7H)-yl)benzamide (19)

$^1$H-NMR (400 Mhz, DMSO-d$_6$), ppm: 2.57 (s, 3H); 3.05 (bs, 4H); 3.71 (s, 3H); 3.73 (s, 3H); 6.34 (d, j=9.6 Hz, 1H); 6.97 (d, j=1.7 Hz, 1H); 7.16 (m, 2H); 7.34 (m, 2H); 8.00 (m, 2H); 8.03 (d, j=9.6 Hz, 1H); 9.06 (t, j=6.0 Hz, 1H);

From 4-(2-[4-(4-fluorophenyl)-1-piperazinyl]-4-methyl-7-oxopyrido[2,3-d]pyrimidin-8(7H)-yl)benzoyl chloride:

N-benzyl-4-(2-[4-(4-fluorophenyl)-1-piperazinyl]-4-methyl-7-oxopyrido[2,3-d]pyrimidin-8(7H)-yl)benzamide (20)

$^1$H-NMR (400 Mhz, DMSO-d$_6$), ppm: 2.58 (s, 3H); 3.0, 3.6 (two bs, 8H); 4.51 (d, j=6.0 Hz, 2H); 6.34 (d, j=9.6 Hz, 1H); 6.96 (m, 4H); 7.30 (m, 7H); 8.01 (m, 2H); 8.03 (d, j=9.6 Hz, 1H); 9.15 (t, j=6.0 Hz, 1H);

4-(2-[4-(4-fluorophenyl)-1-piperazinyl]-4-methyl-7-oxopyrido[2,3-d]pyrimidin-8(7H)-yl)-N-(2-furylmethyl)benzamide (21)

$^1$H-NMR (400 Mhz, DMSO-d$_6$), ppm: 2.58 (s, 3H); 3.0, 3.60 (two bs, 8H); 4.49 (d, j=5.7 Hz, 2H); 6.34 (d, j=9.6 Hz, 1H); 6.40 (dd, j=1.8, 3.2 Hz, 1H); 6.95 (m, 4H); 7.34 (m, 2H); 7.99 (m, 2H); 8.04 (d, j=9.6 Hz, 1H); 9.07 (t, j=5.7 Hz, 1H);

From 4-(4-methyl-7-oxo-2-[4-(2-pyridinyl)-1-piperazinyl]pyrido[2,3-d]pyrimidin-8(7H)-yl)benzoyl chloride:

N-benzyl-4-(4-methyl-7-oxo-2-[4-(2-pyridinyl)-1-piperazinyl]pyrido[2,3-d]pyrimidin-8(7H)-yl)benzamide (22)

$^1$H-NMR (400 Mhz, DMSO-d$_6$), ppm: 2.58 (s, 3H); 3.1–4.0 (bs, 8H); 4.51 (d, j=6.0 Hz, 2H); 6.34 (d, j=9.6 Hz, 1H); 6.61 (ddd, j=7.0, 4.9, 0.6 Hz, 1H); 7.2–7.4 (m, 7H); 8.04 (m, 4H); 9.1 (t, j=6.0 Hz, 1H);

4-(4-methyl-7-oxo-2-[4-(2-pyridinyl)-1-piperazinyl]pyrido[2,3-d]pyrimidin-8(7H)-yl)-N-(3-pyridinylmethyl)benzamide (23)

$^1$H-NMR (400 Mhz, DMSO-d$_6$), ppm: 2.58 (s, 3H); 3.0–4.0 (bs, 8H); 4.53 (d, j=6.0 Hz, 2H); 6.34 (d, j=9.6 Hz, 1H); 6.61 (ddd, j=7.1, 4.9, 0.6 Hz, 1H); 7.37 (m, 3H); 8.04 (m, 4H); 8.46 (dd, j=4.8, 1.7 Hz, 1H); 9.20 (t, j=6.0 Hz, 1H);

N-(2-furylmethyl)-4-(4-methyl-7-oxo-2-[4-(2-pyridinyl)-1-piperazinyl]pyrido[2,3-d]pyrimidin-8(7H)-yl)benzamide (24)

$^1$H-NMR (400 Mhz, DMSO-d$_6$), ppm: 2.58 (s, 3H); 3.1–4.0 (bs, 8H); 4.50 (d, j=5.9 Hz, 2H); 6.34 (d, j=9.6 Hz, 1H); 6.41 (dd, j=1.9, 3.2 Hz, 1H); 6.61 (ddd, j=7.1, 4.9, 0.7 Hz, 1H); 7.37 (m, 2H); 7.9–8.1 (m, 4H); 9.08 (t, j=5.9 Hz, 1H);

N-(3,4-dimethoxybenzyl)-4-(4-methyl-7-oxo-2-[4-(2-pyridinyl)-1-piperazinyl]pyrido[2,3-d]pyrimidin-8(7H)-yl)benzamide (25)

$^1$H-NMR (400 Mhz, DMSO-d$_6$), ppm: 2.58 (s, 3H); 3.2–3.5 (bs, 8H); 3.71 (s, 3H); 3.74 (s, 3H); 4.44 (d, j=6.0 Hz, 2H); 6.34 (d, j=9.6 Hz, 1H); 6.61 (ddd, j=7.1, 4.9, 0.7 Hz, 1H); 6.97 (d, j=1.7 Hz, 1H); 7.35 (m, 2H); 8.03 (m, 4H); 9.06 (t, j=6.0 Hz, 1H);

4-(4-methyl-7-oxo-2-[4-(2-pyridinyl)-1-piperazinyl]pyrido[2,3-d]pyrimidin-8(7H)-yl)-N-(2-naphthylmethyl)benzamide (26)

$^1$H-NMR (400 Mhz, DMSO-d$_6$), ppm: 2.58 (s, 3H); 3.2–4.0 (bs, 8H); 4.99 (d, j=5.8 Hz, 2H); 6.34 (d, j=9.6 Hz, 1H); 6.61 (ddd, j=7.0, 4.8, 0.7 Hz, 1H); 7.35 (m, 2H); 8.03 (m, 3H); 8.21 (d, j=8.2 Hz, 1H); 9.18 (t, j=5.8 Hz, 1H);

From 4-(4-methyl-7-oxo-2-[4-(2-pyrimidinyl)-1-piperazinyl]pyrido[2,3-d]pyrimidin-8(7H)-yl)benzoyl chloride:

N-benzyl-4-(4-methyl-7-oxo-2-[4-(2-pyrimidinyl)-1-piperazinyl]pyrido[2,3-d]pyrimidin-8(7H)-yl)benzamide (27)

$^1$H-NMR (400 Mhz, DMSO-d$_6$), ppm: 2.58 (s, 3H); 3.66 (bs, 4H); 4.52 (d, j=5.9 Hz, 2H); 6.35 (d, j=9.6 Hz, 1H); 6.62 (t, j=4.8 Hz, 1H); 7.2–7.4 (m, 7H); 8.01 (m, 2H); 8.04 (d, j=9.6 Hz, 1H); 9.14 (t, j=5.9 Hz, 1H);

N-(2-furylmethyl)-4-(4-methyl-7-oxo-2-[4-(2-pyrimidinyl)-1-piperazinyl]pyrido[2,3-d]pyrimidin-8(7H)-yl)benzamide (28)

$^1$H-NMR (400 Mhz, DMSO-d$_6$), ppm: 2.58 (s, 3H); 3.66 (bs, 4H); 6.35 (d, j=9.6 Hz, 1H); 6.62 (t, j=4.7 Hz, 1H); 7.34 (m, 2H); 7.58 (dd, j=0.9, 1.8 Hz, 1H); 7.98 (m, 2H); 8.04 (d, j=9.6 Hz, 1H); 9.06 (t, j=5.8 Hz, 1H);

N-(3,4-dimethoxybenzyl)-4-(4-methyl-7-oxo-2-[4-(2-pyrimidinyl)-1-piperazinyl]pyrido[2,3-d]pyrimidin-8(7H)-yl)benzamide (29)

$^1$H-NMR (400 Mhz, DMSO-d$_6$), ppm: 2.58 (s, 3H); 3.66 (bs, 4H); 3.81 (s, 3H); 3.85 (s, 3H); 4.44 (d, j=5.9 Hz, 2H); 6.35 (d, j=9.6 Hz, 1H); 6.62 (t, j=4.8 Hz, 1H); 6.97 (d, j=1.8 Hz, 1H); 7.35 (m, 2H); 7.99 (m, 2H); 8.04 (d, j=9.6 Hz, 1H); 9.05 (t, j=5.9 Hz, 1H);

4-(4-methyl-7-oxo-2-[4-(2-pyrimidinyl)-1-piperazinyl]pyrido[2,3-d]pyrimidin-8(7H)-yl)-N-(3-pyridinylmethyl)benzamide (30)

$^1$H-NMR (400 Mhz, DMSO-d$_6$), ppm: 2.58 (s, 3H); 3.66 (bs, 4H); 4.53 (d, j=5.9 Hz, 2H); 6.35 (d, j=9.6 Hz, 1H); 6.62 (t, j=4.8 Hz, 1H); 7.35 (m, 3H); 7.99 (m, 2H); 8.04 (d, j=9.6 Hz, 1H); 8.46 (dd, j=1.7, 4.7 Hz, 1H); 9.18 (t, j=5.9 Hz, 1H);

N-(2,4-difluorobenzyl)-4-(4-methyl-7-oxo-2-[4-(2-pyrimidinyl)-1-piperazinyl]pyrido[2,3-d]pyrimidin-8(7H)-yl)benzamide (31)

$^1$H-NMR (400 Mhz, DMSO-d$_6$), ppm: 2.58 (s, 3H); 3.66 (bs, 4H); 6.35 (d, j=9.6 Hz, 1H); 6.62 (t, j=4.7 Hz, 1H); 7.35 (m, 2H); 7.46 (m, 1H); 8.00 (m, 2H); 8.04 (d, j=9.6 Hz, 1H); 9.11 (t, j=5.8 Hz, 1H);

4-(4-methyl-7-oxo-2-[4-(2-pyrimidinyl)-1-piperazinyl]pyrido[2,3-d]pyrimidin-8(7H)-yl)-N-(1-naphthylmethyl)benzamide (32)

$^1$H-NMR (400 Mhz, DMSO-d$_6$), ppm: 2.58 (s, 3H); 3.66 (bs, 4H); 6.35 (d, j=9.6 Hz, 1H); 6.62 (t, j=4.8 Hz, 1H); 7.35 (m, 2H); 8.05 (m, 4H); 8.21 (d, j=8.5 Hz, 1H); 9.16 (t, j=5.7 Hz, 1H);

From 4-(2-(3,4-dihydro-2(1H)-isoquinolinyl)-4-methyl-7-oxopyrido[2,3-d]pyrimidin-8(7H)-yl)benzoyl chloride:

N-cyclopropyl-4-(2-(3,4-dihydro-2(1H)-isoquinolinyl)-4-methyl-7-oxopyrido[2,3-d]pyrimidin-8(7H)-yl)benzamide (33)

¹H-NMR (400 Mhz, DMSO-d$_6$), ppm: 2.58 (s, 3H); 2.90 (m, 1H); 3.4–5.1 (bs, 4H); 6.33 (d, j=9.6 Hz, 1H); 7.33 (m, 2H); 7.11 (m, 3H); 7.95 (m, 2H); 8.03 (d, j=9.6 Hz, 1H); 8.54 (d, j=4.3 Hz, 1H);

4-(2-(3,4-dihydro-2(1H)-isoquinolinyl)-4-methyl-7-oxopyrido[2,3-d]pyrimidin-8(7H)-yl)-N-(3,4-dimethoxyphenyl)benzamide (34)

¹H-NMR (400 Mhz, DMSO-d$_6$), ppm: 2.52 (s, 3H); 3.4–5.0 (bs, 4H); 3.74 (s, 3H); 3.77 (s, 3H); 6.35 (d, j=9.6 Hz, 1H); 6.94 (d, j=8.8 Hz, 1H); 7.11 (m, 3H); 7.42 (m, 2H); 8.05 (d, j=9.6 Hz, 1H); 8.09 (m, 2H); 10.22 (s, 1H);

4-(2-(3,4-dihydro-2(1H)-isoquinolinyl)-4-methyl-7-oxopyrido[2,3-d]pyrimidin-8(7H)-yl)-N,N-dimethylbenzamide (35)

¹H-NMR (400 Mhz, DMSO-d$_6$), ppm: 2.58 (s, 3H); 3.0 (bs, 6H); 3.4–5.0 (bs, 4H); 6.34 (d, j=9.6 Hz, 1H); 7.11 (m, 3H); 7.31 (m, 2H); 7.53 (m, 2H); 8.03 (d, j=9.6 Hz, 1H);

4-(2-(3,4-dihydro-2(1H)-isoquinolinyl)-4-methyl-7-oxopyrido[2,3-d]pyrimidin-8(7H)-yl)-N-(3,4-dimethoxybenzyl)benzamide (36)

¹H-NMR (400 Mhz, DMSO-d$_6$), ppm: 2.58 (s, 3H); 3.72 (s, 3H); 3.74 (s, 3H); 4.45 (d, j=6.0 Hz, 2H); 6.33 (d, j=9.6 Hz, 1H); 6.98 (d, j=1.7 Hz, 1H); 7.11 (m, 2H); 7.35 (m, 2H); 8.02 (m, 2H); 8.03 (d, j=9.6 Hz, 1H); 9.08 (t, j=6.0 Hz, 1H);

Ethyl 4-{[4-(2-(3,4-dihydro-2(1H)-isoquinolinyl)-4-methyl-7-oxopyrido[2,3-d]pyrimidin-8(7H)-yl)benzoyl]amino}benzoate (37)

¹H-NMR (400 Mhz, DMSO-d$_6$), ppm: 2.60 (s, 3H); 4.30 (q, j=7.1 Hz, 2H); 6.35 (d, j=9.6 Hz, 1H); 7.11 (m, 3H); 7.45 (m, 2H); 8.05 (d, j=9.6 Hz, 1H); 8.12 (m, 2H); 10.67 (s, 1H);

N-(3-cyanophenyl)-4-(2-(3,4-dihydro-2(1H)-isoquinolinyl)-4-methyl-7-oxopyrido[2,3-d]pyrimidin-8(7H)-yl)benzamide (38)

¹H-NMR (400 Mhz, DMSO-d$_6$), ppm: 2.60 (s, 3H); 3.2–5.1 (bs, 4H); 6.35 (d, j=9.6 Hz, 1H); 7.11 (m, 3H); 7.46 (m, 2H); 7.59 (m, 2H); 8.05 (d, j=9.6 Hz, 1H); 8.12 (m, 2H); 10.67 (s, 1H);

N-cyclohexyl-4-(2-(3,4-dihydro-2(1H)-isoquinolinyl)-4-methyl-7-oxopyrido[2,3-d]pyrimidin-8(7H)-yl)benzamide (39)

¹H-NMR (400 Mhz, DMSO-d$_6$), ppm: 1.0–1.9 (m, 10H); 2.58 (s, 3H); 3.4–5.1 (bs, 6H); 6.33 (d, j=9.6 Hz, 1H); 7.11 (m, 3H); 7.33 (m, 2H); 7.97 (m, 2H); 8.05 (d, j=9.6 Hz, 1H); 8.12 (d, j=8.1 Hz, 1H);

N-(3,4-dichlorophenyl)-4-(2-(3,4-dihydro-2(1H)-isoquinolinyl)-4-methyl-7-oxopyrido[2,3-d]pyrimidin-8(7H)-yl)benzamide (40)

¹H-NMR (400 Mhz, DMSO-d$_6$), ppm: 2.59 (s, 3H); 3.3–5.1 (bs, 4H); 6.35 (d, j=9.6 Hz, 1H); 7.11 (m, 3H); 7.45 (m, 2H); 7.80 (dd, j=2.4, 8.8 Hz, 1H); 8.05 (d, j=9.6 Hz, 1H); 8.10 (m, 2H); 10.61 (s, 1H);

Example 14 methyl 4-({8-[4-(methoxycarbonyl)phenyl]-4-methyl-7-oxo-7,8-dihydropyrido[2,3-d]pyrimidin-2-yl}amino)benzoate (41)

Experimental scheme VII

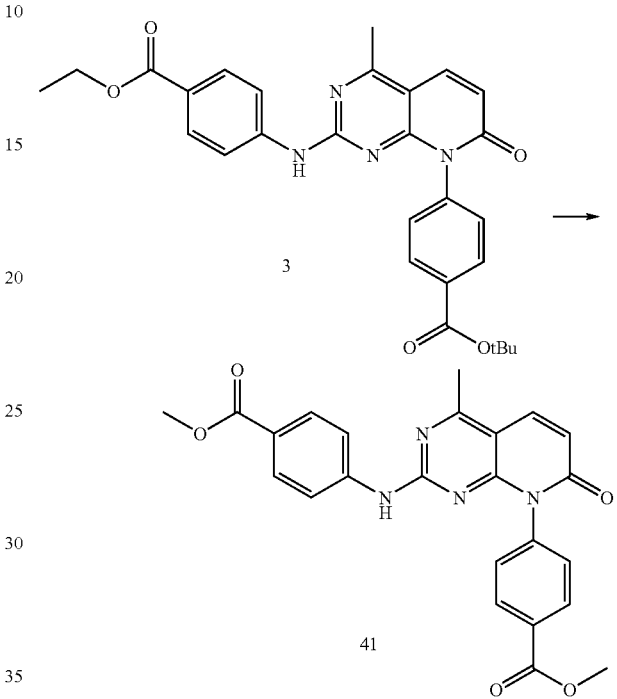

A solution of compound 3 (0.100 g; 0.200 mmol) and 96% H$_2$SO$_4$ (1 mL) in 100 mL of methanol was stirred under reflux for 24 h. The reaction mixture was concentrated, diluted with methylene chloride, and washed with aqueous sodium bicarbonate. The organic phase was dried over anhydrous sodium sulphate, concentrated and purified by silica gel column chromatography (eluant: CH$_2$Cl$_2$/CH$_3$OH=190/10) to yield compound 41 (0.05 g; 56%).

¹H-NMR (400 Mhz, DMSO-d$_6$), ppm: 2.65 (s, 3H); 3.77 (s, 3H); 3.98 (s, 3H); 6.52 (d, j=9.6 Hz, 1H); 7.28 (m, 2H); 7.46 (m, 2H); 7.52 (m, 2H); 8.15 (d, j=9.6 Hz, 1H); 8.19 (m, 2H); 10.35 (s, 1H);

Analogously the following compound has been prepared:

Ethyl 4-({8-[4-(ethoxycarbonyl)phenyl]-4-methyl-7-oxo-7,8-dihydropyrido[2,3-d]pyrimidin-2-yl}amino)benzoate (42)

Solid Phase Method

Analysis

All compounds synthesized with the method described below were characterized by mass spectrometry (MS) and ¹H-NMR. LC-MS confirmed that in each case the principle component had a molecular ion corresponding to the expected product. The compounds showed an average HPLC area % of about 80%.

HPLC Conditions:

Column: Waters Symmetry Shield RP 18 3.5 mm, 4.6×50 mm;

Column temperature: Room temperature;
Mobile phase A: Ammonium acetate 5 mM buffer made to pH 5 with acetic acid/acetonitrile 9:1 (v:v);
Mobile phase B: Ammonium acetate 5 mM buffer made to pH 5 with acetic acid/acetonitrile 1:9 (v:v);
Elution: Gradient from 0 to 100% of B in 7 minutes, then isocratic at 100% of B for other 2 min., followed by a gradient from 100% to 0% of B in 0.1 min. and by a further isocratic at 100% of A for 0.9 min.;
Flow rate: 1 ml/min;
Detection: UV in the range 215–400 nm and MS;
Sample preparation: The sample is dissolved in DMSO at a concentration 10 mM; 20 µl of this solution are diluted to 1 ml with the mixture ammonium acetate buffer 5 mM, pH 5/acetonitrile 1:1 (v:v);

Injection volume: 10 µl

NMR Analysis

NMR spectra are automatically acquired and processed in quantitative conditions (long relaxation delay, high digital resolution, pre-acquisition delays optimized for a flat baseline, post-acquisition baseline correction and linear prediction of the first three data points of the fid) on a 400 MHz MERCURY Vx instrument equipped with a sample changer.

Process for the solid phase synthesis of compound (140):

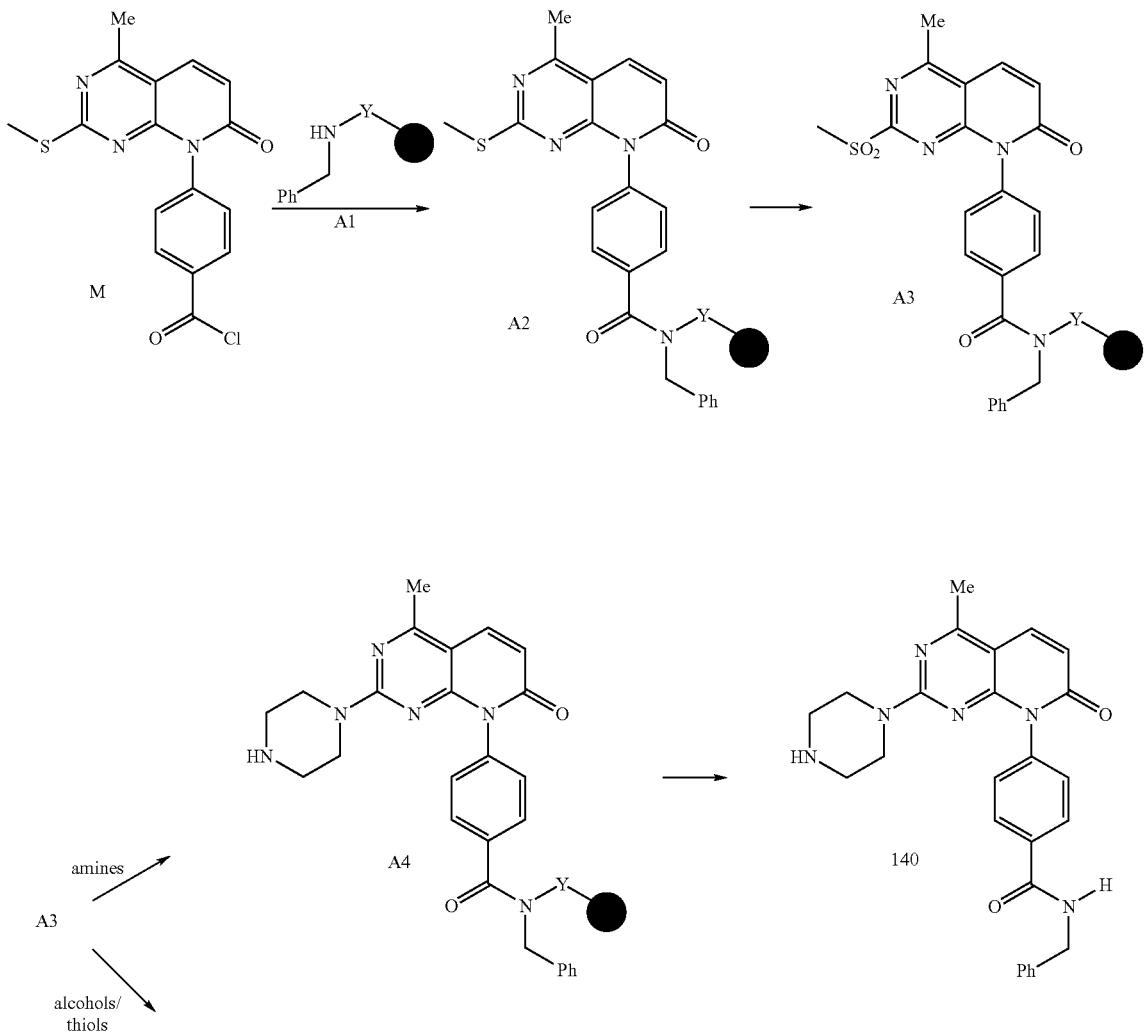

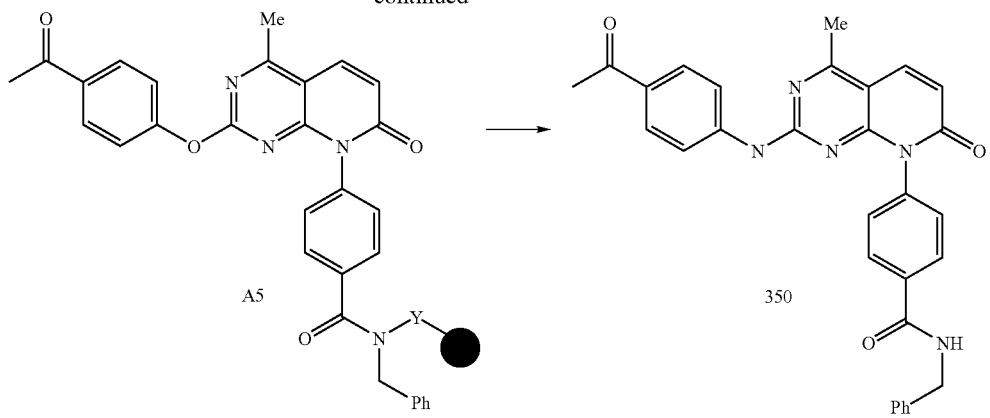

Example 15

Polymer Supported Benzylamine by Reductive Amination (A1)

To a suspension of 4-(4-Formyl-3-methoxyphenoxy)butyryl AM resin (500 mg, 0.40 mmol) in 5 ml of THF/DCM (4:1, v/v) was added benzylamine (260 μl, 2.4 mmol) and AcOH (135 μl, 2.4 mmol). Shaking continued for 15 min, then NaHB(OAc)$_3$ (250 mg, 1.20 mmol) was added and shaking continued over-night. The resin was washed with MeOH (2×1 min), DMF (2×1 min), DCM (1×1 min), MeOH (1×1 min) and DCM (3×1 min). The resin was dried at 30° C. at 10 Torr for 2 h and was ready for use.

According to the previous method the following amines have been polymer supported:
3,4-dimethoxybenzylamine;
4-(trifluoromethyl)benzylamine;
methyl 4-(aminomethyl)benzoate;
2,4-difluorobenzylamine;
4-(methylsulfonyl)benzylamine;
cyclohexylmethylamine;
tetrahydro-2-furanylmethylamine;
2-furylmethylamine;
2-(4-morpholinyl)ethylamine;
N,N-dimethyl-1,3-propanediamine;
2-phenylethylamine;
3,4-dimethoxyaniline;
2-methyl-1-propanamine;
octylamine;
cyclopropylamine
amino group (introduced by coupling of acyl chloride (M) to Rink Amide Resin; Novabiochem, 0.94 mmol/g)

Example 16 polymer supported N-benzyl-4-(4-methyl-2-(methylsulfanyl)-7-oxopyrido[2,3-d]pyrimidin-8(7H)-yl) benzamide (A2)

To a suspension of polymer supported benzylamine (A1, 0.4 mmol) in DCM (15 ml) and NEt$_3$ (0.82 ml, 5.9 mmol) was given the substituted benzoyl chloride (M, 0.90 mmol). The mixture was shaken over-night and filtered. The resin was washed in the following order: DMF (3×1 min), DCM/MeOH (1:1, v/v, 3×1 min), DCM (3×1 min), MeOH (1×1 min), DCM (1×1 min), MeOH (1×1 min) and DCM (3×1 min). The resin was dried for 2 h under vacuo (10 Torr) in an oven (30° C.).

Example 17 polymer supported N-benzyl-4-(4-methyl-2-(methylsulfonyl)-7-oxopyrido[2,3-d]pyrimidin-8(7H)-yl) benzamide (A3)

The resin (ca. 45 mg, 0.0214 mmol) was suspended in DCM (1 ml) and treated for 1.25 h with MCPBA (14.3 mg, 0.064 mmol). The resin was filtered and washed with dioxane (2×1 min) and DCM (2×1 min).

Example 18 polymer supported N-benzyl-4-(4-methyl-7-oxo-2-(1-piperazinyl)pyrido[2,3-d]pyrimidin-8(7H)-yl) benzamide (A4)—(General Procedure for Amines)

The resin (A3), 0.0214 mmol) was suspended in THF (1 ml) and NEt$_3$ (14 mg, 0.14 mmol). To this mixture was added piperazine (21 mg, 0.128 mmol) and shaking continued for 18 h. The resin was washed with THF (2×1 min), DMF (3×1 min, 60° C.) and with DCM (3×1 min) at rt.

Example 19 polymer supported ethyl 4-[(8-{4-[(benzylamino) carbonyl]phenyl}-4-methyl-7-oxo-7,8-dihydropyrido[ 2,3-d]pyrimidin-2-yl)oxy]benzoate (A5)— (General Procedure for Alcohols and Thiols)

Ethyl 4-hydroxybenzoate (0.128 mmol) was suspended in THF (1 ml) and NaH (2.9 mg, 0.12 mmol) was added. After formation of the subsequent sodium salt, suspended in THF, the resin (A3) was added and shaking continued for 18 h. The resin was washed with THF (2×1 min), DMF (3×1 min, 60° C.) and with DCM (3×1 min).

Example 20

N-benzyl-4-(4-methyl-7-oxo-2-(1-piperazinyl)pyrido [2,3-d]pyrimidin-8(7H)-yl)benzamide (140)

Resin (A4) was treated with a mixture of TFA/DCM (1 ml, 50%, v/v) for 75 min. The resin was filtered, washed with DCM (1×1 min) and the combined organic phases were evaporated giving the expected N-benzyl-4-(4-methyl-7-oxo-2-(1-piperazinyl)pyrido[2,3-d]pyrimidin-8(7H)-yl)benzamide (140).

By analogous procedure starting from the appropriate polymer supported intermediates and from the appropriate reagents, the following compounds have been prepared:

(1H-NMR Signals of the Common Scaffold are Reported Below):

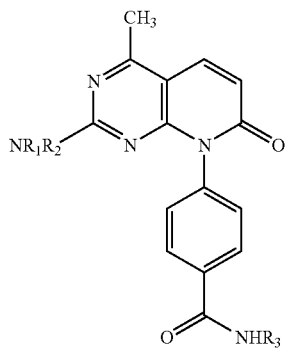

1H NMR (400 MHz, dmso-d6): 2.54 (s, 3H); 6.3 (d, j=9.6 Hz, 1H); 7.3 (m, 2H); 7.9 (m, 2H); 8.0 (d, j=9.6 Hz, 1H);

4-[2-(4-Acetyl-phenoxy)-4-methyl-7-oxo-7H-pyrido[2,3-d]pyrimidin-8-yl]-N-benzyl-benzamide (350)

| N° | Compound Name | 1H-NMR (400 Mhz, DMSO-d6), ppm |
|---|---|---|
| 43 | 4-(2-Isobutylamino-4-methyl-7-oxo-7H-pyrido[2,3-d]pyrimidin-8-yl)-N-octyl-benzamide (43) | |
| 44 | 4-(2-Isobutylamino-4-methyl-7-oxo-7H-pyrido[2,3-d]pyrimidin-8-yl)-N-phenyl-benzamide (44) | |
| 45 | 4-[2-(3,4-dihydro-1H-isoquinolin-2-yl)-4-methyl-7-oxo-7H-pyrido[2,3-d]pyrimidin-8-yl]-N-[2-(4-oxy-morpholin-4-yl)-ethyl]-benzamide (45) | |
| 46 | 4-(2-(3,4-dihydro-2(1H)-isoquinolinyl)-4-methyl-7-oxopyrido[2,3-d]pyrimidin-8(7H)-yl)-N-[3-(dimethylamino-N-oxido)propyl]benzamide (46) | |
| 47 | 4-[2-(2-Methoxy-ethylamino)-4-methyl-7-oxo-7H-pyrido[2,3-d]pyrimidin-8-yl]-N-[2-(4-oxy-morpholin-4-yl)-ethyl]-benzamide (47) | |
| 48 | N-[3-(dimethylamino-N-oxido)propyl]-4-(2-[(2-methoxyethyl)amino]-4-methyl-7-oxopyrido[2,3-d]pyrimidin-8(7H)-yl)benzamide (48) | |
| 49 | N-[3-(dimethylamino-N-oxido)propyl]-4-(2-[(2-furylmethyl)amino]-4-methyl-7-oxopyrido[2,3-d]pyrimidyl-8(7H)-yl)benzamide (49) | |
| 50 | 4-(2-[(2-furylmethyl)amino]-4-methyl-7-oxopyrido[2,3-d]pyrimidin-8(7H)-yl)-N-(2-phenylethyl)benzamide (50) | |
| 51 | 4-(2-[(2-furylmethyl)amino]-4-methyl-7-oxopyrido[2,3-d]pyrimidin-8(7H)-yl)-N-isobutylbenzamide (51) | |
| 52 | N-[3-(dimethylamino-N-oxido)propyl]-4-(2-[(2-ethylhexyl)amino]-4-methyl-7-oxopyrido[2,3-d]pyrimidin-8(7H)-yl)benzamide (52) | |
| 53 | 4-(2-[(2-ethylhexyl)amino]-4-methyl-7-oxopyrido[2,3-d]pyrimidin-8(7H)-yl)-N-(2-phenylethyl)benzamide (53) | |
| 54 | 4-(2-{[2-(acetylamino)ethyl]amino}-4-methyl-7-oxopyrido[2,3-d]pyrimidin-8(7H)-yl)-N-[3-(dimethylamino-N-oxido)propyl]benzamide (54) | |
| 55 | 4-(2-{[2-(acetylamino)ethyl]amino}-4-methyl-7-oxopyrido[2,3-d]pyrimidin-8(7H)-yl)-N-(tetrahydro-2-furanylmethyl)benzamide (55) | |
| 56 | 4-(2-(benzylamino)-4-methyl-7-oxopyrido[2,3-d]pyrimidin-8(7H)-yl)-N-[3-(dimethylamino-N-oxido)propyl]benzamide (56) | |
| 57 | 4-(2-(benzylamino)-4-methyl-7-oxopyrido[2,3-d]pyrimidin-8(7H)-yl)-N-isobutylbenzamide (57) | |
| 58 | 4-(2-[(2-aminoethyl)amino]-4-methyl-7-oxopyrido[2,3-d]pyrimidin-8(7H)-yl)-N-[3-(dimethylamino-N-oxido)propyl]benzamide (58) | |
| 59 | 4-(2-[(2-aminoethyl)amino]-4-methyl-7-oxopyrido[2,3-d]pyrimidin-8(7H)-yl)-N-(2-furylmethyl)benzamide (59) | |
| 60 | 4-(4-methyl-7-oxo-2-[4-(2-pyrimidinyl)-1-piperazinyl]pyrido[2,3-d]pyrimidin-8(7H)-yl)-N-[2-(4-oxido-4-morpholinyl)ethyl]benzamide (60) | |
| 61 | N-[3-(dimethylamino-N-oxido)propyl]-4-(4-methyl-7-oxo-2-[4-(2-pyrimidinyl)-1-piperazinyl]pyrido[2,3-d]pyrimidin-8(7H)-yl)benzamide (61) | |
| 62 | 4-(4-methyl-7-oxo-2-(1-piperazinyl)pyrido[2,3-d]pyrimidin-8(7H)-yl)-N-[2-(4-oxido-4-morpholinyl)ethyl]benzamide (62) | |
| 63 | 4-(4-methyl-7-oxo-2-(1-pyrrolidinyl)pyrido[2,3-d]pyrimidin-8(7H)-yl)-N-[2-(4-oxido-4-morpholinyl)ethyl]benzamide (63) | |
| 64 | 4-(2-[(2-hydroxyethyl)amino]-4-methyl-7-oxopyrido[2,3-d]pyrimidin-8(7H)-yl)-N-(tetrahydro-2-furanylmethyl)benzamide (64) | |
| 65 | 4-(2-{[2-(2-methoxyphenyl)ethyl]amino}-4-methyl-7-oxopyrido[2,3-d]pyrimidin-8(7H)-yl)-N-[2-(4-oxido-4-morpholinyl)ethyl]benzamide (65) | |
| 66 | N-[3-(dimethylamino-N-oxido)propyl]-4-(2-{[2-(2-methoxyphenyl)ethyl]amino}-4-methyl-7-oxopyrido[2,3-d]pyrimidin-8(7H)-yl)benzamide (66) | |
| 67 | N-(2-furylmethyl)-4-(2-{[2-(2-methoxyphenyl)ethyl]amino}-4-methyl-7-oxopyrido[2,3-d]pyrimidin-8(7H)-yl)benzamide (67) | |
| 68 | 4-(2-(3,4-dihydro-2(1H)-isoquinolinyl)-4-methyl-7-oxopyrido[2,3-d]pyrimidin-8(7H)-yl)-N-(2-furylmethyl)benzamide (68) | 4.51 (d, j = 5.7 Hz, 2H); 6.31 (m, 1H) 6.41 (m, 1H) 7.1 (m, 4H); 7.58 (m, 1H) 9.08 (t, j = 5.7, 1H) |
| 69 | 4-(2-(3,4-dihydro-2(1H)-isoquinolinyl)-4-methyl-7-oxopyrido[2,3-d]pyrimidin-8(7H)-yl)-N-octylbenzamide (69) | 0.84 (m, 3H); 3.2–5.1 (bs, 8H); 7.11 (m, 3H); 8.54 (t, j = 5.5 Hz, 1H) |
| 70 | N-benzyl-4-(2-(3,4-dihydro-2(1H)-isoquinolinyl)-4-methyl-7-oxopyrido[2,3-d]pyrimidin-8(7H)- | 3.2–5.1 (bs, 6H); 4.53 (d, J = 5.9 Hz, 2H); |

| N° | Compound Name | 1H-NMR (400 Mhz, DMSO-d6), ppm |
|---|---|---|
| | yl)benzamide (70) | 7.11 (m, 3H); 9.16 (t, j = 5.9 Hz, 1H); |
| 71 | 4-(2-(3,4-dihydro-2(1H)-isoquinolinyl)-4-methyl-7-oxopyrido[2,3-d]pyrimidin-8(7H)-yl)-N-(2-phenylethyl)benzamide (71) | 2.89 (t, J = 7.4 Hz, 2H); 3.2–5.1 (bs, 6H) 3.53 (m, 2H); 7.11 (m, 3H); 8.67 (t, j = 5.7 Hz, 1H); |
| 72 | 4-(2-(3,4-dihydro-2(1H)-isoquinolinyl)-4-methyl-7-oxopyrido[2,3-d]pyrimidin-8(7H)-yl)-N-isobutylbenzamide (72) | 0.91 (d, j = 6.7 Hz, 6H); 3.1–5.1 (bs, 8H); 7.11 (m, 3H); 8.57 (t, j = 5.9 Hz, 1H) |
| 73 | 4-(2-(3,4-dihydro-2(1H)-isoquinolinyl)-4-methyl-7-oxopyrido[2,3-d]pyrimidin-8(7H)-yl)-N-(tetrahydro-2-furanylmethyl)benzamide (73) | 3.64 (m, 1H); 3.79 (m, 1H); 4.02 (m, 1H); 7.11 (m, 3H); 8.64 (t, j = 5.9 Hz, 1H); |
| 74 | N-(cyclohexylmethyl)-4-(2-(3,4-dihydro-2(1H)-isoquinolinyl)-4-methyl-7-oxopyrido[2,3-d]pyrimidin-8(7H)-yl)benzamide (74) | 0.9–1.8 (m, 11H); 3.1–5.1 (bs, 8H); 7.11 (m, 3H); 8.54 (t, j = 5.8 Hz, 1H) |
| 75 | N-cyclopropyl-4-(4-methyl-2-{[2-(4-morpholinyl)ethyl]amino}-7-oxopyrido[2,3-d]pyrimidin-8(7H)-yl)benzamide (75) | 2.87 (m, 1H); 2.5–4.0 (bs, 12H); 7.74 (bs, 1H); 8.52 (t, j = 5.5 Hz, 1H) |
| 76 | 4-(4-methyl-2-{[2-(4-morpholinyl)ethyl]amino}-7-oxopyrido[2,3-d]pyrimidin-8(7H)-yl)-N-octylbenzamide (76) | 0.85 (m, 3H); 2.5–4.0 (bs, 14H); 7.74 (bs, 1H); 8.51 (t, j = 5.5 Hz, 1H) |
| 77 | N-(2-furylmethyl)-4-(4-methyl-2-{[2-(4-morpholinyl)ethyl]amino}-7-oxopyrido[2,3-d]pyrimidin-8(7H)-yl)benzamide (77) | 2.5–4.0 (bs, 12H); 4.49 (d, J = 5.6 Hz, 2H); 6.40 (dd, J = 3.2, 1.8 Hz, 1H); 7.74 (bs, 1H); 9.06 (t, J = 5.6 Hz, 1H) |
| 78 | N-(3,4-dimethoxyphenyl)-4-(4-methyl 2-{[2-(4-morpholinyl)ethyl]amino}-7-oxopyrido[2,3-d]pyrimidin-8(7H)-yl)benzamide (78) | 2.5–4.0 (bs, 12H); 3.74 (s, 3H); 3.75 (s, 3H); 6.93 (d, J = 8.8 Hz, 1H); 7.76 (bs, 1H); 10.2 (s, 1H); |
| 79 | N-benzyl-4-(4-methyl-2-{[2-(4-morpholinyl)ethyl]amino}-7-oxopyrido[2,3-d]pyrimidin-8(7H)-yl)benzamide (79) | |
| 80 | 4-(4-methyl-2-{[2-(4-morpholinyl)ethyl]amino}-7-oxopyrido[2,3-d]pyrimidin-8(7H)-yl)-N-(2-phenylethyl)benzamide (80) | |
| 81 | N-isobutyl-4-(4-methyl-2-{[2-(4-morpholinyl)ethyl]amino}-7-oxopyrido[2,3-d]pyrimidin-8(7H)-yl)benzamide (81) | |
| 82 | 4-(4-methyl-2-{[2-(4-morpholinyl)ethyl]amino}-7-oxopyrido[2,3-d]pyrimidin-8(7H)-yl)-N-(tetrahydro-2-furanylmethyl)benzamide (82) | |
| 83 | N-(cyclohexylmethyl)-4-(4-methyl-2-{[2-(4-morpholinyl)ethyl]amino}-7-oxopyrido[2,3-d]pyrimidin-8(7H)-yl)benzamide (83) | |
| 84 | N-cyclopropyl-4-(2-[(2-methoxyethyl)amino]-4-methyl-7-oxopyrido[2,3-d]pyrimidin-8(7H)-yl)benzamide (84) | |
| 85 | 4-(2-[(2-methoxyethyl)amino]-4-methyl-7-oxopyrido[2,3-d]pyrimidin-8(7H)-yl)-N-octylbenzamide (85) | |
| 86 | N-(2-furylmethyl)-4-(2-[(2-methoxyethyl)amino]-4-methyl-7-oxopyrido[2,3-d]pyrimidin-8(7H)-yl)benzamide (86) | |
| 87 | N-(3,4-dimethoxyphenyl)-4-(2-[(2-methoxyethyl)amino]-4-methyl-7-oxopyrido[2,3-d]pyrimidin-8(7H)-yl)benzamide (87) | |
| 88 | N-benzyl-4-(2-[(2-methoxyethyl)amino]-4-methyl-7-oxopyrido[2,3-d]pyrimidin-8(7H)-yl)benzamide (88) | |
| 89 | 4-(2-[(2-methoxyethyl)amino]-4-methyl-7-oxopyrido[2,3-d]pyrimidin-8(7H)-yl)-N-(2-phenylethyl)benzamide (89) | |
| 90 | N-isobutyl-4-(2-[(2-methoxyethyl)amino]-4-methyl-7-oxopyrido[2,3-d]pyrimidin-8(7H)-yl)benzamide (90) | 0.89 (d, j = 6.2 Hz, 6H); 1.85 (m, 1H); 2.97 (s, 3H); 3.10 (m, 2H); 7.61 (bs, 1H); 8.51 (t, j = 5.7 Hz, 1H) |
| 91 | 4-(2-[(2-methoxyethyl)amino]-4-methyl-7-oxopyrido[2,3-d]pyrimidin-8(7H)-yl)-N-(tetrahydro-2-furanylmethyl)benzamide (91) | 8.59 (t, j = 5.7, 1H); 7.62 (bs, 1H); 3.98 (m, 1H); 3.77 (m, 1H); 3.62 (m, 1H); 3.33 (m, 2H); 2.98 (s, 3H); 2.0–1.5 (m, 4H) |
| 92 | N-(cyclohexylmethyl)-4-(2-[(2-methoxyethyl)amino]-4-methyl-7-oxopyrido[2,3-d]pyrimidin-8(7H)-yl)benzamide (92) | 0.7–1.8 (m, 11H); 2.98 (s, 3H); 3.12 (m, 2H); 7.61 (bs, 1H); 8.48 (t, j = 5.7 Hz, 1H) |
| 93 | N-cyclopropyl-4-(2-[(2-furylmethyl)amino]-4-methyl-7-oxopyrido[2,3-d]pyrimidin-8(7H)-yl)benzamide (93) | |
| 94 | 4-(2-[(2-furylmethyl)amino]-4-methyl-7-oxopyrido[2,3-d]pyrimidin-8(7H)-yl)-N-octylbenzamide (94) | |
| 95 | N-(2-furylmethyl)-4-(2-[(2-furylmethyl)amino]-4-methyl-7-oxopyrido[2,3-d]pyrimidin-8(7H)-yl)benzamide (95) | |
| 96 | N-(3,4-dimethoxyphenyl)-4-(2-[(2-furylmethyl)amino]-4-methyl-7-oxopyrido[2,3-d]pyrimidin-8(7H)-yl)benzamide (96) | |
| 97 | N-benzyl-4-(2-[(2-furylmethyl)amino]-4-methyl-7-oxopyrido[2,3-d]pyrimidin-8(7H)-yl)benzamide (97) | |
| 98 | 4-(2-[(2-furylmethyl)amino]-4-methyl-7-oxopyrido[2,3-d]pyrimidin-8(7H)-yl)-N-(tetrahydro-2-furanylmethyl)benzamide (98) | 1.5–2.0 (m, 4H); 3.62 (m, 1H); 3.77 (m, 1H); 3.98 (m, 1H), 7.96 (bs, 1H); 8.61 (bs, 1H) |
| 99 | N-(cyclohexylmethyl)-4-(2-[(2-furylmethyl)amino]-4-methyl-7-oxopyrido[2,3-d]pyrimidin-8(7H)-yl)benzamide (99) | 0.7–1.8 (m, 11H) 3.12 (t, 2H) 3.98 (d, j = 5.7 Hz, 2H); 7.96 (bs, 1H); 8.49 (t, j = 5.7 Hz, 1H) |
| 100 | N-cyclopropyl-4-(2-[(2-ethylhexyl)amino]-4-methyl-7- | 0.55 (t, j = 7.1 Hz, 3H); |

-continued

| N° | Compound Name | 1H-NMR (400 Mhz, DMSO-d6), ppm |
|---|---|---|
| | oxopyrido[2,3-d]pyrimidin-8(7H)-yl)benzamide (100) | 0.55 (m, 2H); 0.70 (m, 2H); 0.78 (t, j = 7.1 Hz, 3H); 2.85 (m, 1H); 7.70 (t, j = 5.8 Hz, 1H); 8.45 (d, j = 4.2 Hz, 1H) |
| 101 | N-benzyl-4-(2-[(2-ethylhexyl)amino]-4-methyl-7-oxopyrido[2,3-d]pyrimidin-8(7H)-yl)benzamide (101) | 0.53 (t, j = 7.1 Hz, 3H); 0.75 (t, j = 7.1 Hz, 3H); 2.73 (t, J = 5.9 Hz, 2H); 4.50 (d, j = 5.9 Hz, 2H); 7.1–7.4 (m, 5H); 7.70 (t, j = 5.9 Hz, 1H) 9.08 (t, j = 5.9 Hz, 1H) |
| 102 | 4-(2-[(2-ethylhexyl)amino]-4-methyl-7-oxopyrido[2,3-d]pyrimidin-8(7H)-yl)-N-(2-furylmethyl)benzamide (102) | 0.52 (t, j = 7.1 Hz, 3H) 0.74 (t, j = 7.1 Hz, 3H); 4.47 (m, 2H); 6.25 (m, 1H); 6.39 (m, 1H); 7.55 (m, 1H); 7.69 (t, j = 5.6 Hz, 1H); 9.0 (t, j = 5.7 Hz, 1H) |
| 103 | N-(3,4-dimethoxyphenyl)-4-(2-[(2-ethylhexyl)amino]-4-methyl-7-oxopyrido[2,3-d]pyrimidin-8(7H)-yl)benzamide (103) | 0.57 (t, j = 7.1 Hz, 3H); 0.73 (t, j = 7.1 Hz, 3H); 3.73 (s, 3H); 3.74 (s, 3H) 6.93 (d, j = 8.8 Hz, 1H) 7.33 (dd, j = 2.2, 8.8 Hz, 1H); 7.47 (d, j = 2.2 Hz, 1H); 7.72 (t, j = 5.6 Hz, 1H); 10.10 (s, 1H) |
| 104 | 4-(2-[(2-ethylhexyl)amino]-4-methyl-7-oxopyrido[2,3-d]pyrimidin-8(7H)-yl)-N-isobutylbenzamide (104) | 0.54 (t, j = 7.1 Hz, 3H); 0.76 (t, j = 7.1 Hz, 3H); 0.89 (d, j = 7.3 Hz, 6H); 1.85 (m, 1H); 3.09 (m, 2H); 7.72 (t, j = 5.9 Hz, 1H); 8.48 (t, j = 5.6 Hz, 1H) |
| 105 | N-(cyclohexylmethyl)-4-(2-[(2-ethylhexyl)amino]-4-methyl-7-oxopyrido[2,3-d]pyrimidin-8(7H)-yl)benzamide (105) | 0.54 (t, j = 7.1 Hz, 3H); 0.76 (t, j = 7.1 Hz, 3H); 2.72 (m, 2H); 3.12 (m, 2H); 7.68 (t, j = 5.8 Hz, 1H); 8.45 (t, j = 5.6 Hz, 1H) |
| 106 | 4-(2-{[2-(acetylamino)ethyl]amino}-4-methyl-7-oxopyrido[2,3-d]pyrimidin-8(7H)-yl)-N-cyclopropylbenzamide (106) | 0.58 (m, 2H); 0.70 (m, 2H); 1.73 (s, 3H); 2.85 (m, 1H); 7.54 (bs, 1H); 8.49 bs, 1H) |
| 107 | 4-(2-{[2-(acetylamino)ethyl]amino}-4-methyl-7-oxopyrido[2,3-d]pyrimidin-8(7H)-yl)-N-octylbenzamide (107) | |
| 108 | 4-(2-{[2-(acetylamino)ethyl]amino}-4-methyl-7-oxopyrido[2,3-d]pyrimidin-8(7H)-yl)-N-(2-furylmethyl)benzamide (108) | 1.72 (s, 3H); 4.48 (d, j = 5.7 Hz, 2H); 6.28 (m, 1H); 6.39 (m, 1H); 7.54 (bs, 1H); 7.57 (m, 1H); 9.03 (t, j = 5.7 Hz, 1H) |
| 109 | 4-(2-{[2-(acetylamino)ethyl]amino}-4-methyl-7-oxopyrido[2,3-d]pyrimidin-8(7H)-yl)-N-(3,4-dimethoxyphenyl)benzamide (109) | |
| 110 | 4-(2-{[2-(acetylamino)ethyl]amino}-4-methyl-7-oxopyrido[2,3-d]pyrimidin-8(7H)-yl)-N-benzylbenzamide (110) | 1.72 (s, 3H); 4.50 (d, j = 5.7 Hz, 2H); 7.2–7.4 (m, 5H); 7.55 (bs, 1H) 9.11 (t, j = 5.7 Hz, 1H) |
| 111 | 4-(2-{[2-(acetylamino)ethyl]amino}-4-methyl-7-oxopyrido[2,3-d]pyrimidin-8(7H)-yl)-N-(2-phenylethyl)benzamide (111) | 1.73 (s, 3H); 2.86 (t, 2H); 3.50 (m, 2H); 7.27 (m, 5H); 7.55 (bs, 1H); 8.62 (bs, 1H) |
| 112 | 4-(2-{[2-(acetylamino)ethyl]amino}-4-methyl-7-oxopyrido[2,3-d]pyrimidin-8(7H)-yl)-N-isobutylbenzamide (112) | 0.90 (d, j = 6.7 Hz, 6H); 1.73 (s, 3H); 1.85 (m, 1H); 3.10 (t, j = 5.7 Hz, 2H); 7.55 (bs, 1H); 8.52 (t, j = 5.7 Hz) |
| 113 | 4-(2-{[2-(acetylamino)ethyl]amino}-4-methyl-7-oxopyrido[2,3-d]pyrimidin-8(7H)-yl)-N-(cyclohexylmethyl)benzamide (113) | 0.7–1.8 (m, 11H); 1.73 (s, 3H); 3.12 (m, 2H); 7.55 (bs, 1H); 8.49 (t, j = 5.7 Hz, 1H) |
| 114 | 4-(2-(benzylamino)-4-methyl-7-oxopyrido[2,3-d]pyrimidin-(7H)-yl)-N-cyclopropylbenzamide (114) | 0.58 (m, 2H); 0.70 (m, 2H); 2.87 (m, 1H); 3.95 (d, j = 6.0 Hz, 2H); 7.0–7.3 (m, 5H); 8.24 (t, j = 6.0 Hz, 1H); 8.52 (d, j = 4 Hz, 1H) |
| 115 | 4-(2-(benzylamino)-4-methyl-7-oxopyrido[2,3-d]pyrimidin-8(7H)-yl)-N-octylbenzamide (115) | 0.7–1.6 (m, 15H); 3.95 (d, j = 5.6 Hz, 2H); 7.0–7.3 (m, 5H); 8.25 (t, j = 5.6 Hz, 1H); 8.52 (bs, 1H) |
| 116 | 4-(2-(benzylamino)-4-methyl-7-oxopyrido[2,3-d]pyrimidin-8(7H)-yl)-N-(2-furylmethyl)benzamide (116) | |
| 117 | 4-(2-(benzylamino)-4-methyl-7-oxopyrido[2,3-d]pyrimidin-8(7H)-yl)-N-(3,4-dimethoxyphenyl)benzamide (117) | 3.73 (s, 3H); 3.75 (s, 3H); 3.98 (d, j = 5.6 Hz, 2H); 6.8 (m, 1H); 7.10/m, 1H); 7.5 (m, 1H); 8.26 (t, j = 5.6 Hz, 1H); 10.19 (s, 1H) |
| 118 | N-benzyl-4-(2-(benzylamino)-4-methyl-7-oxopyrido[2,3-d]pyrimidin-8(7H)-yl)benzamide (118) | 3.95 (d, j = 5.7 Hz, 2H); 4.51 (d, j = 5.9 Hz, 2H); 7.0–7.3 (m, 10H); 8.26 (t, 5.9 Hz, 1H); 9.15 (t, j = 5.7 Hz, 1H) |
| 119 | 4-(2-(benzylamino)-4-methyl-7-oxopyrido[2,3-d]pyrimidin-8(7H)-yl)- | 3.51 (m, 2H); 3.95 (d, j = 6.0 |

-continued

| N° | Compound Name | 1H-NMR (400 Mhz, DMSO-d6), ppm |
|---|---|---|
| | N-(2-phenylethyl)benzamide (119) | Hz, 2H); 8.25 (t, j = 6.0 Hz, 1H); 8.66 (t, j = 5.6 Hz, 1H); |
| 120 | 4-(2-(benzylamino)-4-methyl-7-oxopyrido[2,3-d]pyrimidin-8(7H)-yl)-N-(tetrahydro-2-furanylmethyl)benzamide (120) | 3.62 (m, 1H); 3.77 (m, 1H); 3.98 (m, 2H); 7.10 (m, 2H); 8.63 (t, j = 5.6 Hz, 1H); |
| 121 | 4-(2-(benzylamino)-4-methyl-7 oxopyrido[2,3-d]pyrimidin-8(7H)-yl)-N-(cyclohexylmethyl)benzamide (121) | 0.8–1.8 (m, 11H,); 3.95 (d, j = 6.1 Hz, 2H); 7.10 (m, 2H); 8.23 (t, j = 6.1 Hz, 1H); 8.55 (t, j = 5.6 Hz, 1H); |
| 122 | 4-(2-[(2-aminoethyl)amino]-4-methyl-7-oxopyrido[2,3-d]pyrimidin-8(7H)-yl)-N-cyclopropylbenzamide (122) | 2.55 (m, 2H); 2.86 (m, 1H); 2.9–3.1 (m, 2H); 8.48 (bs, 1H) |
| 123 | 4-(2-[(2-aminoethyl)amino]-4-methyl-7-oxopyrido[2,3-d]pyrimidin-8(7H)-yl)-N-octylbenzamide (123) | 0.85 (t, j = 7.0 Hz, 3H); 2.55 (m, 2H); 2.8–3.1 (m, 2H); 8.48 (t, j = 5.6 Hz, 1H) |
| 124 | 4-(2-[(2-aminoethyl)amino]-4-methyl-7-oxopyrido[2,3-d]pyrimidin-8(7H)-yl)-N-(3,4-dimethoxyphenyl)benzamide (124) | 2.55 (m, 2H); 3.73 (s, 3H); 3.75 (s, 3H); 7.34 (dd, j = 8.8, 2.3 Hz, 1H); 10.2 (bs, 1H); |
| 125 | 4-(2-[(2-aminoethyl)amino]-4-methyl-7-oxopyrido[2,3-d]pyrimidin-8(7H)-yl)-N-benzylbenzamide (125) | 2.55 (m, 2H); 2.8–3.1 (m, 2H); 4.50 (d, j = 6.0 Hz, 2H); 9.1 (bs, 1H); |
| 126 | 4-(2-[(2-aminoethyl)amino]-4-methyl-7-oxopyrido[2,3-d]pyrimidin-8(7H)-yl)-N-(2-phenylethyl)benzamide (126) | 2.55 (m, 2H); 2.86 (t, j = 7.3 Hz, 2H); 2.9–3.5 (m, 4H); 8.6 (t, j = 5.6 Hz, 1H); |
| 127 | 4-(2-[(2-aminoethyl)amino]-4-methyl-7-oxopyrido[2,3-d]pyrimidin-8(7H)-yl)-N-isobutylbenzamide (127) | 0.90 (d, j = 6.6 Hz, 6H); 1.86 (m, 1H); 2.55 (m, 2H); 2.8–3.2 (m, 4H) |
| 128 | N-cyclopropyl-4-(4-methyl-7-oxo-2-[4-(2-pyrimidinyl)-1-piperazinyl]pyrido[2,3-d]pyrimidin-8(7H)-yl)benzamide (128) | 2.86 (m, 1H); 3.65 (bs, 4H); 6.62 (t, j = 4.7 Hz, 1H) |
| 129 | 4-(2-[(2-aminoethyl)amino-4-methyl-7-oxopyrido[2,3-d]pyrimidin-8(7H)-yl)-N-(cyclohexylmethyl)benzamide (129) | 0.8–1.8 (m, 11H); 3.13 (m, 2H); 7.3 (bs, 1H); 7.4–7.8 (bs, 1H); 8.5 (bs, 1H) |
| 130 | 4-(4-methyl-7-oxo-2-[4-(2-pyrimidinyl)-1-piperazinyl]pyrido[2,3-d]pyrimidin-8(7H)-yl)-N-octylbenzamide (130) | 0.8–1.6 (m, 15H); 3.33 (bs, 2H); 3.66 (bs, 2H); 6.62 (t, j = 4.9 Hz, 1H); 8.33 (d, j = 4.9 Hz, 2H); 8.52 (t, j = 5.9 Hz, 1H) |
| 131 | N-(3,4-dimethoxyphenyl)-4-(4-methyl-7-oxo-2-[4-(2-pyrimidinyl)-1-piperazinyl]pyrido[2,3-d]pyrimidin-8(7H)-yl)benzamide (131) | 3.33 (bs, 2H); 3.68 (bs, 2H); 3.74 (s, 3H); 3.76 (s, 3H); 6.61 (t, j = 4.7 Hz, 1H); 6.9 (d, j = 9 Hz, 1H); 7.36 (dd, j = 2.2, 9.0 Hz, 1H); 7.5 (d, j = 2.2 Hz, 1H); 8.32 (d, j = 4.7 Hz, 2H); 10.2 (s, 1H) |
| 132 | 4-(4-methyl-7-oxo-2-[4-(2-pyrimidinyl)-1-piperazinyl]pyrido[2,3-d]pyrimidin-8(7H)-yl)-N-(2-phenylethyl)benzamide (132) | 2.98 (m, 2H); 3.30 (bs, 2H); 3.51 (m, 2H); 3.67 (bs, 2H); 6.62 (t, j = 4.7 Hz, 1H); 7.1–7.4 (m, 5H); 8.34 (d, j = 4.7 Hz, 2H); 8.65 (t, j = 6.0 Hz, 1H) |
| 133 | N-isobutyl-4-(4-methyl-7-oxo-2-[4-(2-pyrimidinyl)-1-piperazinyl]pyrido[2,3-d]pyrimidin-8(7H)-yl)benzamide (133) | 0.92 (d, j= 6.7 Hz, 6H); 1.88 (m, 1H); 3.12 (m, 2H); 3.30 (bs, 2H); 3.66 (bs, 2H); 6.62 (t, j = 4.7 Hz, 1H); 8.33 (d, j = 4.7 Hz, 2H); 8.54 (t, j = 5.8 Hz, 1H) |
| 134 | 4-(4-methyl-7-oxo-2-[4-(2-pyrimidinyl)-1-piperazinyl]pyrido[2,3-d]pyrimidin-8(7H)-yl)-N-(tetrahydro-2-furanylmethyl)benzamide (134) | |
| 135 | N-(cyclohexylmethyl)-4-(4-methyl-7-oxo-2-[4-(2-pyrimidinyl)-1-piperazinyl]pyrido[2,3-d]pyrimidin-8(7H)-yl)benzamide (135) | |
| 136 | N-cyclopropyl-4-(4-methyl-7-oxo-2-(1-piperazinyl)pyrido[2,3-d]pyrimidin-8(7H)-yl)benzamide (136) | |
| 137 | 4-(4-methyl-7-oxo-2-(1-piperazinyl)pyrido[2,3-d]pyrimidin-8(7H)-yl)-N-octylbenzamide (137) | 0.85 (t, 3H); 1.26, 1.53 (m, 12H); 2.9 (m, 4H); 3.3 (m, 4H); 8.53 (t, j = 5.6 Hz, 1H 8.67 (bs, 1H) |
| 138 | N-(2-furylmethyl)-4-(4-methyl-7-oxo-2-(1-piperazinyl)pyrido[2,3-d]pyrimidin-8(7H)-yl)benzamide (138) | |
| 139 | N-(3,4-dimethoxyphenyl)-4-(4-methyl-7-oxo-2-(1-piperazinyl)pyrido[2,3-d]pyrimidin-8(7H)-yl)benzamide (139) | 3.74 (s, 3H); 3.74 (s, 3H); 6.93 (d, j = 8.4 Hz, 1H); 7.34 (dd, j = 2.6, 8.4 Hz, 1H); 7.48 (d, j = 2.6 Hz); 10.19 (s, 1H) |
| 141 | 4-(4-methyl-7-oxo-2-(1-piperazinyl)pyrido[2,3-d]pyrimidin-8(7H)-yl)-N-(2-phenylethyl)benzamide (141) | 2.86 (m, 2H); 3.04 (m, 4H); 3.50 (m, 2H); 7.1–7.4 (m, 5H); 8.66 (t, j = 5.6 Hz, 1H); 8.74 (bs, 1H) |
| 142 | N-isobutyl-4-(4-methyl-7-oxo-2-(1-piperazinyl)pyrido[2,3-d]pyrimidin-8(7H)-yl)benzamide (142) | 0.90 (d, j = 6.6 Hz, 6H); 1.86 (m, 1H); 3.04 (m, 4H); 3.10 (m, 2H); 3.3–3.7 (m, 4H); 8.54 (t, j = 5.6 Hz, 1H); 8.74 (bs, 1H) |

-continued

| N° | Compound Name | 1H-NMR (400 Mhz, DMSO-d6), ppm |
|---|---|---|
| 143 | 4-(4-methyl-7-oxo-2-(1-piperazinyl)pyrido[2,3-d]pyrimidin-8(7H)-yl)-N-(tetrahydro-2-furanylmethyl)benzamide (143) | 1.5–2.0 (m, 4H); 3.04 (m, 4H); 3.3 (m, 4H); 3.63 (m, 2H); 3.77 (m, 2H); 3.99 (m, 1H); 8.62 (t, j = 5.6 Hz, 1H); 8.73 (bs, 1H) |
| 144 | N-(cyclohexylmethyl)-4-(4-methyl-7-oxo-2-(1-piperazinyl)pyrido[2,3-d]pyrimidin-8(7H)-yl)benzamide (144) | 0.8–1.8 (m, 11H); 3.04 (bs, 4H); 3.12 (t, j = 6.0 Hz, 2H); 3.3–3.7 (m, 4H); 8.51 (t, j = 6.0 Hz, 1H); 8.73 (bs, 1H) |
| 145 | 4-(2-(allylamino)-4-methyl-7-oxopyrido[2,3-d]pyrimidin-8(7H)-yl)-N-cyclopropylbenzamide (145) | |
| 146 | 4-(2-(allylamino)-4-methyl-7-oxopyrido[2,3-d]pyrimidin-8(7H)-yl)-N-octylbenzamide (146) | |
| 147 | 4-(2-(allylamino)-4-methyl-7-oxopyrido[2,3-d]pyrimidin-8(7H)-yl)-N-(2-furylmethyl)benzamide (147) | |
| 148 | 4-(2-(allylamino)-4-methyl-7-oxopyrido[2,3-d]pyrimidin-8(7H)-yl)-N-(3,4-dimethoxyphenyl)benzamide (148) | 3.73 (s, 3H); 3.75 (s, 3H); 4.7–5.1 (bs, 2H); 5.5–5.9 (bs, 1H); 6.93 (d, j = 8.8 Hz, 1H); 7.8 (bs, 1H); 10.17 (s, 1H); |
| 149 | 4-(2-(allylamino)-4-methyl-7-oxopyrido[2,3-d]pyrimidin-8(7H)-yl)-N-benzylbenzamide (149) | 4.50 (d, j = 6.0 Hz, 2H); 4.6–5.1 (bs, 2H); 5.4–5.9 (bs, 1H); 7.79 (bs, 1H); 9.11 (t, j = 6.0 Hz, 1H); |
| 150 | 4-(2-(allylamino)-4-methyl-7-oxopyrido[2,3-d]pyrimidin-8(7H)-yl)-N-(2-phenylethyl)benzamide (150) | 2.86 (t, j = 7.2 Hz, 2H); 3.50 (m, 2H); 4.6–5.1 (bs, 2H); 5.4–5.9 (bs, 1H); 7.78 (bs, 1H); 8.62 (t, j = 5.5 Hz, 1H); |
| 151 | 4-(2-(allylamino)-4-methyl-7-oxopyrido[2,3-d]pyrimidin-8(7H)-yl)-N-isobutylbenzamide (151) | 0.89 (d, j = 6.7 Hz, 6H); 3.10 (dd, j = 5.8, 6.8 Hz, 2H); 4.6–5.1 (bs, 2H); 5.4–5.9 (bs, 1H); 7.78 (bs, 1H); 8.51 (t, j = 5.8 Hz, 1H); |
| 152 | 4-(2-(allylamino)-4-methyl-7-oxopyrido[2,3-d]pyrimidin-8(7H)-yl)-N-(tetrahydro-2-furanylmethyl)benzamide (152) | 3.62 (m, 1H); 3.77 (m, 1H); 3.99 (m, 1H); 4.6–5.1 (bs, 2H); 5.4–5.9 (bs, 1H); 7.78 (bs, 1H); 8.59 (t, j = 5.9 Hz, 1H); |
| 153 | 4-(2-(allylamino)-4-methyl-7-oxopyrido[2,3-d]pyrimidin-8(7H)-yl)-N-(cyclohexylmethyl)benzamide (153) | 3.12 (m, 2H); 4.6–5.1 (bs, 2H); 5.4–5.9 (bs, 1H); 7.78 (bs, 1H); 8.49 (d, j = 5.8 Hz, 1H); |
| 154 | N-cyclopropyl-4-(4-methyl-7-oxo-2-(1-pyrrolidinyl)pyrido[2,3-d]pyrimidin-8(7H)-yl)benzamide (154) | 1.6–1.9 (m, 4H); 2.87 (m, 1H); 2.96 (m, 2H); 8.51 (d, j = 4.1 Hz, 1H); |
| 155 | 4-(4-methyl-7-oxo-2-(1-pyrrolidinyl)pyrido[2,3-d]pyrimidin-8(7H)-yl)-N-octylbenzamide (155) | 0.85 (t, j = 7.0 Hz, 3H); 2.96 (m, 2H); 3.46 (m, 2H); 3.3 (m, 2H); 8.50 (t, j = 5.6 Hz, 1H); |
| 156 | N-(2-furylmethyl)-4-(4-methyl-7-oxo-2-(1-pyrrolidinyl)pyrido[2,3-d]pyrimidin-8(7H)-yl)benzamide (156) | 1.6–1.9 (m, 4H); 4.48 (d, j = 5.6 Hz, 2H); 6.39 (dd, j = 1.8, 3.2, 1H); 9.04 (t, j = 5.6 Hz, 1H); |
| 157 | N-(3,4-dimethoxyphenyl)-4-(4-methyl-7-oxo-2-(1-pyrroladinyl)pyrido[2,3-d]pyrimidin-8(7H)-yl)benzamide (157) | 2.99 (m, 2H); 3.48 (m, 2H); 3.73 (s, 3H); 3.75 (s, 3H); 6.93 (d, j = 8.8 Hz, 1H); 10.18 (s, 1H); |
| 158 | N-benzyl-4-(4-methyl-7-oxo-2-(1-pyrrolidinyl)pyrido[2,3-d]pyrimidin-8(7H)-yl)benzamide (158) | 2.97 (m, 2H); 3.46 (m, 2H); 4.50 (d, j = 6.0 Hz, 2H); 9.10 (t, j = 6.0 Hz, 1H); |
| 159 | 4-(4-methyl-7-oxo-2-(1-pyrrolidinyl)pyrido[2,3-d]pyrimidin-8(7H)-yl)-N-(2-phenylethyl)benzamide (159) | 2.96 (m, 2H); 2.87 (t, j = 7.4 Hz, 2H); 3.50 (m, 4H); 8.64 (t, j = 5.5 Hz, 1H); |
| 160 | N-isobutyl-4-(4-methyl-7-oxo-2-(1-pyrrolidinyl)pyrido[2,3-d]pyrimidin-8(7H)-yl)benzamide (160) | 0.90 (d, j = 6.7 Hz, 6H); 2.97 (m, 2H); 3.10 (dd, j = 5.9, 6.9 Hz, 2H); 3.47 (m, 2H); 8.52 (t, j = 5.9 Hz, 1H); |
| 161 | 4-(4-methyl-7-oxo-2-(1-pyrrolidinyl)pyrido[2,3-d]pyrimidin-8(7H)-yl)-N-(tetrahydro-2-furanylmethyl)benzamide (161) | 2.96 (m, 2H); 3.47 (m, 2H); 3.63 (m, 1H); 3.78 (m, 1H); 4.00 (m, 1H); 8.61 (t, j = 5.8 Hz, 1H); |
| 162 | N-(cyclohexylmethyl)-4-(4-methyl-7-oxo-2-(1-pyrrolidinyl)pyrido[2,3-d]pyrimidin-8(7H)-yl)benzamide (162) | 0.8–2.0 (m, 15H); 2.96 (m, 2H); 3.47 (m, 2H); 8.49 (t, j = 5.8 Hz, 1H); |
| 163 | N-benzyl-4-(2-{[2-(2-methoxyphenyl)ethyl]amino}-4-methyl-7-oxopyrido[2,3-d]pyrimidin-8(7H)-yl)benzamide (163) | 3.66 (s, 3H); 4.52 (d, j = 6.0 Hz, 2H); 6.58 (t, j = 7.3 Hz, 1H); 7.77 (t, j = 5.5 Hz, 1H); 9.13 (t, j = 6.0 Hz, 1H); |
| 164 | N-cyclopropyl-4-(2-[(2-hydroxyethyl)amino]-4-methyl-7-oxopyrido[2,3-d]pyrimidin-8(7H)-yl)benzamide (164) | 2.86 (m, 1H); 2.9–3.4 (m, 4H); 8.49 (d, j = 4.2 Hz, 1H); |
| 165 | 4-(2-[(2-hydroxyethyl)amino]-4-methyl-7-oxopyrido[2,3-d]pyrimidin-8(7H)-yl)-N-octylbenzamide (165) | 0.85 (t, j = 7.0 Hz, 3H); 2.9–3.4 (m, 6H); 8.49 (t, j = 5.6 Hz, 1H); |
| 166 | N-(2-furylmethyl)-4-(2-[(2-hydroxyethyl)amino]-4-methyl-7-oxopyrido[2,3-d]pyrimidin-8(7H)-yl)benzamide (166) | 2.9–3.4 (m, 4H); 4.48 (d, j = 5.9 Hz, 2H); 7.56 (dd, j = 1.8, 0.9, 1H); 9.03 |

| N° | Compound Name | 1H-NMR (400 Mhz, DMSO-d6), ppm |
|---|---|---|
| 167 | N-(3,4-dimethoxyphenyl)-4-(2-[(2-hydroxyethyl)amino]-4-methyl-7-oxopyrido[2,3-d]pyrimidin-8(7H)-yl)benzamide (167) | (t, j = 5.9 Hz, 1H); 2.9–3.4 (m, 4H); 3.73 (s, 3H); 3.75 (s, 3H); 6.93 (d, j = 8.8 Hz, 1H); 10.17 (s, 1H); |
| 168 | N-benzyl-4-(2-[(2-hydroxyethyl)amino]-4-methyl-7-oxopyrido[2,3-d]pyrimidin-8(7H)-yl)benzamide (168) | 3.1–3.5 (m, 4H); 4.50 (d, j = 5.9 Hz, 2H); 9.11 (t, j = 5.9 Hz, 1H); |
| 169 | 4-(2-[(2-hydroxyethyl)amino]-4-methyl-7-oxopyrido[2,3-d]pyrimidin-8(7H)-yl)-N-(2-phenylethyl)benzamide (169) | 2.9–3.4 (m, 4H); 2.86 (t, j = 7.1 Hz, 2H); 3.50 (m, 2H); 8.63 (bs, 1H); |
| 170 | 4-(2-[(2-hydroxyethyl)amino]-4-methyl-7-oxopyrido[2,3-d]pyrimidin-8(7H)-yl)-N-isobutylbenzamide (170) | 0.90 (d, j = 6.7 Hz, 6H); 1.86 (m, 1H); 3.10 (dd, j = 5.9, 6.9 Hz, 2H); 8.52 (t, j = 5.9 Hz, 1H); |
| 171 | N-(cyclohexylmethyl)-4-(2-[(2-hydroxyethyl)amino]-4-methyl-7-oxopyrido[2,3-d]pyrimidin-8(7H)-yl)benzamide (171) | 0.8–1.8 (m, 11H); 2.9–3.4 (m, 6H); 8.48 (t, j = 5.9 Hz, 1H); |
| 172 | N-cyclopropyl-4-(2-{[2-(2-methoxyphenyl)ethyl]amino}-4-methyl-7-oxopyrido[2,3-d]pyrimidin-8(7H)-yl)benzamide (172) | 0.5–0.8 (m, 4H); 3.68 (s, 3H); 6.68 (t, j = 7.3 Hz, 1H); 7.77 (t, j = 5.9 Hz, 1H); 8.51 (d, j = 4.0 Hz, 1H); |
| 173 | 4-(2-{[2-(2-methoxyphenyl)ethyl]amino}-4-methyl-7-oxopyrido[2,3-d]pyrimidin-8(7H)-yl)-N-octylbenzamide (173) | 0.85 (t, j = 7.1 Hz, 3H); 3.67 (s, 3H); 6.68 (t, j = 7.4 Hz, 1H); 7.77 (t, j = 6.0 Hz, 1H); 8.52 (t, j = 5.8 Hz, 1H); |
| 174 | N-(3,4-dimethoxyphenyl)-4-(2-{[2-(2-methoxyphenyl)ethyl]amino}-4-methyl-7-oxopyrido[2,3-d]pyrimidin-8(7H)-yl)benzamide (174) | 3.68 (s, 3H); 3.75 (s, 3H); 3.76 (s, 3H); 6.68 (t, j = 7.4 Hz, 1H); 7.78 (t, j = 6.0 Hz, 1H); 10.16 (s, 1H) |
| 175 | 4-(2-{[2-(2-methoxyphenyl)ethyl]amino}-4-methyl-7-oxopyrido[2,3-d]pyrimidin-8(7H)-yl)-N-(2-phenylethyl)benzamide (175) | 2.87 (m, 2H); 3.50 (m, 2H); 3.67 (s, 3H); 6.69 (t, j = 7.4 Hz, 1H); 7.75 (t, j = 6.0 Hz, 1H); 8.66 (t, j = 5.6 Hz, 1H) |
| 176 | N-isobutyl-4-(2-{[2-(2-methoxyphenyl)ethyl]amino}-4-methyl-7-oxopyrido[2,3-d]pyrimidin-8(7H)-yl)benzamide (176) | 0.91 (d, j = 6.6 Hz, 6H); 3.67 (s, 3H); 6.68 (t, j = 7.4 Hz, 1H); 7.77 (t, j = 5.9 Hz, 1H); 8.54 (t, j = 5.7 Hz, 1H) |
| 177 | 4-(2-{[2-(2-methoxyphenyl)ethyl]amino}-4-methyl-7-oxopyrido[2,3-d]pyrimidin-8(7H)-yl)-N-(tetrahydro-2-furanylmethyl)benzamide (177) | 3.64 (m, 1H); 3.78 (s, 3H); 4.01 (m, 1H); 6.70 (t, j = 7.4 Hz, 1H); 7.76 (t, j = 5.9 Hz, 1H); 8.62 (t, j = 5.7 Hz, 1H); |
| 178 | N-(cyclohexylmethyl)-4-(2-{[2-(2-methoxyphenyl)ethyl]amino}-4-methyl-7-oxopyrido[2,3-d]pyrimidin-8(7H)-yl)benzamide (178) | 0.8–1.8 (m, 11H,); 3.67 (s, 3H); 6.37 (d, j = 7.5 Hz, 1H); 7.77 (t, j = 5.6 Hz, 1H); 8.52 (t, j = 5.8 Hz, 1H); |
| 179 | (2S)-1-(8-{4-[(cyclopropylamino)carbonyl]phenyl}-4-methyl-7-oxo-7,8-dihydropyrido[2,3-d]pyrimidin-2-yl)-2-pyrrolidinecarboxylic acid (179) | two rotational isomers are present: 2.86 (m, 1H); 3.87 (dd, j = 3.1, 8.4 Hz, 0.5H); 4.43 (dd, j = 3.8, 8.7 Hz, 0.5H); 8.33 (d, j = 4.4 Hz, 0.5H); 8.52 (d, j = 4.4 Hz, 0.5H); |
| 180 | (2S)-1-(4-methyl-8-{4-[(octylamino)carbonyl]phenyl}-7-oxo-7,8-dihydropyrido[2,3-d]pyrimidin-2-yl)-2-pyrrolidinecarboxylic acid (180) | two rotational isomers are present: 0.85 (t, j = 7.0 Hz, 3H); 3.26 (m, 2H); 3.88 (dd, j = 3.8, 8.7 Hz, 0.5H); 4.43 (dd, j = 3.8, 8.7 Hz, 0.5H); 8.32 (t, j = 5.6 Hz, 0.5H); 8.51 (t, j = 5.6 Hz, 1H) |
| 181 | (2S)-1-[8-(4-{[(2-furylmethyl)amino]carbonyl}phenyl)-4-methyl-7-oxo-7,8-dihydropyrido[2,3-d]pyrimidin-2-yl]-2-pyrrolidinecarboxylic acid (181) | |
| 182 | (2S)-1-(8-{4-[(3,4-dimethoxyamino)carbonyl]phenyl}-4-methyl-7-oxo-7,8-dihydropyrido[2,3-d]pyrimidin-2-yl)-2-pyrrolidinecarboxylic acid (182) | |
| 183 | (2S)-1-(8-{4-[(benzylamino)carbonyl]phenyl}-4-methyl-7-oxo-7,8-dihydropyrido[2,3-d]pyrimidin-2-yl)-2-pyrrolidinecarboxylic acid (183) | |
| 184 | (2S)-1-[4-methyl-7-oxo-8-(4-{[(2-phenylethyl)amino]carbonyl}phenyl)-7,8-dihydropyrido[2,3-d]pyrimidin-2-yl]-2-pyrrolidinecarboxylic acid (184) | |
| 185 | (2S)-1-(8-{4-[(isobutylamino)carbonyl]phenyl}-4-methyl-7-oxo-7,8-dihydropyrido[2,3-d]pyrimidin-2-yl)-2-pyrrolidinecarboxylic acid (185) | |
| 186 | (2S)-1-[4-methyl-7-oxo-8-(4-{[(tetrahydro-2-furanylmethyl)amino]carbonyl}phenyl)-7,8-dihydropyrido[2,3-d]pyrimidin-2-yl]2-pyrrolidinecarboxylic acid(186) | |
| 187 | (2S)-1-[8-(4-{[(cyclohexylmethyl)amino]carbonyl}phenyl)-4-methyl-7-oxo-7,8-dihydropyrido[2,3-d]pyrimidin-2-yl]-2-pyrrolidinecarboxylic acid (187) | |
| 188 | N-cyclopropyl-4-(2-{[3-(dimethylamino)propyl]amino}-4-methyl-7-oxopyrido[2,3-d]pyrimidin-8(7H)-yl)benzamide (188) | |
| 189 | 4-(2-{[3-(dimethylamino)propyl]amino}-4-methyl-7-oxopyrido[2,3-d]pyrimidin-8(7H)-yl)-N-octylbenzamide (189) | |

-continued

| N° | Compound Name | 1H-NMR (400 Mhz, DMSO-d6), ppm |
|---|---|---|
| 190 | 4-(2-{[3-(dimethylamino)propyl]amino}-4-methyl-7-oxopyrido[2,3-d]pyrimidin-8(7H)-yl)-N-(2-furylmethyl)benzamide (190) | |
| 191 | N-(3,4-dimethoxyphenyl)-4-(2-{[3-(dimethylamino)propyl]amino}-4-methyl-7-oxopyrido[2,3-d]pyrimidin-8(7H)-yl)benzamide (191) | |
| 192 | N-benzyl-4-(2-{[3-(dimethylamino)propyl]amino}-4-methyl-7-oxopyrido[2,3-d]pyrimidin-8(7H)-yl)benzamide (192) | |
| 193 | 4-(2-{[3-(dimethylamino)propyl]amino}-4-methyl-7-oxopyrido[2,3-d]pyrimidin-8(7H)-yl)-N-(2-phenylethyl)benzamide (193) | |
| 194 | 4-(2-{[3-(dimethylamino)propyl]amino}-4-methyl-7-oxopyrido[2,3-d]pyrimidin-8(7H)-yl)-N-isobutylbenzamide (194) | |
| 195 | 4-(2-{[3-(dimethylamino)propyl]amino}-4-methyl-7-oxopyrido[2,3-d]pyrimidin-8(7H)-yl)-N-(tetrahydro-2-furanylmethyl)benzamide (195) | |
| 196 | N-(cyclohexylmethyl)-4-(2-{[3-(dimethylamino)propyl]amino}-4-methyl-7-oxopyrido[2,3-d]pyrimidin-8(7H)-yl)benzamide (196) | |
| 197 | 4-(2-[(2-ethylhexyl)amino]-4-methyl-7-oxopyrido[2,3-d]pyrimidin-8(7H)-yl)-N-octylbenzamide (197) | |
| 198 | 4-(2-[(2-aminoethyl)amino]-4-methyl-7-oxopyrido[2,3-d]pyrimidin-8(7H)-yl)-N-(tetrahydro-2-furanylmethyl)benzamide (198) | |

| Compound Name | Retention Time (min) |
|---|---|
| 4-[2-(4-Benzyl-piperazin-1-yl)-4-methyl-7-oxo-7H-pyrido[2,3-d]pyrimidin-8-yl]-benzamide; | 2.63 |
| 4-[4-Methyl-7-oxo-2-(4-phenyl-piperazin-1-yl)-7H-pyrido[2,3-d]pyrimidin-8-yl]-benzamide; | 3.2 |
| 4-[4-Methyl-2-(4-methyl-piperazin-1-yl)-7-oxo-7H-pyrido[2,3-d]pyrimidin-8-yl]-benzamide; | 1.35 |
| 4-[8-(4-Carbamoyl-phenyl)-4-methyl-7-oxo-7,8-dihydro-pyrido[2,3-d]pyrimidin-2-yl]-piperazine-1-carboxylic acid ethyl ester; | 2.57 |
| 4-[4-Methyl-7-oxo-2-(4-pyridin-2-yl-piperazin-1-yl)-7H-pyrido[2,3-d]pyrimidin-8-yl]-benzamide; | 2.76 |
| 4-[2-(4-Formyl-piperazin-1-yl)-4-methyl-7-oxo-7H-pyrido[2,3-d]pyrimidin-8-yl]-benzamide; | 1.9 |
| 4-{2-[4-(4-Fluoro-phenyl)-piperazin-1-yl]-4-methyl-7-oxo-7H-pyrido[2,3-d]pyrimidin-8-yl}-benzamide; | 3.28 |
| 4-{2-[4-(4-Hydroxy-phenyl)-piperazin-1-yl]-4-methyl-7-oxo-7H-pyrido[2,3-d]pyrimidin-8-yl}-benzamide; | 2.57 |
| 4-[2-(4-Benzyl-piperazin-1-yl)-4-methyl-7-oxo-7H-pyrido[2,3-d]pyrimidin-8-yl]-N-(3,4-dimethoxy-benzyl)-benzamide; | 3.5 |
| N-(3,4-Dimethoxy-benzyl)-4-[4-methyl-7-oxo-2-(4-phenyl-piperazin-1-yl)-7H-pyrido[2,3-d]pyrimidin-8-yl]-benzamide; | 3.83 |
| N-(3,4-Dimethoxy-benzyl)-4-[4-methyl-2-(4-methyl-piperazin-1-yl)-7-oxo-7H-pyrido[2,3-d]pyrimidin-8-yl]-benzamide; | 2.09 |
| 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid ethyl ester; | 3.21 |
| N-(3,4-Dimethoxy-benzyl)-4-[4-methyl-7-oxo-2-(4-pyridin-2-yl-piperazin-1-yl)-7H-pyrido[2,3-d]pyrimidin-8-yl]-benzamide; | 3.47 |
| N-(3,4-Dimethoxy-benzyl)-4-[2-(4-formyl-piperazin-1-yl)-4-methyl-7-oxo-7H-pyrido[2,3-d]pyrimidin-8-yl]-benzamide; | 2.55 |
| N-(3,4-Dimethoxy-benzyl)-4-{2-[4-(4-fluoro-phenyl)-piperazin-1-yl]-4-methyl-7-oxo-7H-pyrido[2,3-d]pyrimidin-8-yl}-benzamide; | 3.91 |
| N-(3,4-Dimethoxy-benzyl)-4-{2-[4-(4-hydroxy-phenyl)-piperazin-1-yl]-4-methyl-7-oxo-7H-pyrido[2,3-d]pyrimidin-8-yl}-benzamide; | 3.2 |
| N-Benzyl-4-[2-(4-benzyl-piperazin-1-yl)-4-methyl-7-oxo-7H-pyrido[2,3-d]pyrimidin-8-yl]-benzamide | 3.8 |
| N-Benzyl-4-[4-methyl-7-oxo-2-(4-phenyl-piperazin-1-yl)-7H-pyrido[2,3-d]pyrimidin-8-yl]-benzamide; | 4.1 |
| N-Benzyl-4-[4-methyl-2-(4-methyl-piperazin-1-yl)-7-oxo-7H-pyrido[2,3-d]pyrimidin-8-yl]-benzamide; | 2.24 |
| 4-[8-(4-Benzylcarbamoyl-phenyl)-4-methyl-7-oxo-7,8-dihydro-pyrido[2,3-d]pyrimidin-2-yl]-piperazine-1-carboxylic acid ethyl ester; | 3.44 |
| N-Benzyl-4-[4-methyl-7-oxo-2-(4-pyridin-2-yl-piperazin-1-yl)-7H-pyrido[2,3-d]pyrimidin-8-yl]-benzamide; | 3.71 |
| N-Benzyl-4-[2-(4-formyl-piperazin-1-yl)-4-methyl-7-oxo-7H-pyrido[2,3-d]pyrimidin-8-yl]-benzamide; | 2.71 |
| N-Benzyl-4-{2-[4-(4-fluoro-phenyl)-piperazin-1-yl]-4-methyl-7-oxo-7H-pyrido[2,3-d]pyrimidin-8-yl}-benzamide; | 4.16 |
| N-Benzyl-4-{2-[4-(4-hydroxy-phenyl)-piperazin-1-yl]-4-methyl-7-oxo-7H-pyrido[2,3-d]pyrimidin-8-yl}-benzamide; | 3.42 |
| 4-[2-(4-Benzyl-piperazin-1-yl)-4-methyl-7-oxo-7H-pyrido[2,3-d]pyrimidin-8-yl]-N-cyclopropyl-benzamide; | 3.11 |
| N-Cyclopropyl-4-[4-methyl-7-oxo-2-(4-phenyl-piperazin-1-yl)-7H-pyrido[2,3-d]pyrimidin-8-yl]-benzamide; | 3.59 |
| N-Cyclopropyl-4-[4-methyl-2-(4-methyl-piperazin-1-yl)-7-oxo-7H-pyrido[2,3-d]pyrimidin-8-yl]-benzamide; | 1.67 |
| 4-[8-(4-Cyclopropylcarbamoyl-phenyl)-4-methyl-7-oxo-7,8-dihydro-pyrido[2,3-d]pyrimidin-2-yl]-piperazine-1-carboxylic acid ethyl ester; | 2.91 |
| N-Cyclopropyl-4-[4-methyl-7-oxo-2-(4-pyridin-2-yl-piperazin-1-yl)-7H-pyrido[2,3-d]pyrimidin-8-yl]-benzamide; | 3.15 |
| N-Cyclopropyl-4-{2-[4-(4-fluoro-phenyl)-piperazin-1-yl]-4-methyl-7-oxo-7H-pyrido[2,3-d]pyrimidin-8-yl}-benzamide; | 3.68 |
| N-Cyclopropyl-4-{2-[4-(4-hydroxy-phenyl)-piperazin-1-yl]-4-methyl-7-oxo-7H-pyrido[2,3-d]pyrimidin-8-yl}-benzamide; | 2.9 |
| 4-[2-(4-Benzyl-piperazin-1-yl)-4-methyl-7-oxo-7H-pyrido[2,3-d]pyrimidin-8-yl]-N-(4-trifluoromethyl-benzyl)-benzamide; | 4.21 |
| 4-[4-Methyl-7-oxo-2-(4-phenyl-piperazin-1-yl)-7H-pyrido[2,3-d]pyrimidin-8-yl]-N-(4-trifluoromethyl-benzyl)-benzamide; | 4.4 |
| 4-[4-Methyl-2-(4-methyl-piperazin-1-yl)-7-oxo-7H-pyridol[2,3-d]pyrimidin-8-yl]-N-(4-trifluoromethyl-benzyl)-benzamide; | 2.8 |
| 4-{Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid ethyl ester; | 3.81 |
| 4-[4-Methyl-7-oxo-2-(4-pyridin-2-yl-piperazin-1-yl)-7H-pyrido[2,3-d]pyrimidin-8-yl]-N-(4-trifluoromethyl-benzyl)-benzamide; | 4.07 |

| Compound Name | Retention Time (min) |
|---|---|
| 4-[2-(4-Formyl-piperazin-1-yl)-4-methyl-7-oxo-7H-pyrido[2,3-d]pyrimidin-8-yl]-N-(4-trifluoromethyl-benzyl)-benzamide; | 3.15 |
| 4-{2-[4-(4-Hydroxy-phenyl)-piperazin-1-yl]-4-methyl-7-oxo-7H-pyrido[2,3-d]pyrimidin-8-yl}-N-(4-trifluoromethyl-benzyl)-benzamide; | 3.78 |
| 4-({4-[2-(4-Benzyl-piperazin-1-yl)-4-methyl-7-oxo-7H-pyrido[2,3-d]pyrimidin-8-yl]-benzoylamino}-methyl)-benzoic acid methyl ester; | 3.77 |
| 4-({4-[4-Methyl-7-oxo-2-(4-phenyl-piperazin-1-yl)-7H-pyrido[2,3-d]pyrimidin-8-yl]-benzoylamino}-methyl)benzoic acid methyl ester; | 4.03 |
| 4-({4-[4-Methyl-2-(4-methyl-piperazin-1-yl-7-oxo-7H-pyrido[2,3-d]pyrimidin-8-yl]-benzoylamino}-methyl)-benzoic acid methyl ester; | 2.33 |
| 4-{8-[4-(4-Methoxycarbonyl-benzylcarbamoyl)-phenyl]-4-methyl-7-oxo-7,8-dihydro-pyrido[2,3-d]pyrimidin-2-yl}-piperazine-1-carboxylic acid ethyl ester; | 3.41 |
| 4-({4-[4-Methyl-7-oxo-2-(4-pyridin-2-yl-piperazin-1-yl)-7H-pyrido[2,3-d]pyrimidin-8-yl]-benzoylamino}-methyl)-benzoic acid methyl ester; | 3.67 |
| 4-[(4-{2-[4-(4-Hydroxy-phenyl)-piperazin-1-yl]-4-methyl-7-oxo-7H-pyrido[2,3-d]pyrimidin-8-yl}-benzoylamino)-methyl]-benzoic acid methyl ester; | 3.4 |
| 4-[2-(4-Benzyl-piperazin-1-yl)-4-methyl-7-oxo-7H-pyrido[2,3-d]pyrimidin-8-yl]-N-(2,4-difluoro-benzyl)-benzamide; | 3.96 |
| N-(2,4-Difluoro-benzyl)-4-[4-methyl-7-oxo-2-(4-phenyl-piperazin-1-yl)-7H-pyrido[2,3-d]pyrimidin-8-yl]-benzamide; | 4.21 |
| N-(2,4-Difluoro-benzyl)-4-[4-methyl-2-(4-methyl-piperazin-1-yl)-7-oxo-7H-pyrido[2,3-d]pyrimidin-8-yl]-benzamide; | 2.44 |
| 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid ethyl ester; | 3.58 |
| N-(2,4-Difluoro-benzyl)-4-[4-methyl-7-oxo-2-(4-pyridin-2-yl-piperazin-1-yl)-7H-pyrido[2,3-d]pyrimidin-8-yl]-benzamide; | 3.85 |
| N-(2,4-Difluoro-benyl)-4-{2-[4-(4-fluoro-phenyl)-piperazin-1-yl]-4-methyl-7-oxo-7H-pyrido[2,3-d]pyrimidin-8-yl}-benzamide; | 4.26 |
| N-(2,4-Difluoro-benzyl)-4-{2-[4-(4-hydroxy-phenyl)-piperazin-1-yl]-4-methyl-7-oxo-7H-pyrido[2,3-d]pyrimidin-8-yl}-benzamide; | 3.56 |
| 4-[2-(4-Benzyl-piperazin-1-yl)-4-methyl-7-oxo-7H-pyrido[2,3-d]pyrimidin-8-yl]-N-(4-methanesulfonyl-benzyl)-benzamide; | 3.29 |
| N-(4-Methanesulfonyl-benzyl)-4-[4-methyl-2-(4-phenyl-piperazin-1-yl)-7H-pyrido[2,3-d]pyrimidin-8-yl]-benzamide; | 3.64 |
| N-(4-Methanesulfonyl-benzyl-4-[4-methyl-2-(4-methyl-piperazin-1-yl)-7-oxo-7H-pyrido[2,3-d]pyrimidin-8-yl]-benzamide; | 1.95 |
| 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid ethyl ester; | 3.05 |
| N-(4-Methanesulfonyl-benzyl)-4-[4-methyl-7-oxo-2-(4-pyridin-2-yl-piperazin-1-yl)-7H-pyrido[2,3-d]pyrimidin-8-yl]-benzamide; | 3.28 |
| 4-{2-[4-(4-Fluoro-phenyl)-piperazin-1-yl]-4-methyl-7-oxo-7H-pyrido[2,3-d]pyrimidin-8-yl}-N-(4-methanesulfonyl-benzyl)-benzamide; | 3.7 |
| 4-{2-[4-(4-Hydroxy-phenyl)-piperazin-1-yl]-4-methyl-7-oxo-7H-pyrido[2,3-d]pyrimidin-8-yl}-N-(4-methanesulfonyl-benzyl)-benzamide; | 3.04 |
| 4-{2-[4-(4-Fluoro-benzoyl)-piperidin-1-yl]-4-methyl-7-oxo-7H-pyrido[2,3-d]pyrimidin-8-yl}-benzamide; | 3.29 |
| 4-[2-(4-Benzyl-piperidin-1-yl)-4-methyl-7-oxo-7H-pyrido[2,3-d]pyrimidin-8-yl]-benzamide; | 3.69 |
| 4-{2-[4-(4-Acetyl-phenyl)-piperazin-1-yl]-4-methyl-7-oxo-7H-pyrido[2,3-d]pyrimidin-8-yl}-benzamide; | 2.92 |
| 4-[2-(5-Benzyl-2,5-diaza-bicyclo[2.2.1]hept-2-yl)-4-methyl-7-oxo-7H-pyrido[2,3-d]pyrimidin-8-yl]-benzamide; | 1.96 |
| 4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-benzamide; | 3.12 |
| 4-[2-(4-Acetyl-4-phenyl-piperidin-1-yl)-4-methyl-7-oxo-7H-pyrido[2,3d]pyrimidin-8-yl]-benzamide; | 3.23 |
| 4-[2-(4-Acetyl-piperazin-1-yl)-4-methyl-7-oxo-7H-pyrido[2,3-d]pyrimidin-8-yl]-benzamide; | 1.96 |
| 4-[8-(4-Carbamoyl-phenyl)-4-methyl-7-oxo-7,8-dihydro-pyrido[2,3-d]pyrimidin-2-yl]-piperazine-1-carboxylic acid benzyl ester; | 3.12 |
| 4-(2-{4-[2-(2-Hydroxy-ethoxy)-ethyl]-piperazin-1-yl}-4-methyl-7-oxo-7H-pyrido[2,3-d]pyrimidin-8-yl)-benzamide; | 1.47 |
| 4-[4-Methyl-7-oxo-2-(4-quinolin-2-yl-piperazin-1-yl)-7H-pyrido[2,3-d]pyrimidin-8-yl]-benzamide; | 3.36 |
| N-(3,4-Dimethoxy-benzyl)-4{2-[4-(4-fluoro-benzoyl)-piperidin-1-yl]-4-methyl-7-oxo-7H-pyrido[2,3-d]pyrimidin-8-yl}-benzamide; | 3.86 |
| 4-[2-(4-Benzyl-piperidin-1-yl)-4-methyl-7-oxo-7H-pyrido[2,3-d]pyrimidin-8-yl]-N-(3,4-dimethoxy-benzyl)-benzamide; | 4.27 |
| 4-[2-(4-Benzo[1,3]dioxol-5-ylmethyl-piperazin-1-yl)-4-methyl-7-oxo-7H-pyrido[2,3-d]pyrimidin-8-yl]-N-(3,4-dimethoxy-benzyl)-benzamide; | 3.42 |
| 4-{2-[4-(4-Acetyl-phenyl)-piperazin-1-yl]-4-methyl-7-oxo-7H-pyrido[2,3-d]pyrimidin-8-yl}-N-(3,4-dimethoxy-benzyl)-benzamide; | 3.49 |
| 4-[2-(5-Benzyl-2,5-diaza-bicyclo[2.2.1]hept-2-yl)-4-methyl-7-oxo-7H-pyrido[2,3-d]pyrimidin-8-yl]-N-(3,4-dimethoxy-benzyl)-benzamide; | 2.77 |
| N-(3,4-Dimethoxy-benzyl)-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; | 3.74 |
| 4-[2-(4-Acetyl-4-phenyl-piperidin-1-yl)-4-methyl-7-oxo-7H-pyrido[2,3-d]pyrimidin-8-yl]-N-(3,4-dimethoxy-benzyl)-benzamide; | 3.81 |
| 4-[2-(4-Acetyl-piperazin-1-yl)-4-methyl-7-oxo-7H-pyrido[2,3-d]pyrimidin-8-yl]-N-(3,4-dimethoxy-benzyl)-benzamide; | 2.58 |
| N-(3,4-Dimethoxy-benzyl)-4-{2-[4-(2-hydroxy-ethyl)-piperidin-1-yl]-4-methyl-7-oxo-7H-pyrido[2,3-d]pyrimidin-8-yl}-benzamide; | 2.92 |
| 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid benzyl ester; | 3.69 |
| N-(3,4-Dimethoxy-benzyl)-4-(2{4-[2-(2-hydroxy-ethoxy)-ethyl]-piperazin-1-yl}-4-methyl-7-oxo-7H-pyrido[2,3-d]pyrimidin-8-yl)-benzamide; | 2.16 |
| N-Benzyl-4-{2-[4-(4-fluoro-benzoyl)-piperidin-1-yl]-4-methyl-7-oxo-7H-pyrido[2,3-d]pyrimidin-8-yl}-benzamide; | 4.08 |
| N-Benzyl-4-[2-(4-benzyl-piperidin-1-yl)-4-methyl-7-oxo-7H-pyrido[2,3-d]pyrimidin-8-yl]-benzamide; | 4.53 |
| 4-[2-(4-Benzo[1,3]dioxol-5-ylmethyl-piperazin-1-yl)-4-methyl-7-oxo-7H-pyrido[2,3-d]pyrimidin-8-yl]-N-benzyl-benzamide; | 3.68 |
| 4-{2-[4-(4-Acetyl-phenyl)-piperazin-1-yl]-4-methyl-7-oxo-7H-pyrido[2,3-d]pyrimidin-8-yl}-N-benzyl-benzamide; | 3.73 |
| N-Benzyl-4-[2-(5-benzyl-2,5-diaza-bicyclo[2.2.1]hept-2-yl)-4-methyl-7-oxo-7H-pyrido[2,3-d]pyrimidin-8-yl]-benzamide; | 3.05 |
| N-Benzyl-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; | 3.99 |
| 4-[2-(4-Acetyl-4-phenyl-piperidin-1-yl)-4-methyl-7-oxo-7H-pyrido[2,3-d]pyrimidin-8-yl]-N-benzyl-benzamide; | 4.06 |

| Compound Name | Retention Time (min) |
|---|---|
| 4-[2-(4-Acetyl-piperazin-1-yl)-4-methyl-7-oxo-7H-pyrido[2,3-d]pyrimidin-8-yl]-N-benzyl-benzamide; | 2.76 |
| N-Benzyl-4-{2-[4-(2-hydroxy-ethyl)-piperidin-1-yl]-4-methyl-7-oxo-7H-pyrido[2,3-d]pyrimidin-8-yl}-benzamide; | 3.13 |
| 4-[8-(4-Benzylcarbamoyl-phenyl)-4-methyl-7-oxo-7,8-dihydro-pyrido[2,3-d]pyrimidin-2-yl]-piperazine-1-carboxylic acid benzyl ester; | 3.9 |
| N-Benzyl-4-(2-{4-[2-(2-hydroxy-ethoxy)-ethyl]-piperazin-1-yl}-4-methyl-7-oxo-7H-pyrido[2,3-d]pyrimidin-8-yl)-benzamide; | 2.29 |
| N-Cyclopropyl-4-{2-[4-(4-fluoro-benzoyl)-piperidin-1-yl]-4-methyl-7-oxo-7H-pyrido[2,3-d]pyrimidin-8-yl]-4-benzamide; | 3.63 |
| 4-[2-(4-Benzyl-piperidin-1-yl)-4-methyl-7-oxo-7H-pyrido[2,3-d]pyrimidin-8-yl]-N-cyclopropyl-benzamide; | 4.08 |
| 4-{2-[4-(4-Acetyl-phenyl)-piperazin-1-yl]-4-methyl-7-oxo-7H-pyrido[2,3-d]pyrimidin-8-yl}-N-cyclopropyl-benzamide; | 3.25 |
| 4-[2-(5-Benzyl-2,5-diaza-bicyclo[2.2.1]hept-2-yl)-4-methyl-7-oxo-7H-pyrido[2,3-d]pyrimidin-8-yl]-N-cyclopropyl-benzamide; | 2.34 |
| N-Cyclopropyl-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; | 3.5 |
| 4-[2-(4-Acetyl-4-phenyl-piperidin-1-yl)-4-methyl-7-oxo-7H-pyrido[2,3-d]pyrimidin-8-yl]-N-cyclopropyl-benzamide; | 3.58 |
| 4-[2-(4-Acetyl-piperazin-1-yl)-4-methyl-7-oxo-7H-pyrido[2,3-d]pyrimidin-8-yl]-N-cyclopropyl-benzamide; | 2.22 |
| N-Cyclopropyl-4-{2-[4-(2-hydroxy-ethyl)-piperidin-1-yl]-4-methyl-7-oxo-7H-pyrido[2,3-d]pyrimidin-8-yl}-benzamide; | 2.59 |
| 4-[8-(4-Cyclopropylcarbamoyl-phenyl)-4-methyl-7-oxo-7,8-dihydro-pyrido[2,3-d]pyrimidin-2-yl]-piperazine-1-carboxylic acid benzyl ester; | 3.44 |
| 4-{2-[4-(4-Fluoro-benzoyl)-piperidin-1-yl]-4-methyl-7-oxo-7H-pyrido[2,3-d]pyrimidin-8-yl}-N-(4-trifluoromethyl-benzyl)-benzamide; | 4.37 |
| 4-[2-(4-Benzyl-piperidin-1-yl)-4-methyl-7-oxo-7H-pyrido[2,3-d]pyrimidin-8-yl]-N-(4-trifluoromethyl-benzyl)-benzamide; | 4.78 |
| 4-{2-[4-(4-Acetyl-phenyl)-piperazin-1-yl]-4-methyl-7-oxo-7H-pyrido[2,3-d]pyrimidin-8-yl}-N-(4-trifluoromethyl-benzyl)-benzamide; | 4.04 |
| 4-[2-(5-Benzyl-2,5-diaza-bicyclo[2.2.1]hept-2-yl)-4-methyl-7-oxo-7H-pyrido[2,3-d]pyrimidin-8-yl]-N-(4-trifluoromethyl-benzyl)-benzamide; | 3.58 |
| 4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-N-(4-trifluoromethyl-benzyl)-benzamide; | 4.29 |
| 4-[2-(4-Acetyl-4-phenyl-piperidin-1-yl)-4-methyl-7-oxo-7H-pyrido[2,3-d]pyrimidin-8-yl]-N-(4-trifluoromethyl-benzyl)-benzamide; | 4.36 |
| 4-[2-(4-Acetyl-piperazin-1-yl)-4-methyl-7-oxo-7H-pyrido[2,3-d]pyrimidin-8-yl]-N-(4-trifluoromethyl-benzyl)-benzamide; | 3.19 |
| 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid benzyl ester; | 4.19 |
| 4-(2-{4-[2-(2-Hydroxy-ethoxy)-ethyl]-piperazin-1-yl}-4-methyl-7-oxo-7H-pyrido[2,3-d]pyrimidin-8-yl)-N-(4-trifluoromethyl-benzyl)-benzamide; | 2.79 |
| 4-[(4-{2-[4-(4-Fluoro-benzoyl)-piperidin-1-yl]-4-methyl-7-oxo-7H-pyrido[2,3-d]pyrimidin-8-yl]-benzoylamino)-methyl]-benzoic acid methyl ester; | 4.05 |
| 4-({4-[2-(4-Benzyl-piperidin-1-yl)-4-methyl-7-oxo-7H-pyrido[2,3-d]pyrimidin-8-yl]-benzoylamino}-methyl)-benzoic acid methyl ester; | 4.47 |
| 4-({4-[2-(4-Benzo[1,3]dioxol-5-ylmethyl-piperazin-1-yl)-4-methyl-7-oxo-7H-pyrido[2,3-d]pyrimidin-8-yl]-benzoylamino}-methyl)-benzoic acid methyl ester; | 3.66 |
| 4-[(4-{2-[4-(4-Acetyl-phenyl)-paperazin-1-yl]-4-methyl-7-oxo-7H-pyrido[2,3-d]pyrimidin-8-yl}-benzoylamino)-methyl]-benzoic acid methyl ester; | 3.69 |
| 4-({4-[2-(5-Benzyl-2,5-diaza-bicyclo[2.2.1]hept-2-yl)-4-methyl-7-oxo-7H-pyrido[2,3-d]pyrimidin-8-yl]-benzoylamino}-methyl)-benzoic acid methyl ester; | 3.03 |
| 4-[(4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-benzoylamino)-methyl]-benzoic acid methyl ester; | 3.95 |
| 4-({4-[2-(4-Acetyl-4-phenyl-piperidin-1-yl)-4-methyl-7-oxo-7H-pyrido[2,3-d]pyrimidin-8-yl]-benzoylamino}-methyl)-benzoic acid methyl ester; | 4.03 |
| 4-({4-[2-(4-Acetyl-piperazin-1-yl)-4-methyl-7-oxo-7H-pyrido[2,3-d]pyrimidin-8-yl]-benzoylamino}-methyl)-benzoic acid methyl ester; | 2.76 |
| 4-[(4-{2-[4-(2-Hydroxy-ethyl)-piperidin-1-yl]-4-methyl-7-oxo-7H-pyrido[2,3-d]pyrimidin-8-yl]-benzoylamino)-methyl]-benzoic acid methyl ester; | 3.12 |
| 4-{8-[4-(4-Methoxycarbonyl-benzylcarbamoyl)-phenyl]-4-methyl-7-oxo-7,8-dihydro-pyrido[2,3-d]pyrimidin-2-yl}-piperazine-1-carboxylic acid benzyl ester; | 3.86 |
| 4-{[4-(2-{4-[2-(2-Hydroxy-ethoxy)-ethyl]-piperazin-1-yl}-4-methyl-7-oxo-7H-pyrido[2,3-d]pyrimidin-8-yl)-benzoylamino]-methyl}-benzoic acid methyl ester; | 2.36 |
| N-(2,4-Difluoro-benzyl)-4-{2-[4-(4-fluoro-benzoyl)-piperidin-1-yl]-4-methyl-7-oxo-7H-pyrido[2,3-d]pyrimidin-8-yl}-benzamide; | 4.19 |
| 4-[2-(4-Benzyl-piperidin-1-yl)-4-methyl-7-oxo-7H-pyrido[2,3-d]pyrimidin-8-yl]-N-(2,4-difluoro-benzyl)-benzamide; | 4.61 |
| 4-[2-(4-Benzo[1,3]dioxol-5-ylmethyl-piperazin-1-yl)-4-methyl-7-oxo-7H-pyrido[2,3-d]pyrimidin-8-yl]-N-(2,4-difluoro-benzyl)-benzamide; | 3.86 |
| 4-{2-[4-(4-Acetyl-phenyl)-piperazin-1-yl]-4-methyl-7-oxo-7H-pyrido[2,3-d]pyrimidin-8-yl}-N-(2,4-difluoro-benzyl)-benzamide; | 3.86 |
| 4-[2-(5-Benzyl-2,5-diaza-bicyclo[2.2.1]hept-2-yl)-4-methyl-7-oxo-7H-pyrido[2,3-d]pyrimidin-8-yl]-N-(2,4-difluoro-benzyl)-benzamide; | 3.24 |
| N-(2,4-Difluoro-benzyl)-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide; | 4.1 |
| 4-[2-(4-Acetyl-4-phenyl-piperidin-1-yl)-4-methyl-7-oxo-7H-pyrido[2,3-d]pyrimidin-8-yl]-N-(2,4-difluoro-benzyl)-benzamide; | 4.18 |
| 4-[2-(4-Acetyl-piperazin-1-yl)-4-methyl-7-oxo-7H-pyrido[2,3-d]pyrimidin-8-yl]-N-(2,4-difluoro-benzyl)-benzamide; | 2.91 |
| 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid benzyl ester; | 4.01 |
| N-(2,4-Difluoro-benzyl)-4-(2-{4-[2-(2-hydroxy-ethoxy)-ethyl]-piperazin-1-yl}-4-methyl-7-oxo-7H-pyrido[2,3-d]pyrimidin-8-yl)-benzamide; | 2.47 |
| 4-{2-[4-(4-Fluoro-benzoyl)-piperidin-1-yl]-4-methyl-7-oxo-7H-pyrido[2,3-d]pyrimidin-8-yl}-N-(4-methanesulfonyl-benzyl)-benzamide; | 3.67 |
| 4-[2-(4-Benzyl-piperidin-1-yl)-4-methyl-7-oxo-7H-pyrido[2,3-d]pyrimidin-8-yl]-N-(4-methanesulfonyl-benzyl)-benzamide; | 4.06 |
| 4-[2-(4-Benzo[1,3]dioxol-5-ylmethyl-piperazin-1-yl)-4-methyl-7-oxo-7H-pyrido[2,3-d]pyrimidin-8-yl]-N-(4-methanesulfonyl-benzyl)-benzamide; | 3.23 |
| 4-{2-[4-(4-Acetyl-phenyl)-piperazin-1-yl]-4-methyl-7-oxo-7H-pyrido[2,3-d]pyrimidin-8-yl}-N-(4-methanesulfonyl-benzyl)-benzamide; | 3.32 |
| 4-{2-[5-(4-Fluoro-phenyl)-2,5-diaza-bicyclo[2.2.1]hept-2-yl]-4-methyl-7-oxo-7H- | 3.55 |

| Compound Name | Retention Time (min) |
|---|---|
| pyrido[2,3-d]pyrimidin-8-yl}-N-(4-methanesulfonyl-benzyl)-benzamide; | |
| 4-[2-(4-Acetyl-4-phenyl-piperidin-1-yl)-4-methyl-7-oxo-7H-pyrido[2,3-d]pyrimidin-8-yl]-N-(4-methanesulfonyl-benzyl)-benzamide; | 3.63 |
| 4-[2-(4-Acetyl-piperazin-1-yl)-4-methyl-7-oxo-7H-pyrido[2,3-d]pyrimidin-8-yl]-N-(4-methanesulfonyl-benzyl)-benzamide; | 2.45 |
| 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid benzyl ester; | 3.51 |
| 4-[2-(4-Acetylamino-phenoxy)-4-methyl-7-oxo-7H-pyrido[2,3-d]pyrimidin-8-yl]-benzamide; | 1.96 |
| 4-[2-(4-Carbamoylmethyl-phenoxy)-4-methyl-7-oxo-7H-pyrido[2,3-d]pyrimidin-8-yl]-benzamide; | 1.86 |
| 4-[8-(4-Carbamoyl-phenyl)-4-methyl-7-oxo-7,8-dihydro-pyrido[2,3-d]pyrimidin-2-yloxy]-benzoic acid ethyl ester; | 2.63 |
| 4-[4-Methyl-7-oxo-2-(4-trifluoromethyl-phenoxy)-7H-pyrido[2,3-d]pyrimidin-8-yl]-benzamide; | 2.81 |
| 4-[2-(4-Fluoro-phenoxy)-4-methyl-7-oxo-7H-pyrido[2,3-d]pyrimidin-8-yl]-benzamide; | 2.42 |
| 4-{2-[4-(4-Hydroxy-benzenesulfonyl)-phenoxy]-4-methyl-7-oxo-7H-pyrido[2,3-d]pyrimidin-8-yl}-benzamide; | 2.53 |
| 4-[2-(4-Acetyl-phenoxy)-4-methyl-7-oxo-7H-pyrido[2,3-d]pyrimidin-8-yl]-benzamide; | 2.22 |
| 4-[2-(4-Carbamoylmethyl-phenoxy)-4-methyl-7-oxo-7H-pyrido[2,3-d]pyrimidin-8-yl]-N-(3,4-dimethoxy-benzyl)-benzamide; | 2.44 |
| N-(3,4-Dimethoxy-benzyl)-4-[4-methyl-7-oxo-2-(4-trifluoromethyl-phenoxy)-7H-pyrido[2,3-d]pyrimidin-8-yl]-benzamide; | 3.43 |
| N-(3,4-Dimethoxy-benzyl)-4-[2-(4-fluoro-phenoxy)-4-methyl-7-oxo-7H-pyrido[2,3-d]pyrimidin-8-yl]-benzamide; | 3.14 |
| N-(3,4-Dimethoxy-benzyl)-4-{2-[4-(4-hydroxy-benzenesulfonyl)-phenoxy]-4-methyl-7-oxo-7H-pyrido[2,3-d]pyrimidin-8-yl}-benzamide; | 3.13 |
| 4-[2-(4-Acetyl-phenoxy)-4-methyl-7-oxo-7H-pyrido[2,3-d]pyrimidin-8-yl]-N-(3,4-dimethoxy-benzyl)-benzamide; | 2.95 |
| N-Benzyl-4-[2-(4-carbamoylmethyl-phenoxy)-4-methyl-7-oxo-7H-pyrido[2,3-d]pyrimidin-8-yl]-benzamide; | 2.63 |
| N-Benzyl-4-[2-(4-fluoro-phenoxy)-4-methyl-7-oxo-7H-pyrido[2,3-d]pyrimidin-8-yl]-benzamide; | 3.4 |
| 4-[2-(4-Acetyl-phenoxy)-4-methyl-7-oxo-7H-pyrido[2,3-d]pyrimidin-8-yl]-N-benzyl-benzamide; | 3.64 |
| 4-[2-(4-Acetylamino-phenoxy)-4-methyl-7-oxo-7H-pyrido[2,3-d]pyrimidin-8-yl]-N-cyclopropyl-benzamide; | 2.29 |
| N-(3,4-Dimethoxy-benzyl)-4-[2-(4-fluoro-phenylsulfanyl)-4-methyl-7-oxo-7H-pyrido[2,3-d]pyrimidin-8-yl]-benzamide; | 3.36 |
| N-Benzyl-4-[4-methyl-2-(1-methyl-1H-imidazol-2-ylsulfanyl)-7-oxo-7H-pyrido[2,3-d]pyrimidin-8-yl]-benzamide; | 2.67 |
| N-Benzyl-4-[2-(4-fluoro-phenylsulfanyl)-4-methyl-7-oxo-7H-pyrido[2,3-d]pyrimidin-8-yl]-benzamide; | 3.64 |
| N-Cyclopropyl-4-[2-(4-fluoro-phenylsulfanyl)-4-methyl-7-oxo-7H-pyrido[2,3-d]pyrimidin-8-yl]-benzamide; | 3.07 |
| 4-[4-Methyl-2-(1-methyl-1H-imidazol-2-ylsulfanyl)-7-oxo-7H-pyrido[2,3-d]pyrimidin-8-yl]-N-(4-trifluoromethyl-benzyl)-benzamide; | 3.13 |
| 4-[2-(4-Fluoro-phenylsulfanyl)-4-methyl-7-oxo-7H-pyrido[2,3-d]pyrimidin-8-yl]-N-(4-trifluoromethyl-benzyl)-benzamide; | 3.99 |
| 4-({4-[4-Methyl-2-(1-methyl-1H-imidazol-2-ylsulfanyl)-7-oxo-7H-pyrido[2,3-d]pyrimidin-8-yl]-benzoylamino}-methyl)-benzoic acid methyl ester; | 2.68 |
| 4-({4-[2-(4-Fluoro-phenylsulfanyl)-4-methyl-7-oxo-7H-pyrido[2,3-d]pyrimidin-8-yl]-benzoylamino}-methyl)-benzoic acid methyl ester; | 3.59 |
| N-(2,4-Difluoro-benzyl)-4-[4-methyl-2-(1-methyl-1H-imidazol-2-ylsulfanyl)-7-oxo-7H-pyrido[2,3-d]pyrimidin-8-yl]-benzamide; | 2.84 |
| N-(2,4-Difluoro-benzyl)-4-[2-(4-fluoro-phenylsulfanyl)-4-methyl-7-oxo-7H-pyrido[2,3-d]pyrimidin-8-yl]-benzamide; | 3.78 |
| 4-[2-(4-Fluoro-phenylsulfanyl)-4-methyl-7-oxo-7H-pyrido[2,3-d]pyrimidin-8-yl]-N-(4-methanesulfonyl-benzyl)-benzamide; | 3.16 |
| N-(3,4-Dimethoxy-benzyl)-4-[4-methyl-2-(1-methyl-1H-imidazol-2-ylsulfanyl)-7-oxo-7H-pyrido[2,3-d]pyrimidin-8-yl]-benzamide; | 2.47 |
| 4-[2-(4-Carbamoylmethyl-phenoxy)-4-methyl-7-oxo-7H-pyrido[2,3-d]pyrimidin-8-yl]-N-cyclopropyl-benzamide; | 2.09 |
| N-Cyclopropyl-4-[4-methyl-7-oxo-2-(4-trifluoromethyl-phenoxy)-7H-pyrido[2,3-d]pyrimidin-8-yl]-benzamide; | 3.17 |
| N-Cyclopropyl-4-[2-(4-fluoro-phenoxy)-4-methyl-7-oxo-7H-pyrido[2,3-d]pyrimidin-8-yl]-benzamide; | 2.81 |
| N-Cyclopropyl-4-{2-[4-(4-hydroxy-benzenesulfonyl)-phenoxy]-4-methyl-7-oxo-7H-pyrido[2,3-d]pyrimidin-8-yl}-benzamide; | 2.86 |
| 4-[2-(4-Acetyl-phenoxy)-4-methyl-7-oxo-7H-pyrido[2,3-d]pyrimidin-8-yl]-N-cyclopropyl-benzamide; | 2.57 |
| 4-[2-(4-Carbamoylmethyl-phenoxy)-4-methyl-7-oxo-7H-pyrido[2,3-d]pyrimidin-8-yl]-N-(4-trifluoromethyl-benzyl)-benzamide; | 3.05 |
| 4-{Methyl-7-oxo-8-[4-(4-trifluoromethyl-benzylcarbamoyl)-phenyl]-7,8-dihydro-pyrido[2,3-d]pyrimidin-2-yloxy}-benzoic acid ethyl ester; | 3.93 |
| 4-[4-Methyl-7-oxo-2-(4-trifluoromethyl-phenoxy)-7H-pyrido[2,3-d]pyrimidin-8-yl]-N-(4-trifluoromethyl-benzyl)-benzamide; | 3.98 |
| 4-[2-(4-Fluoro-phenoxy)-4-methyl-7-oxo-7H-pyrido[2,3-d]pyrimidin-8-yl]-N-(4-trifluoromethyl-benzyl)-benzamide; | 3.74 |
| 4-[2-(4-Acetyl-phenoxy)-4-methyl-7-oxo-7H-pyrido[2,3-d]pyrimidin-8-yl]-N-(4-trifluoromethyl-benzyl)-benzamide; | 3.59 |
| 4-({4-[2-(4-Carbamoylmethyl-phenoxy)-4-methyl-7-oxo-7H-pyrido[2,3-d]pyrimidin-8-yl]-benzoylamino}-methyl)-benzoic acid methyl ester; | 2.64 |
| 4-({4-[4-Methyl-7-oxo-2-(4-trifluoromethyl-phenoxy)-7H-pyrido[2,3-d]pyrimidin-8-yl]-benzoylamino}-methyl)-benzoic acid methyl ester; | 3.63 |
| 4-({4-[2-(4-Acetyl-phenoxy)-4-methyl-7-oxo-7H-pyrido[2,3-d]pyrimidin-8-yl]-benzoylamino}-methyl)-benzoic acid methyl ester; | 3.15 |
| 4-[2-(4-Carbamoylmethyl-phenoxy)-4-methyl-7-oxo-7H-pyrido[2,3-d]pyrimidin-8-yl]-N-(2,4-difluoro-benzyl)-benzamide; | 2.76 |
| N-(2,4-Difluoro-benzyl)-4-[4-methyl-7-oxo-2-(4-trifluoromethyl-phenoxy)-7H-pyrido[2,3-d]pyrimidin-8-yl]-benzamide; | 3.77 |
| 4-[2-(4-Acetyl-phenoxy)-4-methyl-7-oxo-7H-pyrido[2,3-d]pyrimidin-8-yl]-N-(2,4-difluoro-benzyl)-benzamide; | 3.33 |
| 4-[2-(4-Carbamoylmethyl-phenoxy)-4-methyl-7-oxo-7H-pyrido[2,3-d]pyrimidin-8-yl]-N-(4-methanesulfonyl-benzyl)-benzamide; | 2.31 |
| 4-{8-[4-(4-Methanesulfonyl-benzylcarbamoyl)-phenyl]-4-methyl-7-oxo-7,8-dihydro-pyrido[2,3-d]pyrimidin-2-yloxy}-benzoic acid ethyl ester; | 3.15 |
| N-(4-Methanesulfonyl-benzyl)-4-[4-methyl-7-oxo-2-(4-trifluoromethyl-phenoxy)-7H-pyrido[2,3-d]pyrimidin-8-yl]-benzamide; | 3.23 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 2.94 |
| 4-[2-(4-Acetyl-phenoxy)-4-methyl-7-oxo-7H-pyrido[2,3-d]pyrimidin-8-yl]-N-(4-methanesulfonyl-benzyl)-benzamide; | 2.78 |

| Compound Name | Retention Time (min) |
|---|---|
| 4-[4-Methyl-2-(octahydro-isoquinolin-2-yl)-7-oxo-7H-pyrido[2,3-d]pyrimidin-8-yl]-benzamide; | 3.61 |
| N-(3,4-Dimethoxy-benzyl)-4-[4-methyl-2-(octahydro-isoquinolin-2-yl)-7-oxo-7H-pyrido[2,3-d]pyrimidin-8-yl]-benzamide; | 4.24 |
| N-Benzyl-4-[4-methyl-2-(octahydro-isoquinolin-2-yl)-7-oxo-7H-pyrido[2,3-d]pyrimidin-8-yl]-benzamide; | 4.55 |
| N-Cyclopropyl-4-[4-methyl-2-(octahydro-isoquinolin-2-yl)-7-oxo-7H-pyrido[2,3-d]pyrimidin-8-yl]-benzamide; | 4.04 |
| 4-[4-Methyl-2-(octahydro-isoquinolin-2-yl)-7-oxo-7H-pyrido[2,3-d]pyrimidin-8-yl]-N-(4-trifluoromethyl-benzyl)-benzamide; | 4.81 |
| 4-({4-[4-Methyl-2-(octahydro-isoquinolin-2-yl)-7-oxo-7H-pyrido[2,3-d]pyrimidin-8-yl]-benzoylamino}-methyl)-benzoic acid methyl ester; | 4.46 |
| N-(2,4-Difluoro-benzyl)-4-[4-methyl-2-(octahydro-isoquinolin-2-yl)-7-oxo-7H-pyrido[2,3-d]pyrimidin-8-yl]-benzamide; | 4.63 |
| N-(4-Methanesulfonyl-benzyl)-4-[4-methyl-2-(octahydro-isoquinolin-2-yl)-7-oxo-7H-pyrido[2,3-d]pyrimidin-8-yl]-benzamide; | 4.01 |
| 4-[4-Methyl-2-(1-methyl-1H-imidazol-2-ylsulfanyl)-7-oxo-7H-pyrido[2,3-d]pyrimidin-8-yl]-benzamide; | 1.64 |
| 4-[2-(1H-Benzoimidazol-2-ylsulfanyl)-4-methyl-7-oxo-7H-pyrido[2,3-d]pyrimidin-8-yl]-benzamide; | 1.86 |
| 4-[2-(4-Fluoro-phenylsulfanyl)-4-methyl-7-oxo-7H-pyrido[2,3-d]pyrimidin-8-yl]-benzamide; | 2.67 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 3.04 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 3.35 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 3.21 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 3.44 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 2.51 |
| 4-[4-Methyl-7-oxo-2-(5-phenyl-1H-[1,2,4]triazol-3-ylsulfanyl)-7H-pyrido[2,3-d]pyrimidin-8-yl]-benzamide; | 2.06 |
| N-(3,4-Dimethoxy-benzyl)-4-[4-methyl-7-oxo-2-(5-phenyl-1H-[1,2,4]triazol-3-ylsulfanyl)-7H-pyrido[2,3-d]pyrimidin-8-yl]-benzamide; | 2.84 |
| 4-[2-(1H-Benzoimidazol-2-ylsulfanyl)-4-methyl-7-oxo-7H-pyrido[2,3-d]pyrimidin-8-yl]-N-(3,4-dimethoxy-benzyl)-benzamide; | 2.63 |
| N-Benzyl-4-[4-methyl-7-oxo-2-(5-phenyl-1H-[1,2,4]triazol-3-ylsulfanyl)-7H-pyrido[2,3-d]pyrimidin-8-yl]-benzamide; | 3.06 |
| 4-[2-(1H-Benzoimidazol-2-ylsulfanyl)-4-methyl-7-oxo-7H-pyrido[2,3-d]pyrimidin-8-yl]-1-N-benzyl-benzamide; | 2.89 |
| N-Cyclopropyl-4-[4-methyl-7-oxo-2-(5-phenyl-1H-[1,2,4]triazol-3-ylsulfanyl)-7H-pyrido[2,3-d]pyrimidin-8-yl]-benzamide; | 2.45 |
| 4-[4-Methyl-7-oxo-2-(5-phenyl-1H-[1,2,4]triazol-3-ylsulfanyl)-7H-pyrido[2,3-d]pyrimidin-8-yl]-N-(4-trifluoromethyl-benzyl)-benzamide; | 3.47 |
| 4-[2-(1H-Benzoimidazol-2-ylsulfanyl)-4-methyl-7-oxo-7H-pyrido[2,3-d]pyrimidin-8-yl]-N-(4-trifluoromethyl-benzyl)-benzamide; | 3.33 |
| 4-({4-[4-Methyl-7-oxo-2-(5-phenyl-1H-[1,2,4]triazol-3-ylsulfanyl)-7H-pyrido[2,3-d]pyrimidin-8-yl]-benzoylamino}-methyl)-benzoic acid methyl ester; | 3.04 |
| 4-({4-[2-(1H-Benzoimidazol-2-ylsulfanyl)-4-methyl-7-oxo-7H-pyrido[2,3-d]pyrimidin-8-yl]-benzoylamino}-methyl)-benzoic acid methyl ester; | 2.86 |
| N-(2,4-Difluoro-benzyl)-4-[4-methyl-7-oxo-2-(5-phenyl-1H-[1,2,4]triazol-3-ylsulfanyl)-7H-pyridol[2,3-d]pyrimidin-8-yl]-benzamide; | 3.21 |
| 4-[2-(1H-Benzoimidazol-2-ylsulfanyl)-4-methyl-7-oxo-7H-pyrido[2,3-d]pyrimidin-8-yl]-N-2,4-difluoro-benzyl)-benzamide; | 3.04 |
| N-(4-Methanesulfonyl-benzyl)-4-[4-methyl-2-(1-methyl-1H-imidazol-2-ylsulfanyl)-7-oxo-7H-pyrido[2,3-d]pyrimidin-8-yl]-benzamide; | 2.32 |
| N-(4-Methanesulfonyl-benzyl)-4-[4-methyl-7-oxo-2-(5-phenyl-1H-[1,2,4]triazol-3-ylsulfanyl)-7H-pyrido[2,3-d]pyrimidin-8-yl]-benzamide; | 2.62 |
| 4-[2-(1H-Benzoimidazol-2-ylsulfanyl)-4-methyl-7-oxo-7H-pyrido[2,3-d]pyrimidin-8-yl]-N-(4-methanesulfonyl-benzyl)-benzamide; | 2.46 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 3.64 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 2.68 |
| 4-[2-(4-Fluoro-phenoxy)-4-methyl-7-oxo-7H-pyrido[2,3-d]pyrimidin-8-yl]-N-(4-methanesulfonyl-benzyl)-benzamide; | 3.34 |
| N-(2,4-Difluoro-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide; | 3.38 |
| 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid cyclohexylamide; | 3.72 |
| 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide; | 4.1 |
| N-(4-Methanesulfonyl-benzyl-)-4-{4-methyl-7-oxo-2-[4-(pyridine-3-carbonyl)-piperazin-1-yl]-7H-pyrido[2,3-d]pyrimidin-8-yl}-benzamide | 2.48 |
| 4-{8-[4-(4-Methanesulfonyl-benzylcarbamoyl)-phenyl]-4-methyl-7-oxo-7,8-dihydropyrido[2,3-d]pyrimidin-2-yl}-piperazine-1-carboxylic acid (3,4-difluoro-phenyl)-amide; | 3.4 |
| 4-{2-[4-(Furan-2-carbonyl)-piperazin-1-yl]-4-methyl-7-oxo-7H-pyrido[2,3-d]pyrimidin-8-yl}-N-(4-methanesulfonyl-benzyl)-benzamide; | 2.83 |
| 4-[2-(4-Benzoyl-piperazin-1-yl)-4-methyl-7-oxo-7H-pyrido[2,3-d]pyrimidin-8-yl]-N-(4-methanesulfonyl-benzyl)-benzamide; | 2.98 |
| N-(4-Methanesulfonyl-benzyl)-4-[4-methyl-7-oxo-2-(4-phenylacetyl-piperazin-1-yl)-7H-pyrido[2,3-d]pyrimidin-8-yl]-benzamide; | 3.09 |
| N-(4-Methanesulfonyl-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide; | 2.92 |
| 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid cyclohexylamide; | 3.2 |
| 4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide; | 3.63 |
| 4-{2-[4-(Furan-2-carbonyl)-piperazin-1-yl]-4-methyl-7-oxo-7H-pyrido[2,3-d]pyrimidin-8-yl}-benzamide; | 2.38 |
| 4-[2-(4-Benzoyl-piperazin-1-yl)-4-methyl-7-oxo-7H-pyrido[2,3-d]pyrimidin-8-yl]-benzamide; | 2.54 |
| 4-{4-Methyl-7-oxo-2-[4-(3,4,5-trimethoxy-benzoyl)-piperazin-1-yl]-7H-pyrido[2,3-d]pyrimidin-8-yl}-benzamide; | 2.49 |
| N-(3,4-Dimethoxy-benzyl)-4-{4-methyl-7-oxo-2-[4-(pyridine-3-carbonyl)-piperazin-1-yl]-7H-pyrido[2,3-d]pyrimidin-8-yl}-benzamide; | 2.61 |
| 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid | 3.58 |

| Compound Name | Retention Time (min) |
|---|---|
| (3,4-difluoro-phenyl)-amide; | |
| N-(3,4-Dimethoxy-benzyl)-4-{2-[4-(furan-2-carbonyl)-piperazin-1-yl]-4-methyl-7-oxo-7H-pyrido[2,3-d]pyrimidin-8-yl}-benzamide; | 2.99 |
| 4-[2-(4-Benzoyl-piperazin-1-yl)-4-methyl-7-oxo-7H-pyrido[2,3-d]pyrimidin-8-yl]-N-(3,4-dimethoxy-benzyl)-benzamide; | 3.12 |
| N-(3,4-Dimethoxy-benzyl)-4-[4-methyl-7-oxo-2-(4-phenylacetyl-piperazin-1-yl)-7H-pyrido[2,3-d]pyrimidin-8-yl]-benzamide; | 3.23 |
| N-(3,4-Dimethoxy-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide; | 3.04 |
| 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid cyclohexylamide; | 3.37 |
| N-Benzyl-4-{4-methyl-7-oxo-2-[4-(pyridine-3-carbonyl)-piperazin-1-yl]-7H-pyrido[2,3-d]pyrimidin-8-yl}-benzamide; | 2.79 |
| 4-[8-(4-Benzylcarbamoyl-phenyl)-4-methyl-7-oxo-7,8-dihydro-pyrido[2,3-d]pyrimidin-2-yl]-piperazine-1-carboxylic acid (3,4-difluoro-phenyl)-amide; | 3.8 |
| N-Benzyl-4-{2-[4-(furan-2-carbonyl)-piperazin-1-yl]-4-methyl-7-oxo-7H-pyrido[2,3-d]pyrimidin-8-yl}-benzamide; | 3.21 |
| 4-[2-(4-Benzoyl-piperazin-1-yl)-4-methyl-7-oxo-7H-pyrido[2,3-d]pyrimidin-8-yl]-N-benzyl-benzamide; | 3.34 |
| N-Benzyl-4-[4-methyl-7-oxo-2-(4-phenylacetyl-piperazin-1-yl)-7H-pyrido[2,3-d]pyrimidin-8-yl]-benzamide; | 3.45 |
| 4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide; | 3.8 |
| N-Benzyl-4-{4-methyl-7-oxo-2-[4-(3,4,5-trimethoxy-benzoyl)-piperazin-1-yl]-7H-pyrido[2,3-d]pyrimidin-8-yl}-benzamide; | 3.24 |
| 4-[8-(4-Benzylcarbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide; | 4 |
| N-Cyclopropyl-4-{4-methyl-7-oxo-2-[4-(pyridine-3-carbonyl)-piperazin-1-yl]-7H-pyrido[2,3-d]pyrimidin-8-yl}-benzamide; | 2.3 |
| 4-[8-(4-Cyclopropylcarbamoyl-phenyl)-4-methyl-7-oxo-7,8-dihydro-pyrido[2,3-d]pyrimidin-2-yl]-piperazine-1-carboxylic acid (3,4-difluoro-phenyl)-amide; | 3.32 |
| N-Cyclopropyl-4{2[4-(furan-2-carbonyl)-piperazin-1-yl]-4-methyl-7-oxo-7H-pyrido[2,3-d]pyrimidin-8-yl}-benzamide; | 2.68 |
| 4-[2-(4-Benzoyl-piperazin-1-yl)-4-methyl-7-oxo-7H-pyrido[2,3-d]pyrimidin-8-yl]-N-cyclopropyl-benzamide; | 2.85 |
| N-Cyclopropyl-4-[4-methyl-7-oxo-2-(4-phenylacetyl-piperazin-1-yl)-7H-pyrido[2,3-d]pyrimidin-8-yl]-benzamide; | 2.97 |
| N-Cyclopropyl-4-{4-methyl-7-oxo-2-[4-(3,4,5-trimethoxy-benzoyl)-piperazin-1-yl]-7H-pyrido[2,3-d]pyrimidin-8-yl}-benzamide; | 2.77 |
| 4-[8-(4-Cyclopropylcarbamoyl-phenyl)-4-methyl-7-oxo-7,8-dihydro-pyrido[2,3-d]pyrimidin-2-yl]-piperazine-1-carboxylic acid cyclohexylamide | 3.09 |
| 4-[8-(4-Cyclopropylcarbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide | 3.57 |
| 4-{4-Methyl-7-oxo-2-[4-(3,4,5-trimethoxy-benzoyl)-piperazin-1-yl]-7H-pyrido[2,3-d]pyrimidin-8-yl}-N-(4-trifluoromethyl-benzyl)-benzamide; | 3.6 |
| 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid cyclohexylamide; | 3.92 |
| 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid (3-trifluoromethyl-phenyl)-amide; | 4.27 |
| 4-[(4-{4-Methyl-7-oxo-2-[4-(pyridine-3-carbonyl)-piperazin-1-yl]-7H-pyrido[2,3-d]pyrimidin-8-yl}-benzoylamino)-methyl]-benzoic acid methyl ester; | 2.79 |
| 4-[(4-{2-[4-(3,4-Difluoro-phenylcarbamoyl)-piperazin-1-yl]-4-methyl-7-oxo-7H-pyrido[2,3-d]pyrimidin-8-yl}-benzoylamino)-methyl]-benzoic acid methyl ester; | 3.75 |
| 4-[(4-{2-[4-(Furan-2-carbonyl)-piperazin-1-yl]-4-methyl-7-oxo-7H-pyrido[2,3-d]pyrimidin-8-yl}-benzoylamino)-methyl]-benzoic acid methyl ester; | 3.17 |
| 4-({5-[2-(4-Benzoyl-piperazin-1-yl)-4-methyl-7-oxo-7H-pyrido[2,3-d]pyrimidin-8-yl]-benzoylamino}-methyl)-benzoic acid methyl ester; | 3.33 |
| 4-({4-[4-Methyl-7-oxo-2-(4-phenylacetyl-piperazin-1-yl)-7H-pyrido[2,3-d]pyrimidin-8-yl]-benzoylamino}-methyl)-benzoic acid methyl ester; | 3.42 |
| 4-[(4-{4-Methyl-7-oxo-2-[4-(3,4,5-trimethoxy-benzoyl)-piperazin-1-yl]-7H-pyrido[2,3-d]pyrimidin-8-yl}-benzoylamino)-methyl]-benzoic acid methyl ester; | 3.23 |
| 4-({4-[2-(4-Cyclohexylcarbamoylipiperazin-1-yl)-4-methyl-7-oxo-7H-pyrido[2,3-d]pyrimidin-8-yl]-benzoylamino}-methyl)-benzoic acid methyl ester; | 3.55 |
| 4-[(4-{4-Methyl-7-oxo-2-[4(3-trifluoromethyl-phenylcarbamoyl)-piperazin-1-yl]-7H-pyrido[2,3-d]pyrimidin-8-yl}-benzoylamino)-methyl]-benzoic acid methyl ester; | 3.97 |
| N-(2,4-Difluoro-benzyl)-4-{4-methyl-7-oxo-2-[4-(pyridine-3-carbonyl)-piperazin-1-yl]-7H-pyrido[2,3-d]pyrimidin-8-yl}-benzamide; | 2.93 |
| 4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide; | 3.9 |
| 4-[8-(4-Carbamoyl-phenyl)-4-methyl-7-oxo-7,8-dihydro-pyrido[2,3-d]pyrimidin-2-yl]-piperazine-1-carboxylic acid (3-trifluoromethyl-phenyl) -amide; | 3.25 |
| N-(2,4-Difluoro-benzyl)-4-{2-[4-(furan-2-carbonyl)-piperazin-1-yl]-4-methyl-7-oxo-7H pyrido[2,3-d]pyrimidin-8-yl-4-benzamide; | 3.33 |
| 4-[2-(4-Benzoyl-piperazin-1-yl)-4-methyl-7-oxo-7H-pyrido[2,3-d]pyrimidin-8-yl]-N-(2,4-difluoro-benzyl)-benzamide; | 3.48 |
| N-(2,4-Difluoro-benzyl)-4-[4-methyl-7-oxo-2-(4-phenylacetyl-piperazin-1-yl)-7H-pyrido[2,3-d]pyrimidin-8-yl]-benzamide; | 3.57 |
| 4-{4-Methyl-7-oxo-2-[4-(pyridine-3-carbonyl)-piperazin-1-yl]-7H-pyrido[2,3-d]pyrimidin-8-yl}-benzamide; | 2.05 |
| 4-[8-(4-Carbamoyl-phenyl)-4-methyl-7-oxo-7,8-dihydro-pyrido[2,3-d]pyrimidin-2-yl]-piperazine-1-carboxylic acid (3,4-difluoro-phenyl)-amide; | 2.99 |
| 4-[4-Methyl-7-oxo-2-(4-phenylacetyl-piperazin-1-yl)-7H-pyrido[2,3-d]pyrimidin-8-yl]-benzamide; | 2.66 |
| 4-[8-(4-Carbamoyl-phenyl)-4-methyl-7-oxo-7,8-dihydro-pyrido[2,3-d]pyrimidin-2-yl]-piperazine-1-carboxylic acid cyclohexylamide; | 2.76 |
| 4-[8-(4-Benzylcarbamoyl-phenyl)-4-methyl-7-oxo-7,8-dihydro-pyrido[2,3-d]pyrimidin-2-yl]-piperazine-1-carboxylic acid cyclohexylamide; | 3.58 |
| 4-{4-Methyl-7-oxo-2-[4-(pyridine-3-carbonyl)-piperazin-1-yl]-7H-pyrido[2,3-d]pyrimidin-8-yl}-N-(4-trifluoromethyl-benzyl)-benzamide; | 3.19 |
| 4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid (3,4-difluoro-phenyl)-amide; | 4.07 |
| 4-{2-[4-(Furan-2-carbonyl)-piperazin-1-yl]-4- | 3.58 |

-continued

| Compound Name | Retention Time (min) |
|---|---|
| methyl-7-oxo-7H-pyrido[2,3-d]pyrimidin-8-yl}-N-(4-trifluoromethyl-benzyl)-benzamide; | |
| 4-[2-(4-Benzoyl-piperazin-1-yl)-4-methyl-7-oxo-7H-pyrido[2,3-d]pyrimidin-8-yl]-N-(4-trifluoromethyl-benzyl)-benzamide; | 3.71 |
| 4-[4-Methyl-7-oxo-2-(4-phenylacetyl-piperazin-1-yl)-7H-pyrido[2,3-d]pyrimidin-8-yl]-N-(4-trifluoromethyl-benzyl)-benzamide; | 3.8 |
| 4-(4-methyl-2-(methylsulfanyl)-7-oxopyrido[2,3-d]pyrimidin-8(7H)-yl)benzoic acid | |

We claim:
1. A pyrido[2,3-d]pyrimidin-7(8H)-one derivative having the following formula (I):

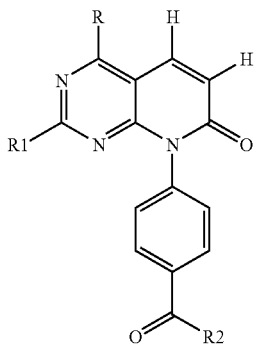

wherein
R represents C1–C6 alkyl or C1–C6 arylalkyl;
R1 represents NR3R4, wherein
R3 represents hydrogen, C1–C6 alkyl, alkenyl, aryl or acyl; and R4 represents hydrogen; unsubstituted C1–C10 alkyl; C1–C10 alkyl substituted by cycloalkyl, C1–C6 alkoxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, alkylsulfonylamino, alkylaminosulfonyl, arylaminosulfonyl, aryloxy, alkylsulfanyl, arylsulfanyl, alkylsulfinyl, arylsulfinyl, alkylsulfonyl or arylsulfonyl; C1–C10 alkyl substituted by phenyl unsubstituted or substituted by from 1 to 3 substituents chosen independently from halogen, C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C10 alkyl substituted by heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; alkenyl; cycloalkyl; cycloalkenyl; phenyl unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, or with heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, and piperidines; fused bicycles selected from the group consisting of 1-naphthyl, 2-naphthyl and dihydronaphthalenyl; monocyclic heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines and pyrrolidines, unsubstituted or substituted by C1–C6 alkyl, aryl, C1–C6 acyl, or arylalkyl; or benzoheterocycles selected from the group consisting of benzofuranyl, benzothiazolyl, benzothiophenyl and benzimidazolyl, unsubstituted or substituted by C1–C6 alkyl, aryl, C1–C6 acyl, or arylalkyl; or
NR3R4 represent a ring of the following type:

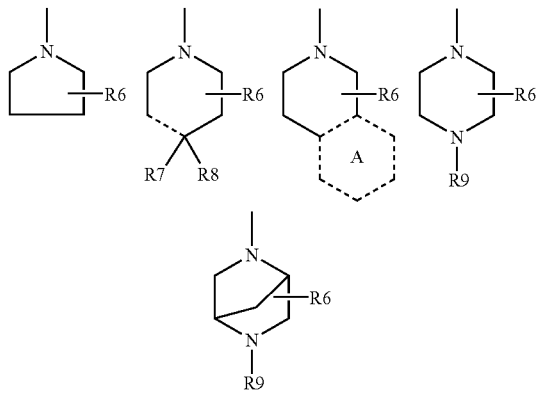

wherein
the symbol - - - - - represents a single or a double bond;
A represents a saturated, unsaturated or aromatic six-membered ring;

R6 represents hydrogen; C1–C6 alkyl unsubstituted or substituted by alkoxy, dialkylamino, arylamino, alkylcarbonyl, arylcarbonyl, substituted or unsubstituted aryl, unsubstituted or substituted heterocycle, alkoxycarbonyl, carboxy, acylamino; alkenyl; cycloalkyl; cyano; alkoxycarbonyl; carboxy; alkylsulfanyl; arylsulfanyl; carbamoyl; alkylcarbamoyl; dialkylcarbamoyl; arylcarbamoyl; acylamino; phenyl unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines, morpholines, piperidines, piperazines, pyrrolidines, indoles, benzofurans, benzothiazoles, benzothiophenes, benzimidazoles and phthalimido, unsubstituted or substituted by C1–C6 alkyl, aryl, C1–C6 acyl, or arylalkyl;

R7 and R8 represent, independently, hydrogen, C1–C6 alkyl (unsubstituted or substituted by alkoxy, hydroxy, amino, monoalkylamino, dialkylamino, arylamino, alkylcarbonyl, unsubstituted or substituted arylcarbonyl, substituted or unsubstituted aryl, unsubstituted or substituted heterocycle, alkoxycarbonyl, carboxy, acylamino); alkenyl; alkynyl; cycloalkyl; hydroxy; alkoxy; aryloxy; amino; alkylamino; arylamino; dialkylamino; diarylamino; alkylarylamino; acyloxy; alkoxycarbonyl; formyl; acyl; carboxy; acylamino; carbamoyl; alkylcarbamoyl; dialkylcarbamoyl; arylcarbamoyl; arylsulfonylamino; alkylaminosulfonyl; arylaminosulfonyl and cyano; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; heterocycles; selected from the group consisting of imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofurans, benzothiazoles, benzothiophenes and benzimidazoles, unsubstituted or substituted by C1–C6 alkyl, aryl, C1–C6 acyl, or arylalkyl; or R7 and R8 taken together represent oxygen, a spirocyclized substituent selected from the group consisting of ethylidendioxy, propylidendioxy, or cycloalkylidene;

R9 represents hydrogen; unsubstituted C1–C10 alkyl; C1–C10 alkyl substituted by cycloalkyl, C1–C6 alkoxy optionally substituted by hydroxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl or arylsulfonyl; C1–C10 alkyl substituted by phenyl unsubstituted or substituted by from 1 to 3 substituents, chosen independently from halogen, C1–C6 alkyl, C1–C6 alkoxy optionally substituted by hydroxy, methylenedioxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl; C1–C10 alkyl substituted by heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofuranes, benzothiazoles, benzothiophenes, benzimidazoles, and quinolines, unsubstituted or substituted by C1–C6 alkyl, aryl, C1–C6 acyl, or arylalkyl; alkenyl; cycloalkyl; cycloalkenyl; formyl; acyl comprising optionally substituted C1–C6 alkylcarbonyl, optionally substituted arylcarbonyl and optionally substituted heterocyclylcarbonyl; C1–C6 alkoxycarbonyl optionally substituted by phenyl; carbamoyl; optionally substituted alkylcarbamoyl; dialkylcarbamoyl; optionally substituted arylcarbamoyl; alkylsulfonyl; arylsulfonyl; phenyl unsubstituted or substituted by from 1 to 3 substituents, chosen independently from halogen, C1–C6 alkyl, C1–C6 acyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, and piperidines, unsubstituted or substituted aryl, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles selected from the group consisting of 1-naphthyl and 2-naphthyl and dihydronaphthalenyls; heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofuranes, benzothiazoles, benzothiophenes, benzimidazoles, and quinolines, unsubstituted or substituted by C1–C6 alkyl, aryl, C1–C6 acyl, or arylalkyl and R2 represents OR', wherein R' is hydrogen, C1C6 alkyl, alkenyl, or aryl; NR"R''', wherein R" represents hydrogen or C1–C6 alkyl, and R''' represents hydrogen; unsubstituted C1–C10 alkyl; alkenyl; cycloalkyl; cycloalkenyl; C1–C6 alkyl substituted with cycloalkyl, C1–C6 alkoxy, C1–C6 acyl, amino, monoalkylamino and monoalkylamino-N-oxides, monoarylamino and monoarylamino N-oxides, dialkylamino and dialkylamino N-oxides, alkylarylamino and alkylarylamino N-oxides, mono heterocycles selected from the group consisting of unsubstituted or substituted morpholinyl, furyl, tetrahydrofuryl, pyridinyl, pyrimidinyl, imidazolyl, pyrazolyl, oxazolyl, pyrrolyl, thiazolyl, piperazinyl, N-alkyl piperazinyl, and the corresponding N-oxides); fused bicycles selected from the group consisting of 1-naphthyl, 2-naphthyl and dihydronaphthalenyls; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C6 alkyl substituted by heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles selected from the group consisting of 1-naphthyl, 2-naphthyl and dihydronaphthalenyls; heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides.

2. A pyrido[2,3-d]pyrimidin-7(8H)-one derivative of claim 1,
wherein
R1 represents OR5, SR5, SOR5 or SO2R5, and wherein R5 represents unsubstituted C1–C6 alkyl; C1–C6 alkyl substituted by cycloalkyl, C1–C6 alkoxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl, arylsulfonyl; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl; C1–C6 alkyl substituted by heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; alkenyl; cycloalkyl; cycloalkenyl; phenyl unsubstituted or substituted by 1 to 3 substituents, chosen independently from halogen, C1–C6 alkyl, perhalogenated C1–C6 alkyl, C1–C6 alkyl substituted by aminocarbonyl or by OH, C1–C6 alkoxy, hydroxy, C1–C6 acyl, carboxy, cyano, nitro, amino, C1–C6 monoalkylamino, monoarylamino, C1–C6 dialkylamino, diarylamino, C1–C6 trialkylammonium halides, C1–C4 acylamino, (C1–C6 alkoxy)carbonyl, alkylsulfanyl, arylsulfanyl, alkylsulfinyl, arylsulfinyl, alkylsulfonyl, arylsulfonyl, alkylsulfonylamino, arylsulfonylamino, alkylaminosulfonyl, arylaminosulfonyl, aryloxy or arylalkyl; mono heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines and pyrrolidines, unsubstituted or substituted by C1–C6 alkyl, aryl, C1–C6 acyl, or arylalkyl; or benzoheterocycles selected from the group consisting of benzofuranyl, benzothiazolyl, benzothiophenyl, benzimidazolyl, unsubstituted or substituted by C1–C6 alkyl, aryl, C1–C6 acyl, or arylalkyl; and wherein R2 represents OR', wherein R' is hydrogen, C1C6 alkyl, alkenyl, or aryl; NR"R'", wherein R" represents hydrogen or C1–C6 alkyl, and R'" represents hydrogen; unsubstituted C1–C10 alkyl; alkenyl; cycloalkyl; cycloalkenyl; C1–C6 alkyl substituted with cycloalkyl, C1–C6 alkoxy, C1–C6 acyl, amino, monoalkylamino and monoalkylamino-N-oxides, monoarylamino and monoarylamino N-oxides, dialkylamino and dialkylamino N-oxides, alkylarylamino and alkylarylamino N-oxides, mono heterocycles selected from the group consisting of unsubstituted or substituted morpholinyl, furyl, tetrahydrofuryl, pyridinyl, pyrimidinyl, imidazolyl, pyrazolyl, oxazolyl, pyrrolyl, thiazolyl, piperazinyl, N-alkyl piperazinyl and the corresponding N-oxides; fused bicycles selected from the group consisting of 1-naphthyl, 2-naphthyl and dihydronaphthalenyls; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C6 alkyl substituted by heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles selected from the group consisting of 1-naphthyl, 2-naphthyl and dihydronaphthalenyls; heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and corresponding N-oxides.

3. A pharmaceutically acceptable salt of a pyrido[2,3-d]pyrimidin-7(8H)-one of formula I

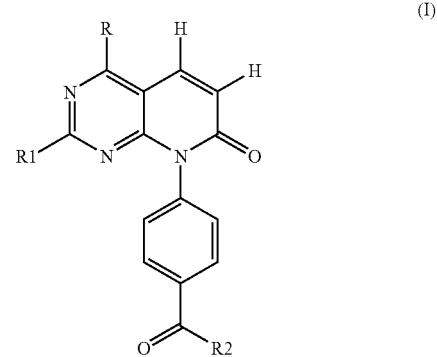

(I)

wherein
R represents C1–C6 alkyl or C1–C6 arylalkyl;
R1 represents NR3R4, wherein
R3 represents hydrogen, C1–C6 alkyl, alkenyl, aryl or acyl; and R4 represents hydrogen; unsubstituted C1–C10 alkyl; C1–C10 alkyl substituted by cycloalkyl, C1–C6 alkoxy, C1–C6 acyl, ammo, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl or arylsulfonyl; C1–C10 alkyl substituted by phenyl unsubstituted or substituted by from 1 to 3 substituents chosen independently from halogen, C1–C6 alkyl, C1–C6 alkoxy, hydroxy, carboxy, cyano, nitro, ammo, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C10 alkyl substituted by heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; alkenyl; cycloalkyl; cycloalkenyl; phenyl unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, or with heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, and piperidines; fused bicycles selected from the group consisting of 1-naphthyl, 2-naphthyl and dihydronaphthalenyl; monocyclic heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines and pyrrolidines, unsubstituted or substituted by C1–C6 alkyl, aryl, C1–C6 acyl, or arylalkyl; or benzoheterocycles selected from the group consisting of benzofuranyl, benzothiazolyl, benzothiophenyl and benzimidazolyl, unsubstituted or substituted by C1–C6 alkyl, aryl, C1–C6 acyl, or arylalkyl; or NR3R4 represent a ring of the following type:

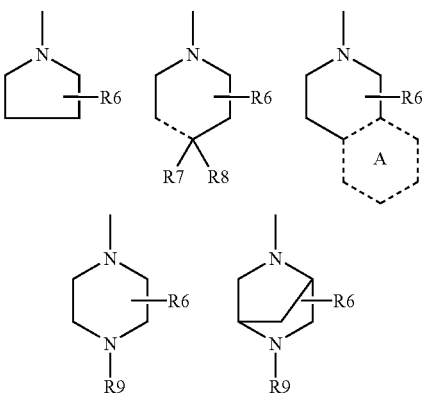

wherein the symbol - - - - - represents a single or a double bond;

A represents a saturated, unsaturated or aromatic six-membered ring;

R6 represents hydrogen; C1–C6 alkyl unsubstituted or substituted by alkoxy, dialkylamino, arylamino, alkylcarbonyl, arylcarbonyl, substituted or unsubstituted aryl, unsubstituted or substituted heterocycle, alkoxycarbonyl, carboxy, acylamino; alkenyl; cycloalkyl; cyano; alkoxycarbonyl; carboxy; alkylsulfanyl; arylsulfanyl; carbamoyl; alkylcarbamoyl; dialkylcarbamoyl; arylcarbamoyl; acylamino; phenyl unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines, morpholines, piperidines, piperazines, pyrrolidines, indoles, benzofurans, benzothiazoles, benzothiophenes, benzimidazoles and phthalimido, unsubstituted or substituted by C1–C6 alkyl, aryl, C1–C6 acyl, or arylalkyl;

R7 and R8 represent, independently, hydrogen, C1–C6 alkyl (unsubstituted or substituted by alkoxy, hydroxy, amino, monoalkylamino, dialkylamino, arylamino, alkylcarbonyl, unsubstituted or substituted arylcarbonyl, substituted or unsubstituted aryl, unsubstituted or substituted heterocycle, alkoxycarbonyl, carboxy, acylamino); alkenyl; alkynyl; cycloalkyl; hydroxy; alkoxy; aryloxy; amino; alkylamino; arylamino; dialkylamino; diarylamino; alkylarylamino; acyloxy; alkoxycarbonyl; formyl; acyl; carboxy; acylamino; carbamoyl; alkylcarbamoyl; dialkylcarbamoyl; arylcarbamoyl; arylsulfonylamino; alkylaminosulfonyl; arylaminosulfonyl and cyano; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; heterocycles, selected from the group consisting of imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofurans, benzothiazoles, benzothiophenes and benzimidazoles, unsubstituted or substituted by C1–C6 alkyl, aryl, C1–C6 acyl, or arylalkyl; or R7 and R8 taken together represent oxygen, a spirocyclized substituent selected from the group consisting of ethylidendioxy, propylidendioxy, or cycloalkylidene;

R9 represents hydrogen; unsubstituted C1–C10 alkyl; C1–C10 alkyl substituted by cycloalkyl, C1–C6 alkoxy optionally substituted by hydroxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl or arylsulfonyl; C1–C10 alkyl substituted by phenyl unsubstituted or substituted by from 1 to 3 substituents, chosen independently from halogen, C1–C6 alkyl, C1–C6 alkoxy optionally substituted by hydroxy, methylenedioxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl; C1–C10 alkyl substituted by heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofuranes, benzothiazoles, benzothiophenes, benzimidazoles, and quinolines, unsubstituted or substituted by C1–C6 alkyl, aryl, C1–C6 acyl, or arylalkyl; alkenyl; cycloalkyl; cycloalkenyl; formyl; acyl comprising optionally substituted C1–C6 alkylcarbonyl, optionally substituted arylcarbonyl and optionally substituted heterocyclylcarbonyl; C1–C6 alkoxycarbonyl optionally substituted by phenyl; carbamoyl; optionally substituted alkylcarbamoyl; dialkylcarbamoyl; optionally substituted arylcarbamoyl; alkylsulfonyl; arylsulfonyl; phenyl unsubstituted or substituted by from 1 to 3 substituents, chosen independently from halogen, C1–C6 alkyl, C1–C6 acyl, perhalogenated C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, and piperidines, unsubstituted or substituted aryl, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles selected from the group consisting of 1-naphthyl and 2-naphthyl and dihydronaphthalenyls; heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines, pyrrolidines, indoles, benzofuranes, benzothiazoles, benzothiophenes, benzimidazoles, and quinolines, unsubstituted or substituted by C1–C6 alkyl, aryl, C1–C6 acyl, or arylalkyl and R2 represents OR', wherein R' is hydrogen, C1C6 alkyl, alkenyl, or aryl; NR''R''', wherein R'' represents hydrogen or C1–C6 alkyl, and R''' represents hydrogen; unsubstituted C1–C10 alkyl; alkenyl; cycloalkyl; cycloalkenyl; C1–C6 alkyl substituted with cycloalkyl, C1–C6 alkoxy, C1–C6 acyl, amino, monoalkylamino and monoalkylamino-N-oxides, monoarylamino and monoarylamino N-oxides, dialkylamino and dialkylamino N-oxides, alkylarylamino and alkylarylamino N-oxides, mono heterocycles selected from the group consisting of unsubstituted or substituted morpholinyl, furyl, tetrahydrofuryl, pyridinyl, pyrimidinyl, imidazolyl, pyrazolyl, oxazolyl, pyrrolyl, thiazolyl, piperazinyl, N-alkyl piperazinyl and the corresponding N-oxides); fused bicycles selected from the group consisting of 1-naphthyl, 2-naphthyl and dihydronaphthalenyls; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C6 alkyl substituted by heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles selected from the group consisting of 1-naphthyl, 2-naphthyl and dihydronaphthalenyls; heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides.

4. A pharmaceutically acceptable salt of a pyrido[2,3-d]pyrimidin-7(8H)-one of formula I

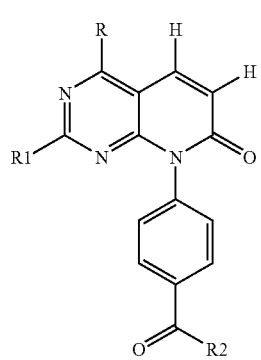

wherein
R1 represents OR5, SR5, SOR5 or SO2R5, and wherein R5 represents unsubstituted C1–C6 alkyl; C1–C6 alkyl substituted by cycloalkyl, C1–C6 alkoxy, C1–C6 acyl, amino, C1–C6 monoalkylamino, monoarylamino, C1–C6 dialkylamino, diarylamino, alkylarylamino, hydroxy, carboxy, cyano, nitro, acylamino, alkoxycarbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, alkylsulfanyl, arylsulfanyl, alkylsulfinyl, arylsulfinyl, alkylsulfonyl, arylsulfonyl; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino, monoarylamino, dialkylamino, alkylarylamino, diarylamino, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl; C1–C6 alkyl substituted by heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; alkenyl; cycloalkyl; cycloalkenyl; phenyl unsubstituted or substituted by 1 to 3 substituents, chosen independently from halogen, C1–C6 alkyl, perhalogenated C1–C6 alkyl, C1–C6 alkyl substituted by aminocarbonyl or by OH, C1–C6 alkoxy, hydroxy, C1–C6 acyl, carboxy, cyano, nitro, amino, C1–C6 monoalkylamino, monoarylamino, C1–C6 dialkylamino, diarylamino, C1–C6 trialkylammonium halides, C1–C4 acylamino, (C1–C6 alkoxy)carbonyl, alkylsulfanyl, arylsulfanyl, alkylsulfinyl, arylsulfinyl, alkylsulfonyl, arylsulfonyl, alkylsulfonylamino, arylsulfonylamino, alkylaminosulfonyl, arylaminosulfonyl, aryloxy or arylalkyl; mono heterocycles selected from the group consisting of imidazoles, pyrazoles, oxazoles, oxadiazoles, pyrroles, furans, thiadiazoles, oxazoles, thiazoles, triazoles, tetrazoles, pyridines, pyrimidines and pyrrolidines, unsubstituted or substituted by C1–C6 alkyl, aryl, C1–C6 acyl, or arylalkyl; or benzoheterocycles selected from the group consisting of benzofuranyl, benzothiazolyl, benzothiophenyl, benzimidazolyl, unsubstituted or substituted by C1–C6 alkyl, aryl, C1–C6 acyl, or arylalkyl; and wherein R2 represents OR', wherein R' is hydrogen, C1C6 alkyl, alkenyl, or aryl; NR"R'", wherein R" represents hydrogen or C1–C6 alkyl, and R'" represents hydrogen; unsubstituted C1–C10 alkyl; alkenyl; cycloalkyl; cycloalkenyl; C1–C6 alkyl substituted with cycloalkyl, C1–C6 alkoxy, C1–C6 acyl, amino, monoalkylamino and monoalkylamino-N-oxides, monoarylamino and monoarylamino N-oxides, dialkylamino and dialkylamino N-oxides, alkylarylamino and alkylarylamino N-oxides, mono heterocycles selected from the group consisting of unsubstituted or substituted morpholinyl, furyl, tetrahydrofuryl, pyridinyl, pyrimidinyl, imidazolyl, pyrazolyl, oxazolyl, pyrrolyl, thiazolyl, piperazinyl, N-alkyl piperazinyl and the corresponding N-oxides); fused bicycles selected from the group consisting of 1-naphtyl, 2-naphtyl and dihydronaphthalenyls; C1–C6 alkyl substituted by phenyl unsubstituted or substituted by 1 to 3 substituents, chosen independently from halogen, C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, aryloxycarbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy or arylalkyl; C1–C6 alkyl substituted by heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides; phenyls unsubstituted or substituted by 1 to 3 substituents, chosen independently from halogen, C1–C6 alkyl, perhalogenated C1–C6 alkyl, C1–C6 alkoxy, hydroxy, carboxy, cyano, nitro, amino, monoalkylamino and the corresponding N-oxides, monoarylamino and the corresponding N-oxides, dialkylamino and the corresponding N-oxides, alkylarylamino and the corresponding N-oxides, diarylamino and the corresponding N-oxides, C1–C6 trialkylammonium halides, alkylsulfanyl, arylsulfanyl, alkylsulfinyl, arylsulfinyl, alkylsulfonyl, arylsulfonyl, C1–C6 acylamino, (C1–C6 alkoxy)carbonyl, carbamoyl, alkylcarbamoyl, dialkylcarbamoyl, arylcarbamoyl, alkylsulfonylamino, arylsulfonylamino, alkylaminosulfonyl, arylaminosulfonyl, aryloxy, arylalkyl, cycloalkyls, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and the corresponding N-oxides, phenyl unsubstituted or substituted by from one to three of the following groups: halogen, C1–C4 alkoxy, hydroxyl, cyano, nitro, straight or branched C1–C6 alkyl, carboxy, (C1–C6 alkoxy)carbonyl, aryloxycarbonyl, amino, C1–C4 dialkylamino, heterocycles selected from the group consisting of imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines and piperidines; fused bicycles selected from the group consisting of 1-naphthyl, 2-naphthyl and dihydronaphthalenyls; heterocycles selected from the group consisting of unsubstituted or substituted imidazoles, pyrazoles, oxadiazoles, pyrroles, furans, thiadiazoles, oxazoles, thiazoles, triazoles, tetrazoles, piperazines, N-alkyl piperazines, triazines, morpholines, pyridines, pyrimidines, pyrrolidines, piperidines and corresponding N-oxides.

5. A pyrido[2,3-d]pyrimidin-7(8H)-ones derivative selected from the group consisting of:

tert-butyl 4-(4-methyl-2-(methylsulfanyl)-7-oxopyrido[2,3-d]pyrimidin-8(7H)-yl)benzoate (1)

tert-butyl 4-(4-methyl-2-(methylsulfonyl)-7-oxopyrido[2,3-d]pyrimidin-8(7H)-yl)benzoate (2)

tert-butyl 4-(2-[4-(ethoxycarbonyl)anilino]-4-methyl-7-oxopyrido[2,3-d]pyrimidin-8(7H)-yl)benzoate (3)

tert-butyl 4-(4-methyl-7-oxo-2-(4-phenyl-1-piperazinyl)pyrido[2,3-d]pyrimidin-8(7H)-yl)benzoate (4)

tert-butyl 4-(2-[4-(4-fluorophenyl)-1-piperazinyl]-4-methyl-7-oxopyrido[2,3-d]pyrimidin-8(7H)-yl)benzoate (5)

tert-butyl 4-(4-methyl-7-oxo-2-[4-(2-pyridinyl)-1-piperazinyl]pyrido[2,3-d]pyrimidin-8(7H)-yl)benzoate (6)

tert-butyl 4-(4-methyl-7-oxo-2-[4-(2-pyrimidinyl)-1-piperazinyl]pyrido[2,3-d]pyrimidin-8(7H)-yl)benzoate (7)

tert-butyl 4-(2-(3,4-dihydro-2(1H)-isoquinolinyl)-4-methyl-7-oxopyrido[2,3-d]pyrimidin-8(7H)-yl)benzoate (8)

4-(2-[4-(ethoxycarbonyl)anilino]-4-methyl-7-oxopyrido[2,3-d]pyrimidin-8(7H)-yl)benzoic acid (9)

4-(4-methyl-7-oxo-2-(4-phenyl-1-piperazinyl)pyrido[2,3-d]pyrimidin-8(7H)-yl)benzoic acid (10)

4-(2-[4-(4-fluorophenyl)-1-piperazinyl]-4-methyl-7-oxopyrido[2,3-d]pyrimidin-8(7H)-yl)benzoic acid (11)

4-(4-methyl-7-oxo-2-[4-(2-pyridinyl)-1-piperazinyl]pyrido[2,3-d]pyrimidin-8(7H)-yl)benzoic acid (12)

4-(4-methyl-7-oxo-2-[4-(2-pyrimidinyl)-1-piperazinyl]pyrido[2,3-d]pyrimidin-8(7H)-yl)benzoic acid (13)

4-(2-(3,4-dihydro-2(1H)-isoquinolinyl)-4-methyl-7-oxopyrido[2,3-d]pyrimidin-8(7H)-yl)benzoic acid (14)

N-benzyl-4-(4-methyl-7-oxo-2-(4-phenyl-1-piperazinyl)pyrido[2,3-d]pyrimidin-8(7H)-yl)benzamide (15)

N-(2-furylmethyl)-4-(4-methyl-7-oxo-2-(4-phenyl-1-piperazinyl)pyrido[2,3-d]pyrimidin-8(7H)-yl)benzamide (16)

4-(4-methyl-7-oxo-2-(4-phenyl-1-piperazinyl)pyrido[2,3-d]pyrimidin-8(7H)-yl)-N-(3-pyridinylmethyl)benzamide (17)

4-(4-methyl-7-oxo-2-(4-phenyl-1-piperazinyl)pyrido[2,3-d]pyrimidin-8(7H)-yl)-N-(1-naphthylmethyl)benzamide (18)

N-(3,4-dimethoxybenzyl)-4-(4-methyl-7-oxo-2-(4-phenyl-1-piperazinyl)pyrido[2,3-d]pyrimidin-8(7H)-yl)benzamide (19)

N-benzyl-4-(2-[4-(4-fluorophenyl)-1-piperazinyl]-4-methyl-7-oxopyrido[2,3-d]pyrimidin-8(7H)-yl)benzamide (20)

4-(2-[4-(4-fluorophenyl)-1-piperazinyl]-4-methyl-7-oxopyrido[2,3-d]pyrimidin-8(7H)-yl)-N-(2-furylmethyl)benzamide (21)

N-benzyl-4-(4-methyl-7-oxo-2-[4-(2-pyridinyl)-1-piperazinyl]pyrido[2,3-d]pyrimidin-8(7H)-yl)benzamide (22)

4-(4-methyl-7-oxo-2-[4-(2-pyridinyl)-1-piperazinyl]pyrido[2,3-d]pyrimidin-8(7H)-yl)-N-(3-pyridinylmethyl)benzamide (23)

N-(2-furylmethyl)-4-(4-methyl-7-oxo-2-[4-(2-pyridinyl)-1-piperazinyl]pyrido[2,3-d]pyrimidin-8(7H)-yl)benzamide (24)

N-(3,4-dimethoxybenzyl)-4-(4-methyl-7-oxo-2-[4-(2-pyridinyl)-1-piperazinyl]pyrido[2,3-d]pyrimidin-8(7H)-yl)benzamide (25)

4-(4-methyl-7-oxo-2-[4-(2-pyridinyl)-1-piperazinyl]pyrido[2,3-d]pyrimidin-8(7H)-yl)-N-(2-naphthylmethyl)benzamide (26)

N-benzyl-4-(4-methyl-7-oxo-2-[4-(2-pyrimidinyl)-1-piperazinyl]pyrido[2,3-d]pyrimidin-8(7H)-yl)benzamide (27)

N-(2-furylmethyl)-4-(4-methyl-7-oxo-2-[4-(2-pyrimidinyl)-1-piperazinyl]pyrido[2,3-d]pyrimidin-8(7H)-yl)benzamide (28)

N-(3,4-dimethoxybenzyl)-4-(4-methyl-7-oxo-2-[4-(2-pyrimidinyl)-1-piperazinyl]pyrido[2,3-d]pyrimidin-8(7H)-yl)benzamide (29)

4-(4-methyl-7-oxo-2-[4-(2-pyrimidinyl)-1-piperazinyl]pyrido[2,3-d]pyrimidin-8(7H)-yl)-N-(3-pyridinylmethyl)benzamide (30)

N-(2,4-difluorobenzyl)-4-(4-methyl-7-oxo-2-[4-(2-pyrimidinyl)-1-piperazinyl]pyrido[2,3-d]pyrimidin-8(7H)-yl)benzamide (31)

4-(4-methyl-7-oxo-2-[4-(2-pyrimidinyl)-1-piperazinyl]pyrido[2,3-d]pyrimidin-8(7H)-yl)-N-(1-naphthylmethyl)benzamide (32)

N-cyclopropyl-4-(2-(3,4-dihydro-2(1H)-isoquinolinyl)-4-methyl-7-oxopyrido[2,3-d]pyrimidin-8(7H)-yl)benzamide (33)

4-(2-(3,4-dihydro-2(1H)-isoquinolinyl)-4-methyl-7-oxopyrido[2,3-d]pyrimidin-8(7H)-yl)-N-(3,4-dimethoxyphenyl)benzamide (34)

4-(2-(3,4-dihydro-2(1H)-isoquinolinyl)-4-methyl-7-oxopyrido[2,3-d]pyrimidin-8(7H)-yl)-N,N-dimethylbenzamide (35)

4-(2-(3,4-dihydro-2(1H)-isoquinolinyl)-4-methyl-7-oxopyrido[2,3-d]pyrimidin-8(7H)-yl)-N-(3,4-dimethoxybenzyl)benzamide (36)

Ethyl 4-{[4-(2-(3,4-dihydro-2(1H)-isoquinolinyl)-4-methyl-7-oxopyrido[2,3-d]pyrimidin-8(7H)-yl)benzoyl]amino}benzoate (37)

N-(3-cyanophenyl)-4-(2-(3,4-dihydro-2(1H)-isoquinolinyl)-4-methyl-7-oxopyridol[2,3-d]pyrimidin-8(7H)-yl)benzamide (38)

N-cyclohexyl-4-(2-(3,4-dihydro-2(1H)-isoquinolinyl)-4-methyl-7-oxopyrido[2,3-d]pyrimidin-8(7H)-yl)benzamide (39)

N-(3,4-dichlorophenyl)-4-(2-(3,4-dihydro-2(1H)-isoquinolinyl)-4-methyl-7-oxopyrido[2,3-d]pyrimidin-8(7H)-yl)benzamide (40)

methyl 4-({8-[4-(methoxycarbonyl)phenyl]-4-methyl-7-oxo-7,8-dihydropyrido[2,3-d]pyrimidin-2-yl}amino)benzoate (41)

Ethyl 4-({8-[4-(ethoxycarbonyl)phenyl]-4-methyl-7-oxo-7,8-dihydropyrido[2,3-d]pyrimidin-2-yl}amino)benzoate (42)

4-(2-Isobutylamino-4-methyl-7-oxo-7H-pyrido[2,3-d]pyrimidin-8-yl)-N-octyl-benzamide (43)

4-(2-Isobutylamino-4-methyl-7-oxo-7H-pyrido[2,3-d]pyrimidin-8-yl)-N-phenyl-benzamide (44)

4-[2-(3,4-Dihydro-1H-isoquinolin-2-yl)-4-methyl-7-oxo-7H-pyrido[2,3-d]pyrimidin-8-yl]-N-[2-(4-oxy-morpholin-4-yl)-ethyl]-benzamide (45)

4-(2-(3,4-dihydro-2(1H)-isoquinolinyl)-4-methyl-7-oxopyrido[2,3-d]pyrimidin-8(7H)-yl)-N-[3-(dimethylamino-N-oxido)propyl]benzamide (46)

4-[2-(2-Methoxy-ethylamino)-4-methyl-7-oxo-7H-pyrido[2,3-d]pyrimidin-8-yl]-N-[2-(4-oxy-morpholin-4-yl)-ethyl]-benzamide (47)

N-[3-(dimethylamino-N-oxido)propyl]-4-(2-[(2-methoxyethyl)amino]-4-methyl-7-oxopyrido[2,3-d]pyrimidin-8(7H)-yl)benzamide (48)

N-[3-(dimethylamino-N-oxido)propyl]-4-(2-[(2-furylmethyl)amino]-4-methyl-7-oxopyrido[2,3-d]pyrimidin-8(7H)-yl)benzamide (49)

4-(2-[(2-furylmethyl)amino]-4-methyl-7-oxopyrido[2,3-d]pyrimidin-8(7H)-yl)-N-(2-phenylethyl)benzamide (50)

4-(2-[(2-furylmethyl)amino]-4-methyl-7-oxopyrido[2,3-d]pyrimidin-8(7H)-yl)-N-isobutylbenzamide (51)

N-[3-(dimethylamino-N-oxido)propyl]-4-(2-[(2-ethylhexyl)amino]-4-methyl-7-oxopyrido[2,3-d]pyrimidin-8(7H)-yl)benzamide (52)

4-(2-[(2-ethylhexyl)amino]-4-methyl-7-oxopyrido[2,3-d]pyrimidin-8(7H)-yl)-N-(2-phenylethyl)benzamide (53)

4-(2-{[2-(acetylamino)ethyl]amino}-4-methyl-7-oxopyrido[2,3-d]pyrimidin-8(7H)-yl)-N-[3-(dimethylamino-N-oxido)propyl]benzamide (54)

4-(2-{[2-(acetylamino)ethyl]amino}-4-methyl-7-oxopyrido[2,3-d]pyrimidin-8(7H)-yl)-N-(tetrahydro-2-furanylmethyl)benzamide (55)

4-(2-(benzylamino)-4-methyl-7-oxopyrido[2,3-d]pyrimidin-8(7H)-yl)-N-[3-(dimethylamino-N-oxido)propyl]benzamide (56)

4-(2-(benzylamino)-4-methyl-7-oxopyrido[2,3-d]pyrimidin-8(7H)-yl)-N-isobutylbenzamide (57)

4-(2-[(2-aminoethyl)amino]-4-methyl-7-oxopyrido[2,3-d]pyrimidin-8(7H)-yl)-N-[3-(dimethylamino-N-oxido)propyl]benzamide (58)

4-(2-[(2-aminoethyl)amino]-4-methyl-7-oxopyrido[2,3-d]pyrimidin-8(7H)-yl)-N-(2-furylmethyl)benzamide (59)

4-(4-methyl-7-oxo-2-[4-(2-pyrimidinyl)-1-piperazinyl]pyrido[2,3-d]pyrimidin-8(7H)-yl)-N-[2-(4-oxido-4-morpholinyl)ethyl]benzamide (60)

N-[3-(dimethylamino-N-oxido)propyl]-4-(4-methyl-7-oxo-2-[4-(2-pyrimidinyl)-1-piperazinyl]pyrido[2,3-d]pyrimidin-8(7H)-yl)benzamide (61)

4-(4-methyl-7-oxo-2-(1-piperazinyl)pyrido[2,3-d]pyrimidin-8(7H)-yl)-N-[2-(4-oxido-4-morpholinyl)ethyl]benzamide (62)

4-(4-methyl-7-oxo-2-(1-pyrrolidinyl)pyrido[2,3-d]pyrimidin-8(7H)-yl)-N-[2-(4-oxido-4-morpholinyl)ethyl]benzamide (63)

4-(2-[(2-hydroxyethyl)amino]-4-methyl-7-oxopyrido[2,3-d]pyrimidin-8(7H)-yl)-N-(tetrahydro-2-furanylmethyl)benzamide (64)

4-(2-{[2-(2-methoxyphenyl)ethyl]amino}-4-methyl-7-oxopyrido[2,3-d]pyrimidin-8(7H)-yl)-N-[2-(4-oxido-4-morpholinyl)ethyl]benzamide (65)

N-[3-(dimethylamino-N-oxido)propyl]-4-(2-{[2-(2-methoxyphenyl)ethyl]amino}-4-methyl-7-oxopyrido[2,3-d]pyrimidin-8(7H)-yl)benzamide (66)

N-(2-furylmethyl)-4-(2-{[2-(2-methoxyphenyl)ethyl]amino}-4-methyl-7-oxopyrido[2,3-d]pyrimidin-8(7H)-yl)benzamide (67)

4-(2-(3,4-dihydro-2(1H)-isoquinolinyl)-4-methyl-7-oxopyrido[2,3-d]pyrimidin-8(7H)-yl)-N-(2-furylmethyl)benzamide (68)

4-(2-(3,4-dihydro-2(1H)-isoquinolinyl)-4-methyl-7-oxopyrido[2,3-d]pyrimidin-8(7H)-yl)-N-octylbenzamide (69)

N-benzyl-4-(2-(3,4-dihydro-2(1H)-isoquinolinyl)-4-methyl-7-oxopyrido[2,3-d]pyrimidin-8(7H)-yl)benzamide (70)

4-(2-(3,4-dihydro-2(1H)-isoquinolinyl)-4-methyl-7-oxopyrido[2,3-d]pyrimidin-8(7H)-yl)-N-(2-phenylethyl)benzamide (71)

4-(2-(3,4-dihydro-2(1H)-isoquinolinyl)-4-methyl-7-oxopyrido[2,3-d]pyrimidin-8(7H)-yl)-N-isobutylbenzamide (72)

4-(2-(3,4-dihydro-2(1H)-isoquinolinyl)-4-methyl-7-oxopyrido[2,3-d]pyrimidin-8(7H)-yl)-N-(tetrahydro-2-furanylmethyl)benzamide (73)

N-(cyclohexylmethyl)-4-(2-(3,4-dihydro-2(1H)-isoquinolinyl)-4-methyl-7-oxopyrido[2,3-d]pyrimidin-8(7H)-yl)benzamide (74)

N-cyclopropyl-4-(4-methyl-2-{[2-(4-morpholinyl)ethyl]amino}-7-oxopyrido[2,3-d]pyrimidin-8(7H)-yl)benzamide (75)

4-(4-methyl-2-{[2-(4-morpholinyl)ethyl]amino}-7-oxopyrido[2,3-d]pyrimidin-8(7H)-yl)-N-octylbenzamide (76)

N-(2-furylmethyl)-4-(4-methyl-2-{[2-(4-morpholinyl)ethyl]amino}-7-oxopyrido[2,3-d]pyrimidin-8(7H)-yl)benzamide (77)

N-(3,4-dimethoxyphenyl)-4-(4-methyl-2-{[2-(4-morpholinyl)ethyl]amino}-7-oxopyrido[2,3-d]pyrimidin-8(7H)-yl)benzamide (78)

N-benzyl-4-(4-methyl-2-{[2-(4-morpholinyl)ethyl]amino}-7-oxopyrido[2,3-d]pyrimidin-8(7H)-yl)benzamide (79)

4-(4-methyl-2-{[2-(4-morpholinyl)ethyl]amino}-7-oxopyrido[2,3-d]pyrimidin-8(7H)-yl)-N-(2-phenylethyl)benzamide (80)

N-isobutyl-4-(4-methyl-2-{[2-(4-morpholinyl)ethyl]amino}-7-oxopyrido[2,3-d]pyrimidin-8(7H)-yl)benzamide (81)

4-(4-methyl-2-{[2-(4-morpholinyl)ethyl]amino}-7-oxopyrido[2,3-d]pyrimidin-8(7H)-yl)-N-(tetrahydro-2-furanylmethyl)benzamide (82)

N-(cyclohexylmethyl)-4-(4-methyl-2-{[2-(4-morpholinyl)ethyl]amino}-7-oxopyrido[2,3-d]pyrimidin-8(7H)-yl)benzamide (83)

N-cyclopropyl-4-(2-[(2-methoxyethyl)amino]-4-methyl-7-oxopyrido[2,3-d]pyrimidin-8(7H)-yl)benzamide (84)

4-(2-[(2-methoxyethyl)amino]-4-methyl-7-oxopyrido[2,3-d]pyrimidin-8(7H)-yl)-N-octylbenzamide (85)

N-(2-furylmethyl)-4-(2-[(2-methoxyethyl)amino]-4-methyl-7-oxopyrido[2,3-d]pyrimidin-8(7H)-yl)benzamide (86)

N-(3,4-dimethoxyphenyl)-4-(2-[(2-methoxyethyl)amino]-4-methyl-7-oxopyrido[2,3-d]pyrimidin-8(7H)-yl)benzamide (87)

N-benzyl-4-(2-[(2-methoxyethyl)amino]-4-methyl-7-oxopyrido[2,3-d]pyrimidin-8(7H)-yl)benzamide (88)

4-(2-[(2-methoxyethyl)amino]-4-methyl-7-oxopyrido[2,3-d]pyrimidin-8(7H)-yl)-N-(2-phenylethyl)benzamide (89)

N-isobutyl-4-(2-[(2-methoxyethyl)amino]-4-methyl-7-oxopyrido[2,3-d]pyrimidin-8(7H)-yl)benzamide (90)

4-(2-[(2-methoxyethyl)amino]-4-methyl-7-oxopyrido[2,3-d]pyrimidin-8(7H)-yl)-N-(tetrahydro-2-furanylmethyl)benzamide (91)

N-(cyclohexylmethyl)-4-(2-[(2-methoxyethyl)amino]-4-methyl-7-oxopyrido[2,3-d]pyrimidin-8(7H)-yl)benzamide (92)

N-cyclopropyl-4-(2-[(2-furylmethyl)amino]-4-methyl-7-oxopyrido[2,3-d]pyrimidin-8(7H)-yl)benzamide (93)

4-(2-[(2-furylmethyl)amino]-4-methyl-7-oxopyrido[2,3-d]pyrimidin-8(7H)-yl)-N-octylbenzamide (94)

N-(2-furylmethyl)-4-(2-[(2-furylmethyl)amino]-4-methyl-7-oxopyrido[2,3-d]pyrimidin-8(7H)-yl)benzamide (95)

N-(3,4-dimethoxyphenyl)-4-(2-[(2-furylmethyl)amino]-4-methyl-7-oxopyrido[2,3-d]pyrimidin-8(7H)-yl)benzamide (96)

N-benzyl-4-(2-[(2-furylmethyl)amino]-4-methyl-7-oxopyrido[2,3-d]pyrimidin-8(7H)-yl)benzamide (97)

4-(2-[(2-furylmethyl)amino]-4-methyl-7-oxopyrido[2,3-d]pyrimidin-8(7H)-yl)-N-(tetrahydro-2-furanylmethyl)benzamide (98)

N-(cyclohexylmethyl)-4-(2-[(2-furylmethyl)amino]-4-methyl-7-oxopyrido[2,3-d]pyrimidin-8(7H)-yl)benzamide (99)

N-cyclopropyl-4-(2-[(2-ethylhexyl)amino]-4-methyl-7-oxopyrido[2,3-d]pyrimidin-8(7H)-yl)benzamide (100)

N-benzyl-4-(2-[(2-ethylhexyl)amino]-4-methyl-7-oxopyrido[2,3-d]pyrimidin-8(7H)-yl)benzamide (101)

4-(2-[(2-ethylhexyl)amino]-4-methyl-7-oxopyrido[2,3-d]pyrimidin-8(7H)-yl)-N-(2-furylmethyl)benzamide (102)

N-(3,4-dimethoxyphenyl)-4-(2-[(2-ethylhexyl)amino]-4-methyl-7-oxopyrido[2,3-d]pyrimidin-8(7H)-yl)benzamide (103)

4-(2-[(2-ethylhexyl)amino]-4-methyl-7-oxopyrido[2,3-d]pyrimidin-8(7H)-yl)-N-isobutylbenzamide (104)

N-(cyclohexylmethyl)-4-(2-[(2-ethylhexyl)amino]-4-methyl-7-oxopyrido[2,3-d]pyrimidin-8(7H)-yl)benzamide (105)

4-(2-{[2-(acetylamino)ethyl]amino}-4-methyl-7-oxopyrido[2,3-d]pyrimidin-8(7H)-yl)-N-cyclopropylbenzamide (106)

4-(2-{[2-(acetylamino)ethyl]amino}-4-methyl-7-oxopyrido[2,3-d]pyrimidin-8(7H)-yl)-N-octylbenzamide (107)

4-(2-{[2-(acetylamino)ethyl]amino}-4-methyl-7-oxopyrido[2,3-d]pyrimidin-8(7H)-yl)-N-(2-furylmethyl)benzamide (108)

4-(2-{[2-(acetylamino)ethyl]amino}-4-methyl-7-oxopyrido[2,3-d]pyrimidin-8(7H)-yl)-N-(3,4-dimethoxyphenyl)benzamide (109)

4-(2-{[2-(acetylamino)ethyl]amino}-4-methyl-7-oxopyrido[2,3-d]pyrimidin-8(7H)-yl)-N-benzylbenzamide (110)

4-(2-{[2-(acetylamino)ethyl]amino}-4-methyl-7-oxopyrido[2,3-d]pyrimidin-8(7H)-yl)-N-(2-phenylethyl)benzamide (111)

4-(2-{[2-(acetylamino)ethyl]amino}-4-methyl-7-oxopyrido[2,3-d]pyrimidin-8(7H)-yl)-N-isobutylbenzamide (112)

4-(2-{[2-(acetylamino)ethyl]amino}-4-methyl-7-oxopyrido[2,3-d]pyrimidin-8(7H)-yl)-N-(cyclohexylmethyl)benzamide (113)

4-(2-(benzylamino)-4-methyl-7-oxopyrido[2,3-d]pyrimidin-8(7H)-yl)-N-cyclopropylbenzamide (114)

4-(2-(benzylamino)-4-methyl-7-oxopyridol[2,3-d]pyrimidin-8(7H)-yl)-N-octylbenzamide (115)

4-(2-(benzylamino)-4-methyl-7-oxopyrido[2,3-d]pyrimidin-8(7H)-yl)-N-(2-furylmethyl)benzamide (116)

4-(2-(benzylamino)-4-methyl-7-oxopyrido[2,3-d]pyrimidin-8(7H)-yl)-N-(3,4-dimethoxyphenyl)benzamide (117)

N-benzyl-4-(2-(benzylamino)-4-methyl-7-oxopyrido[2,3-d]pyrimidin-8(7H)-yl)benzamide (118)

4-(2-(benzylamino)-4-methyl-7-oxopyrido[2,3-d]pyrimidin-8(7H)-yl)-N-(2-phenylethyl)benzamide (119)

4-(2-(benzylamino)-4-methyl-7-oxopyrido[2,3-d]pyrimidin-8(7H)-yl)-N-(tetrahydro-2-furanylmethyl)benzamide (120)

4-(2-(benzylamino)-4-methyl-7-oxopyrido[2,3-d]pyrimidin-8(7H)-yl)-N-(cyclohexylmethyl)benzamide (121)

4-(2-[(2-aminoethyl)amino]-4-methyl-7-oxopyrido[2,3-d]pyrimidin-8(7H)-yl)-N-cyclopropylbenzamide (122)

4-(2-[(2-aminoethyl)amino]-4-methyl-7-oxopyrido[2,3-d]pyrimidin-8(7H)-yl)-N-octylbenzamide (123)

4-(2-[(2-aminoethyl)amino]-4-methyl-7-oxopyrido[2,3-d]pyrimidin-8(7H)-yl)-N-(3,4-dimethoxyphenyl)benzamide (124)

4-(2-[(2-aminoethyl)amino]-4-methyl-7-oxopyrido[2,3-d]pyrimidin-8(7H)-yl)-N-benzylbenzamide (125)

4-(2-[(2-aminoethyl)amino]-4-methyl-7-oxopyrido[2,3-d]pyrimidin-8(7H)-yl)-N-(2-phenylethyl)benzamide (126)

4-(2-[(2-aminoethyl)amino]-4-methyl-7-oxopyrido[2,3-d]pyrimidin-8(7H)-yl)-N-isobutylbenzamide (127)

N-cyclopropyl-4-(4-methyl-7-oxo-2-[4-(2-pyrimidinyl)-1-piperazinyl]pyrido[2,3-d]pyrimidin-8(7H)-yl)benzamide (128)

4-(2-[(2-aminoethyl)amino]-4-methyl-7-oxopyrido[2,3-d]pyrimidin-8(7H)-yl)-N-(cyclohexylmethyl)benzamide (129)

4-(4-methyl-7-oxo-2-[4-(2-pyrimidinyl)-1-piperazinyl]pyrido[2,3-d]pyrimidin-8(7H)-yl)-N-octylbenzamide (130)

N-(3,4-dimethoxyphenyl)-4-(4-methyl-7-oxo-2-yl)benzamide (131)

4-(4-methyl-7-oxo-2-[4-(2-pyrimidinyl)-1-piperazinyl]pyrido[2,3-d]pyrimidin-8(7H)-yl)-N-(2-phenylethyl)benzamide (132)

N-isobutyl-4-(4-methyl-7-oxo-2-[4-(2-pyrimidinyl)-1-piperazinyl]pyrido[2,3-d]pyrimidin-8(7H)-yl)benzamide (133)

4-(4-methyl-7-oxo-2-[4-(2-pyrimidinyl)-1-piperazinyl]pyrido[2,3-d]pyrimidin-8(7H)-yl)-N-(tetrahydro-2-furanylmethyl)benzamide (134)

N-(cyclohexylmethyl)-4-(4-methyl-7-oxo-2-[4-(2-pyrimidinyl)-1-piperazinyl]pyrido[2,3-d]pyrimidin-8(7H)-yl)benzamide (135)

N-cyclopropyl-4-(4-methyl-7-oxo-2-(1-piperazinyl)pyrido[2,3-d]pyrimidin-8(7H)-yl)benzamide (136)

4-(4-methyl-7-oxo-2-(1-piperazinyl)pyrido[2,3-d]pyrimidin-8(7H)-yl)-N-octylbenzamide (137)

N-(2-furylmethyl)-4-(4-methyl-7-oxo-2-(1-piperazinyl)pyrido[2,3-d]pyrimidin-8(7H)-yl)benzamide (138)

N-(3,4-dimethoxyphenyl)-4-(4-methyl-7-oxo-2-(1-piperazinyl)pyrido[2,3-d]pyrimidin-8(7H)-yl)benzamide (139)

N-benzyl-4-(4-methyl-7-oxo-2-(1-piperazinyl)pyrido[2,3-d]pyrimidin-8(7H)-yl)benzamide (140)

4-(4-methyl-7-oxo-2-(1-piperazinyl)pyrido[2,3-d]pyrimidin-8(7H)-yl)-N-(2-phenylethyl)benzamide (141)

N-isobutyl-4-(4-methyl-7-oxo-2-(1-piperazinyl)pyrido[2,3-d]pyrimidin-8(7H)-yl)benzamide (142)

4-(4-methyl-7-oxo-2-(1-piperazinyl)pyrido[2,3-d]pyrimidin-8(7H)-yl)-N-(tetrahydro-2-furanylmethyl)benzamide (143)

N-(cyclohexylmethyl)-4-(4-methyl-7-oxo-2-(1-piperazinyl)pyrido[2,3-d]pyrimidin-8(7H)-yl)benzamide (144)

4-(2-(allylamino)-4-methyl-7-oxopyrido[2,3-d]pyrimidin-8(7H)-yl)-N-cyclopropylbenzamide (145)

4-(2-(allylamino)-4-methyl-7-oxopyrido[2,3-d]pyrimidin-8(7H)-yl)-N-octylbenzamide (146)

4-(2-(allylamino)-4-methyl-7-oxopyrido[2,3-d]pyrimidin-8(7H)-yl)-N-(2-furylmethyl)benzamide (147)

4-(2-(allylamino)-4-methyl-7-oxopyrido[2,3-d]pyrimidin-8(7H)-yl)-N-(3,4-dimethoxyphenyl)benzamide (148)

4-(2-(allylamino)-4-methyl-7-oxopyrido[2,3-d]pyrimidin-8(7H)-yl)-N-benzylbenzamide (149)

4-(2-(allylamino)-4-methyl-7-oxopyrido[2,3-d]pyrimidin-8(7H)-yl)-N-(2-phenylethyl)benzamide (150)

4-(2-(allylamino)-4-methyl-7-oxopyrido[2,3-d]pyrimidin-8(7H)-yl)-N-isobutylbenzamide (151)

4-(2-(allylamino)-4-methyl-7-oxopyrido[2,3-d]pyrimidin-8(7H)-yl)-N-(tetrahydro-2-furanylmethyl)benzamide (152)

4-(2-(allylamino)-4-methyl-7-oxopyrido[2,3-d]pyrimidin-8(7H)-yl)-N-(cyclohexylmethyl)benzamide (153)

N-cyclopropyl-4-(4-methyl-7-oxo-2-(1-pyrrolidinyl)pyrido[2,3-d]pyrimidin-8(7H)-yl)benzamide (154)

4-(4-methyl-7-oxo-2-(1-pyrrolidinyl)pyrido[2,3-d]pyrimidin-8(7H)-yl)-N-octylbenzamide (155)

N-(2-furylmethyl)-4-(4-methyl-7-oxo-2-(1-pyrrolidinyl)pyrido[2,3-d]pyrimidin-8(7H)-yl)benzamide (156)

N-(3,4-dimethoxyphenyl)-4-(4-methyl-7-oxo-2-(1-pyrrolidinyl)pyrido[2,3-d]pyrimidin-8(7H)-yl)benzamide (157)

N-benzyl-4-(4-methyl-7-oxo-2-(1-pyrrolidinyl)pyrido[2,3-d]pyrimidin-8(7H)-yl)benzamide (158)

4-(4-methyl-7-oxo-2-(1-pyrrolidinyl)pyrido[2,3-d]pyrimidin-8(7H)-yl)-N-(2-phenylethyl)benzamide (159)

N-isobutyl-4-(4-methyl-7-oxo-2-(1-pyrrolidinyl)pyrido[2,3-d]pyrimidin-8(7H)-yl)benzamide (160)

4-(4-methyl-7-oxo-2-(1-pyrrolidinyl)pyrido[2,3-d]pyrimidin-8(7H)-yl)-N-(tetrahydro-2-furanylmethyl)benzamide (161)

N-(cyclohexylmethyl)-4-(4-methyl-7-oxo-2-(1-pyrrolidinyl)pyrido[2,3-d]pyrimidin-8(7H)-yl)benzamide (162)

N-benzyl-4-(2-{[2-(2-methoxyphenyl)ethyl]amino}-4-methyl-7-oxopyrido[2,3-d]pyrimidin-8(7H)-yl)benzamide (163)

N-cyclopropyl-4-(2-[(2-hydroxyethyl)amino]-4-methyl-7-oxopyrido[2,3-d]pyrimidin-8(7H)-yl)benzamide (164)

4-(2-[(2-hydroxyethyl)amino]-4-methyl-7-oxopyrido[2,3-d]pyrimidin-8(7H)-yl)-N-octylbenzamide (165)

N-(2-furylmethyl)-4-(2-[(2-hydroxyethyl)amino]-4-methyl-7-oxopyrido[2,3-d]pyrimidin-8(7H)-yl)benzamide (166)

N-(3,4-dimethoxyphenyl)-4-(2-[(2-hydroxyethyl)amino]-4-methyl-7-oxopyrido[2,3-d]pyrimidin-8(7H)-yl)benzamide (167)

N-benzyl-4-(2-[(2-hydroxyethyl)amino]-4-methyl-7-oxopyrido[2,3-d]pyrimidin-8(7H)-yl)benzamide (168)

4-(2-[(2-hydroxyethyl)amino]-4-methyl-7-oxopyrido[2,3-d]pyrimidin-8(7H)-yl)-N-(2-phenylethyl)benzamide (169)

4-(2-[(2-hydroxyethyl)amino]-4-methyl-7-oxopyrido[2,3-d]pyrimidin-8(7H)-yl)-N-isobutylbenzamide (170)

N-(cyclohexylmethyl)-4-(2-[(2-hydroxyethyl)amino]-4-methyl-7-oxopyrido[2,3-d]pyrimidin-8(7H)-yl)benzamide (171)

N-cyclopropyl-4-(2-{[2-(2-methoxyphenyl)ethyl]amino}-4-methyl-7-oxopyrido[2,3-d]pyrimidin-8(7H)-yl)benzamide (172)

4-(2-{[2-(2-methoxyphenyl)ethyl]amino}-4-methyl-7-oxopyrido[2,3-d]pyrimidin-8(7H)-yl)-N-octylbenzamide (173)

N-(3,4-dimethoxyphenyl)-4-(2-{[2-(2-methoxyphenyl)ethyl]amino}-4-methyl-7-oxopyridol[2,3-d]pyrimidin-8(7H)-yl)benzamide (174)

4-(2-{[2-(2-methoxyphenyl)ethyl]amino}-4-methyl-7-oxopyrido[2,3-d]pyrimidin-8(7H)-yl)-N-(2-phenylethyl)benzamide (175)

N-isobutyl-4-(2-{[2-(2-methoxyphenyl)ethyl]amino}-4-methyl-7-oxopyrido[2,3-d]pyrimidin-8(7H)-yl)benzamide (176)

4-(2-{[2-(2-methoxyphenyl)ethyl]amino}-4-methyl-7-oxopyrido[2,3-d]pyrimidin-8(7H)-yl)-N-(tetrahydro-2-furanylmethyl)benzamide (177)

N-(cyclohexylmethyl)-4-(2-{[2-(2-methoxyphenyl)ethyl]amino}-4-methyl-7-oxopyrido[2,3-d]pyrimidin-8(7H)-yl)benzamide (178)

(2S)-1-(8-{4-[(cyclopropylamino)carbonyl]phenyl}-4-methyl-7-oxo-7,8-dihydropyrido[2,3-d]pyrimidin-2-yl)-2-pyrrolidinecarboxylic acid (179)

(2S)-1-(4-methyl-8-{4-[(octylamino)carbonyl]phenyl}-7-oxo-7,8-dihydropyrido[2,3-d]pyrimidin-2-yl)-2-pyrrolidinecarboxylic acid (180)

(2S)-1-[8-(4-{[(2-furylmethyl)amino]carbonyl}phenyl)-4-methyl-7-oxo-7,8-dihydropyrido[2,3-d]pyrimidin-2-yl]-2-pyrrolidinecarboxylic acid (181)

(2S)-1-(8-{4-[(3,4-dimethoxyanilino)carbonyl]phenyl}-4-methyl-7-oxo-7,8-dihydropyrido[2,3-d]pyrimidin-2-yl)-2-pyrrolidinecarboxylic acid (182)

(2S)-1-(8-{4-[(benzylamino)carbonyl]phenyl}-4-methyl-7-oxo-7,8-dihydropyrido[2,3-d]pyrimidin-2-yl)-2-pyrrolidinecarboxylic acid (183)

(2S)-1-[4-methyl-7-oxo-8-(4-{[(2-phenylethyl)amino]carbonyl}phenyl)-7,8-dihydropyrido[2,3-d]pyrimidin-2-yl]-2-pyrrolidinecarboxylic acid (184)

(2S)-1-(8-{4-[(isobutylamino)carbonyl]phenyl}-4-methyl-7-oxo-7,8-dihydropyrido[2,3-d]pyrimidin-2-yl)-2-pyrrolidinecarboxylic acid (185)

(2S)-1-[4-methyl-7-oxo-8-(4-{[(tetrahydro-2-furanylmethyl)amino]carbonyl}phenyl)-7,8-dihydropyrido[2,3-d]pyrimidin-2-yl]-2-pyrrolidinecarboxylic acid (186)

(2S)-1-[8-(4-{[(cyclohexylmethyl)amino]carbonyl}phenyl)-4-methyl-7-oxo-7,8-dihydropyrido[2,3-d]pyrimidin-2-yl]-2-pyrrolidinecarboxylic acid (187)

N-cyclopropyl-4-(2-{[3-(dimethylamino)propyl]amino}-4-methyl-7-oxopyrido[2,3-d]pyrimidin-8(7H)-yl)benzamide (188)

4-(2-{[3-(dimethylamino)propyl]amino}-4-methyl-7-oxopyrido[2,3-d]pyrimidin-8(7H)-yl)-N-octylbenzamide (189)

4-(2-{[3-(dimethylamino)propyl]amino}-4-methyl-7-oxopyrido[2,3-d]pyrimidin-8(7H)-yl)-N-(2-furylmethyl)benzamide (190)

N-(3,4-dimethoxyphenyl)-4-(2-{[3-(dimethylamino)propyl]amino}-4-methyl-7-oxopyrido[2,3-d]pyrimidin-8(7H)-yl)benzamide (191)

N-benzyl-4-(2-{[3-(dimethylamino)propyl]amino}-4-methyl-7-oxopyrido[2,3-d]pyrimidin-8(7H)-yl)benzamide (192)

4-(2-{[3-(dimethylamino)propyl]amino}-4-methyl-7-oxopyrido[2,3-d]pyrimidin-8(7H)-yl)-N-(2-phenylethyl)benzamide (193)

4-(2-{[3-(dimethylamino)propyl]amino}-4-methyl-7-oxopyrido[2,3-d]pyrimidin-8(7H)-yl)-N-isobutylbenzamide (194)

4-(2-{[3-(dimethylamino)propyl]amino}-4-methyl-7-oxopyrido[2,3-d]pyrimidin-8(7H)-yl)-N-(tetrahydro-2-furanylmethyl)benzamide (195)

N-(cyclohexylmethyl)-4-(2-{[3-(dimethylamino)propyl]amino}-4-methyl-7-oxopyrido[2,3-d]pyrimidin-8(7H)-yl)benzamide (196)

4-(2-[(2-ethylhexyl)amino]-4-methyl-7-oxopyrido[2,3-d]pyrimidin-8(7H)-yl)-N-octylbenzamide (197)

4-(2-[(2-aminoethyl)amino]-4-methyl-7-oxopyrido[2,3-d]pyrimidin-8(7H)-yl)-N-(tetrahydro-2-furanylmethyl)benzamide (198)

4-[2-(4-Benzyl-piperazin-1-yl)-4-methyl-7-oxo-7H-pyrido[2,3-d]pyrimidin-8-yl]-benzamide;

4-[4-Methyl-7-oxo-2-(4-phenyl-piperazin-1-yl)-7H-pyrido[2,3-d]pyrimidin-8-yl]-benzamide;

4-[4-Methyl-2-(4-methyl-piperazin-1-yl)-7-oxo-7H-pyrido[2,3-d]pyrimidin-8-yl]-benzamide;

4-[8-(4-Carbamoyl-phenyl)-4-methyl-7-oxo-7,8-dihydropyrido[2,3-d]pyrimidin-2-yl]-piperazine-1-carboxylic acid ethyl ester;

4-[4-Methyl-7-oxo-2-(4-pyridin-2-yl-piperazin-1-yl)-7H-pyrido[2,3-d]pyrimidin-8-yl]-benzamide;

4-[2-(4-Formyl-piperazin-1-yl)-4-methyl-7-oxo-7H-pyrido[2,3-d]pyrimidin-8-yl]-benzamide;

4-{2-[4-(4-Fluoro-phenyl)-piperazin-1-yl]-4-methyl-7-oxo-7H-pyrido[2,3-d]pyrimidin-8-yl}-benzamide;

4-{2-[4-(4-Hydroxy-phenyl)-piperazin-1-yl]-4-methyl-7-oxo-7H-pyrido[2,3-d]pyrimidin-8-yl}-benzamide;

4-[2-(4-Benzyl-piperazin-1-yl)-4-methyl-7-oxo-7H-pyrido[2,3-d]pyrimidin-8-yl]-N-(3,4-dimethoxy-benzyl)-benzamide;

N-(3,4-Dimethoxy-benzyl)-4-[4-methyl-7-oxo-2-(4-phenyl-piperazin-1-yl)-7H-pyrido[2,3-d]pyrimidin-8-yl]-benzamide;

N-(3,4-Dimethoxy-benzyl)-4-[4-methyl-2-(4-methyl-piperazin-1-yl)-7-oxo-7H-pyrido[2,3-d]pyrimidin-8-yl]-benzamide;

4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid ethyl ester;

N-(3,4-Dimethoxy-benzyl)-4-[4-methyl-7-oxo-2-(4-pyridin-2-yl-piperazin-1-yl)-7H-pyrido[2,3-d]pyrimidin-8-yl]-benzamide;

N-(3,4-Dimethoxy-benzyl)-4-[2-(4-formyl-piperazin-1-yl)-4-methyl-7-oxo-7H-pyrido[2,3-d]pyrimidin-8-yl]-benzamide;

N-(3,4-Dimethoxy-benzyl)-4-{2-[4-(4-fluoro-phenyl)-piperazin-1-yl]-4-methyl-7-oxo-7H-pyrido[2,3-d]pyrimidin-8-yl}-benzamide;

N-(3,4-Dimethoxy-benzyl)-4-{2-[4-(4-hydroxy-phenyl)-piperazin-1-yl]-4-methyl-7-oxo-7H-pyrido[2,3-d]pyrimidin-8-yl}-benzamide;

N-Benzyl-4-[2-(4-benzyl-piperazin-1-yl)-4-methyl-7-oxo-7H-pyrido[2,3-d]pyrimidin-8-yl]-benzamide N-Benzyl-4-[4-methyl-7-oxo-2-(4-phenyl-piperazin-1-yl)-7H-pyrido[2,3-d]pyrimidin-8-yl]-benzamide;

N-Benzyl-4-[4-methyl-2-(4-methyl-piperazin-1-yl)-7-oxo-7H-pyrido[2,3-d]pyrimidin-8-yl]-benzamide;

4-[8-(4-Benzylcarbamoyl-phenyl)-4-methyl-7-oxo-7,8-dihydro-pyrido[2,3-d]pyrimidin-2-yl]-piperazine-1-carboxylic acid ethyl ester;

N-Benzyl-4-[4-methyl-7-oxo-2-(4-pyridin-2-yl-piperazin-1-yl)-7H-pyrido[2,3-d]pyrimidin-8-yl]-benzamide;

N-Benzyl-4-[2-(4-formyl-piperazin-1-yl)-4-methyl-7-oxo-7H-pyrido[2,3-d]pyrimidin-8-yl]-benzamide;
N-Benzyl-4-{2-[4-(4-fluoro-phenyl)-piperazin-1-yl]-4-methyl-7-oxo-7H-pyrido[2,3-d]pyrimidin-8-yl}-benzamide;
N-Benzyl-4-{2-[4-(4-hydroxy-phenyl)-piperazin-1-yl]-4-methyl-7-oxo-7H-pyrido[2,3-d]pyrimidin-8-yl}-benzamide;
4-[2-(4-Benzyl-piperazin-1-yl)-4-methyl-7-oxo-7H-pyrido[2,3-d]pyrimidin-8-yl]-N-cyclopropyl-benzamide;
N-Cyclopropyl-4-[4-methyl-7-oxo-2-(4-phenyl-piperazin-1-yl)-7H-pyrido[2,3-d]pyrimidin-8-yl]-benzamide;
N-Cyclopropyl-4-[4-methyl-2-(4-methyl-piperazin-1-yl)-7-oxo-7H-pyrido[2,3-d]pyrimidin-8-yl]-benzamide;
4-[8-(4-Cyclopropylcarbamoyl-phenyl)-4-methyl-7-oxo-7,8-dihydro-pyrido[2,3-d]pyrimidin-2-yl]-piperazine-1-carboxylic acid ethyl ester;
N-Cyclopropyl-4-[4-methyl-7-oxo-2-(4-pyridin-2-yl-piperazin-1-yl)-7H-pyrido[2,3-d]pyrimidin-8-yl]-benzamide;
N-Cyclopropyl-4-{2-[4-(4-fluoro-phenyl)-piperazin-1-yl]-4-methyl-7-oxo-7H-pyrido[2,3-d]pyrimidin-8-yl}-benzamide;
N-Cyclopropyl-4-{2-[4-(4-hydroxy-phenyl)-piperazin-1-yl]-4-methyl-7-oxo-7H-pyrido[2,3-d]pyrimidin-8-yl}-benzamide;
4-[2-(4-Benzyl-piperazin-1-yl)-4-methyl-7-oxo-7H-pyrido[2,3-d]pyrimidin-8-yl]-N-(4-trifluoromethyl-benzyl)-benzamide;
4-[4-Methyl-7-oxo-2-(4-phenyl-piperazin-1-yl)-7H-pyrido[2,3-d]pyrimidin-8-yl]-N-(4-trifluoromethyl-benzyl)-benzamide;
4-[4-Methyl-2-(4-methyl-piperazin-1-yl)-7-oxo-7H-pyrido[2,3-d]pyrimidin-8-yl]-N-(4-trifluoromethyl-benzyl)-benzamide;
4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid ethyl ester;
4-[4-Methyl-7-oxo-2-(4-pyridin-2-yl-piperazin-1-yl)-7H-pyrido[2,3-d]pyrimidin-8-yl]-N-(4-trifluoromethyl-benzyl)-benzamide;
4-[2-(4-Formyl-piperazin-1-yl)-4-methyl-7-oxo-7H-pyrido[2,3-d]pyrimidin-8-yl]-N-(4-trifluoromethyl-benzyl)-benzamide;
4-{2-[4-(4-Hydroxy-phenyl)-piperazin-1-yl]-4-methyl-7-oxo-7H-pyrido[2,3-d]pyrimidin-8-yl}-N-(4-trifluoromethyl-benzyl)-benzamide;
4-({4-[2-(4-Benzyl-piperazin-1-yl)-4-methyl-7-oxo-7H-pyrido[2,3-d]pyrimidin-8-yl]-benzoylamino}-methyl)-benzoic acid methyl ester;
4-({4-[4-Methyl-7-oxo-2-(4-phenyl-piperazin-1-yl)-7H-pyrido[2,3-d]pyrimidin-8-yl]-benzoylamino}-methyl)-benzoic acid methyl ester;
4-({4-[4-Methyl-2-(4-methyl-piperazin-1-yl)-7-oxo-7H-pyrido[2,3-d]pyrimidin-8-yl]-benzoylamino}-methyl)-benzoic acid methyl ester;
4-{8-[4-(4-Methoxycarbonyl-benzylcarbamoyl)-phenyl]-4-methyl-7-oxo-7,8-dihydro-pyrido[2,3-d]pyrimidin-2-yl}-piperazine-1-carboxylic acid ethyl ester;
4-({4-[4-Methyl-7-oxo-2-(4-pyridin-2-yl-piperazin-1-yl)-7H-pyrido[2,3-d]pyrimidin-8-yl]-benzoylamino}-methyl)-benzoic acid methyl ester;
4-[(4-{2-[4-(4-Hydroxy-phenyl)-piperazin-1-yl]-4-methyl-7-oxo-7H-pyrido[2,3-d]pyrimidin-8-yl}-benzoylamino)-methyl]-benzoic acid methyl ester;
4-[2-(4-Benzyl-piperazin-1-yl)-4-methyl-7-oxo-7H-pyrido[2,3-d]pyrimidin-8-yl]-N-(2,4-difluoro-benzyl)-benzamide;
N-(2,4-Difluoro-benzyl)-4-[4-methyl-7-oxo-2-(4-phenyl-piperazin-1-yl)-7H-pyrido[2,3-d]pyrimidin-8-yl]-benzamide;
N-(2,4-Difluoro-benzyl)-4-[4-methyl-2-(4-methyl-piperazin-1-yl)-7-oxo-7H-pyrido[2,3-d]pyrimidin-8-yl]-benzamide;
4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid ethyl ester;
N-(2,4-Difluoro-benzyl)-4-[4-methyl-7-oxo-2-(4-pyridin-2-yl-piperazin-1-yl)-7H-pyrido[2,3-d]pyrimidin-8-yl]-benzamide;
N-(2,4-Difluoro-benzyl)-4-{2-[4-(4-fluoro-phenyl)-piperazin-1-yl]-4-methyl-7-oxo-7H-pyrido[2,3-d]pyrimidin-8-yl}-benzamide;
N-(2,4-Difluoro-benzyl)-4-{2-[4-(4-hydroxy-phenyl)-piperazin-1-yl]-4-methyl-7-oxo-7H-pyrido[2,3-d]pyrimidin-8-yl}-benzamide;
4-[2-(4-Benzyl-piperazin-1-yl)-4-methyl-7-oxo-7H-pyrido[2,3-d]pyrimidin-8-yl]-N-(4-methanesulfonyl-benzyl)-benzamide;
N-(4-Methanesulfonyl-benzyl)-4-[4-methyl-7-oxo-2-(4-phenyl-piperazin-1-yl)-7H-pyrido[2,3-d]pyrimidin-8-yl]-benzamide;
N-(4-Methanesulfonyl-benzyl)-4-[4-methyl-2-(4-methyl-piperazin-1-yl)-7-oxo-7H-pyrido[2,3-d]pyrimidin-8-yl]-benzamide;
4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid ethyl ester;
N-(4-Methanesulfonyl-benzyl)-4-[4-methyl-7-oxo-2-(4-pyridin-2-yl-piperazin-1-yl)-7H-pyrido[2,3-d]pyrimidin-8-yl]-benzamide;
4-{2-[4-(4-Fluoro-phenyl)-piperazin-1-yl]-4-methyl-7-oxo-7H-pyrido[2,3-d]pyrimidin-8-yl}-N-(4-methanesulfonyl-benzyl)-benzamide;
4-{2-[4-(4-Hydroxy-phenyl)-piperazin-1-yl]-4-methyl-7-oxo-7H-pyrido[2,3-d]pyrimidin-8-yl}-N-(4-methanesulfonyl-benzyl)-benzamide;
4-{2-[4-(4-Fluoro-benzoyl)-piperidin-1-yl]-4-methyl-7-oxo-7H-pyrido[2,3-d]pyrimidin-8-yl}-benzamide;
4-{2-[4-(4-Benzyl-piperidin-1-yl)-4-methyl-7-oxo-7H-pyrido[2,3-d]pyrimidin-8-yl]-benzamide;
4-{2-[4-(4-Acetyl-phenyl)-piperazin-1-yl]-4-methyl-7-oxo-7H-pyrido[2,3-d]pyrimidin-8-yl}-benzamide;
4-[2-(5-Benzyl-2,5-diaza-bicyclo[2.2.1]hept-2-yl)-4-methyl-7-oxo-7H-pyrido[2,3-d]pyrimidin-8-yl]-benzamide;
4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-benzamide;
4-[2-(4-Acetyl-4-phenyl-piperidin-1-yl)-4-methyl-7-oxo-7H-pyrido[2,3-d]pyrimidin-8-yl]-benzamide;
4-[2-(4-Acetyl-piperazin-1-yl)-4-methyl-7-oxo-7H-pyrido[2,3-d]pyrimidin-8-yl]-benzamide;
4-[8-(4-Carbamoyl-phenyl)-4-methyl-7-oxo-7,8-dihydro-pyrido[2,3-d]pyrimidin-2-yl]-piperazine-1-carboxylic acid benzyl ester;
4-(2-{4-[2-(2-Hydroxy-ethoxy)-ethyl]-piperazin-1-yl}-4-methyl-7-oxo-7H-pyrido[2,3-d]pyrimidin-8-yl)-benzamide;
4-[4-Methyl-7-oxo-2-(4-quinolin-2-yl-piperazin-1-yl)-7H-pyrido[2,3-d]pyrimidin-8-yl]-benzamide;

N-(3,4-Dimethoxy-benzyl)-4-{2-[4-(4-fluoro-benzoyl)-piperidin-1-yl]-4-methyl-7-oxo-7H-pyrido[2,3-d]pyrimidin-8-yl}-benzamide;

4-[2-(4-Benzyl-piperidin-1-yl)-4-methyl-7-oxo-7H-pyrido[2,3-d]pyrimidin-8-yl]-N-(3,4-dimethoxy-benzyl)-benzamide;

4-[2-(4-Benzo[1,3]dioxol-5-ylmethyl-piperazin-1-yl)-4-methyl-7-oxo-7H-pyrido[2,3-d]pyrimidin-8-yl]-N-(3,4-dimethoxy-benzyl)-benzamide;

4-{2-[4-(4-Acetyl-phenyl)-piperazin-1-yl]-4-methyl-7-oxo-7H-pyrido[2,3-d]pyrimidin-8-yl}-N-(3,4-dimethoxy-benzyl)-benzamide;

4-[2-(5-Benzyl-2,5-diaza-bicyclo[2.2.1]hept-2-yl)-4-methyl-7-oxo-7H-pyrido[2,3-d]pyrimidin-8-yl]-N-(3,4-dimethoxy-benzyl)-benzamide;

N-(3,4-Dimethoxy-benzyl)-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide;

4-[2-(4-Acetyl-4-phenyl-piperidin-1-yl)-4-methyl-7-oxo-7H-pyrido[2,3-d]pyrimidin-8-yl]-N-(3,4-dimethoxy-benzyl)-benzamide;

4-[2-(4-Acetyl-piperazin-1-yl)-4-methyl-7-oxo-7H-pyrido[2,3-d]pyrimidin-8-yl]-N-(3,4-dimethoxy-benzyl)-benzamide;

N-(3,4-Dimethoxy-benzyl)-4-{2-[4-(2-hydroxy-ethyl)-piperidin-1-yl]-4-methyl-7-oxo-7H-pyrido[2,3-d]pyrimidin-8-yl}-benzamide;

4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid benzyl ester;

N-(3,4-Dimethoxy-benzyl)-4-(2-{4-[2-(2-hydroxy-ethoxy)-ethyl]-piperazin-1-yl}-4-methyl-7-oxo-7H-pyrido[2,3-d]pyrimidin-8-yl)-benzamide;

N-Benzyl-4-{2-[4-(4-fluoro-benzoyl)-piperidin-1-yl]-4-methyl-7-oxo-7H-pyrido[2,3-d]pyrimidin-8-yl}-benzamide;

N-Benzyl-4-[2-(4-benzyl-piperidin-1-yl)-4-methyl-7-oxo-7H-pyrido[2,3-d]pyrimidin-8-yl]-benzamide;

4-[2-(4-Benzo[1,3]dioxol-5-ylmethyl-piperazin-1-yl)-4-methyl-7-oxo-7H-pyrido[2,3-d]pyrimidin-8-yl]-N-benzyl-benzamide;

4-{2-[4-(4-Acetyl-phenyl)-piperazin-1-yl]-4-methyl-7-oxo-7H-pyrido[2,3-d]pyrimidin-8-yl}-N-benzyl-benzamide;

N-Benzyl-4-[2-(5-benzyl-2,5-diaza-bicyclo[2.2.1]hept-2-yl)-4-methyl-7-oxo-7H-pyrido[2,3-d]pyrimidin-8-yl]-benzamide;

N-Benzyl-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide;

4-[2-(4-Acetyl-4-phenyl-piperidin-1-yl)-4-methyl-7-oxo-7H-pyrido[2,3-d]pyrimidin-8-yl]-N-benzyl-benzamide;

4-[2-(4-Acetyl-piperazin-1-yl)-4-methyl-7-oxo-7H-pyrido[2,3-d]pyrimidin-8-yl]-N-benzyl-benzamide;

N-Benzyl-4-{2-[4-(2-hydroxy-ethyl)-piperidin-1-yl]-4-methyl-7-oxo-7H-pyrido[2,3-d]pyrimidin-8-yl}-benzamide;

4-[8-(4-Benzylcarbamoyl-phenyl)-4-methyl-7-oxo-7,8-dihydro-pyrido[2,3-d]pyrimidin-2-yl]-piperazine-1-carboxylic acid benzyl ester;

N-Benzyl-4-(2-{4-[2-(2-hydroxy-ethoxy)-ethyl]-piperazin-1-yl}-4-methyl-7-oxo-7H-pyrido[2,3-d]pyrimidin-8-yl)-benzamide;

N-Cyclopropyl-4-{2-[4-(4-fluoro-benzoyl)-piperidin-1-yl]-4-methyl-7-oxo-7H-pyrido[2,3-d]pyrimidin-8-yl}-benzamide;

4-[2-(4-Benzyl-piperidin-1-yl)-4-methyl-7-oxo-7H-pyrido[2,3-d]pyrimidin-8-yl]-N-cyclopropyl-benzamide;

4-{2-[4-(4-Acetyl-phenyl)-piperazin-1-yl]-4-methyl-7-oxo-7H-pyrido[2,3-d]pyrimidin-8-yl}-N-cyclopropyl-benzamide;

4-[2-(5-Benzyl-2,5-diaza-bicyclo[2.2.1]hept-2-yl)-4-methyl-7-oxo-7H-pyrido[2,3-d]pyrimidin-8-yl]-N-cyclopropyl-benzamide;

N-Cyclopropyl-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide;

4-[2-(4-Acetyl-4-phenyl-piperidin-1-yl)-4-methyl-7-oxo-7H-pyrido[2,3-d]pyrimidin-8-yl]-N-cyclopropyl-benzamide;

4-[2-(4-Acetyl-piperazin-1-yl)-4-methyl-7-oxo-7H-pyrido[2,3-d]pyrimidin-8-yl]-N-cyclopropyl-benzamide;

N-Cyclopropyl-4-{2-[4-(2-hydroxy-ethyl)-piperidin-1-yl]-4-methyl-7-oxo-7H-pyrido[2,3-d]pyrimidin-8-yl}-benzamide;

4-[8-(4-Cyclopropylcarbamoyl-phenyl)-4-methyl-7-oxo-7,8-dihydro-pyrido[2,3-d]pyrimidin-2-yl]-piperazine-1-carboxylic acid benzyl ester;

4-{2-[4-(4-Fluoro-benzoyl)-piperidin-1-yl]-4-methyl-7-oxo-7H-pyrido[2,3-d]pyrimidin-8-yl}-N-(4-trifluoromethyl-benzyl)-benzamide;

4-[2-(4-Benzyl-piperidin-1-yl)-4-methyl-7-oxo-7H-pyrido[2,3-d]pyrimidin-8-yl]-N-(4-trifluoromethyl-benzyl)-benzamide;

4-[2-[4-(4-Acetyl-phenyl)-piperazin-1-yl]-4-methyl-7-oxo-7H-pyrido[2,3-d]pyrimidin-8-yl}-N-(4-trifluoromethyl-benzyl)-benzamide;

4-[2-(5-Benzyl-2,5-diaza-bicyclo[2.2.1]hept-2-yl)-4-methyl-7-oxo-7H-pyrido[2,3-d]pyrimidin-8-yl]-N-(4-trifluoromethyl-benzyl)-benzamide;

4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-N-(4-trifluoromethyl-benzyl)-benzamide;

4-[2-(4-Acetyl-4-phenyl-piperidin-1-yl)-4-methyl-7-oxo-7H-pyrido[2,3-d]pyrimidin-8-yl]-N-(4-trifluoromethyl-benzyl)-benzamide;

4-[2-(4-Acetyl-piperazin-1-yl)-4-methyl-7-oxo-7H-pyrido[2,3-d]pyrimidin-8-yl]-N-(4-trifluoromethyl-benzyl)-benzamide;

4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid benzyl ester;

4-(2-{4-[2-(2-Hydroxy-ethoxy)-ethyl]-piperazin-1-yl}-4-methyl-7-oxo-7H-pyrido[2,3-d]pyrimidin-8-yl)-N-(4-trifluoromethyl-benzyl)-benzamide;

4-[(4-{2-[4-(4-Fluoro-benzoyl)-piperidin-1-yl]-4-methyl-7-oxo-7H-pyrido[2,3-d]pyrimidin-8-yl}-benzoylamino)-methyl]-benzoic acid methyl ester;

4-({4-[2-(4-Benzyl-piperidin-1-yl)-4-methyl-7-oxo-7H-pyrido[2,3-d]pyrimidin-8-yl]-benzoylamino}-methyl)-benzoic acid methyl ester;

4-({4-[2-(4-Benzo[1,3]dioxol-5-ylmethyl-piperazin-1-yl)-4-methyl-7-oxo-7H-pyrido[2,3-d]pyrimidin-8-yl]-benzoylamino}-methyl)-benzoic acid methyl ester;

4-[(4-{2-[4-(4-Acetyl-phenyl)-piperazin-1-yl]-4-methyl-7-oxo-7H-pyrido[2,3-d]pyrimidin-8-yl}-benzoylamino)-methyl]-benzoic acid methyl ester;

4-({4-[2-(5-Benzyl-2,5-diaza-bicyclo[2.2.1]hept-2-yl)-4-methyl-7-oxo-7H-pyrido[2,3-d]pyrimidin-8-yl]-benzoylamino}-methyl)-benzoic acid methyl ester;

4-[(4-{2-[5-(4-Fluoro-phenyl)-2,5-diaza-bicyclo[2.2.1]
hept-2-yl]-4-methyl-7-oxo-7H-pyrido[2,3-d]pyrimidin-8-yl}-benzoylamino)-methyl]-benzoic acid methyl ester;
4-({4-[2-(4-Acetyl-4-phenyl-piperidin-1-yl)-4-methyl-7-oxo-7H-pyrido[2,3-d]pyrimidin-8-yl]-benzoylamino}-methyl)-benzoic acid methyl ester;
4-({4-[2-(4-Acetyl-piperazin-1-yl)-4-methyl-7-oxo-7H-pyrido[2,3-d]pyrimidin-8-yl]-benzoylamino}-methyl)-benzoic acid methyl ester;
4-[(4-{2-[4-(2-Hydroxy-ethyl)-piperidin-1-yl]-4-methyl-7-oxo-7H-pyrido[2,3-d]pyrimidin-8-yl}-benzoylamino)-methyl]-benzoic acid methyl ester;
4-{8-[4-(4-Methoxycarbonyl-benzylcarbamoyl)-phenyl]-4-methyl-7-oxo-7,8-dihydro-pyrido[2,3-d]pyrimidin-2-yl}-piperazine-1-carboxylic acid benzyl ester;
4-{[4-(2-{4-[2-(2-Hydroxy-ethoxy)-ethyl]-piperazin-1-yl}-4-methyl-7-oxo-7H-pyrido[2,3-d]pyrimidin-8-yl)-benzoylamino]-methyl}-benzoic acid methyl ester;
N-(2,4-Difluoro-benzyl)-4-{2-[4-(4-fluoro-benzoyl)-piperidin-1-yl]-4-methyl-7-oxo-7H-pyrido[2,3-d]pyrimidin-8-yl}-benzamide;
4-[2-(4-Benzyl-piperidin-1-yl)-4-methyl-7-oxo-7H-pyrido[2,3-d]pyrimidin-8-yl]-N-(2,4-difluoro-benzyl)-benzamide;
4-[2-(4-Benzo[1,3]dioxol-5-ylmethyl-piperazin-1-yl)-4-methyl-7-oxo-7H-pyrido[2,3-d]pyrimidin-8-yl]-N-(2,4-difluoro-benzyl)-benzamide;
4-{2-[4-(4-Acetyl-phenyl)-piperazin-1-yl]-4-methyl-7-oxo-7H-pyrido[2,3-d]pyrimidin-8-yl}-N-(2,4-difluoro-benzyl)-benzamide;
4-[2-(5-Benzyl-2,5-diaza-bicyclo[2.2.1]hept-2-yl)-4-methyl-7-oxo-7H-pyrido[2,3-d]pyrimidin-8-yl]-N-(2,4-difluoro-benzyl)-benzamide;
N-(2,4-Difluoro-benzyl)-4-{2-[5-(4-fluoro-phenyl)-2,5-diaza-bicyclo[2.2.1]hept-2-yl]-4-methyl-7-oxo-7H-pyrido[2,3-d]pyrimidin-8-yl}-benzamide;
4-[2-(4-Acetyl-4-phenyl-piperidin-1-yl)-4-methyl-7-oxo-7H-pyrido[2,3-d]pyrimidin-8-yl]-N-(2,4-difluoro-benzyl)-benzamide;
4-[2-(4-Acetyl-piperazin-1-yl)-4-methyl-7-oxo-7H-pyrido[2,3-d]pyrimidin-8-yl]-N-(2,4-difluoro-benzyl)-benzamide;
4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid benzyl ester;
N-(2,4-Difluoro-benzyl)-4-(2-{4-[2-(2-hydroxy-ethoxy)-ethyl]-piperazin-1-yl}-4-methyl-7-oxo-7H-pyrido[2,3-d]pyrimidin-8-yl)-benzamide;
4-{2-[4-(4-Fluoro-benzoyl)-piperidin-1-yl]-4-methyl-7-oxo-7H-pyrido[2,3-d]pyrimidin-8-yl}-N-(4-methanesulfonyl-benzyl)-benzamide;
4-[2-(4-Benzyl-piperidin-1-yl)-4-methyl-7-oxo-7H-pyrido[2,3-d]pyrimidin-8-yl]-N-(4-methanesulfonyl-benzyl)-benzamide;
4-[2-(4-Benzo[1,3]dioxol-5-ylmethyl-piperazin-1-yl)-4-methyl-7-oxo-7H-pyrido[2,3-d]pyrimidin-8-yl]-N-(4-methanesulfonyl-benzyl)-benzamide;
4-{2-[4-(4-Acetyl-phenyl)-piperazin-1-yl]-4-methyl-7-oxo-7H-pyrido[2,3-d]pyrimidin-8-yl}-N-(4-methanesulfonyl-benzyl)-benzamide;
4-{2-[5-(4-Fluoro-phenyl)-2,5-diaza-bicyclo[2.2.1]hept-2-yl]-4-methyl-7-oxo-7H-pyrido[2,3-d]pyrimidin-8-yl}-N-(4-methanesulfonyl-benzyl)-benzamide;
4-[2-(4-Acetyl-4-phenyl-piperidin-1-yl)-4-methyl-7-oxo-7H-pyrido[2,3-d]pyrimidin-8-yl]-N-(4-methanesulfonyl-benzyl)-benzamide;
4-[2-(4-Acetyl-piperazin-1-yl)-4-methyl-7-oxo-7H-pyrido[2,3-d]pyrimidin-8-yl]-N-(4-methanesulfonyl-benzyl)-benzamide;
4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid benzyl ester;
4-[2-(4-Acetylamino-phenoxy)-4-methyl-7-oxo-7H-pyrido[2,3-d]pyrimidin-8-yl]-benzamide;
4-[2-(4-Carbamoylmethyl-phenoxy)-4-methyl-7-oxo-7H-pyrido[2,3-d]pyrimidin-8-yl]-benzamide;
4-[8-(4-Carbamoyl-phenyl)-4-methyl-7-oxo-7,8-dihydro-pyrido[2,3-d]pyrimidin-2-yloxy]-benzoic acid ethyl ester;
4-[4-Methyl-7-oxo-2-(4-trifluoromethyl-phenoxy)-7H-pyrido[2,3-d]pyrimidin-8-yl]-benzamide;
4-[2-(4-Fluoro-phenoxy)-4-methyl-7-oxo-7H-pyrido[2,3-d]pyrimidin-8-yl]-benzamide;
4-{2-[4-(4-Hydroxy-benzenesulfonyl)-phenoxy]-4-methyl-7-oxo-7H-pyrido[2,3-d]pyrimidin-8-yl}-benzamide;
4-[2-(4-Acetyl-phenoxy)-4-methyl-7-oxo-7H-pyrido[2,3-d]pyrimidin-8-yl]-benzamide;
4-[2-(4-Carbamoylmethyl-phenoxy)-4-methyl-7-oxo-7H-pyrido[2,3-d]pyrimidin-8-yl]-N-(3,4-dimethoxy-benzyl)-benzamide;
N-(3,4-Dimethoxy-benzyl)-4-[4-methyl-7-oxo-2-(4-trifluoromethyl-phenoxy)-7H-pyrido[2,3-d]pyrimidin-8-yl]-benzamide;
N-(3,4-Dimethoxy-benzyl)-4-[2-(4-fluoro-phenoxy)-4-methyl-7-oxo-7H-pyrido[2,3-d]pyrimidin-8-yl]-benzamide;
N-(3,4-Dimethoxy-benzyl)-4-{2-[4-(4-hydroxy-benzenesulfonyl)-phenoxy]-4-methyl-7-oxo-7H-pyrido[2,3-d]pyrimidin-8-yl}-benzamide;
4-[2-(4-Acetyl-phenoxy)-4-methyl-7-oxo-7H-pyrido[2,3-d]pyrimidin-8-yl]-N-(3,4-dimethoxy-benzyl)-benzamide;
N-Benzyl-4-[2-(4-carbamoylmethyl-phenoxy)-4-methyl-7-oxo-7H-pyrido[2,3-d]pyrimidin-8-yl]-benzamide;
N-Benzyl-4-[2-(4-fluoro-phenoxy)-4-methyl-7-oxo-7H-pyrido[2,3-d]pyrimidin-8-yl]-benzamide;
4-[2-(4-Acetyl-phenoxy)-4-methyl-7-oxo-7H-pyrido[2,3-d]pyrimidin-8-yl]-N-benzyl-benzamide;
4-[2-(4-Acetylamino-phenoxy)-4-methyl-7-oxo-7H-pyrido[2,3-d]pyrimidin-8-yl]-N-cyclopropyl-benzamide;
N-(3,4-Dimethoxy-benzyl)-4-[2-(4-fluoro-phenylsulfanyl)-4-methyl-7-oxo-7H-pyrido[2,3-d]pyrimidin-8-yl]-benzamide;
N-Benzyl-4-[4-methyl-2-(1-methyl-1H-imidazol-2-ylsulfanyl)-7-oxo-7H-pyrido[2,3-d]pyrimidin-8-yl]-benzamide;
N-Benzyl-4-[2-(4-fluoro-phenylsulfanyl)-4-methyl-7-oxo-7H-pyrido[2,3-d]pyrimidin-8-yl]-benzamide;
N-Cyclopropyl-4-[2-(4-fluoro-phenylsulfanyl)-4-methyl-7-oxo-7H-pyrido[2,3-d]pyrimidin-8-yl]-benzamide;
4-[4-Methyl-2-(1-methyl-1H-imidazol-2-ylsulfanyl)-7-oxo-7H-pyrido[2,3-d]pyrimidin-8-yl]-N-(4-trifluoromethyl-benzyl)-benzamide;
4-[2-(4-Fluoro-phenylsulfanyl)-4-methyl-7-oxo-7H-pyrido[2,3-d]pyrimidin-8-yl]-N-(4-trifluoromethyl-benzyl)-benzamide;
4-({4-[4-Methyl-2-(1-methyl-1H-imidazol-2-ylsulfanyl)-7-oxo-7H-pyrido[2,3-d]pyrimidin-8-yl]-benzoylamino}-methyl)-benzoic acid methyl ester;
4-({4-[2-(4-Fluoro-phenylsulfanyl)-4-methyl-7-oxo-7H-pyrido[2,3-d]pyrimidin-8-yl]-benzoylamino}-methyl)-benzoic acid methyl ester;

N-(2,4-Difluoro-benzyl)-4-[4-methyl-2-(1-methyl-1H-imidazol-2-ylsulfanyl)-7-oxo-7H-pyrido[2,3-d]pyrimidin-8-yl]-benzamide;
N-(2,4-Difluoro-benzyl)-4-[2-(4-fluoro-phenylsulfanyl)-4-methyl-7-oxo-7H-pyrido[2,3-d]pyrimidin-8-yl]-benzamide;
4-[2-(4-Fluoro-phenylsulfanyl)-4-methyl-7-oxo-7H-pyrido[2,3-d]pyrimidin-8-yl]-N-(4-methanesulfonyl-benzyl)-benzamide;
N-(3,4-Dimethoxy-benzyl)-4-[4-methyl-2-(1-methyl-1H-imidazol-2-ylsulfanyl)-7-oxo-7H-pyrido[2,3-d]pyrimidin-8-yl]-benzamide;
4-[2-(4-Carbamoylmethyl-phenoxy)-4-methyl-7-oxo-7H-pyrido[2,3-d]pyrimidin-8-yl]-N-cyclopropyl-benzamide;
N-Cyclopropyl-4-[4-methyl-7-oxo-2-(4-trifluoromethyl-phenoxy)-7H-pyrido[2,3-d]pyrimidin-8-yl]-benzamide;
N-Cyclopropyl-4-[2-(4-fluoro-phenoxy)-4-methyl-7-oxo-7H-pyrido[2,3-d]pyrimidin-8-yl]-benzamide;
N-Cyclopropyl-4-{2-[4-(4-hydroxy-benzenesulfonyl)-phenoxy]-4-methyl-7-oxo-7H-pyrido[2,3-d]pyrimidin-8-yl}-benzamide;
4-[2-(4-Acetyl-phenoxy)-4-methyl-7-oxo-7H-pyrido[2,3-d]pyrimidin-8-yl]-N-cyclopropyl-benzamide;
4-[2-(4-Carbamoylmethyl-phenoxy)-4-methyl-7-oxo-7H-pyrido[2,3-d]pyrimidin-8-yl]-N-(4-trifluoromethyl-benzyl)-benzamide;
4-{4-Methyl-7-oxo-8-[4-(4-trifluoromethyl-benzylcarbamoyl)-phenyl]-7,8-dihydro-pyrido[2,3-d]pyrimidin-2-yloxy}-benzoic acid ethyl ester;
4-[4-Methyl-7-oxo-2-(4-trifluoromethyl-phenoxy)-7H-pyrido[2,3-d]pyrimidin-8-yl]-N-(4-trifluoromethyl-benzyl)-benzamide;
4-[2-(4-Fluoro-phenoxy)-4-methyl-7-oxo-7H-pyrido[2,3-d]pyrimidin-8-yl]-N-(4-trifluoromethyl-benzyl)-benzamide;
4-[2-(4-Acetyl-phenoxy)-4-methyl-7-oxo-7H-pyrido[2,3-d]pyrimidin-8-yl]-N-(4-trifluoromethyl-benzyl)-benzamide;
4-({4-[2-(4-Carbamoylmethyl-phenoxy)-4-methyl-7-oxo-7H-pyrido[2,3-d]pyrimidin-8-yl]-benzoylamino}-methyl)-benzoic acid methyl ester;
4-({4-[4-Methyl-7-oxo-2-(4-trifluoromethyl-phenoxy)-7H-pyrido[2,3-d]pyrimidin-8-yl]-benzoylamino}-methyl)-benzoic acid methyl ester;
4-({4-[2-(4-Acetyl-phenoxy)-4-methyl-7-oxo-7H-pyrido[2,3-d]pyrimidin-8-yl]-benzoylamino}-methyl)-benzoic acid methyl ester;
4-[2-(4-Carbamoylmethyl-phenoxy)-4-methyl-7-oxo-7H-pyrido[2,3-d]pyrimidin-8-yl]-N-(2,4-difluoro-benzyl)-benzamide;
N-(2,4-Difluoro-benzyl)-4-[4-methyl-7-oxo-2-(4-trifluoromethyl-phenoxy)-7H-pyrido[2,3-d]pyrimidin-8-yl]-benzamide;
4-[2-(4-Acetyl-phenoxy)-4-methyl-7-oxo-7H-pyrido[2,3-d]pyrimidin-8-yl]-N-(2,4-difluoro-benzyl)-benzamide;
4-[2-(4-Carbamoylmethyl-phenoxy)-4-methyl-7-oxo-7H-pyrido[2,3-d]pyrimidin-8-yl]-N-(4-methanesulfonyl-benzyl)-benzamide;
4-{8-[4-(4-Methanesulfonyl-benzylcarbamoyl)-phenyl]-4-methyl-7-oxo-7,8-dihydro-pyrido[2,3-d]pyrimidin-2-yloxy}-benzoic acid ethyl ester;
N-(4-Methanesulfonyl-benzyl)-4-[4-methyl-7-oxo-2-(4-trifluoromethyl-phenoxy)-7H-pyrido[2,3-d]pyrimidin-8-yl]-benzamide;
4-[2-(4-Fluoro-phenoxy)-4-methyl-7-oxo-7H-pyrido[2,3-d]pyrimidin-8-yl]-N-(4-methanesulfonyl-benzyl)-benzamide;
4-[2-(4-Acetyl-phenoxy)-4-methyl-7-oxo-7H-pyrido[2,3-d]pyrimidin-8-yl]-N-(4-methanesulfonyl-benzyl)-benzamide;
4-[4-Methyl-2-(octahydro-isoquinolin-2-yl)-7-oxo-7H-pyrido[2,3-d]pyrimidin-8-yl]-benzamide;
N-(3,4-Dimethoxy-benzyl)-4-[4-methyl-2-(octahydro-isoquinolin-2-yl)-7-oxo-7H-pyrido[2,3-d]pyrimidin-8-yl]-benzamide;
N-Benzyl-4-[4-methyl-2-(octahydro-isoquinolin-2-yl)-7-oxo-7H-pyrido[2,3-d]pyrimidin-8-yl]-benzamide;
N-Cyclopropyl-4-[4-methyl-2-(octahydro-isoquinolin-2-yl)-7-oxo-7H-pyrido[2,3-d]pyrimidin-8-yl]-benzamide;
4-[4-Methyl-2-(octahydro-isoquinolin-2-yl)-7-oxo-7H-pyrido[2,3-d]pyrimidin-8-yl]-N-(4-trifluoromethyl-benzyl)-benzamide;
4-({4-[4-Methyl-2-(octahydro-isoquinolin-2-yl)-7-oxo-7H-pyrido[2,3-d]pyrimidin-8-yl]-benzoylamino}-methyl)-benzoic acid methyl ester;
N-(2,4-Difluoro-benzyl)-4-[4-methyl-2-(octahydro-isoquinolin-2-yl)-7-oxo-7H-pyrido[2,3-d]pyrimidin-8-yl]-benzamide;
N-(4-Methanesulfonyl-benzyl)-4-[4-methyl-2-(octahydro-isoquinolin-2-yl)-7-oxo-7H-pyrido[2,3-d]pyrimidin-8-yl]-benzamide;
4-[4-Methyl-2-(1-methyl-1H-imidazol-2-ylsulfanyl)-7-oxo-711-pyrido[2,3-d]pyrimidin-8-yl]-benzamide;
4-[2-(1H-Benzoimidazol-2-ylsulfanyl)-4-methyl-7-oxo-7H-pyrido[2,3-d]pyrimidin-8-yl]-benzamide;
4-[2-(4-Fluoro-phenylsulfanyl)-4-methyl-7-oxo-7H-pyrido[2,3-d]pyrimidin-8-yl]-benzamide;
4-[2-(4-Fluoro-phenoxy)-4-methyl-7-oxo-7H-pyrido[2,3-d]pyrimidin-8-yl]-N-(4-methanesulfonyl-benzyl)-benzamide;
4-[2-(4-Fluoro-phenoxy)-4-methyl-7-oxo-7H-pyrido[2,3-d]pyrimidin-8-yl]-N-(4-methanesulfonyl-benzyl)-benzamide;
4-[2-(4-Fluoro-phenoxy)-4-methyl-7-oxo-7H-pyrido[2,3-d]pyrimidin-8-yl]-N-(4-methanesulfonyl-benzyl)-benzamide;
4-[2-(4-Fluoro-phenoxy)-4-methyl-7-oxo-7H-pyrido[2,3-d]pyrimidin-8-yl]-N-(4-methanesulfonyl-benzyl)-benzamide;
4-[2-(4-Fluoro-phenoxy)-4-methyl-7-oxo-7H-pyrido[2,3-d]pyrimidin-8-yl]-N-(4-methanesulfonyl-benzyl)-benzamide;
4-[4-Methyl-7-oxo-2-(5-phenyl-1H-[1,2,4]triazol-3-ylsulfanyl)-7H-pyrido[2,3-d]pyrimidin-8-yl]-benzamide;
N-(3,4-Dimethoxy-benzyl)-4-[4-methyl-7-oxo-2-(5-phenyl-1H-[1,2,4]triazol-3-ylsulfanyl)-7H-pyrido[2,3-d]pyrimidin-8-yl]-benzamide;
4-[2-(1H-Benzoimidazol-2-ylsulfanyl)-4-methyl-7-oxo-7H-pyrido[2,3-d]pyrimidin-8-yl]-N-(3,4-dimethoxy-benzyl)-benzamide;
N-Benzyl-4-[4-methyl-7-oxo-2-(5-phenyl-1H-[1,2,4]triazol-3-ylsulfanyl)-7H-pyrido[2,3-d]pyrimidin-8-yl]-benzamide;
4-[2-(1H-Benzoimidazol-2-ylsulfanyl)-4-methyl-7-oxo-7H-pyrido[2,3-d]pyrimidin-8-yl]-N-benzyl-benzamide;
N-Cyclopropyl-4-[4-methyl-7-oxo-2-(5-phenyl-1H-[1,2,4]triazol-3-ylsulfanyl)-7H-pyrido[2,3-d]pyrimidin-8-yl]-benzamide;

4-[4-Methyl-7-oxo-2-(5-phenyl-1H-[1,2,4]triazol-3-yl-sulfanyl)-7H-pyrido[2,3-d]pyrimidin-8-yl]-N-(4-trifluoromethyl-benzyl)-benzamide;

4-[2-(1H-Benzoimidazol-2-ylsulfanyl)-4-methyl-7-oxo-7H-pyrido[2,3-d]pyrimidin-8-yl]-N-(4-trifluoromethyl-benzyl)-benzamide;

4-({4-[4-Methyl-7-oxo-2-(5-phenyl-1H-[1,2,4]triazol-3-ylsulfanyl)-7H-pyrido[2,3-d]pyrimidin-8-yl]-benzoylamino}-methyl)-benzoic acid methyl ester;

4-({4-[2-(1H-Benzoimidazol-2-ylsulfanyl)-4-methyl-7-oxo-7H-pyrido[2,3-d]pyrimidin-8-yl]-benzoylamino}-methyl)-benzoic acid methyl ester;

N-(2,4-Difluoro-benzyl)-4-[4-methyl-7-oxo-2-(5-phenyl-1H-[1,2,4]triazol-3-ylsulfanyl)-7H-pyrido[2,3-d]pyrimidin-8-yl]-benzamide;

4-[2-(1H-Benzoimidazol-2-ylsulfanyl)-4-methyl-7-oxo-7H-pyrido[2,3-d]pyrimidin-8-yl]-N-(2,4-difluoro-benzyl)-benzamide;

N-(4-Methanesulfonyl-benzyl)-4-[4-methyl-2-(1-methyl-1H-imidazol-2-ylsulfanyl)-7-oxo-7H-pyrido[2,3-d]pyrimidin-8-yl]-benzamide;

N-(4-Methanesulfonyl-benzyl)-4-[4-methyl-7-oxo-2-(5-phenyl-1H-[1,2,4]triazol-3-ylsulfanyl)-7H-pyrido[2,3-d]pyrimidin-8-yl]-benzamide;

4-[2-(1H-Benzoimidazol-2-ylsulfanyl)-4-methyl-7-oxo-7H-pyrido[2,3-d]pyrimidin-8-yl]-N-(4-methanesulfonyl-benzyl)-benzamide;

4-[2-(4-Fluoro-phenoxy)-4-methyl-7-oxo-7H-pyrido[2,3-d]pyrimidin-8-yl]-N-(4-methanesulfonyl-benzyl)-benzamide;

4-[2-(4-Fluoro-phenoxy)-4-methyl-7-oxo-7H-pyrido[2,3-d]pyrimidin-8-yl]-N-(4-methanesulfonyl-benzyl)-benzamide;

4-[2-(4-Fluoro-phenoxy)-4-methyl-7-oxo-7H-pyrido[2,3-d]pyrimidin-8-yl]-N-(4-methanesulfonyl-benzyl)-benzamide;

N-(2,4-Difluoro-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide;

4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid cyclohexylamide;

4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide;

N-(4-Methanesulfonyl-benzyl)-4-{4-methyl-7-oxo-2-[4-(pyridine-3-carbonyl)-piperazin-1-yl]-7H-pyrido[2,3-d]pyrimidin-8-yl}-benzamide;

4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide;

4-{2-[4-(Furan-2-carbonyl)-piperazin-1-yl]-4-methyl-7-oxo-7H-pyrido[2,3-d]pyrimidin-8-yl}-N-(4-methanesulfonyl-benzyl)-benzamide;

4-[2-(4-Benzoyl-piperazin-1-yl)-4-methyl-7-oxo-7H-pyrido[2,3-d]pyrimidin-8-yl]-N-(4-methanesulfonyl-benzyl)-benzamide;

N-(4-Methanesulfonyl-benzyl)-4-[4-methyl-7-oxo-2-(4-phenylacetyl-piperazin-1-yl)-7H-pyrido[2,3-d]pyrimidin-8-yl]-benzamide;

N-(4-Methanesulfonyl-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide;

4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid cyclohexylamide;

4-{8-[4-(4-Methanesulfonyl-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide;

4-{2-[4-(Furan-2-carbonyl)-piperazin-1-yl]-4-methyl-7-oxo-7H-pyrido[2,3-d]pyrimidin-8-yl}-benzamide;

4-[2-(4-Benzoyl-piperazin-1-yl)-4-methyl-7-oxo-7H-pyrido[2,3-d]pyrimidin-8-yl]-benzamide;

4-{4-Methyl-7-oxo-2-[4-(3,4,5-trimethoxy-benzoyl)-piperazin-1-yl]-7H-pyrido[2,3-d]pyrimidin-8-yl}-benzamide;

N-(3,4-Dimethoxy-benzyl)-4-{4-methyl-7-oxo-2-[4-(pyridine-3-carbonyl)-piperazin-1-yl]-7H-pyrido[2,3-d]pyrimidin-8-yl}-benzamide;

4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide;

N-(3,4-Dimethoxy-benzyl)-4-{2-[4-(furan-2-carbonyl)-piperazin-1-yl]-4-methyl-7-oxo-7H-pyrido[2,3-d]pyrimidin-8-yl}-benzamide;

4-[2-(4-Benzoyl-piperazin-1-yl)-4-methyl-7-oxo-7H-pyrido[2,3-d]pyrimidin-8-yl]-N-(3,4-dimethoxy-benzyl)-benzamide;

N-(3,4-Dimethoxy-benzyl)-4-[4-methyl-7-oxo-2-(4-phenylacetyl-piperazin-1-yl)-7H-pyrido[2,3-d]pyrimidin-8-yl]-benzamide;

N-(3,4-Dimethoxy-benzyl)-4-{4-methyl-7-oxo-2-[4-(3,4,5-trimethoxy-benzoyl)-piperazin-1-yl]-7H-pyrido[2,3-d]pyrimidin-8-yl}-benzamide;

4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid cyclohexylamide;

N-Benzyl-4-{4-methyl-7-oxo-2-[4-(pyridine-3-carbonyl)-piperazin-1-yl]-7H-pyrido[2,3-d]pyrimidin-8-yl}-benzamide;

4-[8-(4-Benzylcarbamoyl-phenyl)-4-methyl-7-oxo-7,8-dihydro-pyrido[2,3-d]pyrimidin-2-yl]-piperazine-1-carboxylic acid (3,4-difluoro-phenyl)-amide;

N-Benzyl-4-{2-[4-(furan-2-carbonyl)-piperazin-1-yl]-4-methyl-7-oxo-7H-pyrido[2,3-d]pyrimidin-8-yl}-benzamide;

4-[2-(4-Benzoyl-piperazin-1-yl)-4-methyl-7-oxo-7H-pyrido[2,3-d]pyrimidin-8-yl]-N-benzyl-benzamide;

N-Benzyl-4-[4-methyl-7-oxo-2-(4-phenylacetyl-piperazin-1-yl)-7H-pyrido[2,3-d]pyrimidin-8-yl]-benzamide;

4-{8-[4-(3,4-Dimethoxy-benzylcarbamoyl)-phenyl]-4-methyl-7-oxo-7,8-dihydro-pyrido[2,3-d]pyrimidin-2-yl}-piperazine-1-carboxylic acid (3-trifluoromethyl-phenyl)-amide;

N-Benzyl-4-{4-methyl-7-oxo-2-[4-(3,4,5-trimethoxy-benzoyl)-piperazin-1-yl]-7H-pyrido[2,3-d]pyrimidin-8-yl}-benzamide;

4-[8-(4-Benzylcarbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide;

N-Cyclopropyl-4-{4-methyl-7-oxo-2-[4-(pyridine-3-carbonyl)-piperazin-1-yl]-7H-pyrido[2,3-d]pyrimidin-8-yl}-benzamide;

4-[8-(4-Cyclopropylcarbamoyl-phenyl)-4-methyl-7-oxo-7,8-dihydro-pyrido[2,3-d]pyrimidin-2-yl]-piperazine-1-carboxylic acid (3,4-difluoro-phenyl)-amide;

N-Cyclopropyl-4-{2-[4-(furan-2-carbonyl)-piperazin-1-yl]-4-methyl-7-oxo-7H-pyrido[2,3-d]pyrimidin-8-yl}-benzamide;

4-[2-(4-Benzoyl-piperazin-1-yl)-4-methyl-7-oxo-7H-pyrido[2,3-d]pyrimidin-8-yl]-N-cyclopropyl-benzamide;

N-Cyclopropyl-4-[4-methyl-7-oxo-2-(4-phenylacetyl-piperazin-1-yl)-7H-pyrido[2,3-d]pyrimidin-8-yl]-benzamide;

N-Cyclopropyl-4-{4-methyl-7-oxo-2-[4-(3,4,5-trimethoxy-benzoyl)-piperazin-1-yl]-7H-pyrido[2,3-d]pyrimidin-8-yl}-benzamide;

4-[8-(4-Cyclopropylcarbamoyl-phenyl)-4-methyl-7-oxo-7,8-dihydro-pyrido[2,3-d]pyrimidin-2-yl]-piperazine-1-carboxylic acid cyclohexylamide 4-[8-(4-Cyclopropylcarbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide 4-{4-Methyl-7-oxo-2-[4-(3,4,5-trimethoxy-benzoyl)-piperazin-1-yl]-7H-pyrido[2,3-d]pyrimidin-8-yl}-N-(4-trifluoromethyl-benzyl)-benzamide;

4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid cyclohexylamide;

4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid (3-trifluoromethyl-phenyl)-amide;

4-[(4-{4-Methyl-7-oxo-2-[4-(pyridine-3-carbonyl)-piperazin-1-yl]-7H-pyrido[2,3-d]pyrimidin-8-yl}-benzoylamino)-methyl]-benzoic acid methyl ester;

4-[(4-{2-[4-(3,4-Difluoro-phenylcarbamoyl)-piperazin-1-yl]-4-methyl-7-oxo-7H-pyrido[2,3-d]pyrimidin-8-yl}-benzoylamino)-methyl]-benzoic acid methyl ester;

4-[(4-{2-[4-(Furan-2-carbonyl)-piperazin-1-yl]-4-methyl-7-oxo-7H-pyrido[2,3-d]pyrimidin-8-yl}-benzoylamino)-methyl]-benzoic acid methyl ester;

4-({4-[2-(4-Benzoyl-piperazin-1-yl)-4-methyl-7-oxo-7H-pyrido[2,3-d]pyrimidin-8-yl]-benzoylamino}-methyl)-benzoic acid methyl ester;

4-({4-[4-Methyl-7-oxo-2-(4-phenylacetyl-piperazin-1-yl)-7H-pyrido[2,3-d]pyrimidin-8-yl]-benzoylamino}-methyl)-benzoic acid methyl ester;

4-[(4-{4-Methyl-7-oxo-2-[4-(3,4,5-trimethoxy-benzoyl)-piperazin-1-yl]-7H-pyrido[2,3-d]pyrimidin-8-yl}-benzoylamino)-methyl]-benzoic acid methyl ester;

4-({4-[2-(4-Cyclohexylcarbamoyl-piperazin-1-yl)-4-methyl-7-oxo-7H-pyrido[2,3-d]pyrimidin-8-yl]-benzoylamino}-methyl)-benzoic acid methyl ester;

4-[(4-{4-Methyl-7-oxo-2-[4-(3-trifluoromethyl-phenylcarbamoyl)-piperazin-1-yl]-7H-pyrido[2,3-d]pyrimidin-8-yl}-benzoylamino)-methyl]-benzoic acid methyl ester;

N-(2,4-Difluoro-benzyl)-4-{4-methyl-7-oxo-2-[4-(pyridine-3-carbonyl)-piperazin-1-yl]-7H-pyrido[2,3-d]pyrimidin-8-yl}-benzamide;

4-{8-[4-(2,4-Difluoro-benzylcarbamoyl)-phenyl]-4-methyl-7-oxo-7,8-dihydro-pyrido[2,3-d]pyrimidin-2-yl}-piperazine-1-carboxylic acid (3,4-difluoro-phenyl)-amide;

4-[8-(4-Carbamoyl-phenyl)-4-methyl-7-oxo-7,8-dihydro-pyrido[2,3-d]pyrimidin-2-yl]-piperazine-1-carboxylic acid (3-trifluoromethyl-phenyl)-amide;

N-(2,4-Difluoro-benzyl)-4-{2-[4-(furan-2-carbonyl)-piperazin-1-yl]-4-methyl-7-oxo-7H-pyrido[2,3-d]pyrimidin-8-yl}-benzamide 4-[2-(4-Benzoyl-piperazin-1-yl)-4-methyl-7-oxo-7H-pyrido[2,3-d]pyrimidin-8-yl]-N-(2,4-difluoro-benzyl)-benzamide;

N-(2,4-Difluoro-benzyl)-4-[4-methyl-7-oxo-2-(4-phenylacetyl-piperazin-1-yl)-7H-pyrido[2,3-d]pyrimidin-8-yl]-benzamide;

4-{4-Methyl-7-oxo-2-[4-(pyridine-3-carbonyl)-piperazin-1-yl]-7H-pyrido[2,3-d]pyrimidin-8-yl}-benzamide;

4-[8-(4-Carbamoyl-phenyl)-4-methyl-7-oxo-7,8-dihydro-pyrido[2,3-d]pyrimidin-2-yl]-piperazine-1-carboxylic acid (3,4-difluoro-phenyl)-amide;

4-[4-Methyl-7-oxo-2-(4-phenylacetyl-piperazin-1-yl)-7H-pyrido[2,3-d]pyrimidin-8-yl]-benzamide;

4-[8-(4-Carbamoyl-phenyl)-4-methyl-7-oxo-7,8-dihydro-pyrido[2,3-d]pyrimidin-2-yl]-piperazine-1-carboxylic acid cyclohexylamide;

4-[8-(4-Benzylcarbamoyl-phenyl)-4-methyl-7-oxo-7,8-dihydro-pyrido[2,3-d]pyrimidin-2-yl]-piperazine-1-carboxylic acid cyclohexylamide;

4-{4-Methyl-7-oxo-2-[4-(pyridine-3-carbonyl)-piperazin-1-yl]-7H-pyrido[2,3-d]pyrimidin-8-yl}-N-(4-trifluoromethyl-benzyl)-benzamide;

4-{4-Methyl-7-oxo-8-[4-(4-trifluoromethyl-benzylcarbamoyl)-phenyl]-7,8-dihydro-pyrido[2,3-d]pyrimidin-2-yl}-piperazine-1-carboxylic acid (3,4-difluoro-phenyl)-amide;

4-{2-[4-(Furan-2-carbonyl)-piperazin-1-yl]-4-methyl-7-oxo-7H-pyrido[2,3-d]pyrimidin-8-yl}-N-(4-trifluoromethyl-benzyl)-benzamide;

4-[2-(4-Benzoyl-piperazin-1-yl)-4-methyl-7-oxo-7H-pyrido[2,3-d]pyrimidin-8-yl]-N-(4-trifluoromethyl-benzyl)-benzamide;

4-[4-Methyl-7-oxo-2-(4-phenylacetyl-piperazin-1-yl)-7H-pyrido[2,3-d]pyrimidin-8-yl]-N-(4-trifluoromethyl-benzyl)-benzamide; and 4-(4-methyl-2-(methylsulfanyl)-7-oxopyrido[2,3-d]pyrimidin-8(7H)-yl)benzoic acid.

6. A method for inhibiting telomerase enzyme comprising contacting the telomerase enzyme with an effective amount of the pyrido[2,3-d]pyrimidin-7(8H)-ones derivative of claim 1.

7. A method for inhibiting telomerase enzyme comprising contacting the telomerase enzyme with an effective amount of the pyrido[2,3-d]pyrimidin-7(8H)-ones derivative of claim 2.

8. A pharmaceutical composition comprising a pharmaceutically acceptable carrier, diluent, or both a pharmaceutically acceptable carrier and a diluent and a pyrido[2,3-d]pyrimidin-7(8H)-one of claim 1.

9. A pharmaceutical composition comprising a pharmaceutically acceptable carrier, diluent, or both a pharmaceutically acceptable carrier and a diluent and a pyrido[2,3-d]pyrimidin-7(8H)-one derivative of claim 2.

* * * * *